(12) United States Patent
Aronov et al.

(10) Patent No.: US 7,446,199 B2
(45) Date of Patent: Nov. 4, 2008

(54) COMPOSITIONS USEFUL AS INHIBITORS OF PROTEIN KINASES

(75) Inventors: Alex Aronov, Watertown, MA (US); David J. Lauffer, Stow, MA (US); Pan Li, Arlington, MA (US); Ronald C. Tomlinson, Sudbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 327 days.

(21) Appl. No.: 10/936,470

(22) Filed: Sep. 7, 2004

(65) Prior Publication Data

US 2005/0137201 A1    Jun. 23, 2005

Related U.S. Application Data

(60) Provisional application No. 60/500,199, filed on Sep. 4, 2003, provisional application No. 60/527,907, filed on Dec. 8, 2003.

(51) Int. Cl.
*C07D 471/04* (2006.01)
*C07D 401/02* (2006.01)
(52) U.S. Cl. .................................. 546/113; 546/272.1
(58) Field of Classification Search ............... 546/272.1
See application file for complete search history.

(56) References Cited

U.S. PATENT DOCUMENTS 5,604,240 A * 2/1997 Chambers et al. ........... 514/300

FOREIGN PATENT DOCUMENTS

| WO | WO 01/12621 A1 | 2/2001 |
| WO | WO 02/10158 A1 | 2/2002 |
| WO | WO 02/083668 A1 | 10/2002 |
| WO | WO 02/102800 A1 | 12/2002 |
| WO | WO 03/004492 A1 | 1/2003 |
| WO | 2004/078756 A2 | 9/2004 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the Internet, URL: http://en.wikipedia.org/wiki/Cancer>.*
Cancer [online], [retrieved on Jul. 6, 2007]. Retrieved from the Internet, URL: http://www.nlm.nih.gov/medlineplus/cancer.html>.*
Cancer [online], [retrieved on Jun. 3, 2008]. Retrieved from the Internet, URL: http://www.cancer.gov/cancertopics/pdq/treatment/renalcell/patient>.*

* cited by examiner

*Primary Examiner*—Rei-tsang Shiao
*Assistant Examiner*—Shawquia Young
(74) *Attorney, Agent, or Firm*—Daniel A. Pearson

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

12 Claims, No Drawings

COMPOSITIONS USEFUL AS INHIBITORS OF PROTEIN KINASES

CROSS-REFERENCE TO RELATED APPLICATIONS

The present application claims the benefit under 35 U.S.C. § 119 of U.S. Provisional patent application No. 60/500,199, filed Sep. 4, 2003, and U.S. Provisional patent application No. 60/527,907, filed Dec. 8, 2003, the entire contents of both applications being incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, cancer and other proliferative disorders. Accordingly, there has been a substantial effort in medicinal chemistry to find protein kinase inhibitors that are effective as therapeutic agents.

The c-Met proto-oncogene encodes the Met receptor tyrosine kinase. The Met receptor is a 190 kDa glycosylated dimeric complex composed of a 50 kDa alpha chain disulfide-linked to a 145 kDa beta chain. The alpha chain is found extracellularly while the beta chain contains transmembrane and cytosolic domains. Met is synthesized as a precursor and is proteolytically cleaved to yield mature alpha and beta subunits. It displays structural similarities to semaphorins and plexins, a ligand-receptor family that is involved in cell-cell interaction. The ligand for Met is hepatocyte growth factor (HGF), a member of the scatter factor family and has some homology to plasminogen [Longati, P. et al., *Curr. Drug Targets* 2001, 2, 41-55); Trusolino, L. and Comoglio, P. *Nature Rev. Cancer* 2002, 2, 289-300].

Met functions in tumorigenesis and tumor metastasis. Chromosomal rearrangements forming Tpr-met fusions in an osteoclast cell line resulted in constitutively active Met receptors and transformation (Cooper, C. S. et al., *Nature* 1984, 311, 29-33). Met mutants exhibiting enhanced kinase activity have been identified in both hereditary and sporadic forms of papillary renal carcinoma (Schmidt, L. et al., *Nat. Genet.* 1997, 16, 68-73; Jeffers, M. et al., *Proc. Nat. Acad. Sci.* 1997, 94, 11445-11500). Expression of Met along with its ligand HGF is transforming, tumorigenic, and metastatic (Jeffers, M. et al., *Oncogene* 1996, 13, 853-856; Michieli, P. et al., *Oncogene* 1999, 18, 5221-5231). HGF/Met has been shown to inhibit anoikis, suspension-induced programmed cell death (apoptosis), in head and neck squamous cell carcinoma cells. Anoikis resistance or anchorage-independent survival is a hallmark of oncogenic transformation of epithelial cells (Zeng, Q. et al., *J. Biol. Chem.* 2002, 277, 25203-25208).

MET is overexpressed in a significant percentage of human cancers and is amplified during the transition between primary tumors and metastasis. To investigate whether this oncogene is directly responsible for the acquisition of the metastatic phenotype, Giordano et al. exploited a single-hit oncogenic version of MET that was able to transform and to confer invasive and metastatic properties to nontumorigenic cells, both in vitro and in nude mice. They found a point mutation in the signal transducer docking site of MET that increased the transforming ability of the oncogene, but abolished its metastatic potential. They concluded that the metastatic potential of the MET oncogene relies on the properties of its multifunctional docking site, and that a single point mutation affecting signal transduction can dissociate neoplastic transformation from metastasis. Giordano, S., et al., *Proc. Nat. Acad. Sci.* 94: 13868-13872, 1997.

c-Met is implicated in various cancers, especially renal. It was found that the beta-subunit of the c-Met protooncogene product is the cell-surface receptor for hepatocyte growth factor. It was also identified that the hepatocyte growth factor receptor is the c-met proto-oncogene product. Bottaro, D. P., et al., *Science* 251: 802-804, 1991.

The nexus between c-Met and colorectal cancer has also been established. Analysis of cMet expression during colorectal cancer progression showed that 50% of the carcinoma specimens analyzed expressed 5-50-fold higher levels of cMet mRMA transcripts and protein versus the adjacent normal colonic mucosa. In addition, when compared to the primary tumor, 70% of colorectal cancer liver metastasis showed cMet over expression. See Long et al., Met Receptor Overexpression and Oncogenic Ki-ras Mutation Cooperate to Enhance Tumorigenicity of Colon Cancer Cells in Vivo. *Mol Cancer Res.* 2003 March; 1(5): 393-401; Fujisaki, et al., CD44 stimulation induces integrin-mediated adhesion of colon cancer cell lines to endothelial cells by up-regulation of integrins and c-Met and activation of integrins. *Cancer Res.* 1999 Sep. 1; 59(17): 4427-34; Hiscox et al., Association of the HGF/SF receptor, c-met, with the cell-surface adhesion molecule, E-cadherin, and catenins in human tumor cells. *Biochem Biophys Res Commun.* 1999 Aug. 2; 261(2): 406-11; Herynk et al., Activation of c-Met in colorectal carcinoma cells leads to constitutive association of tyrosine-phosphorylated beta-cateninz. *Clin Exp Metastasis.* 2003; 20(4): 291-300; Wielenga et al., Expression of c-Met and heparan-sulfate proteoglycan forms of CD44 in colorectal cancer. *Am J Pathol.* 2000 November; 157(5): 1563-73; Di Renzo et al., Overexpression and amplification of the Met/HGF receptor gene during the progression of colorectal cancer. *Clin. Cancer Res.,* 1: 147-154, 1995; and Mao, et al., Activation of c-Src by receptor tyrosine kinases in human colon cancer cells with high metastatic potential. Oncogene, 15: 3083-3090, 1997.

The c-Met is also implicated in glioblastoma. High-grade malignant gliomas are the most common cancers of the central nervous system. Despite treatment with surgical resection, radiation therapy, and chemotherapy, the mean overall survival is<1.5 years, and few patients survive for>3 years. A common reason for treatment failure is their innate resistance to radiation and chemotherapy.

Glioblastoma multiforme is the most common and most malignant glial neoplasm. Despite very aggressive treatment, these malignant gliomas are associated with an average life expectancy of only 9 months. The formation and malignant progression of human gliomas are complex processes and involve genetic mutations, chromosomal multiploidy, and aberrant epigenetic influences of multiple mitogens and angiogenic factors.

Human malignant gliomas frequently express both HGF and cMet, which can establish an autocrine loop of biological significance. Glioma cMet expression correlates with glioma grade, and an analysis of human tumor specimens showed that malignant gliomas have a 7-fold higher HGF content than low-grade gliomas.

Gliomas represent the most common form of primary central nervous system malignancy and are among the tumors most tightly linked with HGF-cMet signaling abnormalities. Multiple studies have demonstrated that human gliomas frequently co-express HGF and cMet and that high levels of expression are associated with malignant progression. HGF gene transfer to glioma cell lines enhances tumorigenicity, tumor growth, and tumor-associated angiogenesis. It has also been shown that blocking HGF-cMet signaling reverses these phenotypes in vivo. It was further shown that HGF-cMet is able to activate Akt and protect glioma cell lines from apopototic death, both in vitro and in vivo.

See Hirose et al., Clinical importance of cMet protein expression in high grade astrocytic tumors. *Neurol. Med.-Chir.* 38:851-859, 1998; Hirose et al., Immunohistochemical examination of cMet protein expression in astrocytic tumors. *Acta Neuropathol.* 95: 345-351, 1998; Koochekpour et al., Met and hepatocyte growth factor expression in human gliomas. Cancer Res. 57: 5391-5398; Laterra et al., HGF expression enhances human glioblastoma tumorigenicity and growth. *Biochem. Biophys. Res. Commun.* 235:743-747; Moriyama et al., Concomitant expression of hepatocyte growth factor, HGF activator and cMet genes in human glioma cells in vitro. *FEBs Lett.* 372:78-82, 1995; Nabeshima et al., Expression of cMet correlates with grade of malignancy in human astrocytic tumors: an immunohistochemical study. *Histopathology* 31: 436-443, 1997; Shiota et al., Coexpression of hepatocyte growth factor and its receptor (cMet) in HGL4 glioblastoma cells. *Lab. Investig.* 53: 511-516, 1996; Welch et al., Hepatocyte growth factor and receptor (cMet) in normal and malignant astrocytic cells. *Anticancer Res.* 19:1635-1640, 1999; Bowers et al., HGF protects against cytoxic death in human glioblastoma via PI3-K and Akt-dependent pathways. *Cancer Res.* 60:4277-4283, 2000.

It was shown that the effect of NK4 (HGF antagonist), on HGF-promoted growth of a human breast cancer resulted in the reduction of tumor invasiveness and motility, weight and volume. Furthermore, in the in-vitro invasion assay and migration assay, both HGF and human fibroblasts, which secrete bioactive HGF, increased the invasiveness and migration of the breast cancer cells (MDA MB 231). See Growth and angiogenesis of human breast cancer in a nude mouse tumour model is reduced by NK4, the HGF antagonist. *Carcinogensis*, May 9, 2003. Furthermore, transgenic mice harboring mutationally activated cMet developed metastic mammary carcinoma. These same activating mutants were able to establish tumors in nude mouse NIH 3T3 xenografts (*PNAS*, Vol 95, pp 14417-14422, November 1998).

Transgenic mice that overexpressed cMet in hepatocytes developed heptocellular carcinoma (HCC) one of the human tumors in which cMet has been implicated previously. Inactivation of the transgene led to regression of even highly advanced tumors, apparently mediated by apoptosis and cessation of cellular proliferation. Numerous cells were proliferating in the liver tumors that were elicited by cMet. Removal of the stimulus from the transgenic hMet led to prompt cessation of cellular proliferation even in the cells of advanced malignancies (*The Journal of Cell Biology, Vol.* 153, 2001, p. 1023-1033).

HGF/Met signaling is involved in cell adhesion and motility in normal cells and plays a major role in the invasive growth that is found in most tissues, including cartilage, bone, blood vessels, and neurons (reviewed in Comoglio, P. M. and Trusolino, L. *J. Clin. Invest.* 2002, 109, 857-862). Dysfunctional activation or increased numbers of Met is likely to contribute to the aberrant cell-cell interactions that lead to migration, proliferation, and survival of cells that is characteristic of tumor metastasis. Activation of Met induces and sustains a variety of tumors [Wang, R. et al., *J. Cell. Biol.* 2001, 153, 1023-1034; Liang, T. J. et al., *J. Clin. Invest.* 1996, 97, 2872-2877; Jeffers, M. et al., *Proc. Nat. Acad. Sci.* 1998, 95, 14417-14422] while loss of Met inhibits growth and invasiveness of tumor cells [Jiang, W. G. et al., *Clin. Cancer Res.* 2001, 7, 2555-2562; Abounader, R. et al., *FASEB J.* 2002 16, 108-110]. Increased expression of Met/HGF is seen in many metastatic tumors including colon (Fazekas, K. et al., *Clin. Exp. Metastasis* 2000, 18, 639-649), breast (Elliott, B. E. et al., 2002, *Can. J. Physiol. Pharmacol.* 80, 91-102), prostate (Knudsen, B. S. et al., *Urology* 2002, 60, 1113-1117), lung (Siegfried, J. M. et al., *Ann. Thorac. Surg.* 1998, 66, 1915-1918), and gastric (Amemiya, H. et al., *Oncology* 2002, 63, 286-296).

Further demonstration of the role Met plays in metastasis was shown by Giordano, et al. (2002) who presented evidence for cross-talk between the semaphorin 4D (SEMA4D; 601866) receptor, plexin B1 (PLXNB1; 601053), and MET during invasive growth in epithelial cells. Binding of SEMA4D to PLXNB1 stimulated tyrosine kinase activity of MET, resulting in tyrosine phosphorylation of both receptors. This effect was not found in cells lacking MET expression. Giordano, S., et al.: The Semaphorin 4D receptor controls invasive growth by coupling with *Met. Nature Cell Biol.* 4: 720-724, 2002.

HGF-Met signaling has also been associated with increased risk of atherosclerosis (Yamamoto, Y. et al., *J. Hypertens.* 2001, 19, 1975-1979; Morishita, R. et al., *Endocr. J.* 2002, 49, 273-284) and increased fibrosis of the lung (Crestani, B. et al., *Lab. Invest.* 2002, 82, 1015-1022.

Glycogen synthase kinase-3 (GSK-3) is a serine/threonine protein kinase comprised of a and b isoforms that are each encoded by distinct genes [Coghlan et al., Chemistry & Biology, 7, 793-803 (2000); Kim and Kimmel, Curr. Opinion Genetics Dev., 10, 508-514 (2000)]. GSK-3 has been implicated in various diseases including diabetes, Alzheimer's disease, CNS disorders such as manic depressive disorder and neurodegenerative diseases, and cardiomyocyte hypertrophy [see, e.g., WO 99/65897; WO 00/38675; Kaytor and Orr, Curr. Opin. Neurobiol., 12, 275-8 (2000); Haq et al., J. Cell Biol., 151, 117-30 (2000); Eldar-Finkelman, Trends Mol. Med., 8, 126-32 (2002)]. These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor b-catenin, the translation initiation factor e1F-2B, as well as ATP citrate lyase, axin, heat shock factor-1, c-Jun, c-myc, c-myb, CREB, and CEPBa. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake [Klein et al., PNAS, 93, 8455-9 (1996); Cross et al., Biochem. J., 303, 21-26 (1994); Cohen, Biochem. Soc. Trans., 21, 555-567 (1993); and Massillon et al., Biochem J. 299, 123-128 (1994); Cohen and Frame, Nat. Rev. Mol. Cell. Biol., 2, 769-76 (2001)]. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes [WO 00/38675]. Therapeutic inhibitors of GSK-3 are therefore useful for treating diabetic patients suffering from an impaired response to insulin.

Apoptosis has been implicated in the pathophysiology of ischemic brain damage (Li et al., 1997; Choi, et al., 1996; Charriaut-Marlangue et al., 1998; Grahm and Chen, 2001; Murphy et al., 1999; Nicotera et al., 1999). Recent publications indicate that activation of GSK-3β may be involved in apoptotic mechanisms (Kaytor and Orr, 2002; Culbert et al., 2001). Studies in rat models of ischemic stroke induced by middle cerebral artery occlusion (MCAO) showed increased GSK-3b expression is following ischemia (Wang et al., Brain Res, 859, 381-5, 2000; Sasaki et al., Neurol Res, 23, 588-92, 2001). Fibroblast growth factor (FGF) reduced ischemic brain injury after permanent middle cerebral artery occlusion (MCO) in rats (Fisher et al. 1995; Song et al. 2002). Indeed, the neuroprotective effects of FGF demonstrated in ischemia models in rats may be mediated by a PI-3 kinase/AKT-dependent inactivation of GSK-3b (Hashimoto et al., 2002). Thus, inhibition of GSK-3β after a cerebral ischemic event may ameliorate ischemic brain damage.

GSK-3 is also implicated in myocardial infarction. See Jonassen et al., Circ Res, 89: 1191, 2001 (The reduction in myocardial infarction by insulin administration at reperfusion is mediated via Akt dependent signaling pathway); Matsui et al., Circulation, 104: 330, 2001 (Akt activation preserves cardiac function and prevents cardiomyocyte injury after transient cardiac ischemia in vivo); Miao et al., J Mol Cell Cardiol, 32: 2397, 2000 (Intracoronary, adenovirus-mediated Akt gene delivery in heart reduced gross infarct size following ischemia-reperfusion injury in vivo); and Fujio et al., Circulation et al., 101: 660, 2000 (Akt signaling inhibits cardiac myocyte apoptosis in vitro and protects against ischemia-reperfusion injury in mouse heart).

GSK-3 activity plays a role in head trauma. See Noshita et al., Neurobiol Dis, 9: 294, 2002 (Upregulation of Akt/PI3-kinase pathway may be crucial for cell survival after traumatic brain injury) and Dietrich et al., J Neurotrauma, 13: 309, 1996 (Posttraumatic administration of bFGF significantly reduced damaged cortical neurons & total contusion volume in a rat model of traumatic brain injury).

GSK-3 is also known to play a role in psychiatric disorders. See Eldar-Finkelman, Trends Mol Med, 8:126, 2002; Li et al., Bipolar Disord, 4: 137, 2002 (LiCl and Valproic acid, antipsychotic, mood stabilizing drugs, decrease GSK3 activities and increase beta-catenin) and Lijam et al., Cell, 90: 895, 1997 (Dishevelled KO mice showed abnormal social behavior and defective sensorimotor gating. Dishevelled, a cytoplasmic protein involved in WNT pathway, inhibits GSK3beta activities).

It has been shown that GSK3 inhibition by lithium and valproic acid induces axonal remodeling and change synaptic connectivity. See Kaytor & Orr, Curr Opin Neurobiol, 12: 275, 2002 (Downregulation of GSK3 causes changes in microtubule-associated proteins: tau, MAP1 & 2) and Hall et al., Mol Cell Neurosci, 20: 257, 2002 (Lithium and valproic acid induces the formation of growth cone-like structures along the axons).

GSK-3 activity is also associated with Alzheimer's disease. This disease is characterized by the presence of the well-known b-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., Curr. Biol., 4, 1077-86 (1994); and Brownlees et al., Neuroreport 8, 3251-55 (1997); Kaytor and Orr, Curr. Opin. Neurobiol., 12, 275-8 (2000)]. In transgenic mice overexpressing GSK3, significant increased Tau hyperphosphorylation and abnormal morphology of neurons were observed [Lucas et al., EMBO J, 20: 27-39 (2001)]. Active GSK3 accumulates in cytoplasm of pretangled neurons, which can lead to neurofibrillary tangles in brains of patients with AD [Pei et al., J Neuropathol Exp Neurol, 58, 1010-19 (1999)]. Therefore, inhibition of GSK-3 slows or halts the generation of neurofibrillary tangles and thus treats or reduces the severity of Alzheimer's disease.

Evidence for the role GSK-3 plays in Alzheimer's disease has been shown in vitro. See Aplin et al. (1996), J Neurochem 67: 699; Sun et al. (2002), Neurosci Lett 321: 61 (GSK3b phosphorylates cytoplasmic domain of Amyloid Precursor Protein (APP) and GSK3b inhibition reduces Ab40 & Ab42 secretion in APP-transfected cells); Takashima et al. (1998), PNAS 95:9637; Kirschenbaum et al. (2001), J Biol Chem 276:7366 (GSK3b complexes with and phosphorylates presenilin-1, which is associated with gamma-secretase activity in the synthesis of Ab from APP); Takashima et al. (1998), Neurosci Res 31:317 (Activation of GSK3b by Ab(25-35) enhances phosphorylation of tau in hippocampal neurons. This observation provides a link between Ab and neurofibrillary tangles composed of hyperphosphorylated tau, another pathological hallmark of AD); Takashima et al. (1993), PNAS 90:7789 (Blockade of GSK3b expression or activity prevents Ab-induced neuro-degeneration of cortical and hippocampal primary cultures); Suhara et al. (2003), Neurobiol Aging. 24:437 (Intracellular Ab42 is toxic to endothelial cells by interfering with activation of Akt/GSK-3b signaling-dependent mechanism); De Ferrari et al. (2003) Mol Psychiatry 8:195 (Lithium protects N2A cells & primary hippocampal neurons from Ab fibrils-induced cytotoxicity, & reduced nuclear translocation/destabilization of b-catenin); and Pigino et al., J Neurosci, 23:4499, 2003 (The mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi et al. (1996), Acta Neuropathol 92: 232; Pei et al. (1999), J Neuropath Exp Neurol 58: 1010 (GSK3b immunoreactivity is elevated in susceptible regions of AD brains); Hernandez et al. (2002), J Neurochem 83: 1529 (Transgenic mice with conditional GSK3b overexpression exhibit cognitive deficits similar to those in transgenic APP mouse models of AD); De Ferrari et al. (2003) Mol Psychiatry 8:195 (Chronic lithium treatment rescued neurodegeneration and behavioral impairments (Morris water maze) caused by intrahippocampal injection of Ab fibrils.); McLaurin et al., Nature Med, 8:1263, 2002 (Immunization with Ab in a transgenic model of AD reduces both AD-like neuropathology and the spatial memory impairments); and Phiel et al. (2003) Nature 423:435 (GSK3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., Journal of Neuroscience (23: 4499, 2003). It was found that GSK3beta phosphorylates kinesin-I light chain, which results in a release of kinesin-1 from membrane-bound organelles, leading to a reduction in fast anterograde axonal transport (Morfini et al., 2002). The authors suggest that the mutations in PS1 may deregulate and increase GSK-3 activity, which in turn, impairs axonal transport in neurons. The consequent reductions in axonal transport in affected neurons ultimately lead to neurodegeneration.

GSK-3 is also associated with amyotrophic lateral sclerosis (ALS). See Williamson and Cleveland, 1999 (Axonal transport is retarded in a very early phase of ALS in mSOD1 mice); Morfini et al., 2002 (GSK3 phosphorylates kinesin light chains and inhibit anterograde axonal transport); Warita et al., Apoptosis, 6: 45, 2001 (The majority of spinal motor neurons lost the immunoreactivities for both PI3-K and Akt in the early and presymptomatic stage that preceded significant loss of the neurons in this SOD1 tg animal model of ALS); and Sanchez et al., 2001 (The inhibition of PI-3K induces neurite retraction mediated by GSK3 activation).

GSK-3 activity is also linked to spinal cord and peripheral nerve injuries. It has been shown that GSK3 inhibition by lithium and valproic acid can induce axonal remodeling and change synaptic connectivity. See Kaytor & Orr, Curr Opin Neurobiol, 12: 275, 2002 (Downregulation of GSK3 causes changes in microtubule-associated proteins: tau, MAP1 & 2) and Hall et al., Mol Cell Neurosci, 20: 257, 2002 (Lithium and valproic acid induces the formation of growth cone-like structures along the axons). See also Grothe et al., Brain Res, 885: 172, 2000 (FGF2 stimulate Schwann cell proliferation and inhibit myelination during axonal growth); Grothe and Nikkhah, 2001 (FGF-2 is up regulated in the proximal and distal nerve stumps within 5 hours after nerve crush); and Sanchez et al., 2001 (The inhibition of PI-3K induces neurite retraction mediated by GSK3 activation).

Another substrate of GSK-3 is b-catenin, which is degraded after phosphorylation by GSK-3. Reduced levels of b-catenin have been reported in schizophrenic patients and have also been associated with other diseases related to increase in neuronal cell death [Zhong et al., Nature, 395, 698-702 (1998); Takashima et al., PNAS, 90, 7789-93 (1993); Pei et al., J. Neuropathol. Exp, 56, 70-78 (1997); and Smith et al., Bio-org. Med. Chem. 11, 635-639 (2001)]. Furthermore, b-catenin and Tcf-4 play a dual role in vascular remodeling by inhibiting vascular smooth muscle cell apoptosis and promoting proliferation (Wang et al., Circ Res, 90: 340, 2002). Accordingly, GSK-3 is associated with angiogenic disorders. See also Liu et al., FASEB J, 16: 950, 2002 (Activation of GSK3 reduces hepatocyte growth factor, leading to altered endothelial cell barrier function and diminished vascular integrity) and Kim et al., J Biol Chem, 277: 41888, 2002 (GSK3beta activation inhibits angiogenesis in vivo using Matrigel plug assay: the inhibition of GSK3beta signaling enhances capillary formation).

Association between GSK-3 and Huntington's disease has been shown. See Carmichael et al., J. Biol. Chem., 277: 33791, 2002 (GSK3beta inhibition protect cells from polyglutamine-induced neuronal and non-neuronal cell death via increases in b-catenin and its associated transcriptional pathway). Overexpression of GSK3 reduced the activation of heat shock transcription factor-1 and heat shock protein HSP70 (Bijur et al., J Biol Chem, 275: 7583, 2000) that are shown to decrease both poly-(Q) aggregates and cell death in in vitro HD model (Wyttenbach et al., Hum Mol Genet, 11: 1137, 2002).

GSK-3 effects the levels of FGF-2 and their receptors are increased during remyelination of brain aggregate cultures remyelinating rat brains. See Copelman et al., 2000, Messersmith, et al., 2000; and Hinks and Franklin, 2000. It was also found that FGF-2 induces process outgrowth by oligodendrocytes implicating involvement of FGF in remyelination (Oh and Yong, 1996; Gogate et al., 1994) and that FGF-2 gene therapy has shown to improve the recovery of experimental allergic encephalomyelitis (EAE) mice (Ruffini, et al., 2001).

GSK-3 has also been associated with hair growth because Wnt/beta-catenin signaling is shown to play a major role in hair follicle morphogenesis and differentiation (Kishimotot et al. Genes Dev, 14:1181, 2000; Millar, J Invest Dermatol, 118:216, 2002). It was found that mice with constitutive overexpression of the inhibitors of Wnt signaling in skin failed to develop hair follicles. Wnt signals are required for the initial development of hair follicles and GSK3 constitutively regulates Wnt pathways by inhibiting beta-catenin. (Andl et al., Dev Cell 2:643, 2002). A transient Wnt signal provides the crucial initial stimulus for the start of a new hair growth cycle, by activating beta-catenin and TCF-regulated gene transcription in epithelial hair follicle precursors (Van Mater et al., Genes Dev, 17:1219, 2003).

Because GSK-3 activity is associated with sperm motility, GSK-3 inhibition is useful as a male contraceptive. It was shown that a decline in sperm GSK3 activity is associated with sperm motility development in bovine and monkey epididymis (Vijayaraghavan et al., Biol Reprod, 54:709, 1996; Smith et al., J Androl, 20:47, 1999). Furthermore, tyrosine & serine/threonine phosphorylation of GSK3 is high in motile compared to immotile sperm in bulls (Vijayaraghavan et al., Biol Reprod, 62:1647, 2000). This effect was also demonstrated with human sperm (Luconi et al., Human Reprod, 16:1931, 2001).

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank Mol. Med. 5: 432-456 (1999) & Seidel, et al., Oncogene 19: 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain (gc) and is activated by IL-2, IL-4, IL-7, IL-9, and IL-15. The proliferation and survival of murine mast cells induced by IL-4 and IL-9 have, in fact, been shown to be dependent on JAK3- and gc-signaling [Suzuki et al., Blood 96: 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al., Nature 346: 274-276 (1990) & Galli, N. Engl. J. Med., 328: 257-265 (1993)]. A crucial role for JAK3 in IgE receptor-mediated mast cell responses in vitro and in vivo has been established [Malaviya, et al., Biochem. Biophys. Res. Commun. 257:807-813 (1999)]. In addition, the prevention of type I hypersensitivity reactions, including anaphylaxis, mediated by mast cell-activation through inhibition of JAK3 has also been reported [Malaviya et al., J. Biol. Chem. 274:27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, transpl. proc. 33: 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus Kinases (JAK 1 & 3) and that IL-4-associated JAK kinases are expressed in the RA synovium [Muller-Ladner, et al., J. Immunol. 164: 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This confirmed that JAK3 plays a role in FALS [Trieu, et al., Biochem. Biophys. Res. Commun. 267: 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al., Clin. Cancer Res. 5: 1569-1582 (1999)]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al., EMBO J. 17: 5321-5333 (1998)].

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al., Proc. Nat. Acad. Sci. U.S.A. 94: 6764-6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al., J. Immunol. 159: 5206-5210 (1997)]. In addition, IL-6-mediated STAT3 activation was blocked by an inhibitor of JAK, leading to sensitization of myeloma cells to apoptosis [Catlett-Falcone, et al., Immunity 10:105-115 (1999)].

Tyrosine kinases are a class of enzymes that mediate intracellular signal transduction pathways. Abnormal activity of these kinases has been shown to contribute to cell proliferation, carcinogenesis and cell differentiation. Thus, agents that modulate the activity of tyrosine kinases are useful for preventing and treating proliferative diseases associated with these enzymes.

Syk is a tyrosine kinase that plays a critical role in Fc∈RI mediated mast cell degranulation and eosinophil activation. Accordingly, Syk kinase is implicated in various allergic disorders, in particular asthma. It has been shown that Syk binds to the phosphorylated gamma chain of the Fc∈RI receptor via N-terminal SH2 domains and is essential for downstream signaling [Taylor et al., *Mol. Cell. Biol.* 1995, 15, 4149].

Inhibition of eosinophil apoptosis has been proposed as a key mechanism for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al., *J. Exp. Med.* 1996, 183, 1407].

The role of Syk in FcgR dependent and independent response in bone marrow derived macrophages has been determined by using irradiated mouse chimeras reconstituted with fetal liver cells from Syk -/- embryos. Syk deficient macrophages were defective in phagocytosis induced by FcgR but showed normal phagocytosis in response to complement [Kiefer et al., *Mol. Cell. Biol.* 1998, 18, 4209]. It has also been reported that aerosolized Syk antisense suppresses Syk expression and mediator release from macrophages [Stenton et al., *J. Immunology* 2000, 164, 3790].

KDR is a tyrosine kinase receptor that also binds VEGF (vascular endothelial growth factor) Neufeld et al., 1999, FASEB J., 13, 9. The binding of VEGF to the KDR receptor leads to angiogenesis, which is the sprouting of capillaries from preexisting blood vessels. High levels of VEGF are found in various cancers causing tumor angiogenesis and permitting the rapid growth of cancerous cells. Therefore, suppressing VEGF activity is a way to inhibit tumor growth, and it has been shown that this can be achieved by inhibiting KDR receptor tyrosine kinase. For example, SU5416 is a selective inhibitor of the tyrosine kinase and was reported to also suppress tumor vascularization and the growth of multiple tumors. Fong et al., 1999, Cancer Res. 59, 99. Other inhibitors of KDR tyrosine kinase for the treatment of cancer have also been reported (WO 98/54093, WO 99/16755, WO 00/12089).

Examples of cancers that may be treated by such inhibitors include brain cancer, genitourinary tract cancer, lymphatic system cancer, stomach cancer, cancer of the larynx, lung cancer, pancreatic cancer, breast cancer, Kaposi's sarcoma, and leukemia. Other diseases and conditions associated with abnormal tyrosine kinase activity include vascular disease, autoimmune diseases, ocular conditions, and inflammatory diseases.

A family of type III receptor tyrosine kinases including Flt3, c-Kit, PDGF-receptor and c-Fms play an important role in the maintenance, growth and development of hematopoietic and non-hematopoietic cells. [Scheijen, B, Griffin J D, Oncogene, 2002, 21, 3314-3333 and Reilly, JT, British Journal of Haematology, 2002, 116, 744-757]. FLT-3 and c-Kit regulate maintenance of stem cell/early progenitor pools as well the development of mature lymphoid and myeloid cells [Lyman, S, Jacobsen, S, Blood, 1998, 91, 1101-1134]. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propagate the activation signal leading to growth, differentiation and survival. Some of the downstream regulators of FLT-3 and c-Kit receptor signaling include, PLCγ, PI3-kinase, Grb-2, SHIP and Src related kinases [Scheijen, B, Griffin J D, Oncogene, 2002, 21, 3314-3333]. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype [Scheijen, B, Griffin J D, Oncogene, 2002, 21, 3314-3333].

c-fms encodes for macrophage colony stimulating factor receptor (M-CSF-1R) which is expressed predominately in the monocytes/macrophage lineage [Dai, XM et al., Blood, 2002, 99, 111-120]. MCSF-1R and its ligand regulate macrophage lineage growth and differentiation. Like the other family members, MCSF-1R contains an intrinsic kinase domain that is activated upon ligand-induced dimerization of the receptor. MCSF-1R is also expressed in non-hematopoietic cells including mammary gland epithelial cells and neurons. Mutations in this receptor are potentially linked to myeloid leukemias and its expression is correlated with metastatic breast, ovarian and endometrial carcinomas [Reilly, J T, British Journal of Haematology, 2002, 116, 744-757 and Kacinski, B M, Mol. Reprod and Devel., 1997, 46, 71-74]. Another possible indication for antagonists of MCSF-1R is osteoporosis [Teitelbaum, S, Science 2000, 289, 1504-1508.

Aurora-2 is a serine/threonine protein kinase that has been implicated in human cancer, such as colon, breast and other solid tumors. This kinase is involved in protein phosphorylation events that regulate the cell cycle. Specifically, Aurora-2 plays a role in controlling the accurate segregation of chromosomes during mitosis. Misregulation of the cell cycle can lead to cellular proliferation and other abnormalities. In human colon cancer tissue, the aurora-2 protein has been found to be overexpressed [Bischoff et al., EMBO J., 17, 3052-3065 (1998); Schumacher et al., J. Cell Biol., 143, 1635-1646 (1998); Kimura et al., J. Biol. Chem., 272, 13766-13771 (1997)].

Transforming growth factor-beta (TGF-beta) activated kinase 1 (TAK-1) is a 67 kDa ubiquitin-dependent serine-threonine kinase that functions as a mitogen-activated protein (MAP) kinase kinase kinase (MAPKKK or MEKK) (Wang, C., et al., Nature 2001, 412, 346-351).

Originally described as stimulated by TGF-beta superfamily members (Yamaguchi K. et al., Science 1995, 270, 2008-2011) TAK-1 is known to also function in signaling from numerous cell modulators including proinflammatory cytokines. TAK-1 is critical for signaling from IL-1beta/TLR ligands (Holtmann H, et al., J. Biol. Chem. 2001, 276, 3508-3516; Jiang Z, et al., J. Biol. Chem. 2003, 278, 16713-16719) and TNF-alpha (Takaesu G. et al., J. Mol. Biol. 2003, 326, 105-115). In addition TAK-1 plays a role in IL-18 (Wald, D., et al., Eur. J. Immunol. 2001, 31, 3747-3754), RANKL (Mizukami J., et al., Mol. Cell. Biol. 2002, 22, 992-1000) and ceramide (Shirakabe K., et al., J. Biol. Chem. 1997, 272, 8141-8144) signaling.

Through interaction with corresponding cell surface receptors these ligands stimulate TAK-1 to relay signals to a variety of pathways such as IKK/NFkappaB, JNK, and p38, that are important regulators of cellular processes including apoptosis (Edlund S., et al., Mol Biol Cell. 2003, 14, 529-544), differentiation (Suzawa, M. et al., Nat Cell Biol 2003, 5, 224-230), and cell cycle progression (Bradham C A, et al., Am J Physiol Gastrointest Liver Physiol. 2001 281, G1279-89).

Modification of signaling pathways can alter cellular processes and contribute to disease. Due to its central role in signaling from numerous cell surface receptors TAK-1 may be an important therapeutic target for a variety of diseases. The cytokines IL-1beta and TNFalpha are important mediators of inflammation in rheumatoid arthritis and other inflammatory diseases (Maini R N. and Taylor P C. Ann. Rev. Med. 2000, 51, 207-229). TAK-1 may be important in regulating disease-relevant cellular responses in these cases (Hammaker D R, et al. J. Immunol. 2004, 172, 1612-1618). TAK-1 affects cellular fibrotic responses (Ono K., et al., Biochem. Biophys. Res. Commun. 2003, 307, 332-337). It may also plays a role in heart failure (Zhang, D., Nat. Med. 2000, 6, 556-563), osteoporosis (Mizukami J, et al., Mol. Cell. Biol. 2002, 22, 992-1000) and survival of hepatocellular carcinoma cells (Arsura M, et al. Oncogene 2003, 22, 412-425). TAK-1 signaling may affect neurite outgrowth (Yanagisawa M., et al. Genes Cells. 2001, 6, 1091-1099) and is involved in control of adipogenesis (Suzawa M., et al. Nat. Cell. Biol. 2003, 5, 224-230) and cardiomyocyte differentiation (Monzen K., et al. J. Cell. Biol. 2001, 153(4), 687-698.

As a result of the biological importance of protein kinases, there is current interest in therapeutically effective protein kinase inhibitors. Accordingly, there is still a great need to develop inhibitors of protein kinases that are useful in treating various diseases or conditions associated with protein kinase activation. In particular, it would be desirable to develop compounds that are useful as inhibitors of c-Met, GSK3, JAK, SYK, KDR, FLT-3, c-Kit, Aurora, or TAK-1 particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of c-Met, GSK3, JAK, SYK, KDR, FLT-3, c-Kit, Aurora, or TAK-1 protein kinases. These compounds have the general formula I:

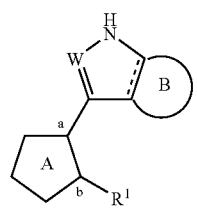

I or a pharmaceutically acceptable salt thereof, wherein W, Ring A, Ring B, and $R^1$ are as defined below. Bonds a and b are marked in Formula I to define the orientation of Ring A. Bond a is the bond between Ring A and the bicylic ring, including Ring B. Bond b is the bond between Ring A and $R^1$. Bonds a and b are also marked on examples of Ring A shown in the following section. All formula and compounds in the present application follow the orientations indicated below by these bonds.

These compounds and pharmaceutically acceptable compositions thereof are useful for treating or preventing a variety of diseases, disorders or conditions, including, but not limited to, cancer and other proliferative disorders.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention:

The present invention relates to a compound of formula I:

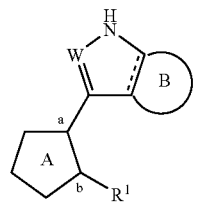

I or a pharmaceutically acceptable salt thereof, wherein:
W is CH or N;
Ring B is an optionally substituted 5-6 membered heteroaryl ring having 0-3 heteroatoms independently selected from nitrogen, oxygen, or sulfur;

$R^1$ is an optionally substituted 6-membered aryl ring having 0-3 nitrogens; and Ring A is an optionally substituted ring selected from:

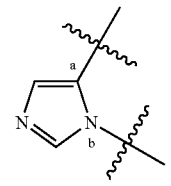

a

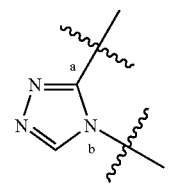

b

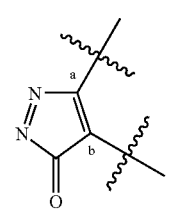

c

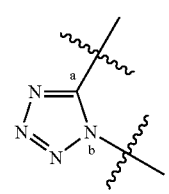

d

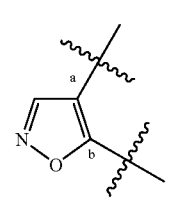

e

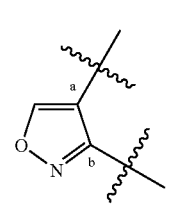

f

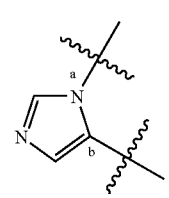

g

-continued

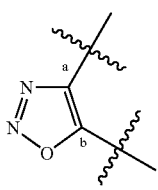
h

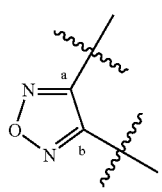
i

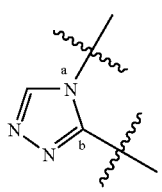
j

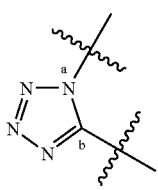
k

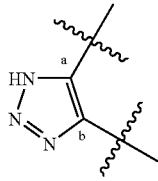
l

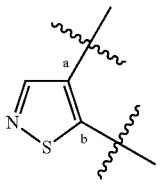
m

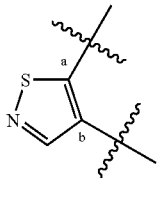
n

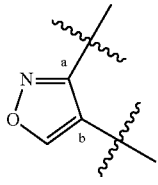
o

-continued

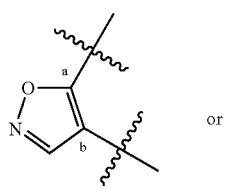
p or

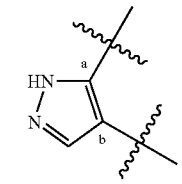
q

If Ring B is a 6-membered ring having no heteroatoms (i.e., is not a phenyl ring), it may form a fused benzo ring. In one embodiment of this invention, if Ring A is (b), (d), or (e), then Ring B is not a 6-membered ring having no heteroatoms (i.e., is not a phenyl ring) and thus does not form a fused benzo ring. In another embodiment, if Ring A is (b), (d), or (e), then Ring B is a pyridyl ring (i.e., Ring B and the ring fused thereto form an azaindole). In a preferred form of this embodiment, the nitrogen atoms in these azaindoles are oriented as in a 7-azaindole (see, e.g., compound 1).

In another embodiment of this invention, if Ring A is (b), then Ring A is not substituted with —SR°.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, alkyl, alkenyl, alkynyl, cycloalkyl, cycloalkenyl, cycloalkynyl groups and hybrids thereof such as (cycloalkyl)alkyl, (cycloalkenyl)alkyl or (cycloalkyl)alkenyl.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl", or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from oxo; halogen; —B(OH)$_2$; —R°; —OR°; —SR°; aryl; heteroaryl; 1,2-methylenedioxy; 1,2-ethylenedioxy; —CO$_2$ (C$_{1-4}$ aliphatic); an optionally substituted 5-6 membered heterocyclic ring; phenyl optionally substituted with R°; —O(phenyl) optionally substituted with R°; —(CH$_2$)$_{1-2}$(phenyl), optionally substituted with R°; —CH=CH(phenyl), optionally substituted with R°; —NO$_2$; —CN; —NHR°; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R°;

wherein each independent occurrence of R° is selected from hydrogen, optionally substituted C$_{1-6}$ aliphatic, an optionally substituted 5-9 membered heteroaryl or heterocyclic ring, phenyl, —O(phenyl), or —CH$_2$(phenyl), an optionally substituted —O(5-6 membered heterocyclic ring), an optionally substituted —CO(5-6 membered heterocyclic ring), or an optionally substituted —CH$_2$(5-6 membered heterocyclic ring); or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur.

Optional substituents on the aliphatic group of R° are selected from aryl, phenyl, heteroaryl, NH2, NH(C$_{1-4}$aliphatic), N(C$_{1-4}$aliphatic)$_2$, NH(CH$_2$)phenyl, halogen, —NHSO$_2$(C$_{1-4}$ aliphatic), C$_{1-4}$aliphatic, OH, O(C$_{1-4}$aliphatic), NO$_2$, CN, CO$_2$H, an optionally substituted —CO(5-6 membered heterocyclic ring), an optionally substituted 5-6 membered heterocyclic ring, CO$_2$(C$_{1-4}$aliphatic), O(haloC$_{1-4}$ aliphatic), or halo(C$_{1-4}$aliphatic), wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), heterocyclic ring, —OH, —CH$_2$OH, NHR*, N(R*)$_2$, CO(heterocyclic ring), R*, NHSO$_2$R* or =NR*, wherein each R* is independently selected from hydrogen or an optionally substituted C$_{1-6}$ aliphatic.

Optional substituents on the aliphatic group of R* are selected from 5-6 membered heterocyclic ring, heteroaryl, aryl, NH2, NHSO$_2$R*, NH(C$_{1-4}$ aliphatic), N(C$_{1-4}$ aliphatic)$_2$, halogen, C$_{1-4}$ aliphatic, OH, O(C$_{1-4}$ aliphatic), CO(5-6 membered heterocyclic ring), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R* is unsubstituted.

Optional substituents on the nitrogen of a non-aromatic heterocyclic ring are selected from —(C$_{1-6}$ aliphatic)$_2$, —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(phenyl), optionally substituted —CH$_2$(phenyl), optionally substituted —(CH$_2$) 1-2 (phenyl); optionally substituted —CH=CH(phenyl); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur.

Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R$^°$ (or R$^+$, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R$^°$ (or R$^+$, or any other variable similarly defined herein) are taken together with the atom(s) to which each variable is bound include, but are not limited to the following: a) two independent occurrences of R$^°$ (or R$^+$, or any other variable similarly defined herein) that are bound to the same atom and are taken together with that atom to form a ring, for example, N(R$^°$)$_2$, where both occurrences of R$^°$ are taken together with the nitrogen atom to form a piperidin-1-yl, piperazin-1-yl, or morpholin-4-yl group; and b) two independent occurrences of R$^°$ (or R$^+$, or any other variable similarly defined herein) that are bound to different atoms and are taken together with both of those atoms to form a ring, for example where a phenyl group is substituted with two occurrences of OR$^°$

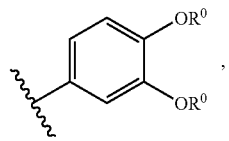

these two occurrences of R$^°$ are taken together with the oxygen atoms to which they are bound to form a fused 6-membered oxygen containing ring:

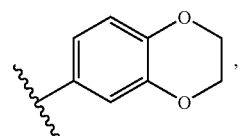

It will be appreciated that a variety of other rings can be formed when two independent occurrences of R$^°$ (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds:

One embodiment of the present invention relates to a compound wherein a compound of formula I:

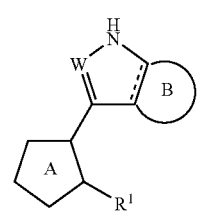

or a pharmaceutically acceptable salt thereof, wherein:

W is CH or N;

Ring B is an optionally substituted 5-6 membered heteroaryl ring having 0-3 heteroatoms independently selected from nitrogen, oxygen, or sulfur;

R$^1$ is an optionally substituted 6-membered aryl ring having 0-3 nitrogens; and Ring A is an optionally substituted ring selected from:
a
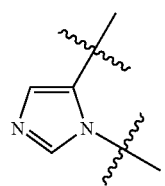
b
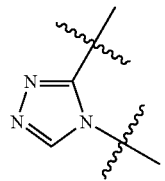
c
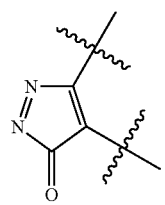
d
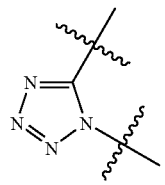
e
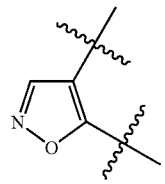
f
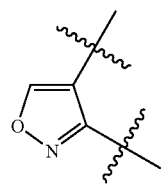
g
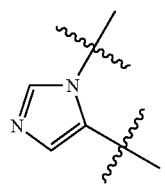
h
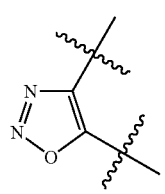
-continued
i
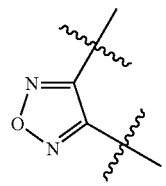
j
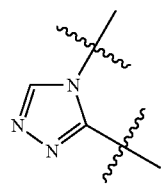
k
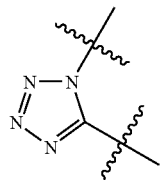
l
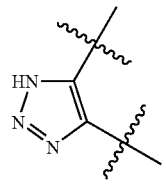
m
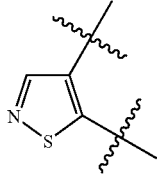
n
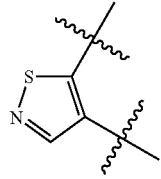
o
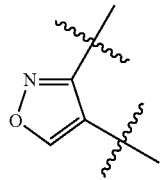
p
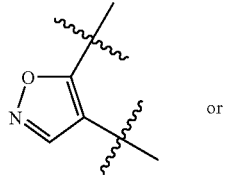
or

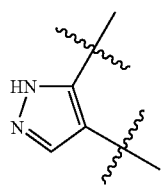
q

Another embodiment of the present invention relates to of formula I:

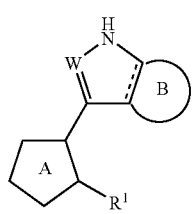
I or a pharmaceutically acceptable salt thereof, wherein:
W is CH or N, wherein the H is optionally replaced with (C$_1$-C$_6$)-alkyl or NH$_2$;
Ring B is an optionally substituted 5- or 6-membered aryl, heteroaryl or heterocyclic ring having 0-3 heteroatoms independently selected from nitrogen, oxygen, or sulfur;
R$^1$ is:
an optionally substituted 6-10-membered aryl or 5-10-membered heteroaryl ring having 0-3 heteroatoms independently selected from nitrogen, oxygen, or sulfur,
a—(C$_1$-C$_4$ aliphatic) substituted with a -6-10-membered aryl or a 5-10-membered heteroaryl ring or a C$_3$-C$_8$ cycloaliphatic or heterocyclic ring, having having 0-3 heteroatoms independently selected from nitrogen, oxygen, or sulfur each aliphatic and each ring being optionally substituted, or
an optionally substituted C$_3$-C$_8$ cycloaliphatic (preferably, cycloalkyl);
Ring A is an optionally substituted ring selected from:

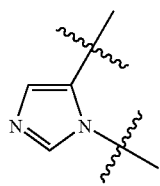
a

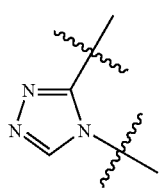
b

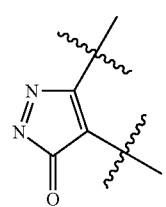
c

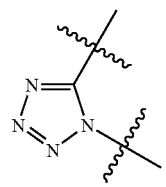
d

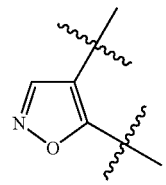
e f

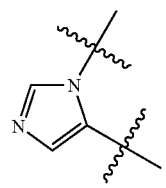
g

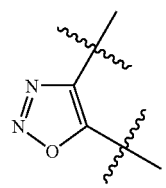
h

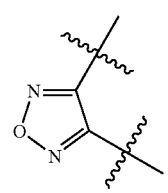
i

-continued j 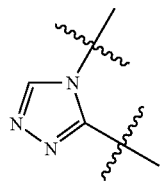

k 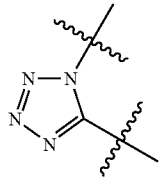

l 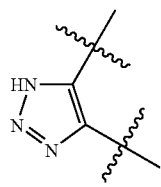

m 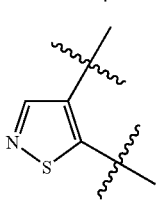

n 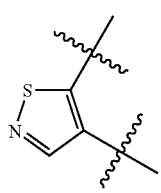

o 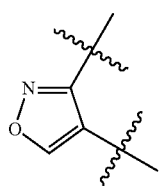

p q 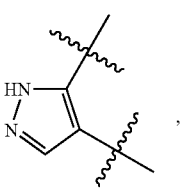, each aryl or heteroaryl is optionally substituted with one or more (preferably, 0, 1, 2, or 3) $R^3$ groups, wherein $R^3$ is halogen; —B(OH)$_2$; —R°; —OR°; —SR°; 1,2-methyl-enedioxy; 1,2-ethylenedioxy; —CO$_2$(C$_{1-4}$ aliphatic); an optionally substituted 5-6 membered heterocyclic ring; phenyl optionally substituted with R°; —O(phenyl) optionally substituted with R°; —(CH$_2$)$_{1-2}$(phenyl), optionally substituted with R°; —CH=CH(phenyl), optionally substituted with R°; —NO$_2$; —CN; —NHR°; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R°;

wherein each independent occurrence of R° is selected from hydrogen, C$_{1-6}$ aliphatic, a 5-10 membered heteroaryl or heterocyclic ring, phenyl, —O(phenyl), —CH$_2$(phenyl), 5 membered heterocyclic ring, wherein each group of R° is optionally substituted with J, wherein J is aryl, phenyl, heteroaryl, NH$_2$, NH(C$_{1-4}$ aliphatic), N(C$_{1-4}$ aliphatic)$_2$, NH(CH$_2$)phenyl, halogen, —NHSO$_2$(C$_{1-4}$ aliphatic), —NHCO$_2$(C$_{1-4}$ aliphatic), C$_{1-4}$ aliphatic, OH, O(C$_{1-4}$ aliphatic), NO$_2$, CN, CO$_2$H, —CO(5-6 memebered heterocyclic ring), 5-6 membered heterocyclic ring, —CO$_2$(C$_{1-4}$ aliphatic), —O(haloC$_{1-4}$ aliphatic), or halo(C$_{1-4}$ aliphatic), or wherein each group of J is optionally substituted with J', wherein J' is NH$_2$, NH(C$_{1-4}$ aliphatic), N(C$_{1-4}$ aliphatic)$_2$, NH(CH$_2$)phenyl, halogen, —NHSO$_2$(C$_{1-4}$ aliphatic), —NHCO$_2$(C$_{1-4}$ aliphatic), C$_{1-4}$ aliphatic, OH, O(C$_{1-4}$ aliphatic), NO$_2$, CN, CO$_2$H, —CO(5-6 membered heterocyclic ring), 5-6 membered heterocyclic ring, —CO$_2$(C$_{1-4}$ aliphatic), —O(haloC$_{1-4}$ aliphatic), or halo(C$_{1-4}$ aliphatic), wherein each the J' groups is optionally substituted with C$_{1-4}$ aliphatic, halogen, wherein each of the C$_{1-4}$ aliphatic groups of J' is unsubstituted;

two R° are taken together with the atom(s) to which each is bound to form a 5-8-membered heterocyclyl, aryl, or heteroaryl ring or a 3-8-membered cycloalkyl ring having 0-3 heteroatoms independently selected from nitrogen, oxygen, or sulfur;

wherein each aliphatic or heteroaliphatic group or non-aromatic heterocyclic ring is optionally substituted with $R^3$, =O, =S, =NNHR*, =NN(R*)$_2$, =NNHC(O)R*, =NNHCO$_2$(alkyl), =NNHSO$_2$(alkyl), or =NR*, wherein each R* is independently selected from hydrogen or an optionally substituted C$_{1-6}$ aliphatic, wherein optional substituents on the aliphatic group of R* are selected from 5-6 membered heterocyclic ring, heteroaryl, aryl, NH$_2$, NHSO$_2$R*, NH(C$_{1-4}$ aliphatic), N(C$_{1-4}$ aliphatic)$_2$, halogen, C$_{1-4}$ aliphatic, OH, O(C$_{1-4}$ aliphatic), CO(5-6 membered heterocyclic ring), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted; and wherein each nitrogen of a non-aromatic heterocyclic ring is optionally substituted with —(C$_{1-6}$ aliphatic)$_2$, —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$;

wherein R⁺ is hydrogen, an optionally substituted $C_{1-6}$ aliphatic, optionally substituted phenyl, optionally substituted —O(phenyl), optionally substituted —CH₂(phenyl), optionally substituted —(CH₂)$_{1-2}$(phenyl); optionally substituted —CH═CH(phenyl); or an unsubstituted 5-6 membered heteroaryl or heterocyclic ring having one to four heteroatoms independently selected from oxygen, nitrogen, or sulfur, wherein optional substituents on the aliphatic group or the phenyl ring of R⁺ are selected from NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of the foregoing $C_{1-4}$ aliphatic groups of R⁺ is unsubstituted, or two R⁺ are taken together with the atom(s) to which each is bound to form a 5-8-membered heterocyclyl, aryl, or heteroaryl ring or a 3-8-membered cycloalkyl ring having 0-3 heteroatoms independently selected from nitrogen, oxygen, or sulfur.

Another embodiment of the present invention relates to a compound of formula I:

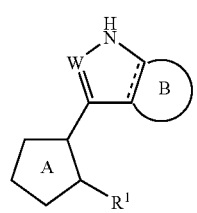

I or a pharmaceutically acceptable salt thereof, wherein:
W is CH, CNH2 or N;
Ring B is an optionally substituted 5- or 6-membered aryl, heteroaryl or heterocyclic ring having 0-3 heteroatoms independently selected from nitrogen, oxygen, or sulfur, wherein Ring B is optionally substituted with one or more oxo, halogen, —OH, —OR°, —NHR°, N(R°)₂, a 5-6 membered heterocyclic ring, —COO($C_{1-4}$ aliphatic), —B(OH)₂, —CO(5-6 membered heterocyclic ring), aryl, heteroaryl, and R°,
wherein each R° is H or $C_{1-6}$ aliphatic independently optionally substituted with phenyl, NH2, NH(C1-4 aliphatic), NH(CH2)phenyl, N(C1-4 aliphatic)₂, heteroaryl, —NHSO2($C_{1-4}$ aliphatic), halogen, an optionally substituted —CO(5-6 membered heterocyclic ring), an optionally substituted 5-6 membered heterocyclic ring, COO aliphatic and OH;
R1 is an optionally substituted 6-membered aryl or heteroaryl ring having 0-3 nitrogens, (C1-C4 aliphatic)-aryl ring, C1-C6 aliphatic,
wherein R1 is optionally substituted with one or more halogen or —OR°, wherein each R° is $C_{1-4}$ aliphatic;
Ring A is an optionally substituted ring selected from:

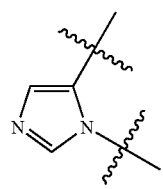

a

-continued

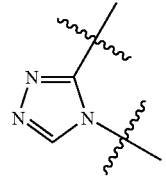

b

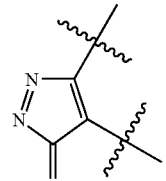

c

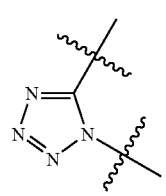

d

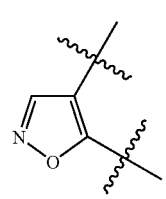

e

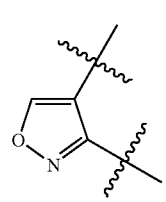

f

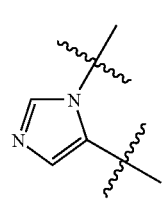

g

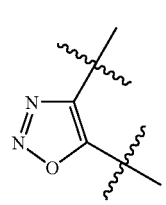

h

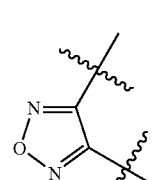

i

-continued j 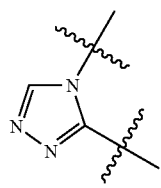

k 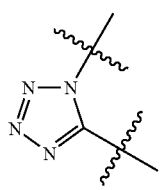

l 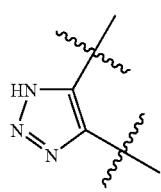

m 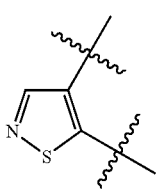

n 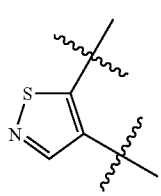

o 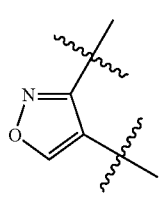

p q 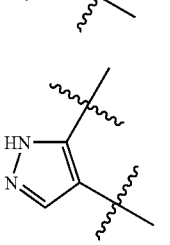, wherein Ring A is optionally substituted with oxo, —OH, $NH_2$, or —$CH_3$; and each aryl or heteroaryl is optionally substituted with one or more halogen; —R°; —OR°; —SR°; 1,2-methylenedioxy; 1,2-ethylenedioxy; phenyl optionally substituted with R°; —O(phenyl) optionally substituted with R°; —$(CH_2)_{1-2}$(phenyl), optionally substituted with R°; —CH=CH(phenyl), optionally substituted with R°; —$NO_2$; —CN; —$N(R°)_2$; —NR°C(O)R°; —NR°C(S)R°; —NR°C(O)N(R°)$_2$; —NR°C(S)N(R°)$_2$; —NR°CO$_2$R°; —NR° NR°C(O)R°; —NR°NR°C(O)N(R°)$_2$; —NR°NR°CO$_2$R°; —C(O)C(O) R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O) R°; —C(O)N(OR°)R°; —C(NOR°)R°; —S(O)$_2$R°; —S(O)$_3$ R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —$(CH_2)_{0-2}$NHC(O)R°;

wherein each independent occurrence of R° is selected from hydrogen, optionally substituted $C_{1-6}$ aliphatic, an optionally substituted 5-9 membered heteroaryl or heterocyclic ring, phenyl, —O(phenyl), —$CH_2$(phenyl), an optionally substituted —O(5-6 membered heterocyclic ring), or an optionally substituted —$CH_2$(5-6 membered heterocyclic ring);

wherein aliphatic groups of R° are optionally substituted with $NH_2$, $NH(C_{1-4}$aliphatic), $N(C_{1-4}$aliphatic)$_2$, halogen, $C_{1-4}$aliphatic, OH, O($C_{1-4}$aliphatic), $NO_2$, CN, $CO_2$H, $CO_2(C_{1-4}$aliphatic), O(halo$C_{1-4}$ aliphatic), or halo$C_{1-4}$aliphatic, wherein each of the foregoing $C_{1-4}$aliphatic groups of R° is unsubstituted, or two R° are taken together with the atom(s) to which each is bound to form a 5-8-membered heterocyclyl, aryl, or heteroaryl ring or a 3-8-membered cycloalkyl ring having 0-3 heteroatoms independently selected from nitrogen, oxygen, or sulfur;

wherein each aliphatic or heteroaliphatic group or non-aromatic heterocyclic ring is optionally substituted with =O, =S, =NNHR*, =NN(R*)$_2$, =NNHC(O)R*, =NNHCO$_2$(alkyl), =NNHSO$_2$(alkyl), heterocyclic ring, —OH, —CH$_2$OH, NHR*, N(R*)$_2$, CO (heterocyclic ring), R*, NHSO$_2$R* or =NR*, wherein each R* is independently selected from hydrogen or an optionally substituted $C_{1-6}$ aliphatic, wherein optional substituents on the aliphatic group of R* are selected from 5-6 membered heterocyclic ring, heteroaryl, aryl, NH2, NHSO$_2$R*, NH($C_{1-4}$ aliphatic), N($C_{1-4}$ aliphatic)$_2$, halogen, $C_{1-4}$ aliphatic, OH, O($C_{1-4}$ aliphatic), CO(5-6 membered heterocyclic ring), $NO_2$, CN, $CO_2$H, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted; and wherein each nitrogen of a non-aromatic heterocyclic ring is optionally substituted with —($C_{1-6}$ aliphatic)$_2$, —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$;

wherein R$^+$ is hydrogen, an optionally substituted $C_{1-6}$ aliphatic, optionally substituted phenyl, optionally substituted —O(phenyl), optionally substituted —$CH_2$(phenyl), optionally substituted —$(CH_2)_1$-2 (phenyl); optionally substituted —CH=CH(phenyl); or an unsubstituted 5-6 membered heteroaryl or heterocyclic ring having one to four heteroatoms independently selected from oxygen, nitrogen, or sulfur, wherein optional substituents on the aliphatic group or the phenyl ring of R$^+$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2$H, $CO_2(C_{1-4}$ aliphatic), O(halo $C_{1-4}$ aliphatic), or halo($C_{1-4}$ aliphatic), wherein each of the foregoing $C_{1-4}$aliphatic groups of $R^+$ is unsubstituted, or two $R^+$ are taken together with the atom(s) to which each is bound to form a 5-8-membered heterocyclyl, aryl, or heteroaryl ring or a 3-8-membered cycloalkyl ring having 0-3 heteroatoms independently selected from nitrogen, oxygen, or sulfur.

Another embodiment of the present invention relates to a compound of formula I:

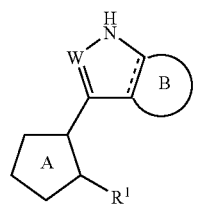

I or a pharmaceutically acceptable salt thereof, wherein:

W is CH, CNH2 or N;

Ring B is an optionally substituted 5- or 6-membered aryl, heteroaryl or heterocyclic ring having 0-3 heteroatoms independently selected from nitrogen, oxygen, or sulfur, wherein Ring B is optionally substituted with one or more oxo, halogen, —OH, —OR°, —NHR°, N(R°)2, a 5-6 membered heterocyclic ring, —COO(C1-4 aliphatic), —B(OH)2, —CO(5-6 membered heterocyclic ring), aryl, heteroaryl, and R°, wherein each R° is H or C1-6 aliphatic independently optionally substituted with phenyl, NH2, NH(CH2)phenyl, NH(C1-4 aliphatic), N(C1-4 aliphatic)2, heteroaryl, COO aliphatic, —NHSO2(C1-4 aliphatic), halogen, an optionally substituted —CO(5-6 membered heterocyclic ring), an optionally substituted 5-6 membered heterocyclic ring, and OH;

R1 is an optionally substituted 6-membered aryl or heteroaryl ring having 0-3 nitrogens, wherein R1 is optionally substituted with one or more halogen or —OR°, wherein each R° is C1-4 aliphatic;

Ring A is an optionally substituted ring selected from:

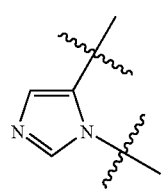

a

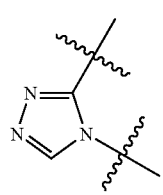

b

-continued

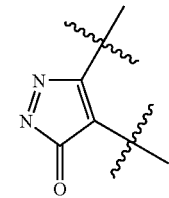

c

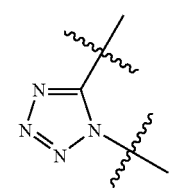

d

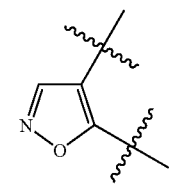

e

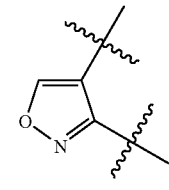

f

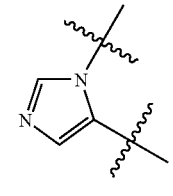

g

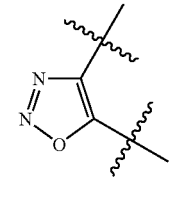

h

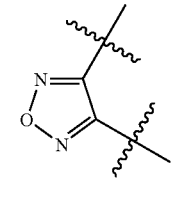

i

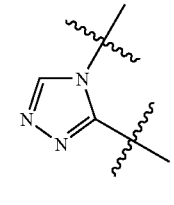

j

-continued

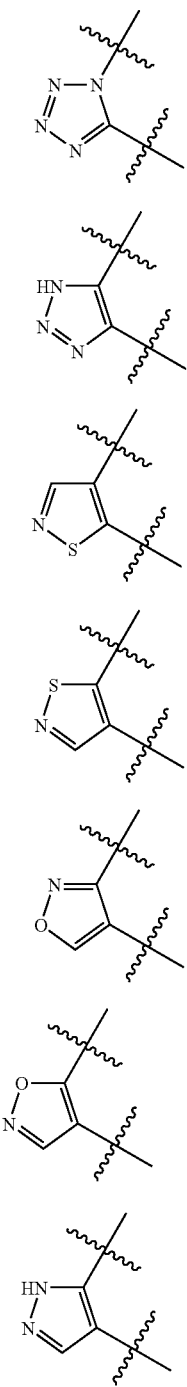

k l m n o p or q wherein Ring A is optionally substituted with oxo, —OH, NH₂, or —CH₃; and each aryl or heteroaryl is optionally substituted with one or more halogen; —R°; —OR°; —CN; NO₂; —N(R°)₂; —NR°C(O)R°; —C(O)N(R°)₂; —S(O)₂R°; or —NR°SO₂R°;

wherein each independent occurrence of R° is selected from hydrogen, optionally substituted $C_{1-6}$ aliphatic, an optionally substituted 6-9 membered heteroaryl or heterocyclic ring, or an optionally substituted —CH₂(5-6 membered heterocyclic ring);

wherein aliphatic groups of R° are optionally substituted with N (unsubstituted $C_{1-4}$aliphatic)₂;

wherein each aliphatic or heteroaliphatic group or non-aromatic heterocyclic ring is optionally substituted with =O, heterocyclic ring, NHR*, N(R*)₂, NHSO₂R*, CO (heterocylic ring), CH₂OH, OH and —R*, wherein each R* H or optionally substituted $C_{1-6}$ aliphatic;

wherein the optional substituents of the aliphatic group of R* are selected from 5-6 membered heterocyclic ring and aryl; and wherein each nitrogen of a non-aromatic heterocyclic ring is optionally substituted with ($C_{1-6}$ aliphatic)₂, —R⁺, —C(O)R⁺;

wherein R⁺ is hydrogen, an optionally substituted $C_{1-6}$ aliphatic, wherein optional substituents on the aliphatic group of R⁺ are CN.

Another embodiment of the present invention relates to a compound of formula I:

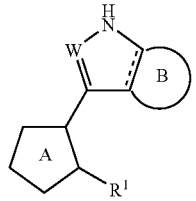

I or a pharmaceutically acceptable salt thereof, wherein:

W is CH, CNH2 or N;

Ring B is an optionally substituted 5- or 6-membered aryl, heteroaryl or heterocyclic ring having 0-3 heteroatoms independently selected from nitrogen, oxygen, or sulfur, wherein Ring B is optionally substituted with one or more oxo; chloro; bromo; fluoro; —CH2OH; —OH; —OCH3; CH3; —NHCH3; —NHCH2CH3; —N(CH3)2; —NH—CH2-tetrahydrofuranyl, pyrrolidinyl; piperidinyl; pyrazolyl; —COO(CH3); —B(OH)2; phenyl; benzyl; pyrindinyl; pyrimidinyl; imidazolyl; H; cyclopropyl; cyclohexyl; cyclohexenyl; —CH2CH3; —CH2N(CH3)2; propynyl substituted with N(CH3)2; ethenyl; ethenyl substituted with triazolyl; —CH2CH2-triazolyl; NH(CH3); NH(CH2)phenyl; N(CH3)2; imidazo-1,2-e-pyridinyl optionally substituted with —SO2(CH3), —NHSO2(CH3); an optionally substituted —CO(piperazinyl) or —CO(pyrrolidinyl), an optionally substituted morpholinyl or triazolyl, or OH;

R1 is an optionally substituted 6-membered aryl or heteroaryl ring having 0-3 nitrogens, wherein R1 is optionally substituted with one or more halogen or —OR°, wherein each R° is C1-4 aliphatic;

Ring A is an optionally substituted ring selected from:

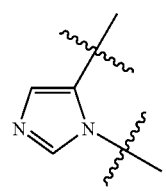

a

-continued
b
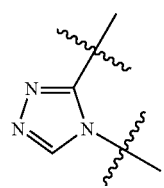
c
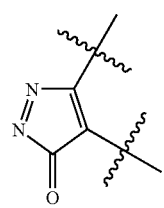
d
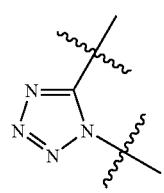
e
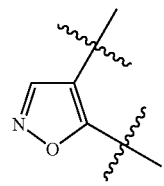
f
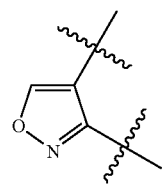
g
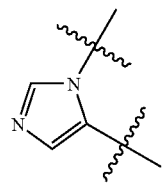
h
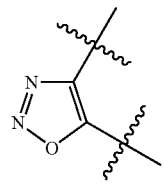
i
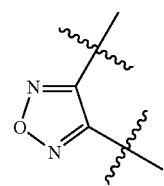
-continued
j
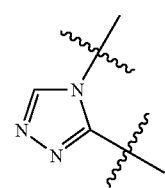
k
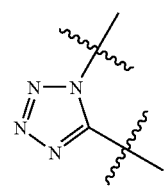
l
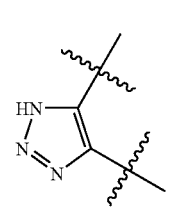
m
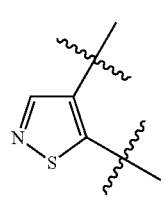
n
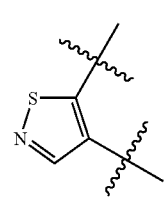
o
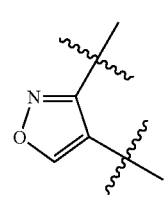
p
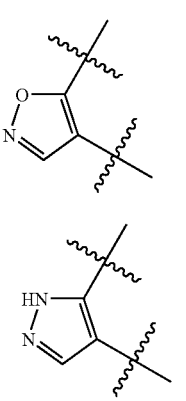
or
q
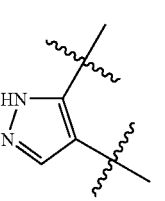
, wherein Ring A is optionally substituted with oxo, —OH, NH$_2$, or —CH$_3$; and each aryl or heteroaryl is optionally substituted with one or more fluoro; chloro; —R$^o$; —OR$^o$; —CN; NO$_2$; —N(CH$_3$)$_2$; —NHCH$_2$CH$_2$N(CH$_3$)$_2$, —NH$_2$, —NHC(O)CH$_3$; —C(O)NH$_2$; —C(O)N(CH$_3$)$_2$—S(O)$_2$CH$_3$; or —NHSO$_2$CH$_3$;

wherein each independent occurrence of R$^o$ is selected from hydrogen, CH$_3$, —CH$_2$(N(CH$_3$)$_2$, optionally substituted pyridinyl, piperindinyl, diazepanyl, morpholinyl, optionally substituted 3,9-diaza-bicyclo [4.2.1] nonane, piperazinyl or pyrrolidinyl, or an optionally substituted —CH$_2$(morpholinyl) or —CH$_2$(piperazinyl);

wherein each aliphatic or heteroaliphatic group or non-aromatic heterocyclic ring is optionally substituted with =O, pyrrolidinyl, OH, NHbenzyl, NH2, and —CO(piperazinyl); and wherein each nitrogen of a non-aromatic heterocyclic ring is optionally substituted with —CH$_3$, —(CH$_3$)$_2$, —H, —CH$_2$CH$_3$, —C(O)CH$_2$CN, —C(O)CH$_3$.

One embodiment of the present invention relates to a compound of formula I wherein W is N.

Another embodiment of the present invention relates to a compound of formula I wherein W is CH.

Another embodiment of the present invention relates to a compound of formula I wherein W is CNH$_2$.

According to one embodiment, the present invention relates to a compound of formula I wherein Ring B is an optionally substituted 5-membered heteroaryl ring having one nitrogen and 0-2 additional heteroatoms independently selected from nitrogen, oxygen, or sulfur.

According to another embodiment, Ring B of formula I is an optionally substituted benzo ring.

According to another embodiment, Ring B of formula I is an optionally substituted 6-membered heteroaryl ring having 1-3 nitrogens.

According to another embodiment, Ring B of formula I is an optionally substituted pyrido ring.

According to yet another embodiment, Ring B of formula I is an optionally substituted pyrimido ring.

Another aspect of the present invention relates to a compound of formula I wherein Ring B is an optionally substituted pyrazino ring.

Another aspect of the present invention relates to a compound of formula I wherein Ring B is an optionally substituted pyridazo ring.

In one embodiment of this invention, substituents on Ring B, when present, include one or more oxo, halogen, —OH, —OR$^o$, —NHR$^o$, N(R$^o$)$_2$, a 5-6 membered heterocyclic ring, —COO(C$_{1-4}$ aliphatic), —B(OH)$_2$, —CO(5-6 membered heterocyclic ring), aryl, heteroaryl, and R$^o$, wherein each R$^o$ is H or C$_{1-6}$ aliphatic independently optionally substituted with phenyl, NH$_2$, NH(C$_{1-4}$ aliphatic), NH(CH$_2$)phenyl, N(C$_{1-4}$ aliphatic)$_2$, heteroaryl, —NHSO$_2$(C$_{1-4}$ aliphatic), halogen, an optionally substituted —CO(5-6 membered heterocyclic ring), an optionally substituted 5-6 membered heterocyclic ring, COO aliphatic and OH.

In another embodiment of this invention, substituents on Ring B, when present, include one or more oxo, halogen, —OH, —OR$^o$, —NHR$^o$, N(R$^o$)$_2$, a 5-6 membered heterocyclic ring, —COO(C$_{1-4}$ aliphatic), —B(OH)$_2$, —CO(5-6 membered heterocyclic ring), aryl, heteroaryl, and R$^o$, wherein each R$^o$ is H or C$_{1-6}$ aliphatic independently optionally substituted with phenyl, NH$_2$, NH(CH$_2$)phenyl, NH(C$_{1-4}$ aliphatic), N(C$_{1-4}$ aliphatic)$_2$, heteroaryl, COO aliphatic, —NHSO$_2$(C$_{1-4}$ aliphatic), halogen, an optionally substituted —CO(5-6 membered heterocyclic ring), an optionally substituted 5-6 membered heterocyclic ring, and OH.

According to another embodiment of this invention, substituents on Ring B, when present, include one or more oxo; chloro; bromo; fluoro; —CH$_2$OH; —OH; —OCH$_3$; CH$_3$; —NHCH$_3$; —NHCH$_2$CH$_3$; —N(CH$_3$)$_2$; —NH—CH$_2$-tetrahydrofuranyl, pyrrolidinyl; piperidinyl; pyrazolyl; —COO (CH$_3$); —B(OH)$_2$; phenyl; benzyl; pyrindinyl; pyrimidinyl; imidazolyl; H; cyclopropyl; cyclohexyl; cyclohexenyl; —CH$_2$CH$_3$; —CH$_2$N(CH$_3$)$_2$; propynyl substituted with N(CH$_3$)$_2$; ethenyl; ethenyl substituted with triazolyl; —CH$_2$CH$_2$-triazolyl; NH(CH$_3$); NH(CH$_2$)phenyl; N(CH$_3$)$_2$; imidazo-1,2-e-pyridinyl optionally substituted with —SO$_2$ (CH$_3$), —NHSO$_2$ (CH$_3$); an optionally substituted —CO (piperazinyl) or —CO(pyrrolidinyl), an optionally substituted morpholinyl or triazolyl, or OH.

In one embodiment of the present invention, R$^1$ is an optionally substituted 6-membered aryl ring. In another embodiment of the present invention, R$^1$ is an optionally substituted 6-membered heteroaryl ring having 1, 2, or 3 nitrogens.

In one embodiment of the present invention, R$^1$ is an—(C$_{1-6}$ aliphatic)—6-membered aryl ring. In another embodiment of the present invention, R$^1$ is an —(C$_{1-6}$ aliphatic)—6-membered heteroaryl ring having 1, 2, or 3 nitrogens. In another embodiment of the present invention, R$^1$ is an—(C$_1$ aliphatic)—6-membered heteroaryl ring having 1, 2, or 3 nitrogens. Preferably, R$^1$ is an—(C$_1$ aliphatic)—6-membered aryl ring.

In one embodiment of the present invention, R$^1$ is an optionally substituted C1-8 aliphatic. Preferably, the aliphatic is a 5-, 6-, 7-, or 8-membered cycloaliphatic (either substituted as defined herein or unsubstituted).

Yet another aspect of the present invention relates to a compound of formula I wherein R$^1$ is an optionally substituted phenyl ring. Examples of substituents on the R$^1$ phenyl ring, when present, include one or more halogen and —OR$^o$, wherein each R$^o$ is C$_{1-4}$ aliphatic. According to one embodiment of the present invention, substituents on the R$^1$ phenyl ring, when present, include one or more chloro, fluoro and —OCH$_3$.

According to another embodiment, the present invention relates to a compound of formula I wherein R$^1$ is an optionally substituted pyridyl or pyrimidinyl ring. Examples of substituents on the ring, when present, include one or more halogen and —OR$^o$, wherein each R$^o$ is C$_{1-4}$ aliphatic. According to one embodiment of the present invention, substituents on the ring, when present, include one or more chloro, fluoro and —OCH$_3$.

Another embodiment of the present invention relates to a compound of formula I wherein Ring A is an optionally substituted ring selected from isoxazolyl, imidazolyl, triazolyl, or tetrazolyl. Examples of substituents on the ring, when present, include one or more halogen and —OR$^o$, wherein each R$^o$ is C$_{1-4}$ aliphatic. According to one embodiment of the present invention, substituents on the ring, when present, include one or more chloro, fluoro and —OCH$_3$.

In another embodiment, if Ring A is an optionally substituted ring q:

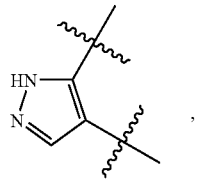

then q is substituted with halo, NO₂, OPCN. In another embodiment, q is not substituted.

Alternatively, if Ring A is an optionally substituted ring q:

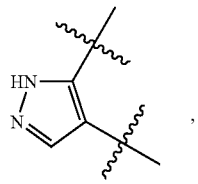

then R' is an optionally substituted 6-membered aryl ring having 0 nitrogens. In yet another alternative embodiment, the aryl ring has 3 nitrogens.

Yet another embodiment relates to a compound of formula I wherein Ring A is selected from the following rings:

a

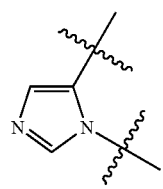

b

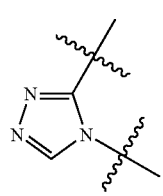

d

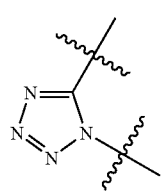

o

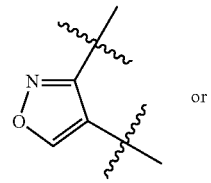

or p

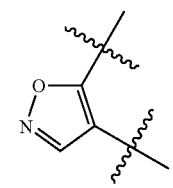

According to another embodiment, Ring A is isoxazolyl.

According to yet another embodiment, Ring A is selected from:

o

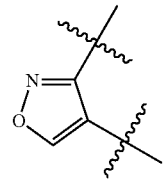

or p

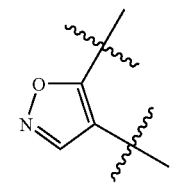

According to one embodiment, the present invention relates to a compound of formula I wherein Ring A is unsubstituted.

According to another embodiment, the present invention relates to a compound of formula I wherein Ring A is optionally substituted with one or more oxo, —OH, —NH₂, or —CH₃.

In certain embodiments of the present invention, substituents (on aryl, aliphatic, heteroaryl, etc.) are depicted in the exemplified compounds. Exemplary structures of formula I are set forth in Table 1, below.

TABLE 1
Examples of Compounds at Formula I:
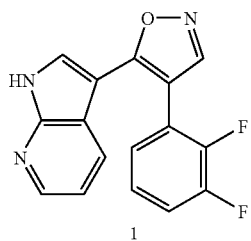
1
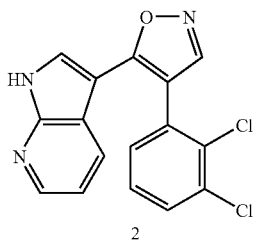
2
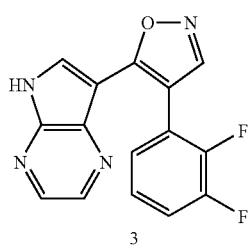
3
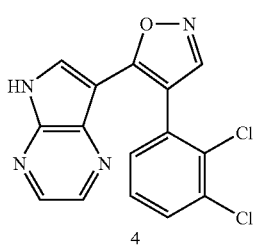
4
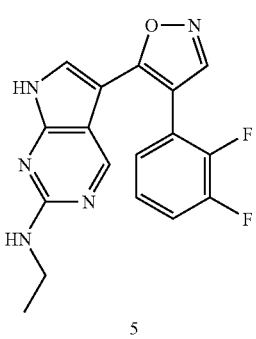
5
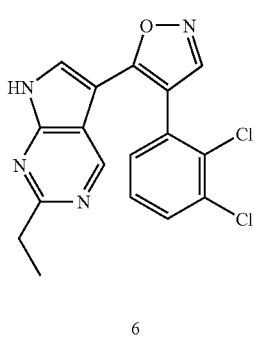
6
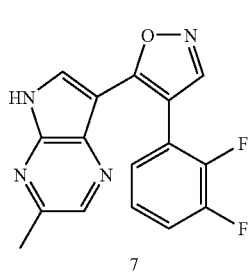
7
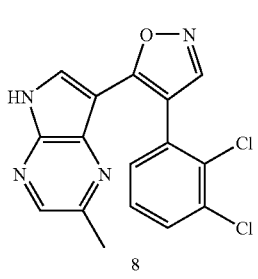
8
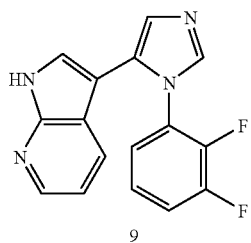
9
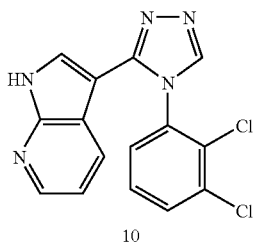
10
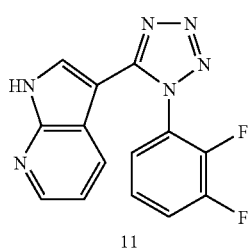
11
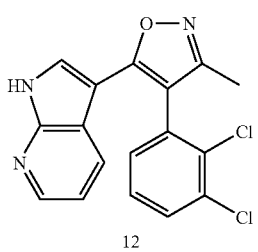
12

TABLE 1-continued
Examples of Compounds at Formula I:
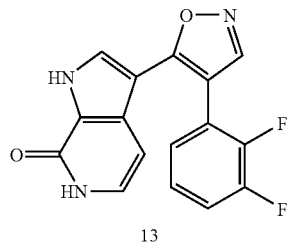
13
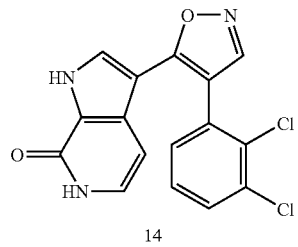
14
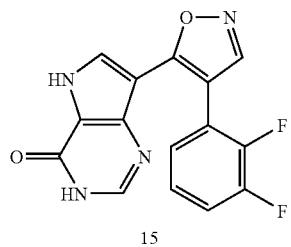
15
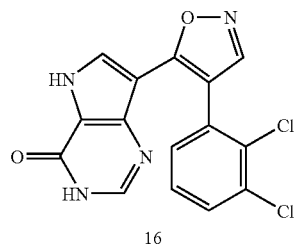
16
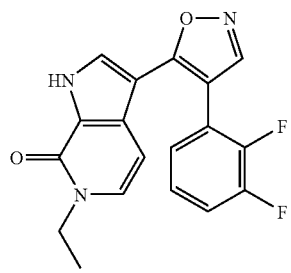
17
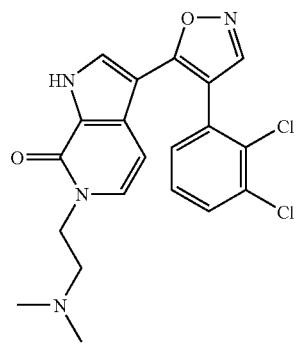
18
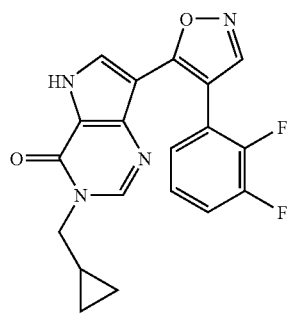
19
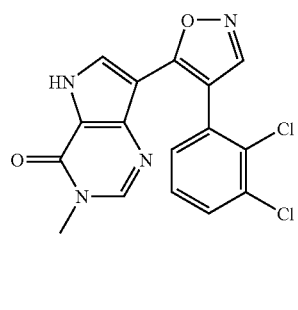
20
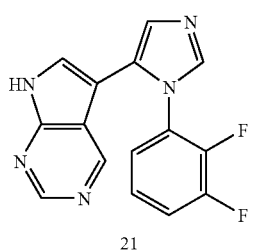
21
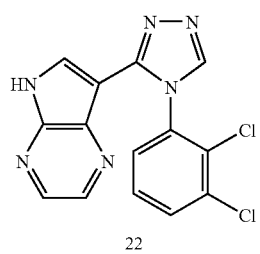
22

TABLE 1-continued
Examples of Compounds at Formula I:
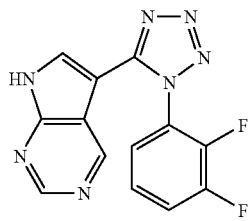
23
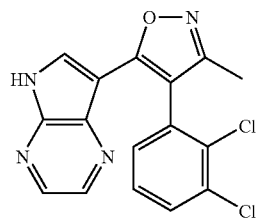
24
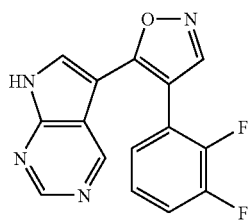
25
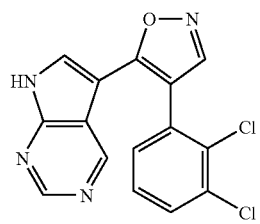
26
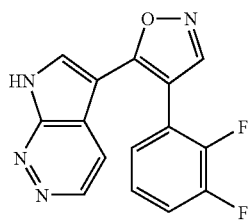
27
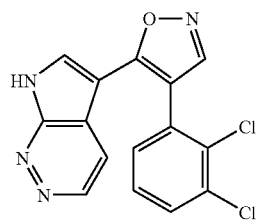
28
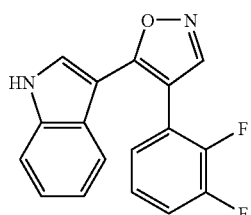
29
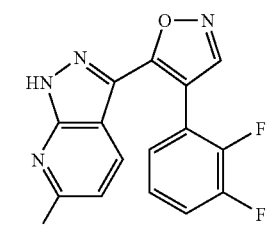
30
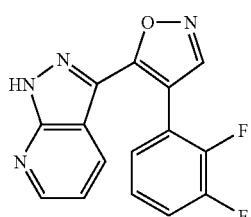
31
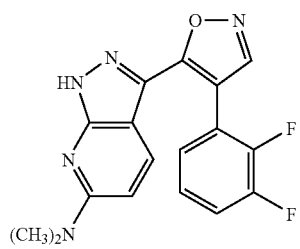
32

TABLE 1-continued

Examples of Compounds at Formula I:

| Compound | Cmpd # |
|---|---|
| | 33 |
| | 34 |
| | 35 |
| | 36 |
| | 37 |
| | 38 |

TABLE 1-continued
Examples of Compounds at Formula I:
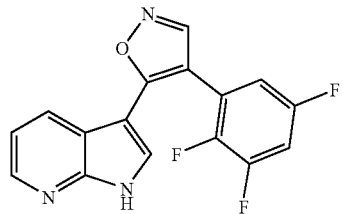 39
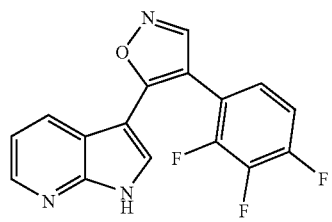 40
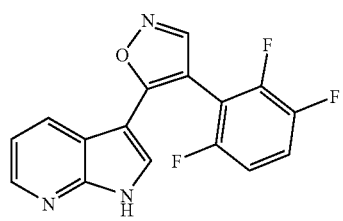 41
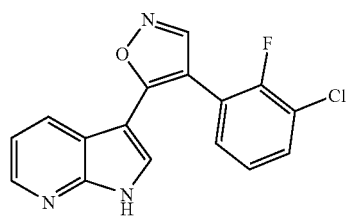 42
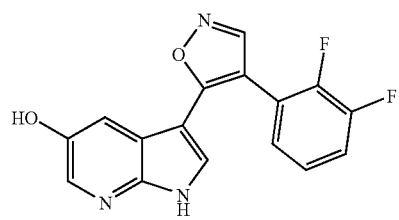 43
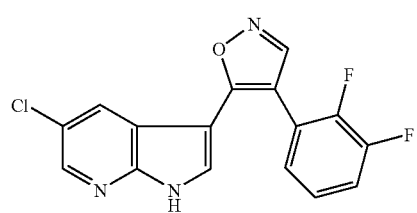 44
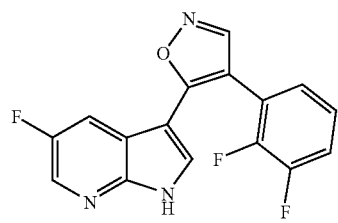 45

TABLE 1-continued
Examples of Compounds at Formula I:
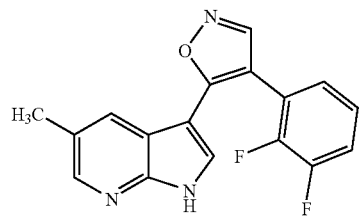
46
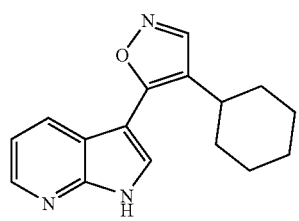
47
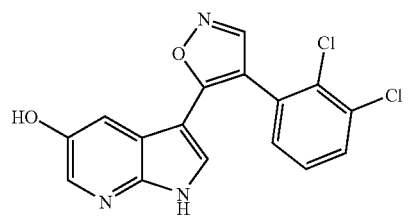
48
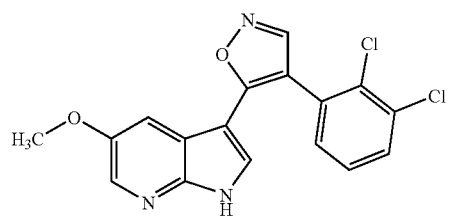
49
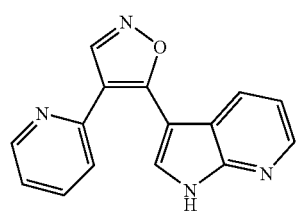
50
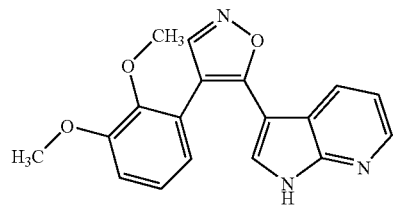
51
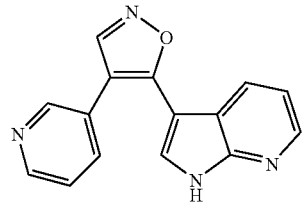
52

TABLE 1-continued
Examples of Compounds at Formula I:
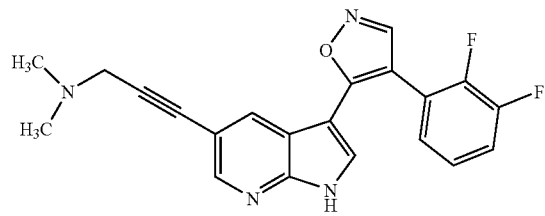
53
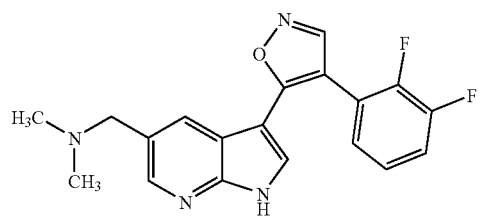
54
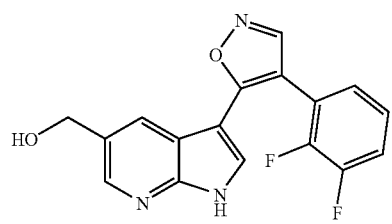
55
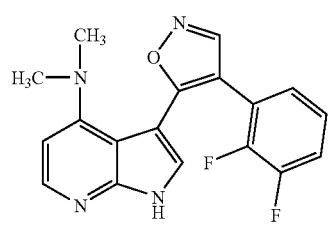
56
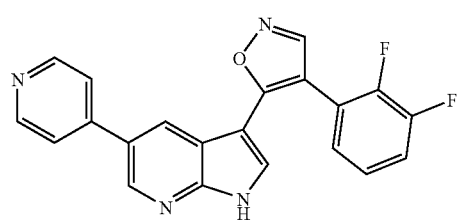
57
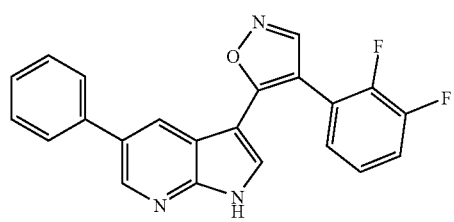
58
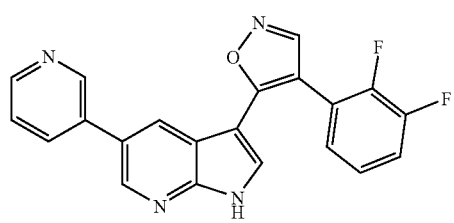
59

TABLE 1-continued
Examples of Compounds at Formula I:
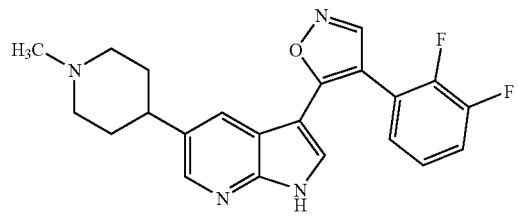 60
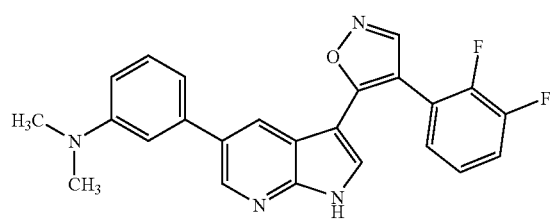 61
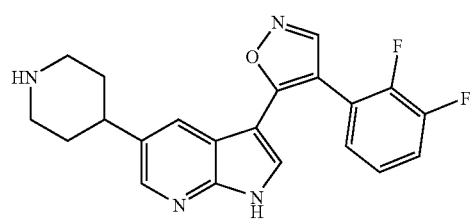 62
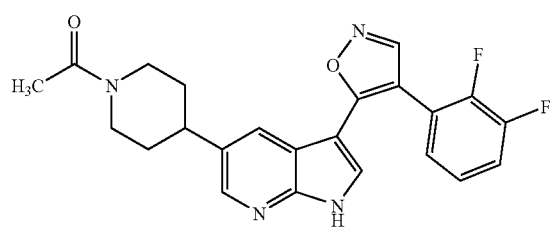 63
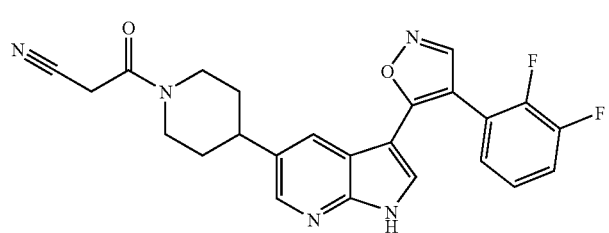 64
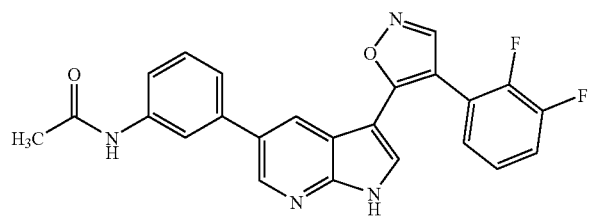 65

TABLE 1-continued

Examples of Compounds at Formula I:

66

67

68

69

70

71

TABLE 1-continued
Examples of Compounds at Formula I:
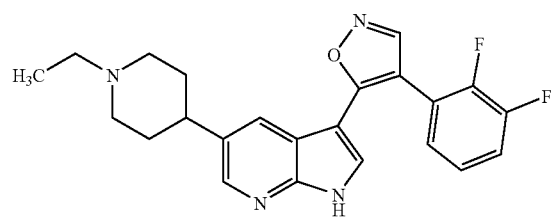 72
 73
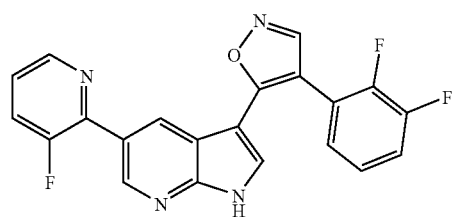 74
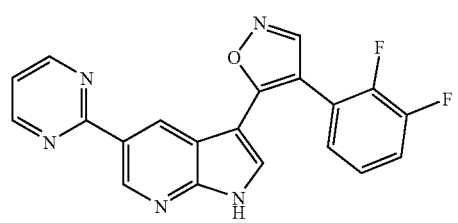 75
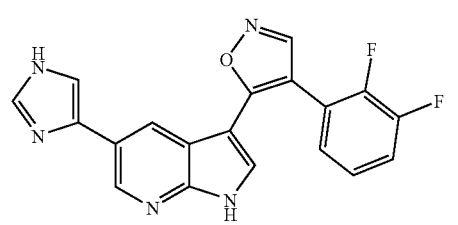 76
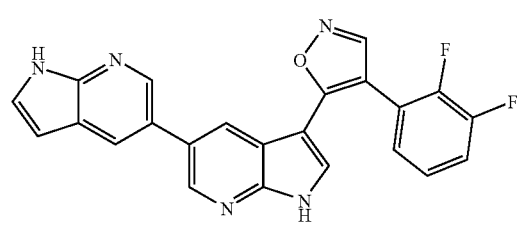 77
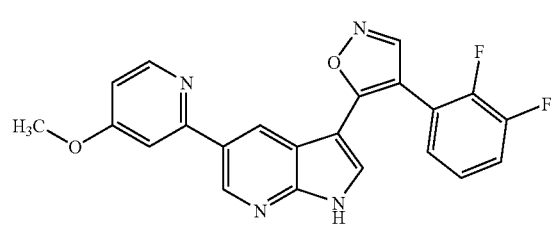 78

TABLE 1-continued

Examples of Compounds at Formula I:

| | |
|---|---|
| (structure) | 79 |
| (structure) | 80 |
| (structure) | 81 |
| (structure) | 82 |
| (structure) | 83 |
| (structure) | 84 |
| (structure) | 85 |

TABLE 1-continued
Examples of Compounds at Formula I:
 86
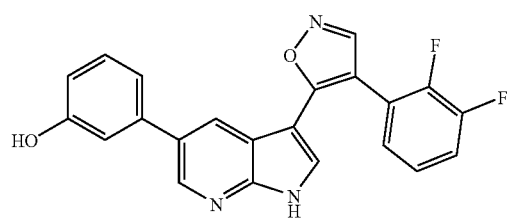 87
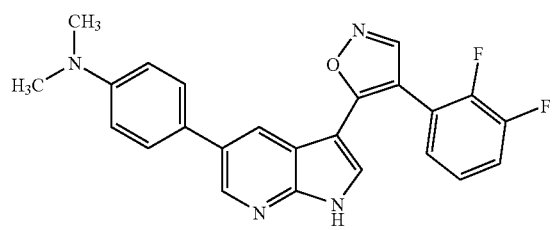 88
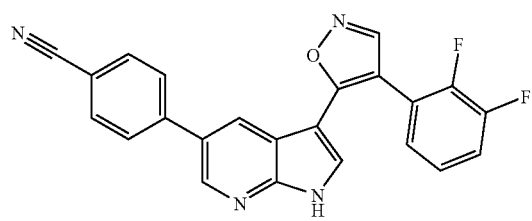 89
 90
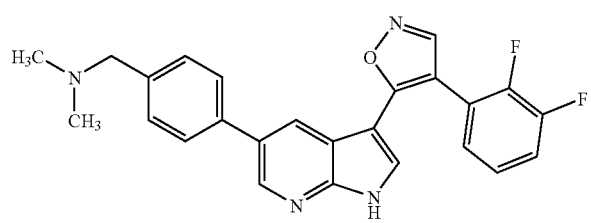 91

TABLE 1-continued
Examples of Compounds at Formula I:
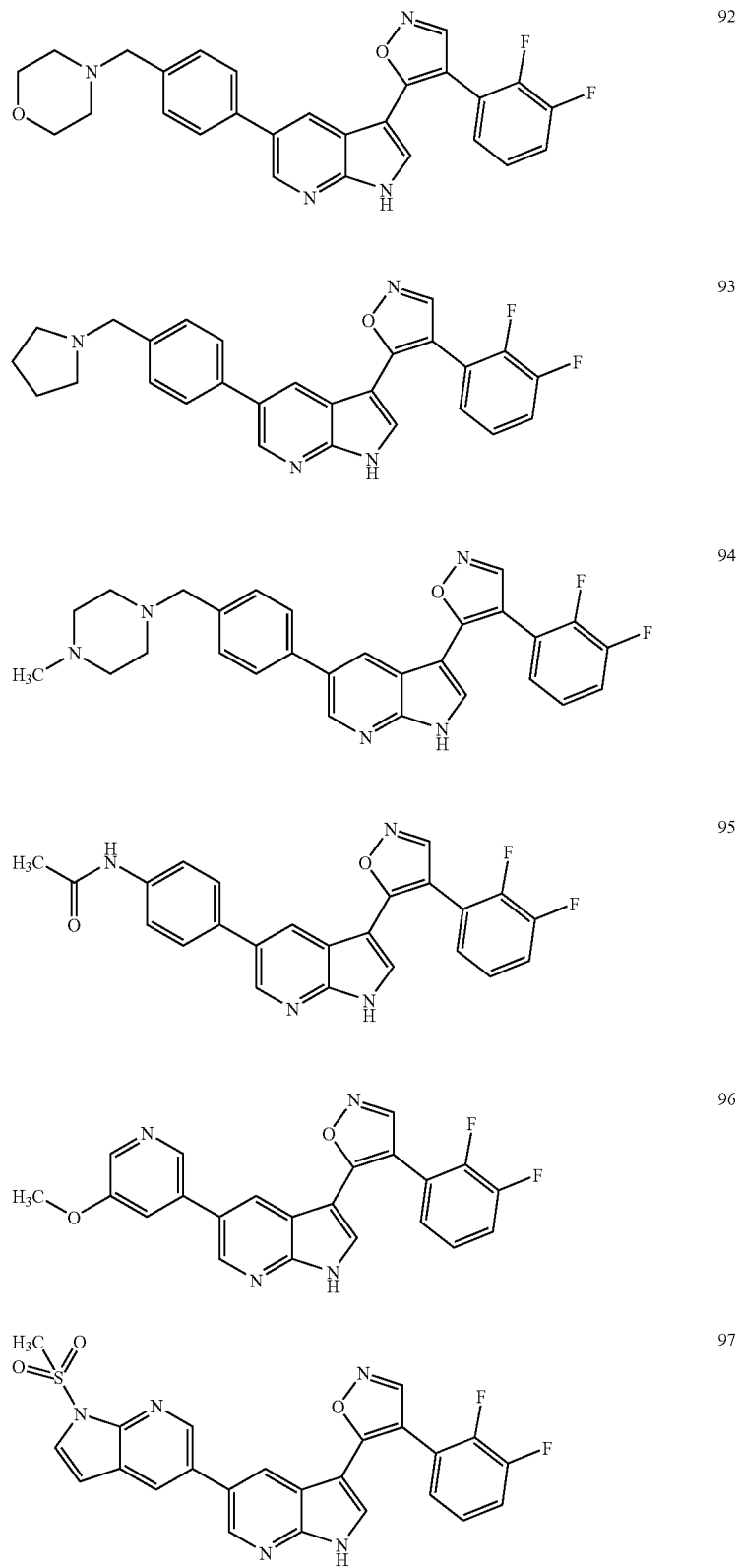

TABLE 1-continued

Examples of Compounds at Formula I:

TABLE 1-continued
Examples of Compounds at Formula I:
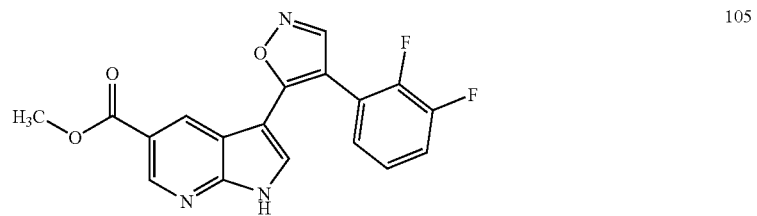
105
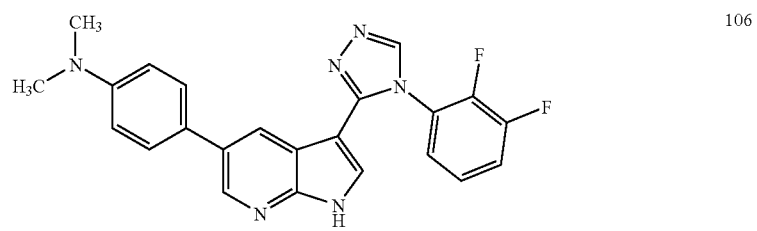
106
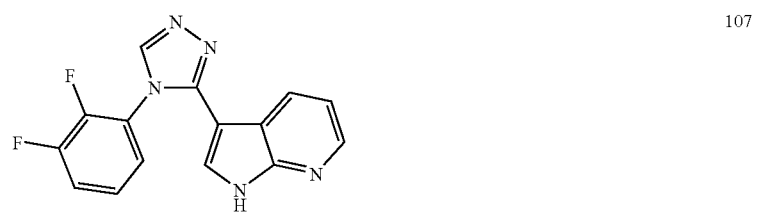
107
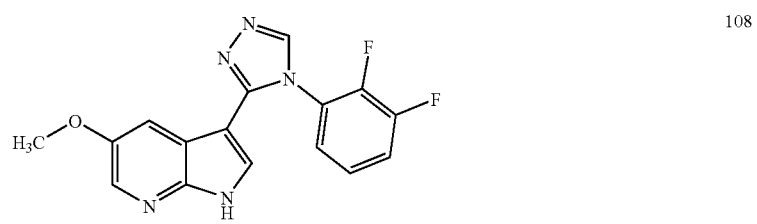
108
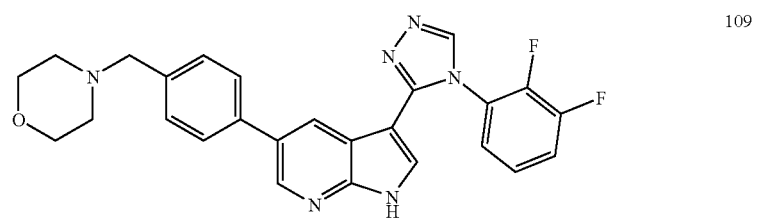
109
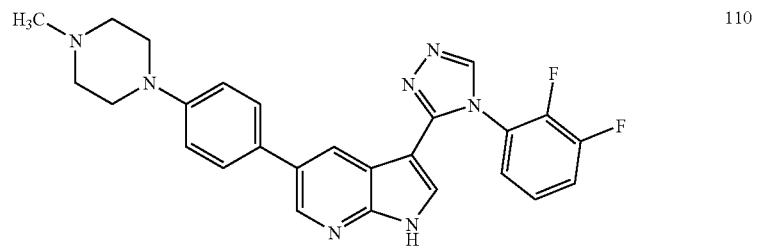
110

TABLE 1-continued
Examples of Compounds at Formula I:
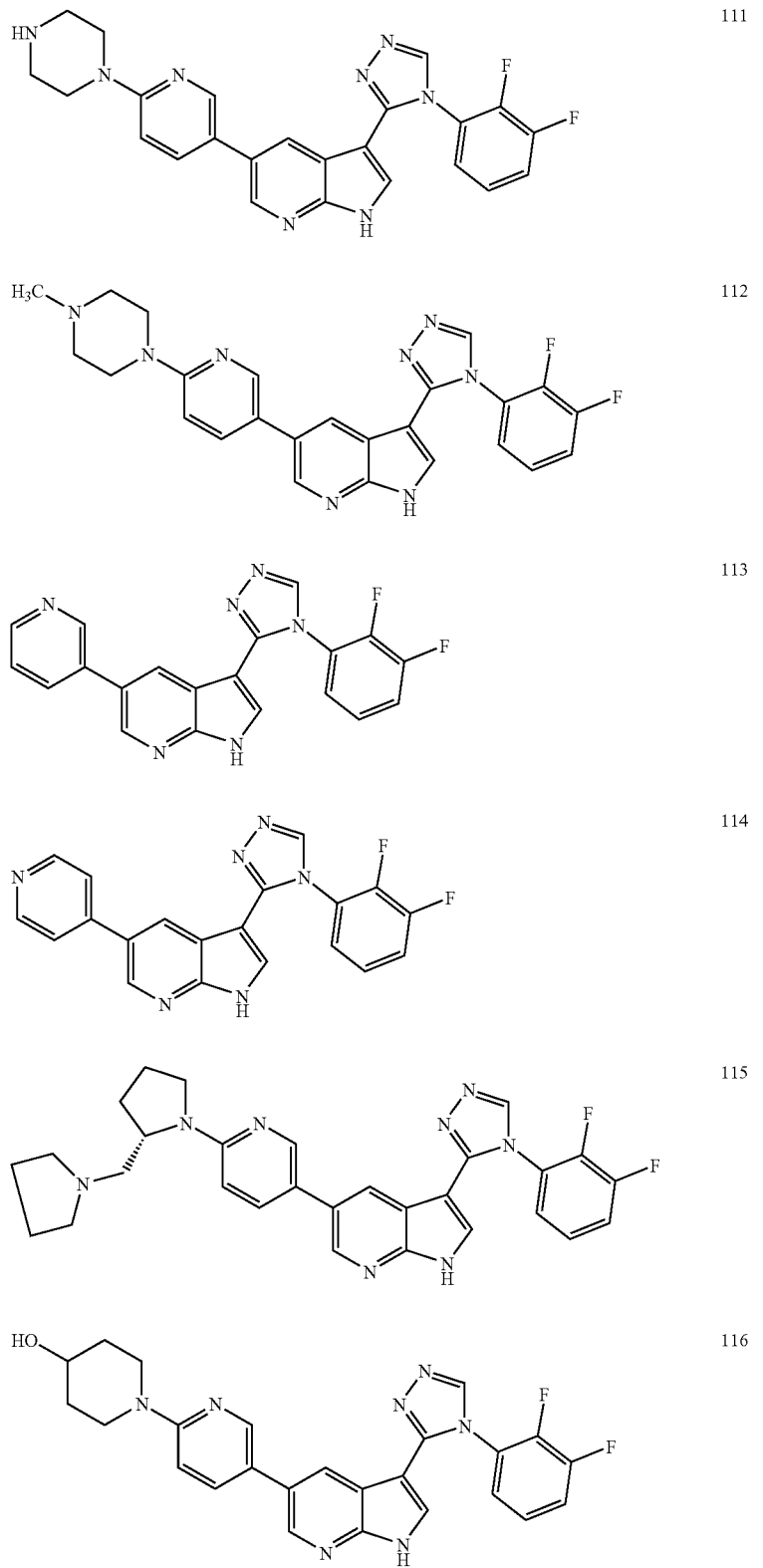
111
112
113
114
115
116

TABLE 1-continued
Examples of Compounds at Formula I:
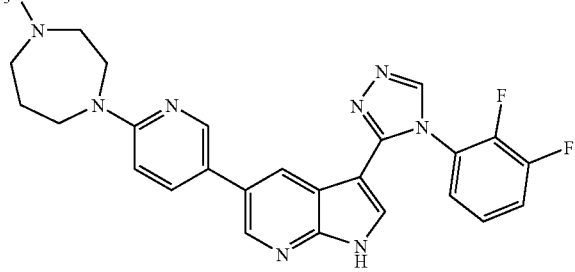  117
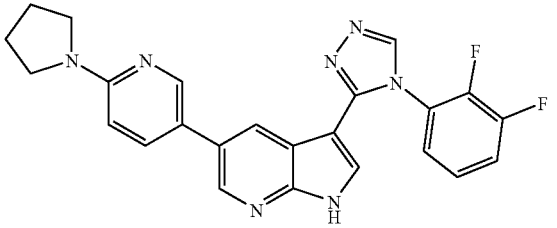  118
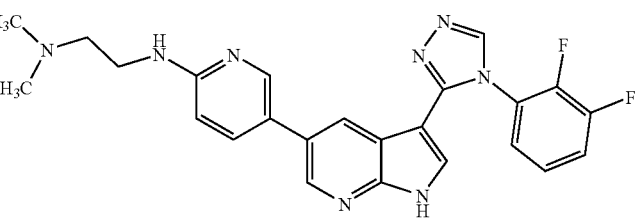  119
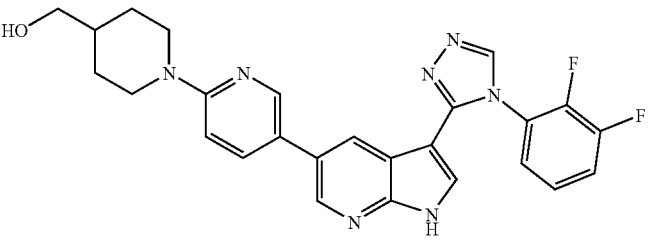  120
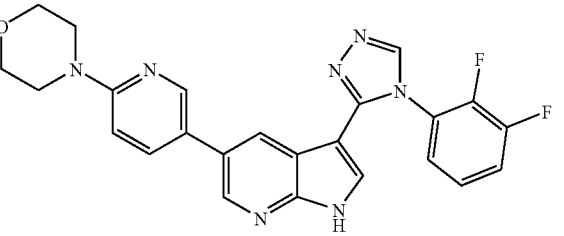  121
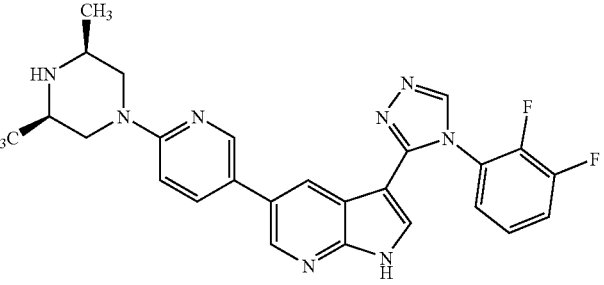  122

TABLE 1-continued
Examples of Compounds at Formula I:
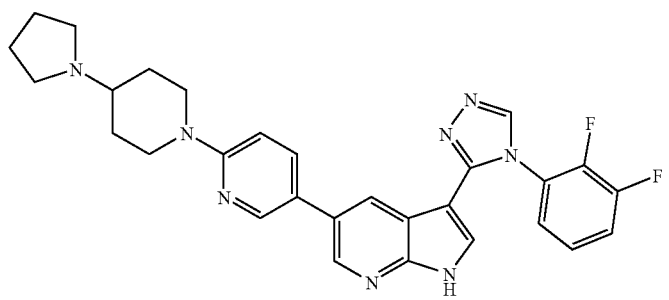
123
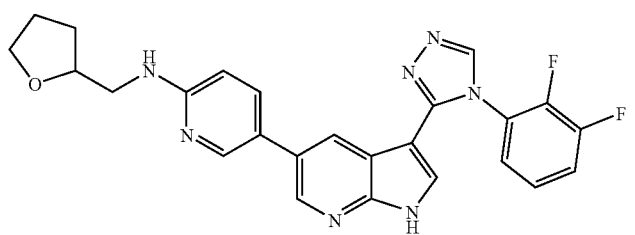
124
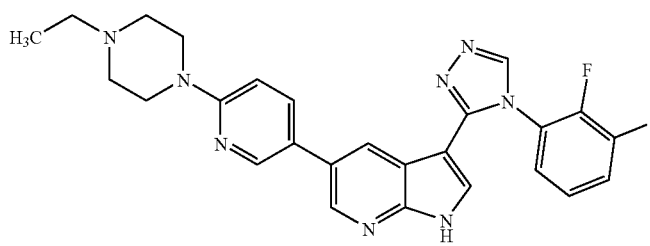
125
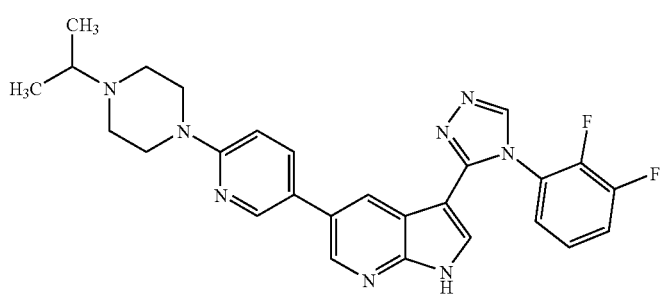
126
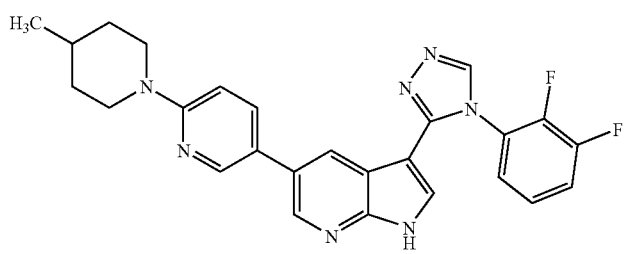
127

TABLE 1-continued
Examples of Compounds at Formula I:
| | |
|---|---|
| 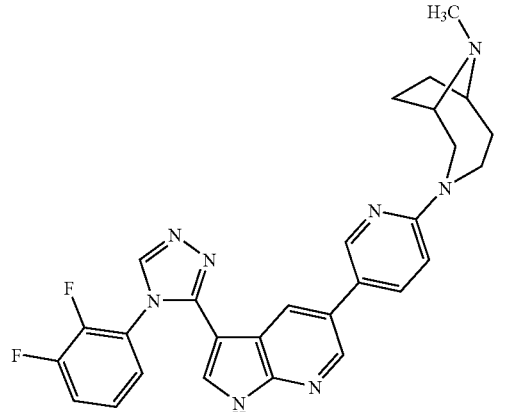 | 128 |
| 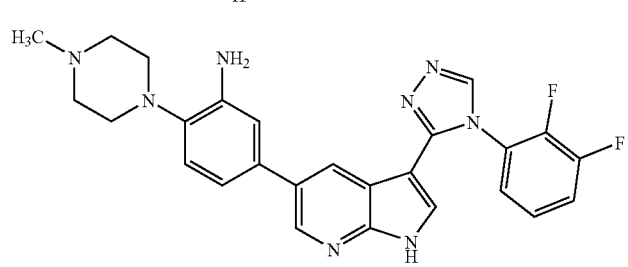 | 129 |
| 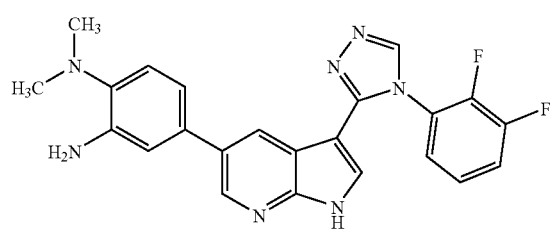 | 130 |
| 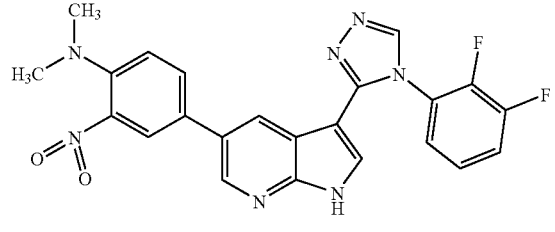 | 131 |
| 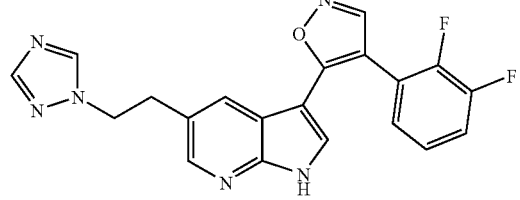 | 132 |
| 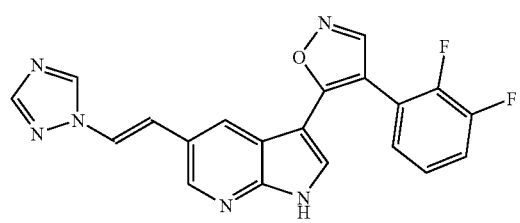 | 133 |

TABLE 1-continued
Examples of Compounds at Formula I:
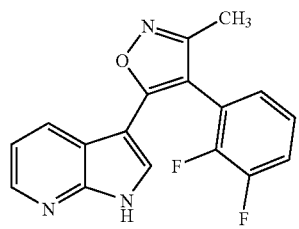
134
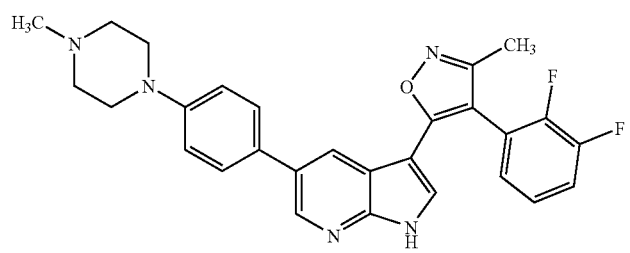
135
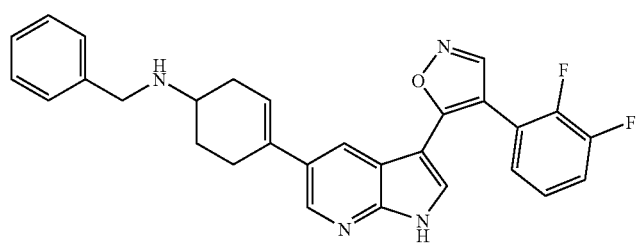
136
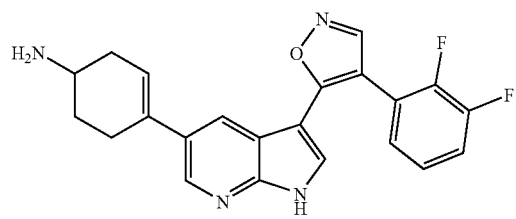
137
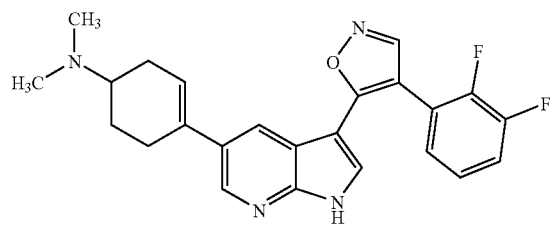
138
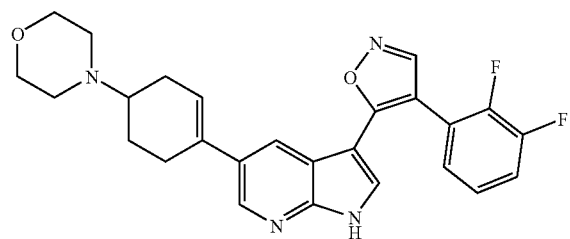
139

TABLE 1-continued
Examples of Compounds at Formula I:
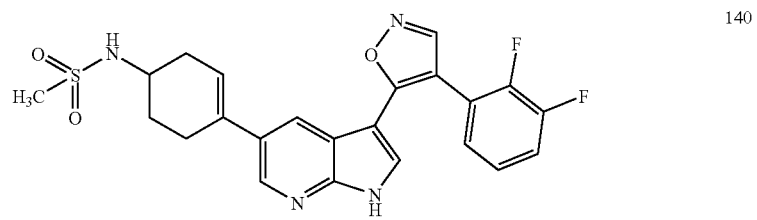
140
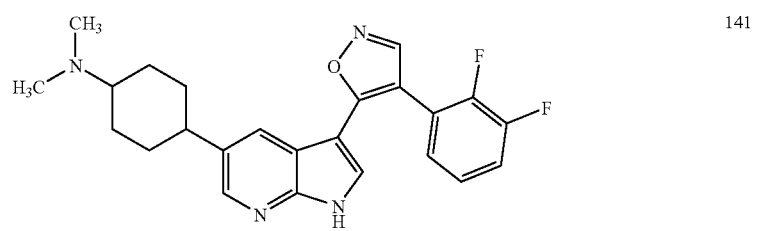
141
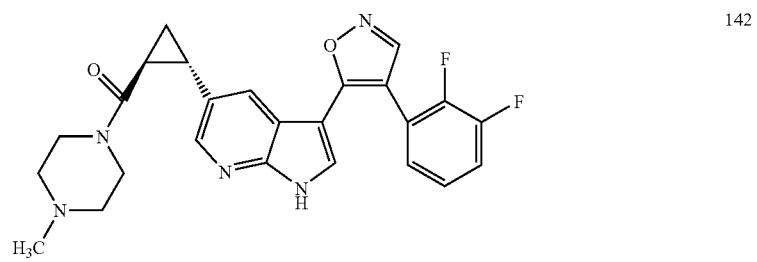
142
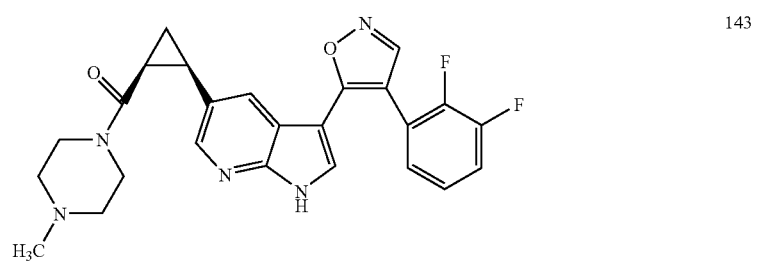
143
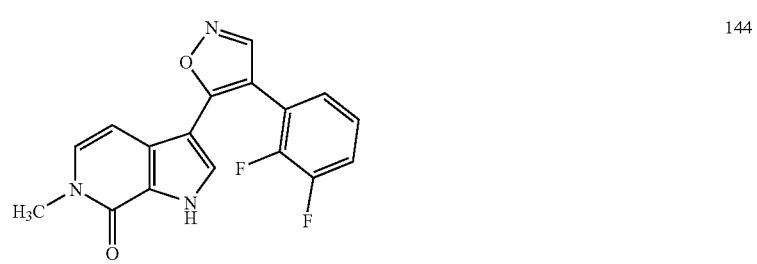
144
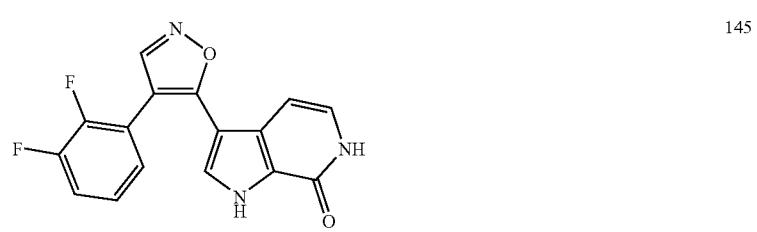
145

TABLE 1-continued
Examples of Compounds at Formula I:
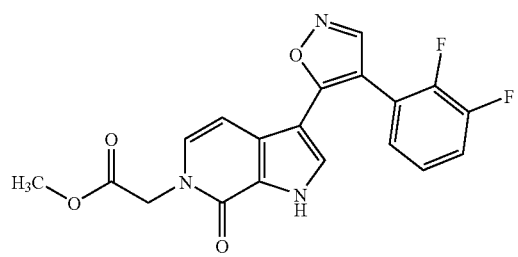
146
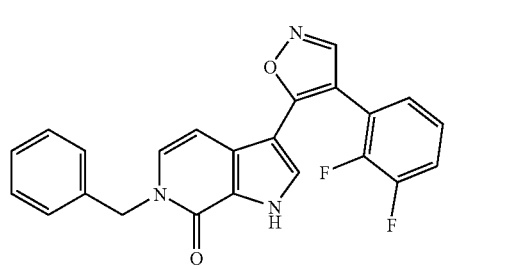
147
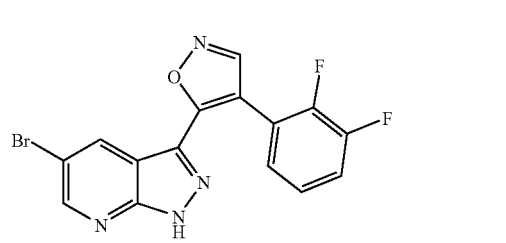
148
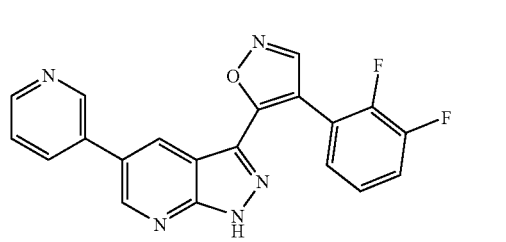
149
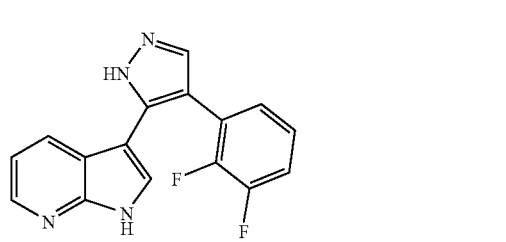
150
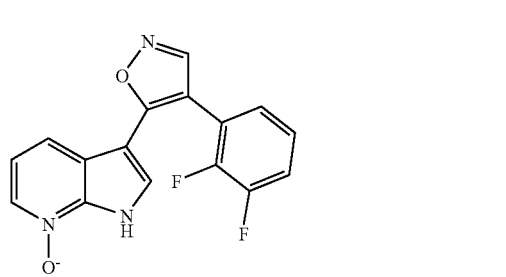
151

TABLE 1-continued
Examples of Compounds at Formula I:
152
153
154
155
4. General Synthetic Methodology
The compounds of this invention may be prepared in general by methods known to those skilled in the art for analogous compounds, as illustrated by the general scheme below, and the preparative examples that follow.
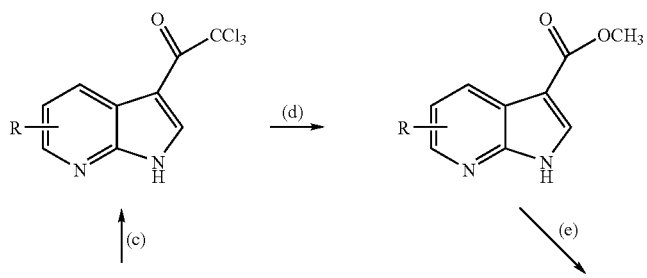
Scheme I

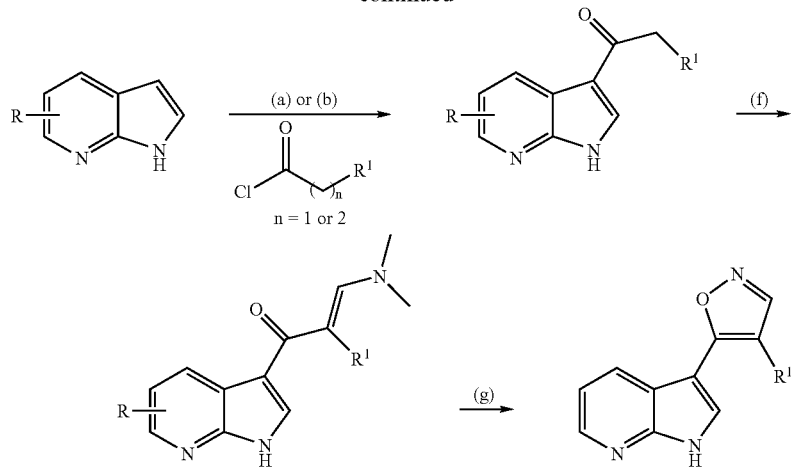

Reagents and conditions: (a) AlCl₃, DCM; (b) AlCl₃, CS₂ 50° C.; (c) Trichloroacetyl chloride, AlCl₃, DCM; (d) Methanol, Et₃N; (e) (i) LHMDS, aryl-acetic acid, THF, −78 C, 1 hr. (ii) reflux (f) Bredereck's reagent, THF; (g) i. hydroxyl amine hydrochloride, NaHCO3, THF reflux, ii. TsOH, THF reflux.

Scheme I above shows a general synthetic route for preparing compounds of the present invention when Ring A is isoxazolyl.

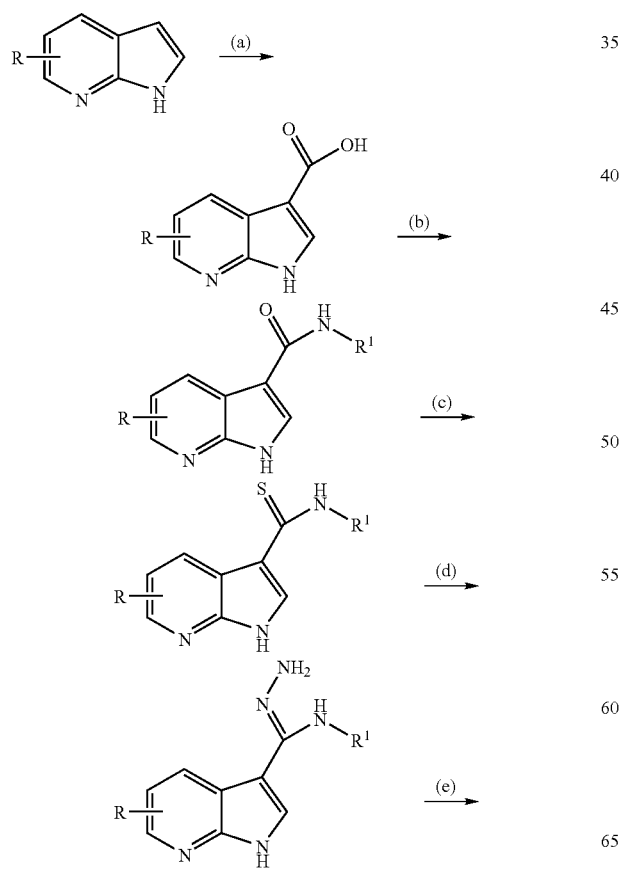

Scheme II

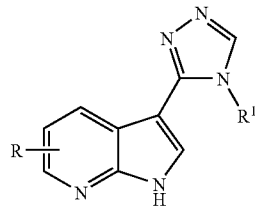

Reagents and conditions: (a) POCl₃, DMF, Jones' Reagent; (b) R¹NH₂, CDI, DMA; (c) Lawesson's reagent; (d) hydrazine; (e) CH(OEt)₃.

Scheme II above shows a general synthetic route for preparing compounds of the present invention when Ring A is triazolyl ring (b).

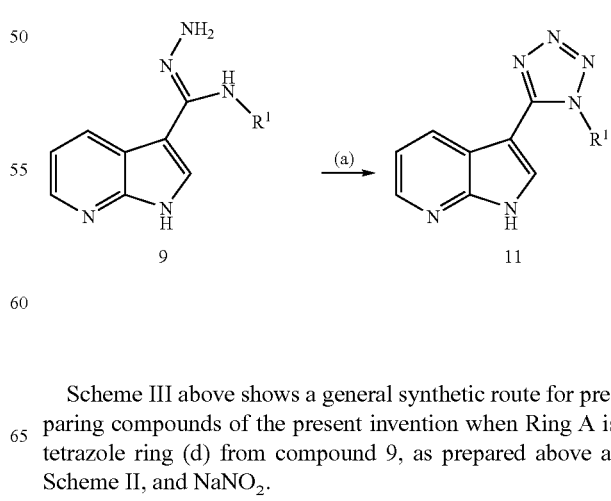

Scheme III

Scheme III above shows a general synthetic route for preparing compounds of the present invention when Ring A is tetrazole ring (d) from compound 9, as prepared above at Scheme II, and NaNO₂.

Scheme IV

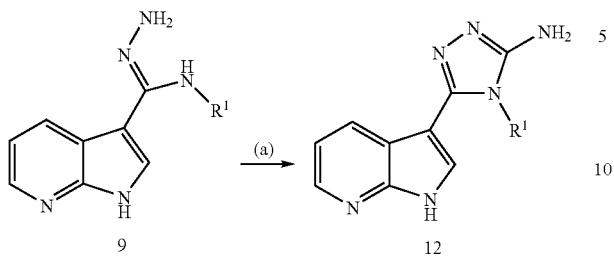

Scheme IV above shows a general synthetic route for preparing compounds of the present invention when Ring A is triazole ring (b), substituted with —NH2, from compound 9 and hydrazine.

Scheme V

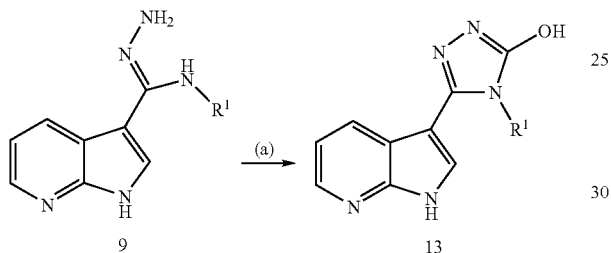

Scheme V above shows a general synthetic route for preparing compounds of the present invention when Ring A is triazole ring (b), substituted with —OH, from compound 9 and CDI.

Scheme VI

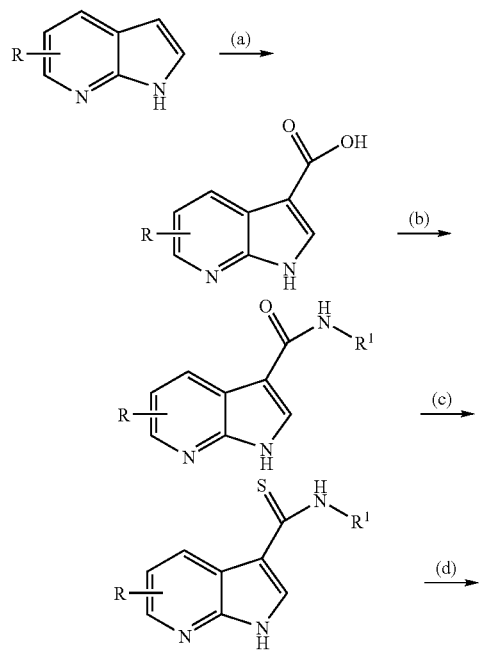

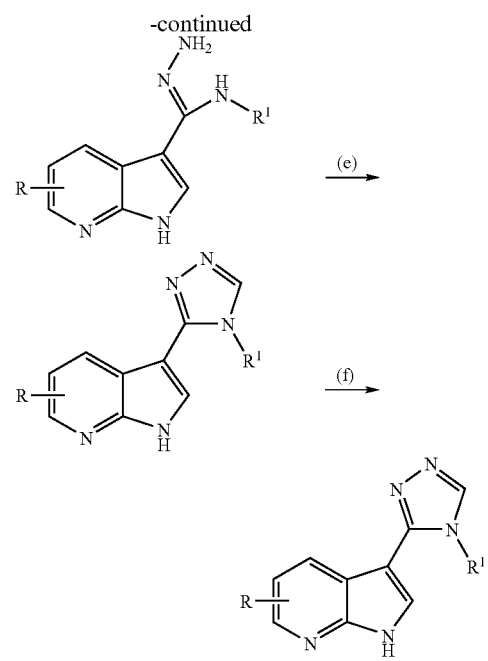

Reagents and Conditions: (a) (i) trichloroacetyl chloride, $AlCl_3$ $CH_2Cl_2$, (ii) $Et_3N$, $H_2O$, RT (b) (i) oxalyl chloride, DMF (cat.), $CH_2Cl_2$, (ii) Ar—NH2, $Et_3N$, $CH_2Cl_2$; (c) Lawesson's reagent, toluene, reflux; (d) hydrazine, EtOH & $CH_2Cl_2$; (e) triethylorthoformate, HCO2H; (f) Suzuki coupling.

Step (f) involves a Suzuki coupling. Optional step (f) may be used to prepare compounds having various R groups. The conditions may be modified as known to skilled practitioners. For example, if R is bromo or iodo, the reagents that may be used in the coupling reaction include R—B(OR)$_2$, 2M $Na_2CO_3$, $PdCl_2$(dppf), and DMF. If R is B(OH)$_2$, the reagents include Ar—X (where X=Br, I, OTf), 2M $Na_2CO_3$, $PdCl_2$ (dppf), and DMF. As would be recognized, step (f) would not be used if the desired final product was one wherein R is bromo, iodo, or B(OR)$_2$.

Although certain exemplary embodiments are depicted and described above and herein, it will be appreciated that compounds of the invention can be prepared according to the methods described generally above using appropriate starting materials by methods generally available to one of ordinary skill in the art.

5. Uses, Formulation and Administration

The compounds and compositions described herein are generally useful for the inhibition of protein kinase activity of one or more enzymes. Further information relating to kinase structure, function and their role in disease or disease symptoms is available at the Protein Kinase Resource website (http://kinases.sdsc.edu/html/index.shtml).

Examples of kinases that are inhibited by the compounds and compositions described herein and against which the methods described herein are useful include, but are not limited to, c-Met, GSK3, JAK, SYK, KDR, FLT-3, c-Kit, Aurora, and TAK-1 and all subtypes of these kinases (e.g., Aurora-2). The compounds and compositions of the invention are therefore also particularly suited for the treatment of diseases and disease symptoms that involve one or more of the aforementioned kinases.

The activity of a compound utilized in this invention as an inhibitor of c-Met, GSK3, JAK, SYK, KDR, FLT-3, c-Kit, Aurora, and/or TAK-1 may be assayed in vitro, in vivo or in a cell line. In vitro assays include assays that determine inhibition of either the phosphorylation activity or ATPase activity of activated c-Met, GSK3, JAK, SYK, KDR, FLT-3, c-Kit, Aurora, and/or TAK-1. Alternate in vitro assays quantitate the ability of the inhibitor to bind to c-Met, GSK3, JAK, SYK, KDR, FLT-3, c-Kit, Aurora, and/or TAK-1. Inhibitor binding may be measured by radiolabelling the inhibitor prior to binding, isolating the inhibitor/c-Met, inhibitor/GSK3, inhibitor/JAK, inhibitor/SYK, inhibitor/KDR, inhibitor/FLT-3, inhibitor/c-Kit, inhibitor/Aurora, and/or inhibitor/TAK-1 complex and determining the amount of radiolabel bound. Alternatively, inhibitor binding may be determined by running a competition experiment where new inhibitors are incubated with c-Met, GSK3, JAK, SYK, KDR, FLT-3, c-Kit, Aurora, and/or TAK-1 bound to known radioligands. Detailed conditions for assaying a compound utilized in this invention as an inhibitor of c-Met, GSK3, JAK, SYK, KDR, FLT-3, c-Kit, Aurora, and/or TAK-1 kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly c-Met, GSK3, JAK, SYK, KDR, FLT-3, c-Kit, Aurora, and/or TAK-1 kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearatez, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in c-Met, GSK3, JAK, SYK, KDR, FLT-3, c-Kit, Aurora, and/or TAK-1 activity between a sample comprising said composition and a c-Met, GSK3, JAK, SYK, KDR, FLT-3, c-Kit, Aurora, and/or TAK-1 kinase and an equivalent sample comprising c-Met, GSK3, JAK, SYK, KDR, FLT-3, c-Kit, Aurora, and/or TAK-1 kinase in the absence of said composition.

As used herein, the term "JAK" is used interchangeably with the terms "JAK kinase" and "a JAK family kinase". In certain embodiments, JAK refers to JAK3 kinase.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of c-Met, GSK3, JAK, SYK, KDR kinase, FLT-3, c-Kit, Aurora, and/or TAK-1.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2Ooctyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting c-Met, GSK3, JAK, SYK, KDR, FLT-3, c-Kit, Aurora, and/or TAK-1 kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from c-Met, GSK3, JAK, SYK, KDR, FLT-3, c-Kit, Aurora, and/or TAK-1 kinase, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting c-Met, GSK3, JAK, SYK, KDR, FLT-3, c-Kit, Aurora, and/or TAK-1 kinase activity in a patient comprising the step of administering to said patient a compound of the present invention, or a composition comprising said compound.

The term "cMET-mediated disease" or "cMET-mediated condition", as used herein, means any disease state or other deleterious condition in which cMET is known to play a role. The terms "cMET-mediated disease" or "cMET-mediated condition" also mean those diseases or conditions that are alleviated by treatment with a cMET inhibitor. Such conditions include, without limitation, atherosclerosis, lung fibrosis, glioblasomas, gastric carcinomas, or a cancer selected from renal, colon, breast, prostate, liver, pancreatic, or lung cancer.

According to one embodiment, the present invention relates to a method of treating or lessening the severity of renal, colon, breast, prostate, or lung cancer, atherosclerosis or lung fibrosis in a patient in need thereof, comprising administering to said patient a compound of the present invention or composition thereof.

According to another embodiment, the present invention relates to a method of treating or lessening the severity of renal cancer in a patient in need thereof, comprising administering to said patient a compound of the present invention or composition thereof.

Another aspect of the present invention relates to a method of inhibiting tumor metastasis in a patient in need thereof, comprising administering to said patient a compound of the present invention or composition thereof.

The term "GSK3-mediated disease" or "condition", as used herein means any disease or other deleterious condition in which GSK3 is known to play a role. Accordingly, another embodiment of the present invention relates to treating or lessening the severity of one or more diseases in which GSK3 is known to play a role. Specifically, the present invention relates to a method of treating or lessening the severity of a disease or condition selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease wherein said method comprises administering to a patient in need thereof a composition according to the present invention.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to a preferred embodiment, the method of the present invention relates to treating or lessening the severity of stroke.

According to another preferred embodiment, the method of the present invention relates to treating or lessening the severity of a neurodegenerative or neurological disorder.

Another aspect of the present invention relates to a method of decreasing sperm motility in a male patient comprising administering to said patient a compound of the present invention or composition thereof.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

According to another embodiment, the invention provides a method for treating or lessening the severity of a JAK-mediated disease or condition in a patient comprising the step of administering to said patient a composition according to the present invention.

The term "JAK-mediated disease", as used herein means any disease or other deleterious condition in which a JAK family kinase is known to play a role. Accordingly, another embodiment of the present invention relates to treating or lessening the severity of one or more diseases in which JAK is known to play a role. Specifically, the present invention relates to a method of treating or lessening the severity of a disease or condition selected from immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas, wherein said method comprises administering to a patient in need thereof a composition according to the present invention.

According to another embodiment, the invention provides a method for treating or lessening the severity of a SYK-mediated disease or condition in a patient comprising the step of administering to said patient a composition according to the present invention.

The term "SYK-mediated disease", as used herein means any disease or other deleterious condition in which a SYK family kinase is known to play a role. Accordingly, another embodiment of the present invention relates to treating or lessening the severity of one or more diseases in which SYK is known to play a role. Specifically, the present invention relates to a method of treating or lessening the severity of a disease or condition selected from allergic disorders, especially asthma.

According to another embodiment, the invention provides a method for treating or lessening the severity of a KDR-mediated disease or condition in a patient comprising the step of administering to said patient a composition according to the present invention.

The term "KDR-mediated disease", as used herein means any disease or other deleterious condition in which a KDR family kinase is known to play a role. Accordingly, another embodiment of the present invention relates to treating or lessening the severity of one or more diseases in which KDR is known to play a role. Specifically, the present invention relates to a method of treating or lessening the severity of a disease or condition selected from cancer such as brain cancer, genitourinary tract cancer, lymphatic system cancer, stomach cancer, cancer of the larynx, lung cancer, pancreatic cancer, breast cancer, Kaposi's sarcoma, and leukemia; endometriosis, benign prostatic hyperplasia; vascular diseases such as restenosis and atherosclerosis; autoimmune diseases such as rheumatoid arthritis and psoriasis; ocular conditions such as proliferative or angiogenic retinopathy and macular degeneration; and inflammatory diseases such as contact dermatitis, asthma and delayed hypersensitivity reactions.

According to another embodiment, the invention provides a method for treating or lessening the severity of a FLT-3-mediated disease or condition in a patient comprising the step of administering to said patient a composition according to the present invention.

The term "FLT-3-mediated disease", as used herein means any disease or other deleterious condition in which a FLT-3 family kinase is known to play a role. Such conditions include, without limitation, hematopoietic disorders, in particular, acute-myelogenous leukemia (AML), acute-promyelocytic leukemia (APL), and acute lymphocytic leukemia (ALL).

According to another embodiment, the invention provides a method for treating or lessening the severity of a FMS-mediated disease or condition in a patient comprising the step of administering to said patient a composition according to the present invention.

The term "FMS-mediated disease", as used herein means any disease or other deleterious condition in which a FMS family kinase is known to play a role. Such conditions include, without limitation, cancer (including, but not limited to, ovarian, endometrial, and breast cancer), inflammatory disorders, and hypertension.

According to another embodiment, the invention provides a method for treating or lessening the severity of a c-KIT-mediated disease or condition in a patient comprising the step of administering to said patient a composition according to the present invention.

The term "c-KIT-mediated disease", as used herein means any disease or other deleterious condition in which a c-KIT family kinase is known to play a role. Such conditions include, without limitation, AML, chronic myelogenous leukemia (CML), mastocytosis, anaplastic large-cell lymphoma, ALL, gastrointestinal stromal tumor (GIST), T-cell lymphoma, adenoid cytsic carcinoma, angiosarcoma, endometrial carcinoma, small cell lung carcinoma, prostate cancer, ovarian cancer, breast carcinoma, thyroid carcinoma, malignant melanoma and colon carcinoma.

According to another embodiment, the invention provides a method for treating or lessening the severity of an AUR-mediated disease or condition in a patient comprising the step of administering to said patient a composition according to the present invention.

The term "AUR-mediated disease" or "AUR-mediated condition", as used herein, means any disease or other deleterious condition in which AUR protein kinase is known to play a role. Such conditions include, without limitation, allergic disorders, especially asthma.

According to another embodiment, the invention provides a method for treating or lessening the severity of a TAK-1-mediated disease or condition in a patient comprising the step of administering to said patient a composition according to the present invention.

The term "TAK-1-mediated condition", as used herein means any disease or other deleterious condition in which TAK-1 is known to play a role. The terms "TAK-1-mediated disease" or "TAK-1-mediated condition" also mean those diseases or conditions that are alleviated by treatment with an TAK inhibitor. Such conditions include, without limitation, autoimmune, inflammatory, proliferative, and hyperproliferative diseases, rheumatoid arthritis, heart failure, osteoporosis, hepatic cancer, neurite outgrowth, adipogenesis, and cardiomyocyte differentiation.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

As used herein, the term "$R_t$ (min)" refers to the HPLC retention time, in minutes, associated with the compound. Unless otherwise indicated, the HPLC method utilized to obtain the reported retention time is as follows:

Column: YMC Pro C18 S-5 120Acolumn, 2.0×50 mm
Gradient: 10-90% acetonitrile+water (0.1% Formic acid)
Flow rate: 1.0 mL/minute
Detection: 225 nm.

Preparation of Azaindoles

General Method A:

Reagents and conditions: (a) $AlCl_3$, DCM; (b) $AlCl_3$, $CS_2$ 50° C.; (c) Trichloroacetyl chloride, $AlCl_3$, DCM; (d) Methanol, $Et_3N$; (e) (i) LHMDS, aryl-acetic acid, THF, −78 C, 1 hr. (ii) reflux (f) Bredereck's reagent, THF; (g). i. hydroxylamine hydrochloride, $NaHCO_3$, THF reflux, ii. TsOH, THF reflux.

Example 1

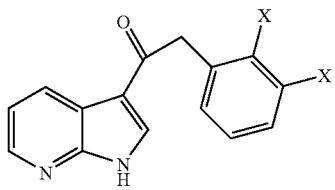

2-(2,3-Difluoro-phenyl)-1-(1H-pyrrolo[2,3-b]pyridin-3-yl)-ethanone

Method A: (X=F)

To 7-azaindole (1 g, 8.5 mmol) and $AlCl_3$ (1.2 g, 9.0 mmol) in methlene chloride at 0° C. was added (2,3-difluorophenyl)-acetyl chloride [prepared by treating (2,3-difluoro-phenyl)-acetic acid (1.5 mg, 8.72 mmol) with oxalyl chloride (0.90 mL)] in methlene chloride. After stirring at room temperature for 2 hours, the solution was poured into ice water and extracted with methlene chloride, dried ($Na_2SO_4$), and concentrated to give 300 mg (13% yield) of title compound used without purification. LCMS $R_t$=3.00 minutes, $MH^+$ 273.1, $M^-$ 271.1.

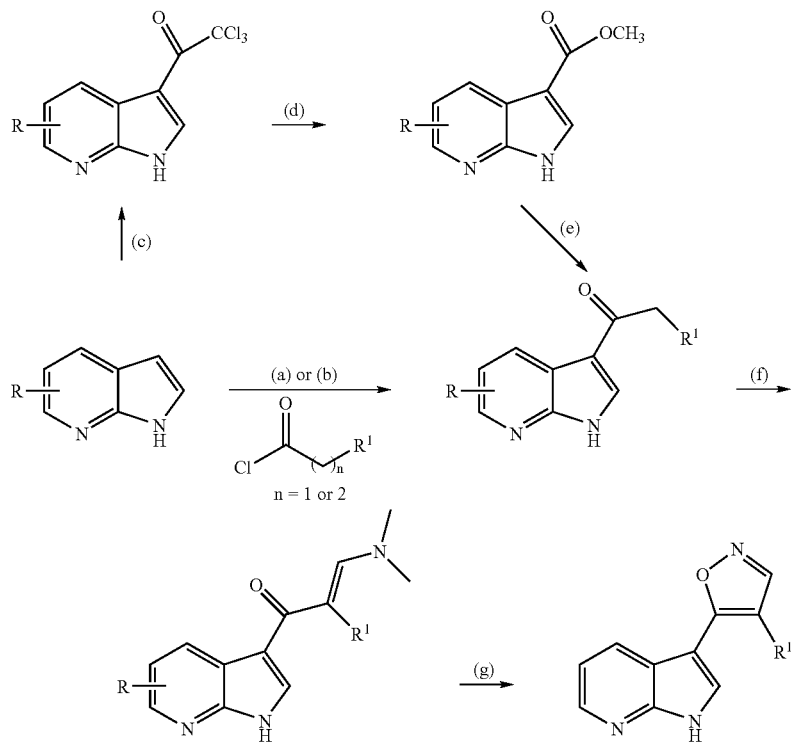

Method B: (X=Cl)

To 7-azaindole (173 mg, 1.46 mmol), AlCl₃ (1.34 g, 11 mmol) in carbon disulfide at 50° C., was added (2,3-dichloro-phenyl)-acetyl chloride [prepared by treating (2,3-dichloro-phenyl)-acetic acid (300 mg, 1.46 mmol) with oxalyl chloride (0.14 mL)] drop wise in CS₂. After heating for 3 hours, the solution was poured into water and extracted with ethyl acetate, dried (Na₂SO₄), and concentrated to give 303 mg (68% yield) of title compound used without purification. LCMS: $R_t$=3.88 mins.; m/e 305.1 (M+H), 303.1 (M−H).

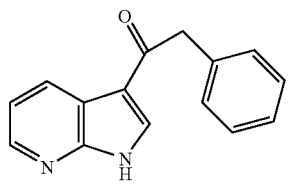

2-Phenyl-1-(1H-pyrrolo[2,3-b]pyridin-3-yl)-etha-none

Modification of Method A: To a mixture of 1H-pyrrolo[2,3-b]pyridine (1.0 g, 8.46 mmol) and AlCl3 (3.4 g, 25.50 mmol) in dry methylene chloride (20 mL) was added phenyl acetyl chloride (3.27 g, 21.15 mmol) at room temperature. The solution was then stirred at room temperature (RT) for 4 hrs. The mixture was poured into iced water and extracted with methylene chloride (3×20 mL). The combined organic layers were dried over MgSO₄, filtered, and evaporated. The residue was then dissolved in MeOH (20 mL) and treated with 6N NaOH (5 mL) at RT for 2 hrs. Evaporated most of the solvent, the residue was acidified with 6N HCl and extracted with EtOAc. The combined organic layers were dried over MgSO4, filtered, and evaporated. The residue was purified by flash column to give desired product (1.3 g, 65%). MS (ES−): m/e=235.2 (M−H); LC/Method A/2.86 min.

Example 2

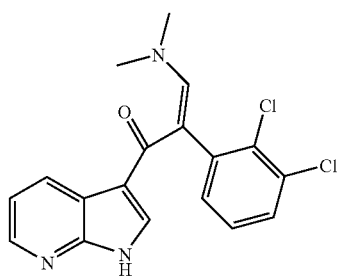

2-(2,3-Dichloro-phenyl)-3-dimethylamino-1-(1H-pyrrolo[2,3-b]pyridin-3-yl)-propenone To 2-(2,3-Dichloro-phenyl)-1-(1H-pyrrolo[2,3-b]pyridin-3-yl)-ethanone (303 mg, 0.991 mmol) in THF 50 mL, was added Bredereck's reagent 952 mg, 2.99 mmol) and the solution was heated to reflux overnight. Concentration afforded title compound used without purification. LCMS: $R_t$=2.64 mins.; m/e 360.1(M+H).

Example 3

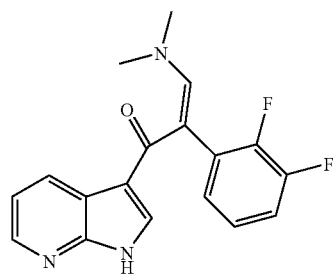

2-(2,3-Difluoro-phenyl)-3-dimethylamino-1-(1H-pyrrolo[2,3-b]pyridin-3-yl)-propenone To 2-(2,3-difluoro-phenyl)-1-(1H-pyrrolo[2,3-b]pyridin-3-yl)-ethanone (125 mg, 0.726 mmol) in THF 40 mL, was added Bredereck's reagent (379 mg, 2.18 mmol) and the solution was heated at reflux overnight. Concentration afforded title compound used without purification. LCMS: $R_t$=2.30 mins.; m/e 328.2(M+H), 326.2 (M−H).

Example 4

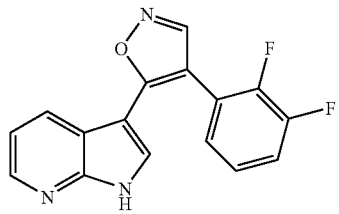

3-[4-(2,3-Difluoro-phenyl)-isoxazol-5-yl]-1H-pyrrolo[2, 3-b]pyridine (1)

To 2-(2,3-dichloro-phenyl)-3-dimethylamino-1-(1H-pyrrolo[2,3-b]pyridin-3-yl)-propenone (358 mg, 0.997 mmol) in THF 100 mL, was added hydroxylamine hydrochloride (76 mg, 1.0 mmol) and NaHCO₃ (84 mg, 1.0 mmol) and the reaction mixture was refluxed for 4 hours. To the red solution was added p-toluene sulfonic acid (189 mg, 0.99 mmol) and the solution was heated for an additional 2 hours. The reaction was poured into water, extracted with ethyl acetate, washed with brine, dried (Na₂SO₄) and concentrated. Purification by flash chromatography (0 to 6% methanol in methylene chloride) to afford the title compound (157 mg, 48% yield). ¹H NMR (500 MHz, DMSO-d6) δ 12.38 (1H, bs), 8.85 (1H, s), 8.34-8.32 (1H, d), 7.89-7.87 (1H, d), 7.76-7.75 (1H, d), 7.51-7.50 (1H, d, d), 7.36-7.33 (1H, m), 7.31-7.28 (1H, m) 7.18-7.15 (1H, m).

LC/MS: $R_t$=3.64 mins.; m/e 298.1(M+H), 296.1 (M−H)

Example 5

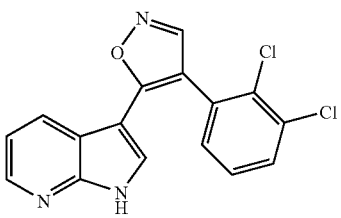

3-[4-(2,3-Dichloro-phenyl)-isoxazol-5-yl]-1H-pyrrolo[2, 3-b]pyridine (2)

To 2-(2,3-dichloro-henyl)-3-dimethylamino-1-(1H-pyrrolo[2, 3-b]pyridin-3-yl)-propenone (238 mg, 0.727 mmol) in THF 75 mL, was added hydroxylamine hydrochloride (56 mg, 0.80 mmol) and NaHCO$_3$ (67 mg, 0.80 mmol) and the reaction mixture was refluxed for 4 hours. To the red solution was added p-toluene sulfonic acid (152 mg, 0.80 mmol) and the solution was heated for an additional 2 hours. The reaction was poured into water, extracted with ethyl acetate, washed with brine, dried (Na$_2$SO$_4$) and concentrated. Purification by flash chromatography (0 to 6% methanol in methylene chloride to afford the title compound (77 mg, 36% yield). $^1$H NMR (500 MHz, DMSO-d6) δ 12.32 (1H, bs), 8.80 (1H, s), 8.33-8.32 (1H, d, d), 7.94-7.93 (1H, d, d), 7.77-7.75 (1H, d, d), 7.52-7.50 (1H, d, d), 7.49-7.48 (1H, d), 7.47-7.44 (1H, m) 7.19-7.16 (1H, d, d).

LC/MS: R$_t$=2.36 mins.; m/e 330.09 (M+H), 328.05 (M−H).

Various methods for the formation of the isoxazole ring were applied:
1. Hydroxylamine hydrochloride (5 equiv.), sodium acetate (6 equiv.), ethanol, reflux.
2. (a) Hydroxylamine hydrochloride, NaHCO$_3$, THF, reflux; (b) p-toluenesulfonic acid, THF, reflux.
3. Hydroxylamine hydrochloride, K$_2$CO$_3$, ethanol, reflux.

The following examples 6-21 were prepared by methods described above (Examples 1-5). A number of starting 5-substituted 7-azaindole derivatives were prepared by similar methods as described in the literature (Heterocycles 1999, 50 (2), 1065; Tetrahedron Letters 1998, 39, 5355).

Example 6

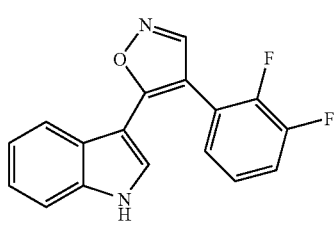

3-[4-(2,3-Difluoro-phenyl)-isoxazol-5-yl]-1H-indole (29)

M+ 297.1; M−295.2; R$_t$=4.06 minutes; $^1$H NMR (DMSO-d6) δ 11.80 (s, 1H), 8.80 (s, 1H), 7.60 (d, 1H), 7.59 (d, 1H), 7.50 (m, 2H), 7.35 (m, 1H), 7.29 (m, 1H), 7.21 (t, 1H), 7.10 (t, 1H). LC/MS: R$_t$ 4.06 mins.; m/e 297.1 (M+H), 295.2 (M−H).

Example 7

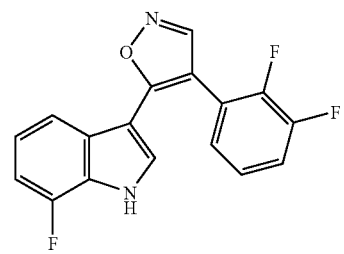

3-[4-(2,3-Difluoro-phenyl)-isoxazol-5-yl]-7-fluoro-1H-indole (33)

$^1$H NMR (500 MHz, DMSO-d6) δ: 12.37 (1H, bs), 8.85 (1H, s), 7.655-7.650 (1H, d), 7.51-7.50 (1H, q), 7.39-7.37 (1H, d), 7.34-7.28 (2H, cm), 7.09-7.06 (2H, m). LC/MS: Rt 4.24 mins.; m/z 315.06 (M+H), 313.17 (M−H).

Example 8

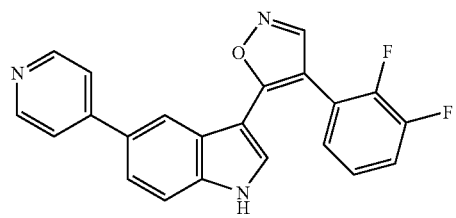

3-[4-(2,3-Difluoro-phenyl)-isoxazol-5-yl]-5-pyridin-4-yl-1H-indole (34)

$^1$H NMR (500 MHz, DMSO-d6) δ: 12.13 (s, 1H), 8.88 (s, 1H), 8.78 (d, 2H), 8.03 (s, 1H), 8.01 (d, 2H), 7.80 (m, 2H), 7.70 (d, 1H), 7.51 (m, 1H), 7.35 (m, 2H)

LC/MS: Rt 2.3 mins.; m/z 374.0 (M+H), 372.1 (M−H).

Example 9

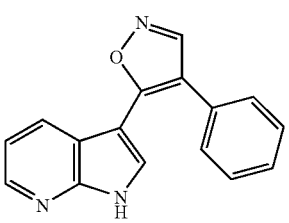

3-[4-Phenyl-isoxazol-5-yl]-1H-pyrrolo[2,3-b]pyridine (35)

To a solution of 2-phenyl-1-(1H-pyrrolo[2,3-b]pyridin-3-yl)-ethanone (200 mg, 0.85 mmol) in dry THF (5 mL) was added tert-butoxy-N,N,N',N'-tetramethyl-methanediamine (Bredereck's reagent) (440 mg, 2.52 mmol). The solution was heated at 60° C. for 3 h and evaporated to dry. The resulting residue was dissolved in ethanol (5 mL). To this ethanol solution was then added hydroxylamine hydrochloride (300 mg, 4.32 mmol) and sodium acetate (420 mg, 5.12 mmol). The mixture was heated under reflux for 10 h, cooled, and poured into aqueous NaHCO3 solution. The crude product was collected by filtration and washed with water. After purification by Gilson HPLC, the pure product was obtained as powder (130 mg, 0.50 mmol, 59%).

$^1$H NMR (500 MHz, DMSO-d6) δ: 12.34 (s, 1H), 8.88 (s, 1H), 8.11 (dd, 1H), 7.84 (d, 1H), 7.75 (dd, 1H), 7.50 (m, 2H), 7.43 (m, 2H), 7.37 (m, 1H), 7.11 (dd, 1H). LC/MS: Rt 3.19 mins.; m/e 262.2 (M+H), 260.2 (M−H)

Example 10

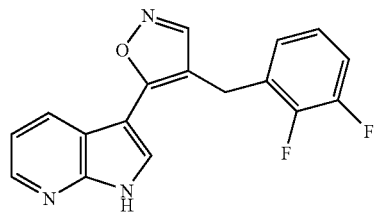

3-[4-(2,3-Difluoro-benzyl)-isoxazol-5-yl]-1H-pyrrolo[2,3-b]pyridine (36)

$^1$H NMR (500 MHz, DMSO-d6) δ: 12.40 (s, 1H), 8.43 (s, 1H), 8.35 (m, 2H), 8.02 (d, 1H), 7.31 (m, 1H), 7.26 (dd, 1H), 7.14 (m, 1H), 7.06 (t, 1H), 4.14 (s, 2H). LC/MS: Rt 3.55 mins.; m/e 312.2 (M+H), 310.2 (M−H).

Example 11

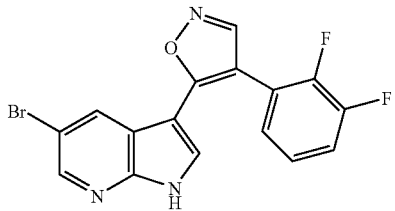

5-Bromo-3-[4-(2,3-difluoro-phenyl)-isoxazol-5-yl]-1H-pyrrolo[2,3-b]pyridine (37)

$^1$H NMR (500 MHz, DMSO-d6) δ: 12.67 (s, 1H), 8.88 (s, 1H), 8.41 (d, 1H), 7.89 (d, 1H), 7.88 (d, 1H), 7.54 (m, 1H), 7.33 (m, 2H). LC/MS: Rt 4.00 mins.; m/e 376 (M+H), 374 (M−H).

Example 12

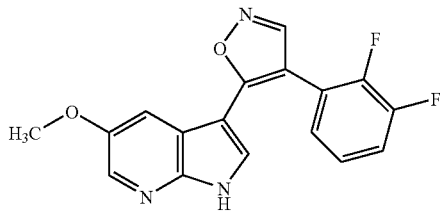

3-[4-(2,3-Difluoro-phenyl)-isoxazol-5-yl]-5-methoxy-1H-pyrrolo[2,3-b]pyridine (38)

The Friedel-Craft reaction of aluminum chloride, 2,3-difluorophenylacetyl chloride, and 5-methoxy-7-azaindole was run at 0 C. The remaining procedures were carried out as described for Example 2-5.

$^1$H NMR (500 MHz, DMSO-d6) δ: 12.31 (s, 1H), 8.85 (s, 1H), 8.07 (d, 1H), 7.76 (d, 1H), 7.51 (m, 1H), 7.32 (m, 2H), 7.21 (d, 1H), 3.69 (s, 3H). LC/MS: Rt 3.5 mins.; m/e 328 (M+H), 326.1 (M−H).

Example 13

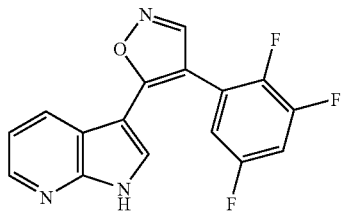

3-[4-(2,3,5-Trifluoro-phenyl)-isoxazol-5-yl]-1H-pyrrolo [2,3-b]pyridine (39)

$^1$H NMR (500 MHz, acetone-d6) δ: 8.69 (d, J=1.2 HZ, 1H), 8.44 (dd, J=4.8, 1.2 HZ, 1H) 8.24 (dd, J=8.0, 1.2 HZ, 1H), 7.97 (s, 1H) 7.33 (m, 2H), 7.24 (m, 1H). LC/MS: Rt 3.5 mins.; m/e 328 (M+H), 326.1(M−H).

Example 14

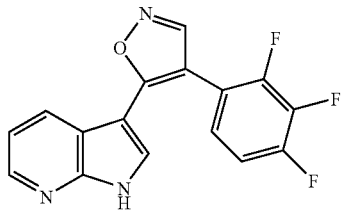

3-[4-(2,3,4-Trifluoro-phenyl)-isoxazol-5-yl]-1H-pyrrolo [2,3-b]pyridine (40)

$^1$H NMR (500 MHz, acetone-d6) δ: 8.63 (d, J=1.0 Hz, 1H) 8.36 (m, 1H), 8.10 (dd, J=8.0, 1.4 Hz, 1H) 7.83 (s, 1H) 7.40 (m, 1H), 7.29 (m, 1H) 7.20 (m, 1H). LC/MS: Rt 3.4 mins.; m/e 316 (M+H), 314.1 (M−H).

Example 15

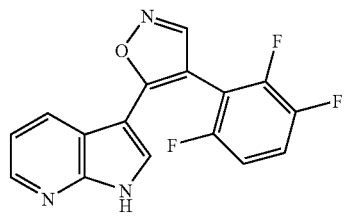

3-[4-(2,3,6-Trifluoro-phenyl)-isoxazol-5-yl]-1H-pyrrolo[2,3-b]pyridine (41)

$^1$H NMR (500 MHz, DMSO-d6) δ: 12.45 (s, 1H), 8.87 (s, 1H), 8.35 (dd, 1H), 8.03 (dd, 1H), 7.71 (d, 1H), 7.65 (ddd, 1H), 7.32 (dddd, 1H), 7.21 (dd, 1H). LC/MS: Rt 3.38 mins.; m/e 316 (M+H), 314.1 (M−H).

Example 16

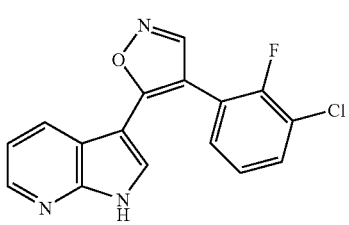

3-[4-(3-Chloro-2-fluoro-phenyl)-isoxazol-5-yl]-1H-pyrrolo[2,3-b]pyridine (42)

$^1$H NMR (500 MHz, DMSO-d6) δ: 12.38 (s, 1H), 8.85 (s, 1H), 8.33 (d, 1H), 7.88 (d, 1H), 7.73 (d, 1H), 7.66 (t, 1H), 7.51 (t, 1H), 7.30 (t, 1H), 7.16 (dd, 1H). LC/MS: Rt 3.37 mins.; m/e 314 (M+H), 312 (M−H).

Example 17

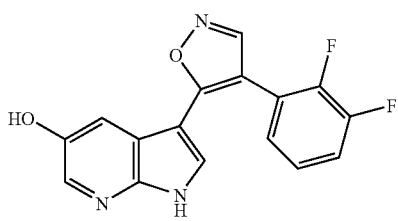

3-[4-(2,3-Difluoro-phenyl)-isoxazol-5-yl]-1H-pyrrolo[2,3-b]pyridin-5-ol (43)

The 5-hydroxy derivative was obtained by the Friedel-Craft reaction of aluminum chloride, 2,3-difluorophenylacetyl chloride and 5-methoxy-7-azaindole at room temperature. The remaining procedures were carried out as described in Examples 2-5 to yield the title product.

$^1$H NMR (500 MHz, DMSO-d6) δ: 12.11 (s, 1H), 9.40 (br, 1H), 8.81 (s, 1H), 7.94 (d, 1H), 7.60 (d, 1H), 7.49 (m, 1H), 7.30 (m, 3H). LC/MS: Rt 2.98 mins.; m/e 314 (M+H), 312.1 (M−H).

Example 18

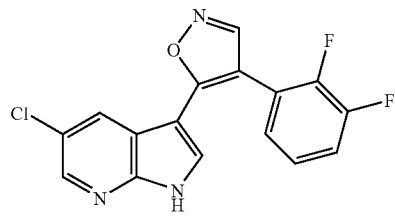

3-[4-(2,3-Difluoro-phenyl)-isoxazol-5-yl]-5-chloro-1H-pyrrolo[2,3-b]pyridine(44)

$^1$H NMR (500 MHz, DMSO-d6) δ: 12.67 (1H, s), 8.88 (1H, s), 8.35 (1H, d), 7.89 (1H, s), 7.79 (1H, d), 7.54 (1H, m), 7.37-7.28 (m, 2H). LC/MS: Rt 4.00 mins.; m/e 331.9 (M+H), 330 (M−H).

Example 19

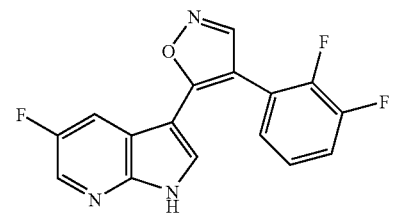

3-[4-(2,3-Difluoro-phenyl)-isoxazol-5-yl]-5-fluoro-1H-pyrrolo[2,3-b]pyridine (45)

$^1$H NMR (500 MHz, DMSO-d6) δ: 12.59 (1H, s); 8.87 (1H, s); 8.34 (1H, s); 7.87, (1H, d); 7.61-7.59 (1H, m); 7.54-7.45 (1H, m); 7.39-7.1, (2H, m); 2.43 (3H, s). LC/MS: Rt 3.69 mins.; m/e 316.2 (M+H), 314.1 (M−H).

Example 20

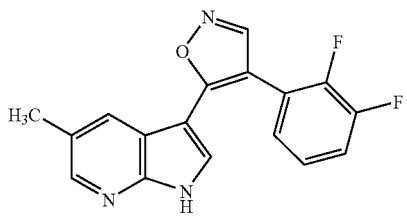

3-[4-(2,3-Difluoro-phenyl)-isoxazol-5-yl]-5-methyl-1H-pyrrolo[2,3-b]pyridine (46)

¹H NMR (500 MHz, DMSO-d6) δ: 12.24 (1H, bs), 8.83 (1H, s), 8.184-8.180 (1H, d), 7.68-7.67 (2H, m), 7.52-7.51 (1H, cm), 7.35-7.29 (2H, cm), 2.38 (3H, s). LC/MS: Rt 3.6 mins.; m/e 312.0 (M+H), 310.1 (M–H).

Example 21

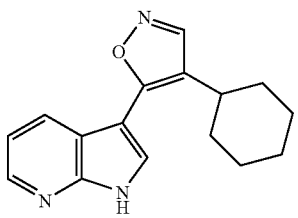

3-(4-Cyclohexyl-isoxazol-5-yl)-1H-pyrrolo[2,3-b]pyridine (47)

¹H NMR (500 MHz, DMSO-d6) δ: 12.38 (s, 1H), 8.59 (s, 1H), 8.36 (dd, 1H), 8.28 (dd, 1H), 7.94 (d, 1H), 7.24 (dd, 1H), 2.81 (m, 1H), 1.90-1.72 (complex, 5H), 1.50-1.24 (complex, 5H). LC/MS: Rt 3.49 mins.; m/e 268.2 (M+H), 266.25 (M–H).

Example 22

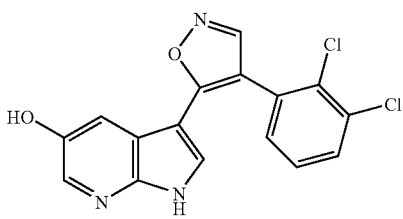

3-[4-(2,3-Dichloro-phenyl)-isoxazol-5-yl]-1H-pyrrolo[2,3-b]pyridin-5-ol (48)

¹H NMR (500 MHz, DMSO-d6) δ: 12.01 (s, 1H), 9.41 (s, 1H), 8.75 (s, 1H), 7.94 (d, J=2.5 Hz, 1H), 7.75 (dd, J=1.5, 7.5 Hz, 1H), 7.49 (dd, J=1.5, 7.5 Hz, 1H), 7.45 (dd, J=8.0, 7.5 Hz, 1H), 7.39 (d, J=2.5 Hz, 1H), 7.30 (s, 1H). LC/MS: Rt 3.3 mins.; 345.9 (M+H), 344 (M–H).

Example 23

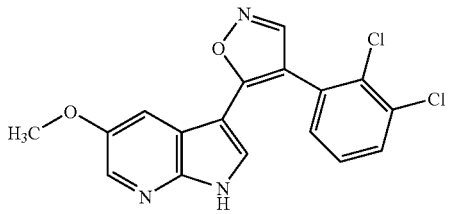

3-[4-(2,3-Dichloro-phenyl)-isoxazol-5-yl]-5-methoxy-1H-pyrrolo[2,3-b]pyridine (49)

¹H NMR (500 MHz, DMSO-d6) δ: 12.24 (s, 1H), 8.80 (s, 1H), 8.05 (d, J=2.5 Hz, 1H), 7.75 (dd, J=1.5, 8.0 Hz, 1H), 7.56 (s, 1H), 7.48 (dd, J=1.5, 7.5 Hz, 1H), 7.44 (dd, J=8.0, 7.5 Hz, 1H), 7.17 (d, J=2.5 Hz, 1H), 3.69 (s, 3H). LC/MS: Rt 3.9 mins.; m/e 359.9 (M+H), 358 (M–H).

Preparation of 3-(4-Pyridin-2-yl-isoxazol-5-yl)-1H-pyrrolo[2,3-b]pyridine, Example 24 (50)

Example 24

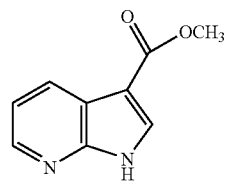

Step A: 1H-Pyrrolo[2,3-b]pyridine-3-carboxylic Acid methyl ester 2,2,2-Trichloro-1-(1H-pyrrolo[2,3-b]pyridin-3-yl)-ethanone was prepared using the procedures described in Method G. To a solution of this trichloro ketone (350 mg, 1.33 mmol) in MeOH (10 mL) was added triethylamine (2 mL) at RT. The resulting solution was stirred at RT for 2 h. The solvent was evaporated under vacuum, the residue was washed with water, and the crude product was dried on the pump for direct use. (200 mg, 1.13 mmol, 85%). MS (ES+): m/e=177.1 (M+H); LC: 2.2 min.

Example 25

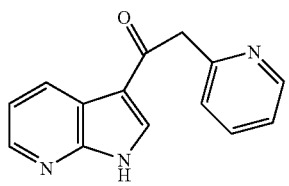

Step B: 2-Pyridin-2-yl-1-(1H-pyrrolo[2,3-b]pyridin-3-yl)-ethanone

To a solution of 1H-pyrrolo[2,3-b]pyridine-3-carboxylic acid methyl ester (200 mg, 1.13 mmol) and 2-pyridinyl-acetic acid hydrochloride (440 mg, 2.53 mmol) in anhydrous THF (10 mL) was added LiHMDS (1.0 M in THF, 10 mL, 10.0 mmol) at −78° C. The solution was stirred at −78° C. for 30 min and was allowed to warm up to RT. After stirring at RT for another 30 min, the reaction mixture was heated under reflux for 14 h. The solvent was then evaporated, the residue was taken up to ethyl acetate (50 mL), and washed with aq. NaHCO3. The organic layer was dried over MgSO4, filtered, and evaporated. The residue was used directly for the next reaction.

Example 26

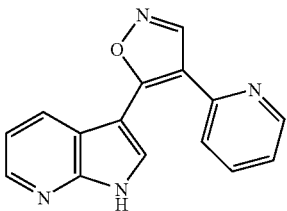

3-(4-Pyridin-2-yl-isoxazol-5-yl)-1H-pyrrolo[2,3-b]pyridine (50)

The residue obtained above was converted to 3-(4-pyridin-2-yl-isoxazol-5-yl)-1H-pyrrolo[2,3-b]pyridine (31 mg, 0.12 mmol) using the isoxazole formation procedures described.
$^1$H NMR (500 MHz, DMSO-d6) δ: 12.49 (s, 1H), 9.15 (s, 1H), 8.87 (d, 1H), 8.76 (d, 1H), 8.38 (dd, 1H), 8.25 (dd, 1H), 7.93 (dt, 1H), 7.80 (d, 1H), 7.41 (ddd, 1H), 7.26 (dd, 1H)

Example 27

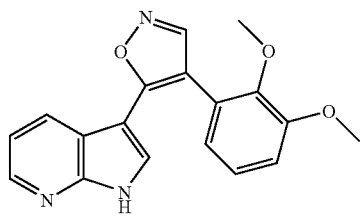

3-[4-(2,3-Dimethoxy-phenyl)-isoxazol-5-yl]-1H-pyrrolo[2,3-b]pyridine (51) was prepared by the procedures described for Example 24.
$^1$H NMR (500 MHz, DMSO-d6) δ: 12.22 (s, 1H), 8.66 (s, 1H), 8.30 (dd, 1H), 7.93 (dd, 1H), 7.55 (d, 1H), 7.13 (m, 3H), 6.90 (dd, 1H), 3.87 (s, 3H), 3.58 (s, 3H). LC/MS: Rt 3.14 mins.; m/e 322.2 (M+H), 320.2 (M−H)

Example 28

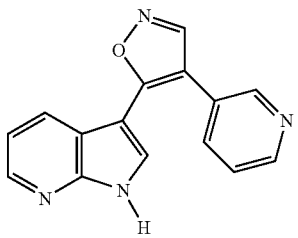

3-(4-Pyridin-3-yl-isoxazol-5-yl)-1H-pyrrolo[2,3-b]pyridine (52) was prepared by the procedures described for Example 24.
$^1$H NMR (500 MHz, DMSO-d6) δ: 12.40 (s, 1H), 8.97 (s, 1H), 8.71 (s, 1H), 8.57 (dd, 1H), 8.33 (dd, 1H), 7.90 (dt, 1H), 7.88 (s, 1H), 7.77 (dd, 1H), 7.45 (dd, 1H), 7.14 (dd, 1H). LC/MS: Rt 1.55 mins.; m/e 263.2 (M+H), 261.2 (M−H).

Preparation of (3-{3-[4-(2,3-Difluoro-phenyl)-isoxazol-5-yl]-1H-pyrrolo[2,3-b]pyridin-5-yl}-prop-2-ynyl)-dimethyl-amine, Example 30 (53)

Step A:

Example 29

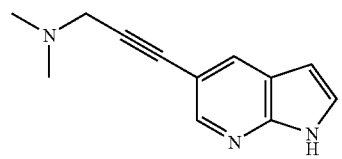

Dimethyl-[3-(1H-pyrrolo[2,3-b]pyridin-5-yl)-prop-2-ynyl]-amine

To a screw top tube, 8.1 mg (0.0425 mmoles) of CuI, 18 mg (0.0256 mmoles) of PdCl$_2$(PPh$_3$)$_2$, and 207 mg (0.8483 mmoles) of 5-Bromo-1H-pyrrolo[2,3-b]pyridine were added. The dry solids were diluted with 1 ml of dry DMF and a stream of N$_2$ was bubbled through the solution for 10 minutes and then 182.6 ul (1.7 mmoles) of Dimethyl-prop-2-ynyl-amine was added and the reaction was stirred in a sealed tube overnight at room temperature. The reaction was diluted with 10 ml of DCM and washed with saturated ammonium chloride solution. The organic layer was separated and dried with MgSO4, filtered, and concentrated to dryness yielding a crude material of 189 mg. MS showed a M+ ion of 200.05 which confirmed the structure above. The crude material was taken to the next step.

Step B:

Example 30

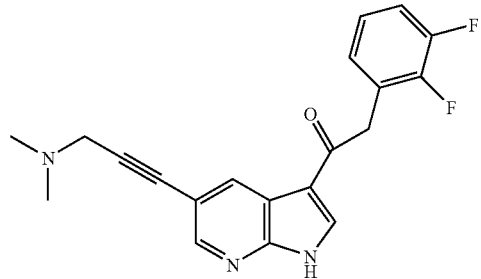

2-(2,3-Difluoro-phenyl)-1-[5-(3-dimethylamino-prop-1-ynyl)-1H-pyrrolo[2,3-b]pyridin-3-yl]-ethanone 189 mg of crude Dimethyl-[3-(1H-pyrrolo[2,3-b]pyridin-5-yl)-prop-2-ynyl]-amine was stirred in 5 ml of DCM with AlCl$_3$ (4 equivalents) for 30 minutes. Two equivalents of (2,3-Difluoro-phenyl)-acetyl chloride were added and the reaction was stirred in a sealed tube overnight. The LC/MS showed the reaction to be complete and was worked-up under standard conditions. Normal phase column chromatography yielded 101 mg of 2-(2,3-Difluoro-phenyl)-1-[5-(3-dimethylamino-prop-1-ynyl)-1H-pyrrolo[2,3-b]pyridin-3-yl]-ethanone with a yield over two steps of 33%. LC/MS retention time of 1.83 minutes. M+ 354.17, M− 352.1

Step C:

Example 31

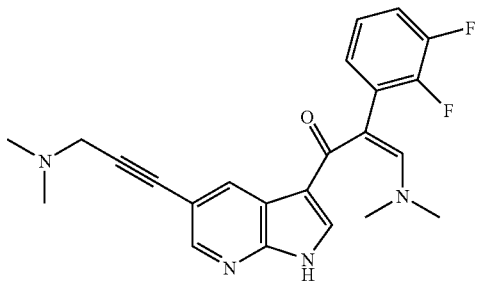

2-(2,3-Difluoro-phenyl)-3-dimethylamino-1-[5-(3-dimethylamino-prop-1-ynyl)-1H-pyrrolo[2,3-b]pyridin-3-yl]-propenone Procedure as described previously. Crude material was taken to the next step. LC/MS retention time 1.99 minutes. M⁺ 409.18.

Step D:

Example 32

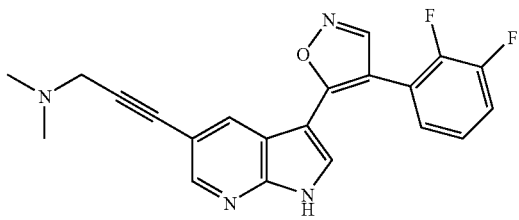

(3-{3-[4-(2,3-Difluoro-phenyl)-isoxazol-5-yl]-1H-pyrrolo[2,3-b]pyridin-5-yl}-prop-2-ynyl)-dimethyl-amine (53)

Procedure as described previously. Purification by reverse phase column chromatography yielding 20 mg (18.7% yield over two steps).

$^1$H-NMR (DMSO-d6, 500 MHz) δ: 12.7 (s, 1H), 10.2 (s, 1H), 8.9 (s, 1H), 8.5 (s, 1H), 8.1 (m, 1H), 7.9 (m, 1H), 7.55 (m, 1H), 7.35 (m, 2H), 4.4 (s, 2H) ppm; MS (FIA) 379.35 (M+H); HPLC 2.16 min. LC/MS: Rt 2.16 mins.; m/e 379.35 (M+H), 377.3 (M−H).

Preparation of {3-[4-(2,3-Difluoro-phenyl)-isoxazol-5-yl]-1H-pyrrolo[2,3-b]pyridin-5-ylmethyl}-dimethyl-amine, Example 35 (54)

Example 33

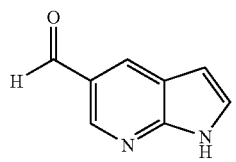

Step A: 1H-Pyrrolo[2,3-b]pyridine-5-carbaldehyde

To 5-Bromo-1H-pyrrolo[2,3-b]pyridine (1.5 g, 7.61 mmol) in THF (200 mL) at −78 C, under nitrogen, was added n-butyl lithium (2.5M in hexanes, 15.2 mmol, 6.1 mL), and the reaction solution was stirred with an overhead motor. After 1 hr, the resulting orange gel was quenched with methylormate (4.56 g, 76 mmol) and the reaction solution was allowed to slowly warm to 23C. The solution was poured into water and extracted with ethyl acetate, dried (Na$_2$SO$_4$) to give 1H-Pyrrolo[2,3-b]pyridine-5-carbaldehyde (0.68 g, 61% yield) as a yellow solid.

$^1$H-NMR (DMSO-d6, 500 MHz) δ: 12.17 (1H, bs), 10.09 (1H, s), 8.77-8.76 (1H, d), 8.49-8.48 (1H, d), 7.65-7.64 (1H, d), 6.68-6.67 (1H, d). LC/MS: Rt 2.18 mins.; m/e 146.9 (M+H), 144.9 (M−H).

Example 34

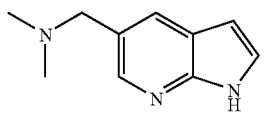

Step B: Dimethyl-(1H-pyrrolo[2,3-b]pyridin-5-ylmethyl)-amine

To 1H-Pyrrolo[2,3-b]pyridine-5-carbaldehyde (114 mg, 0.78 mmol), in methanol (10 ml) was added dimethylamine hydrochloride (127 mg, 1.56 mmol, NaOH (31.2 mg, 0.78 mmol), sodium cyanoborohydride (49 mg, 0.78 mmol) and the solution was stirred under nitrogen for 12 hr. Poured into water (50 mL), extracted with ethyl acetate, dried (Na$_2$SO$_4$) to afforded Dimethyl-(1H-pyrrolo[2,3-b]pyridin-5-ylmethyl)-amine (44 mg, 33% yield) used without purification. MS: m/e 176.1 (M+H).

Example 35

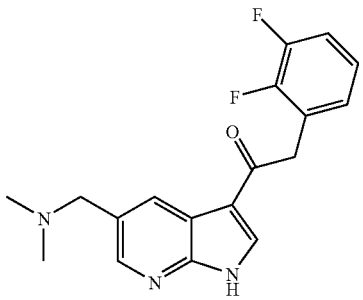

Step C: 2-(2,3-Difluoro-phenyl)-1-(5-dimethylaminomethyl-1H-pyrrolo[2,3-b]pyridin-3-yl)-ethanone Dimethyl- (1H-pyrrolo[2,3-b]pyridin-5-ylmethyl)-amine (44 mg, 0.25 mmol) and AlCl$_3$ (167 mg, 1.25 mmol) in methylene chloride (10 mL) were stirred for 0.5 hr. To this mixture was added 2,3-Difluoro-phenyl)-acetyl chloride (96 mg, 0.50 mmol) and the reaction solution was stirred for 4 hr. Quenched with methanol (20 mL) and water (20 mL) and extracted with ethyl acetate, dried (Na$_2$SO$_4$). Flash chromatography (methylene chloride/methanol) afforded 2-(2,3-Difluoro-phenyl)-1-(5-dimethyl aminomethyl-1H-pyrrolo[2,3-b]pyridin-3-yl)-ethanone (20 mg, 24% yield). LCMS tr=1.64 min, m/z MH+ 330.1, M−328.2

Example 36

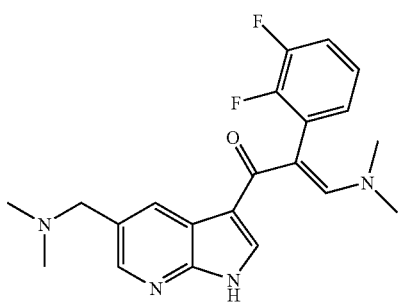

Step D: 2-(2,3-Difluoro-phenyl)-3-dimethylamino-1-(5-dimethylaminomethyl-1H-pyrrolo[2,3-b]pyridin-3-yl) propenone To 2-(2,3-Difluoro-phenyl)-1-(5-dimethylaminomethyl-1H-pyrrolo [2,3-b]pyridin-3-yl)-ethanone (20 mg, 0.061 mmol) in THF (5 mL) was added Bredereck's reagent (53 mg, 0.31 mmol) and the reaction was heated to 80 C in a sealed tube overnight. Concentration under reduced vacuum gave title compound a red oil used as obtained. LC/MS: Rt 1.60 mins.; m/e 385.2(M+H), 358.2(−27), 356.3(M−H)

Example 37

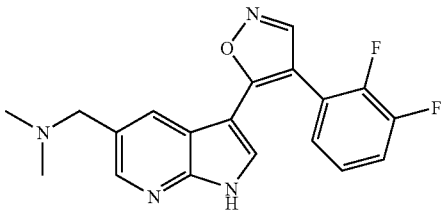

Step E: {3-[4-(2,3-Difluoro-phenyl)-isoxazol-5-yl]-1H-pyrrolo[2,3-b]pyridin-5-ylmethyl}-dimethyl-amine (54)

To 2-(2,3-Difluoro-phenyl)-3-dimethylamino-1-(5-dimethylaminomethyl-1H-pyrrolo[2,3-b]pyridin-3-yl) propenone (23 mg, 0.61 mmol) in ethanol (5 mL) was added sodium acetate (30 mg, 0.37 mmol) and hydroxylamine Hydrochloride (21 mg, 0.30 mmol) and the mixture was heated to 80 C in a sealed tube. After 14 hr, solution was cooled, diluted with ethyl acetate, washed with brine, dried (Na$_2$SO$_4$). Concentrated gave an amber oil. Preparative reverse phase chromatography gave 4.5 mg (21% yield).

$^1$H NMR (500 MHz, DMSO-d6) δ: 12.60 (1H, bs), 9.65 (1H, vbs (TFA)), 8.80 (1H, s), 8.422-8.419 (1H, d), 8.382-8.361 (1H, d), 7.778-7.771 (1H, d), 7.54-7.49 (1H, cm), 7.38-7.28 (2H, cm), 4.46-4.44 (2H, d), 2.76-2.71 (6H, d). LC/MS: Rt 1.98 mins.; m/e 355.2 (M+H), 353.31 (M−H)

Preparation of {3-[4-(2,3-Difluoro-phenyl)-isoxazol-5-yl]-1H-pyrrolo[2,3-b]pyridin-5-yl}-methanol, Example 41 (55)

Example 38

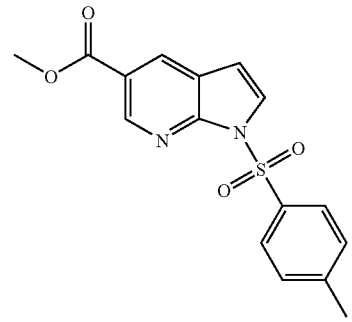

Step A: 1-(Toluene-4-sulfonyl)-1H-pyrrolo[2,3-b] pyridine-5-carboxylic Acid methyl ester Under N$_2$ purge, 5-Bromo-1-(toluene-4-sulfonyl)-1H-pyrrolo[2,3-b]pyridine (1.0 g, 2.8 mmol), Et$_3$N (0.75 mL, 5.4 mmol), Pd(OAc)$_2$ (64 mg, 0.28 mmol), Ph$_3$P (0.45 g, 1.7 mmol) and MeOH (5.0 mL, 120 mmol) were loaded in 20 mL DMF. The vessel was purged with CO 5 minutes and fixed with a condenser tube with CO balloon. The reaction was heated to 100 C for 6 hours and monitored by TLC (r$_f$ 5-Bromo-1-(toluene-4-sulfonyl)-1H-pyrrolo[2,3-b]pyridine=0.72, r$_f$ 1-(Toluene-4-sulfonyl)-1H-pyrrolo[2,3-b]pyridine-5-carboxylic acid methyl ester=0.43, CH$_2$Cl$_2$). After 6 hours, the reaction was removed from heat, diluted to 100 mL with water and extracted with EtOAC (100 mL). The phases were separated and organic was washed with additional water (2×100 mL) and brine (1×100 mL), dried over Na$_2$SO$_4$, filtered, and dried in vacuo. The resulting yellow powder was purified over a short plug of silica gel with CH$_2$Cl$_2$ until all material was recovered. Yield 0.94 g, white powder.

$^1$H NMR (500 MHz, CDCl$_3$) δ: 9.1 (s, 1H), 8.5 (s, 1H), 8.1 (d, 2H), 7.8 (d, 1H), 7.3 (d, 2H), 6.8 (d, 1H), 3.9 (s, 3H), 2.4 (s, 3H).

Example 39

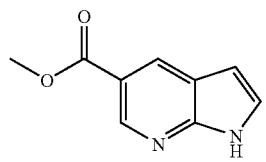

Step B: 1H-Pyrrolo[2,3-b]pyridine-5-carboxylic Acid methyl ester

A suspension of 1-(Toluene-4-sulfonyl)-1H-pyrrolo[2,3-b]pyridine-5-carboxylic acid methyl ester (5.4 g, 16 mmol) in MeOH (100 mL) with NaOMe in MeOH (20 mL, 25% wt., excess) was heated at 65° C. for 1 hour. The resulting material was concentrated from MeOH, diluted with H$_2$O (100 mL), and pH adjusted to 6 with 1N HCl. The aqueous solution was partitioned with EtOAc (100 mL) and the organic extraction was dried over Na$_2$SO$_4$ and dried in vacuo. The residue was purified with flash chromatography over silica gel in an elution from 99:1 CH$_2$Cl$_2$:MeOH to 92:8 CH$_2$Cl$_2$:MeOH. Yield 1.8 g, beige powder.

$^1$H NMR (500 MHz, CDCl$_3$) δ: 9.7 (bs, 1H), 9.0 (s, 1H), 8.7 (s, 1H). 7.4 (t, 1H), 6.6 (t, 1H). 4.0 (s, 3H).

Example 40

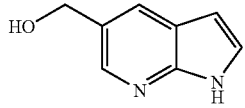

Step C: (1H-Pyrrolo[2,3-b]pyridin-5-yl)-methanol

To 1H-Pyrrolo[2,3-b]pyridine-5-carboxylic acid methyl ester (75 mg, 0.394 mmol) in THF at 0 C was added lithium aluminum hydride (45 mg, 1.18 mmol) and the reaction mixture was slowly allowed to warm to ambient temperature. The reaction was refluxed for 12 hr, allowed to cool and quenched with water. Extraction with ethyl acetate, washed with brine, dried (Na$_2$SO$_4$) to afford (1H-Pyrrolo[2,3-b]pyridin-5-yl)-methanol (57 mg, 98% yield).

$^1$H NMR (500 MHz, DMSO-d6) δ: 11.50 (1H, bs), 8.166-8.163 (1H, d), 7.862-7.860 (1H, d), 7.43-7.42 (1H, d), 6.41-6.40 (1H, d). 5.10-5.08 (1H, t), 4.58-4.57 (2H, d). FIA MS, m/z MH+ 149.1.

Example 41

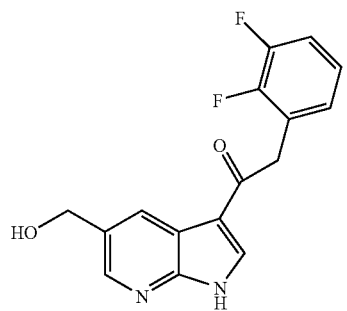

Step D: 2-(2,3-Difluoro-phenyl)-1-(5-hydroxymethyl-1H-pyrrolo[2,3-b]pyridin-3-yl)-ethanone (1H-Pyrrolo[2,3-b]pyridin-5-yl)-methanol (57 mg, 0.39 mmol) and AlCl$_3$ (160 mg, 1.15 mmol) in methylene chloride (5 mL) were stirred for 0.5 hr. To this mixture was added 2,3-Difluoro-phenyl)-acetyl chloride (219 mg, 1.15 mmol) and the reaction solution was stirred for 14 hr. Quenched with methanol (10 mL) and water (10 mL) and extracted with ethyl acetate, dried (Na$_2$SO$_4$). This afforded (2,3-Difluoro-phenyl)-acetic acid 3-[(2,3-difluoro-phenyl)-acetyl]-1H-pyrrolo[2,3-b]pyridin-5-yl(LCMS tr=4.04 min, m/z MH+ 457.0 M−455.1) that was taken up in methanol (5 mL) and treated with 1N NaOH (1 mL) and stirred for 3 hrs. Diluted ethyl acetate and pH adjusted to 7 with 10% NaHSO$_4$. Concentration gave title compound as an off-white solid (93 mg, 80% yield).

$^1$H NMR (500 MHz, DMSO-d6) δ: 12.51 (1H, bs), 8.63 (1H, s), 8.41-8.40 (1H, d), 8.29-8.28 (1H, d), 7.34530 (1H, m), 7.20-7.15 (2H, cm), 5.23-5.20 (1H, q) 4.60-4.53 (2H, d), 4.39-4.38 (2H, s). LC/MS: Rt 2.55 mins.; m/e 303.1 (M+H), 301.2 (M−H).

Example 42

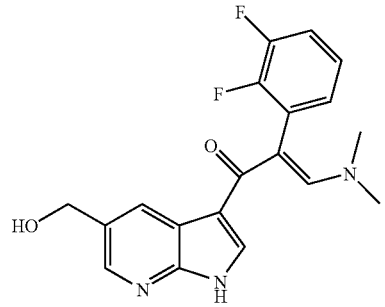

Step E: 2-(2,3-Difluoro-phenyl)-3-dimethylamino-1-(5-hydroxymethyl-1H-pyrrolo[2,3-b]pyridin-3-yl)-propenone To 2-(2,3-Difluoro-phenyl)-1-(5-hydroxymethyl-1H-pyrrolo[2,3-b]pyridin-3-yl)-ethanone (93 mg, 0.31 mmol) in THF (15 mL) was added Bredereck's reagent (500 µL, 2.4 mmol) and the reaction was heated to 80 C overnight. Concentration under reduced vacuum gave title compound a red oil, used as obtained. LC/MS: Rt 2.72 mins.; m/e 359.1 (M+H), 356.2 (M−H).

Example 43

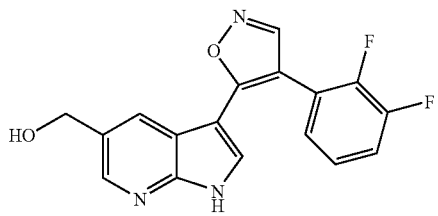

Step F: {3-[4-(2,3-Difluoro-phenyl)-isoxazol-5-yl]-1H-pyrrolo[2,3-b]pyridin-5-yl}-methanol (55)

To 2-(2,3-Difluoro-phenyl)-3-dimethylamino-1-(5-hydroxymethyl-1H-pyrrolo[2,3-b]pyridin-3-yl)-propenone (110 mg, 0.31 mmol) in tetrahydrfuran (20 mL) was added sodium hydrogen carbonate (39 mg, 0.46 mmol) and hydroxylamine Hydrochloride (32 mg, 0.46 mmol) and the mixture was heated to 80 C. After 5 hr p-toluenesulfonic acid (catalytic amount) was added and the reaction mixture was heated for an additional 14 hr. The solution was cooled, diluted with ethyl acetate, washed with brine, dried (Na$_2$SO$_4$). Concentration gave an amber oil. Preparative reverse phase chromatography afforded {3-[4-(2-Fluoro-phenyl)-isoxazol-5-yl]-1H-pyrrolo[2,3-b]pyridin-5-yl}-methanol (3.0 mg, 3% yield).

¹H NMR (500 MHz, DMSO-d6) δ: 12.30 (1H, bs), 8.40 (1H, s), 8.295-8.292 (1H, d), 7.95 (1H, s), 7.685-7.680 (1H, d), 7.54-7.49 (1H, cm), 7.38-7.16 (2H, cm), 7.06 (1H, t), 4.57 (2H, s). LC/MS: Rt 2.81 mins.; m/e 328.1 (M+H), 326.2 (M–H).

Preparation of {3-[4-(2,3-Difluoro-phenyl)-isoxazol-5-yl]-1H-pyrrolo[2,3-b]pyridin-4-yl}-dimethyl-amine, Example 44 (56)

Example 44

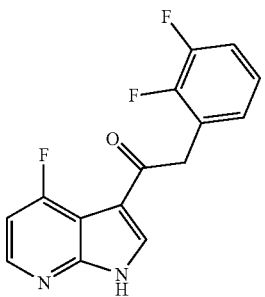

2-(2,3-Difluoro-phenyl)-1-(4-fluoro-1H-pyrrolo[2,3-b]pyridin-3-yl)-ethanone

4-Fluoro-1H-pyrrolo[2,3-b]pyridine (230 mg, 1.69 mmol) (Org. Lett. 2003, 5(26), 5023) and AlCl₃ (678, 5.1 mmol) in methylene chloride (30 mL) were stirred for 0.5 hr. To this mixture was added 2,3-Difluoro-phenyl)-acetyl chloride (644 mg, 3.38 mmol) and the reaction solution was stirred for 14 hr. Quenched with methanol (50 mL) and water (50 mL) and extracted with ethyl acetate, dried (Na₂SO₄). Flash chromatography (methylene chloride/methanol) afforded 2-(2,3-Difluoro-phenyl)-1-(4-fluoro-1H-pyrrolo[2,3-b]pyridin-3-yl)-ethanone (448 mg, 91% yield). LC/MS: Rt 3.16 mins.; m/e 287.1 (M+H), 285.2 (M–H).

Example 45

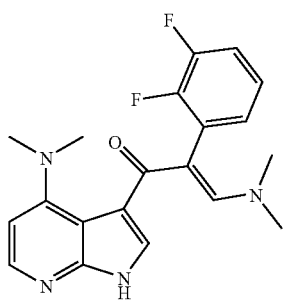

2-(2,3-Difluoro-phenyl)-3-dimethylamino-1-(4-dimethylamino-1H-pyrrolo[2,3-b]pyridin-3-yl)-propenone To 2-(2,3-Difluoro-phenyl)-1-(4-fluoro-1H-pyrrolo[2,3-b]pyridin-3-yl)-ethanone (428 mg, 1.15 mmol) in THF (50 mL) was added Bredereck's reagent (1.6 mL, 7.7 mmol) and the reaction was heated to 80 C overnight. Concentration under reduced vacuum a red oil, used as obtained as a mixture (1:1) of 2-(2,3-Difluoro-phenyl)-3-dimethylamino-1-(4-dimethylamino-1H-pyrrolo[2,3-b]pyridin-3-yl)-propenone and 2-(2,3-Difluoro-phenyl)-3-dimethylamino-1-(4-fluoro-1H-pyrrolo[2,3-b]pyridin-3-yl)-propenone LC/MS: Rt 1.75 mins.; m/e 371.0 (M+H), 342.2 (M–27) and Rt 2.58 mins.; m/e 346.0 (M+H), 344.0 (M–H).

Example 46

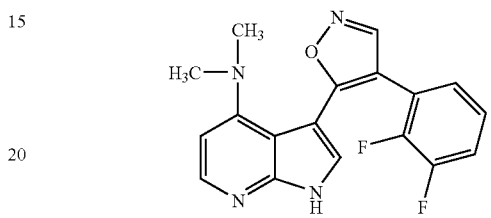

{3-[4-(2,3-Difluoro-phenyl)-isoxazol-5-yl]-1H-pyrrolo[2,3-b]pyridin-4-yl}-dimethyl-amine (56)

To a mixture (1:1) of 2-(2,3-Difluoro-phenyl)-3-dimethylamino-1-(4-dimethyl-amino-1H-pyrrolo[2,3-b]pyridin-3-yl)-propenone and 2-(2,3-Difluoro-phenyl)-3-dimethylamino-1-(4-fluoro-1H-pyrrolo[2,3-b]pyridin-3-yl)-propenone (110 mg, 0.31 mmol) in tetrahydrfuran (20 mL) was added sodium hydrogen carbonate (39 mg, 0.46 mmol) and hydroxylamine Hydrochloride (32 mg, 0.46 mmol) and the mixture was heated to 80C. After 5 hr p-toluenesulfonic acid (catalytic amount) was added and the reaction mixture was heated for an additional 4 hr. The solution was cooled, diluted with ethyl acetate, washed with brine, dried (Na₂SO₄). Concentration gave an amber oil. Preparative reverse phase chromatography afforded {3-[4-(2,3-Difluoro-phenyl)-isoxazol-5-yl]-1H-pyrrolo[2,3-b]pyridin-4-yl}-dimethyl-amine (3.0 mg, 3% yield). HNMR (dmso): 13.3-12.9 (1H, vbs), 9.02 (1H, s), 8.13-8.12 (1H, d), 7.75 (1H, s), 7.44-7.39 (1H, m), 7.23-7.13 (2H, cm), 6.71-6.70 (1H, d), 2.81 (6H, s). LC/MS Rt 2.1 mins.; m/e 341.0 (M+H), 339.1 (M–H General Method B:

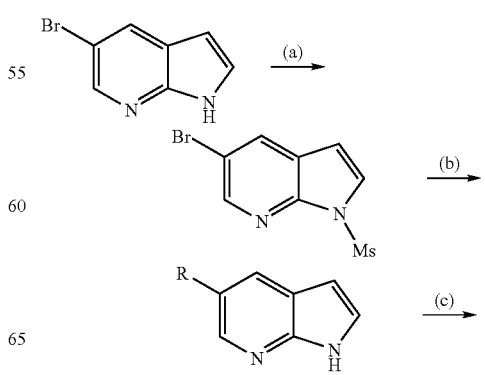

-continued

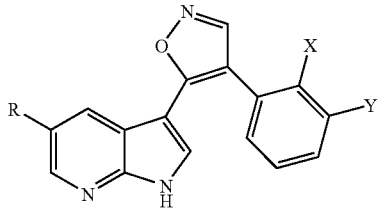

Reagents and Conditions: (a) (i) NaH, THF, RT, (ii) methanesulfonyl chloride; (b) R—B(OR)$_2$, 2M Na$_2$CO$_3$, PdCl$_2$(dppf), DMF; (c) (i) substituted-phenylacetyl chloride, AlCl$_3$, CH$_2$Cl$_2$, (ii) Bredereck's Reagent, THF, reflux, (iii) H$_2$NOH HCl, NaOAc, THF, reflux.

Preparation of 3-[4-(2,3-Difluoro-phenyl)-isoxazol-5-yl]-5-pyridin-4-yl-1H-pyrrolo[2,3-b]pyridine, Example 47 (57)

Example 47

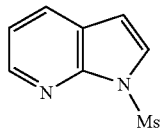

Step A: 5-Bromo-1-methanesulfonyl-1H-pyrrolo[2,3-b]pyridine

To a solution of 5-bromo-1H-pyrrolo[2,3-b]pyridine (600 mg, 3.06 mmol) in dry THF (30 mL) was added NaH (246 mg, 6.12 mmol) at room temperature. The suspension was stirred for 30 min before addition of methanesulfonyl chloride (540 mg, 4.80 mmol). The solution was stirred at room temperature for another 30 min and poured into water (50 mL). The aqueous solution was extracted with ethyl acetate (2×30 mL), the combined organic layers were dried over MgSO4 and filtered, the filtrate was evaporated under vacuum to afford white solid (780 mg, 93%). The crude product was used directly for the next reaction. LC/MS: Rt 3.26 mis.; (m/e=275.0, 276.9 (M+H, M+2+H).

Example 48

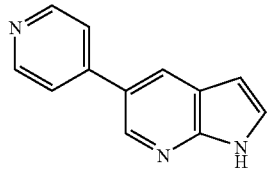

Step B: 5-Pyridin-4-yl-1H-pyrrolo[2,3-b]pyridine

To a solution of 5-bromo-1-methanesulfonyl-1H-pyrrolo[2,3-b]pyridine (140 mg, 0.51 mmol) and 4-pyridinyl boronic acid (125 mg, 1.02 mmol) in DMF (4 mL) was added aqueous Na2CO3 (2M, 1.3 mL, 2.6 mmol). To this suspension was then added PdCl2(dppf) (20 mg, 0.025 mmol) under N2 atmosphere. The flask was then covered with septa, heated at 80° C. for 9 h, and poured into water. The precipitate was collected by filtration, washed with water, and redissolved in MeOH (10 mL). To this Methanol solution was added 6N NaOH solution (2 mL) and the resulting basic reaction mixture was heated at 50° C. for 3 h. After evaporating the MeOH, the aqueous residue was acidified with 6N HCl to pH=2. The precipitate was filtered off and washed with 2N HCl. The acidic filtrate was then neutralized with saturated NaHCO3 solution. The crude product was collected by filtration, washed with water, and dried on the pump for direct use (60 mg, 0.31 mmol). LC/MS: Rt 1.96 mins.; m/e 196.1 (M+H).

Example 49

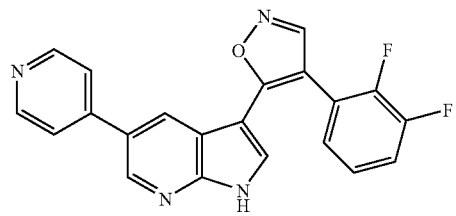

Step C: 3-[4-(2,3-Difluoro-phenyl)-isoxazol-5-yl]-5-pyridin-4-yl-1H-pyrrolo[2,3-b]pyridine (57)

5-Pyridin-4-yl-1H-pyrrolo[2,3-b]pyridine (60 mg, 0.31 mmol) was converted to 3-(4-(2,3-difluoro-phenyl)-isoxazol-5-yl)-5-pyridin-4-y-1H-pyrrolo[2,3-b]pyridine (60 mg, 0.16 mmol) by using Method A.

$^1$H NMR (500 MHz, DMSO-d6) δ: 12.65 (s, 1H), 8.90 (s, 1H), 8.78 (d, 1H), 8.64 (m, 2H), 8.03 (d, 1H), 7.94 (d, 1H), 7.61 (d, 2H), 7.53 (m, 1H), 7.39 (m, 1H), 7.33 (m, 1H), (free base). LC/MS: Rt 2.5 mins.; m/e 375 (M+H), 373 (M−H).

Example 50

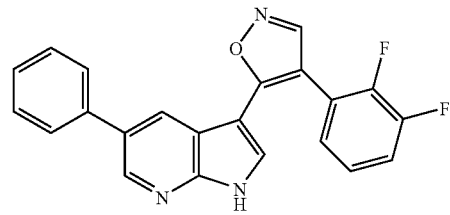

3-[4-(2,3-Difluoro-phenyl)-isoxazol-5-yl]-5-phenyl-1H-pyrrolo[2,3-b]pyridine (58)

$^1$H NMR (500 MHz, DMSO-d6) δ: 12.53 (s, 1H), 8.88 (s, 1H), 8.62 (d, 1H), 7.90 (d, 1H), 7.84 (d, 1H), 7.51 (m, 5H), 7.34 (m, 3H). LC/MS: Rt 4.2 mins.; m/e 374 (M+H), 372.1 (M−H).

Example 51

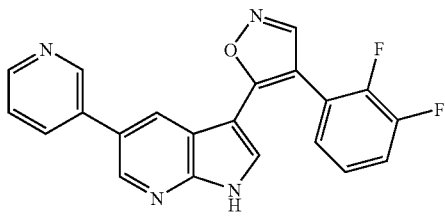

3-[4-(2,3-Difluoro-phenyl)-isoxazol-5-yl]-5-pyridin-3-yl-1H-pyrrolo[2,3-b]pyridine (59)

$^1$H NMR (500 MHz, DMSO-d6) δ: 12.58 (s, 1H), 8.89 (s, 1H), 8.75 (d, 1H), 8.67 (d, 1H), 8.58 (dd, 1H), 7.98 (m, 1H), 7.93 (m, 2H), 7.51 (m, 2H), 7.37 (dd, 1H), 7.31 (m, 1H), 1H. LC/MS: Rt 2.5 mins.; m/e 375 (M+H), 373 (M−H).

Example 52

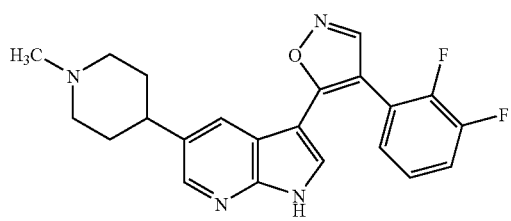

3-[4-(2,3-Difluoro-phenyl)-isoxazol-5-yl]-5-(1-methyl-piperidin-4-yl)-1H-pyrrolo[2,3-b]pyridine (60)

$^1$H NMR (500 MHz, DMSO-d6) δ: 12.40 (s, 1H), 9.55 (br, 1H), 8.87 (s, 1H), 8.26 (d, 1H), 7.76 (d, 1H), 7.72 (d, 1H), 7.51 (m, 1H), 7.32 (m, 2H), 3.53 (d, 2H), 3.09 (m, 2H), 2.92 (m, 1H), 2.84 (d, 3H), 2.03 (d, 2H), 1.84 (m, 2H). LC/MS: Rt 2.1 mins.; m/e 395 (M+H), 393 (M−H).

Example 53

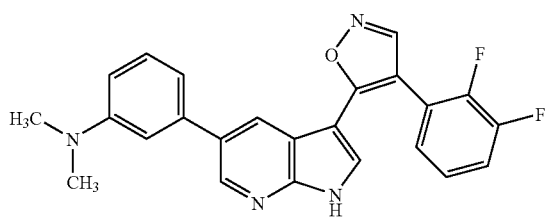

(3-{3-[4-(2,3-Difluoro-phenyl)-isoxazol-5-yl]-1H-pyrrolo[2,3-b]pyridin-5-yl}-phenyl)-dimethyl-amine (61)

$^1$H NMR (500 MHz, DMSO-d6) δ: 12.48 (s, 1H), 8.88 (s, 1H), 8.60 (d, 1H), 7.89 (d, 1H), 7.82 (d, 1H), 7.51 (m, 1H), 7.33 (m, 2H), 7.25 (t, 1H), 6.81 (s, 1H), 6.74 (m, 2H), 2.96 (s, 6H). LC/MS: Rt 3.4 mins.; m/e 417 (M+H), 415 (M−H).

Example 54

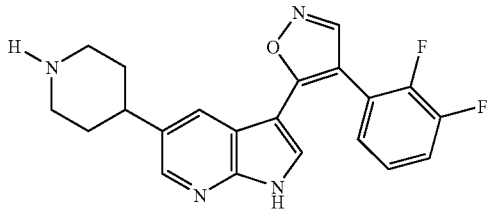

3-[4-(2,3-Difluoro-phenyl)-isoxazol-5-yl]-5-piperidin-4-yl-1H-pyrrolo[2,3-b]pyridine (62)

$^1$H NMR (500 MHz, DMSO-d6) δ: 12.40 (s, 1H), 8.86 (s, 1H), 8.66 (br, d, 1H), 8.34 (br, 1H), 8.25 (d, 1H), 7.75 (d, 1H), 7.74 (d, 1H), 7.52 (m, 1H), 7.33 (m, 2H), 3.40 (br, d, 2H), 3.00 (m, 3H), 1.93 (br, d, 2H), 1.78 (m, 2H). LC/MS: Rt 2.1 mins.; m/e 381 (M+H), 379 (M−H).

Example 55

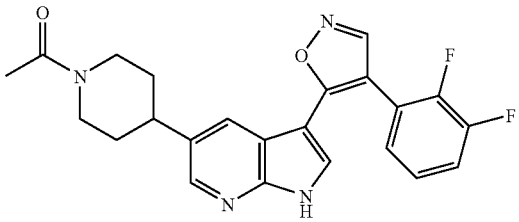

1-(4-{3-[4-(2,3-Difluoro-phenyl)-isoxazol-5-yl]-1H-pyrrolo[2,3-b]pyridin-5-yl}-piperidin-1-yl)-ethanone (63)

$^1$H NMR (500 MHz, DMSO-d6) δ: 12.35 (s, 1H), 8.85 (s, 1H), 8.24 (d, 1H), 7.84 (d, 1H), 7.48 (m, 1H), 7.40 (d, 1H), 7.32 (m, 2H), 4.51 (d, br, 1H), 3.90 (d, br, 1H), 3.11 (td, 1H), 2.85 (tt, 1H), 2.51 (td, 1H), 2.06 (s, 3H), 1.71 (t, br, 2H), 1.46-1.25 (m, 2H). LC/MS: Rt 3.0 mins.; m/e 423 (M+H), 421 (M−H).

Example 56

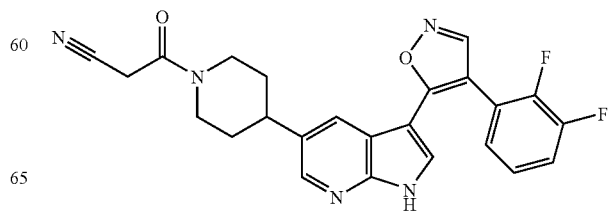

3-(4-{3-[4-(2,3-Difluoro-phenyl)-isoxazol-5-yl]-1H-pyrrolo[2,3-b]pyridin-5-yl}-piperidin-1-yl)-3-oxo-propionitrile (64)

¹H NMR (500 MHz, DMSO-d6) δ: 12.34 (s, 1H), 8.85 (s, 1H), 8.23 (d, 1H), 7.80 (d, 1H), 7.52 (d, 1H), 7.48 (m, 1H), 7.32 (m, 2H), 4.48 (d, br, 1H), 4.05 (s, 2H), 3.78 (d, br, 1H), 3.15 (td, 1H), 2.88 (tt, 1H), 2.69 (td, 1H), 1.75 (d, br, 2H), 1.56 (qd, 1H), 1.35 (qd, 1H). LC/MS: Rt 3.2 mins.; m/e 448 (M+H), 446 (M−H).

Example 57

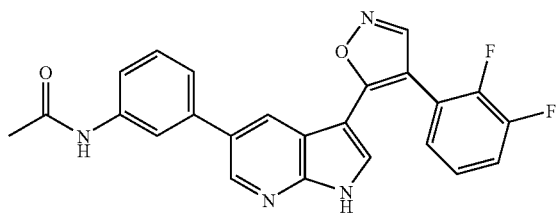

N-(3-{3-[4-(2,3-Difluoro-phenyl)-isoxazol-5-yl]-1H-pyrrolo[2,3-b]pyridin-5-yl}-phenyl)-acetamide (65)

¹H NMR (500 MHz, DMSO-d6) δ: 12.51 (s, 1H), 8.87 (s, 1H), 8.58 (d, 1H), 8.01 (d, 1H), 7.82 (d, overlap, 2H), 7.62 (d, 1H), 7.53 (m, 1H), 7.39 (m, 2H), 7.31 (m, 1H), 7.21 (d, 1H), 2.09 (s, 3H). LC/MS: Rt 3.5 mins; m/e 431 (M+H), 429 (M−H).

Example 58

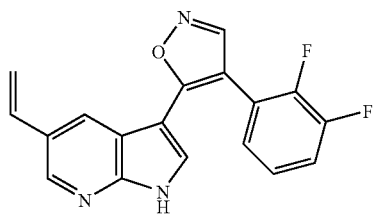

3-[4-(2,3-Difluoro-phenyl)-isoxazol-5-yl]-5-vinyl-1H-pyrrolo[2,3-b]pyridine (66)

¹H NMR (500 MHz, DMSO-d6) δ: 12.44 (s, 1H), 8.87 (s, 1H), 8.46 (s, 1H), 7.81 (s, 1H), 7.78 (s, 1H) 7.51 (m, 1H), 7.32 (m, 2H), 6.80 (dd, J=11.0, 17.5 Hz, 1H), 5.66 (d, J=17.5 Hz, 1H), 5.23 (d, J=11.0 Hz, 1H). LC/MS: Rt 3.8 mins.; m/e 324 (M+H), 322 (M−H).

Example 59

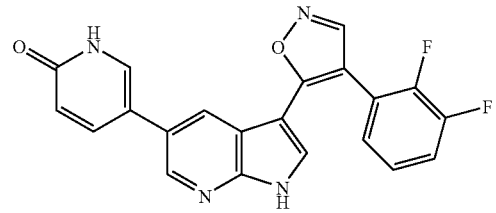

5-{3-[4-(2,3-Difluoro-phenyl)-isoxazol-5-yl]-1H-pyrrolo[2,3-b]pyridin-5-yl}-1H-pyridin-2-one (67)

¹H NMR (500 MHz, DMSO-d6) δ: 12.47 (s, 1H), 8.87 (s, 1H), 8.51 (d, J=2.1 Hz, 1H), 7.85 (d, J=2.7 Hz, 1H), 7.73 (d, J=2.0 Hz, 1H), 7.67 (dd, J=2.7, 9.5 Hz, 1H), 7.57 (d, J=2.4 Hz, 1H), 7.54 (m, 1H), 7.32 (m, 2H), 6.45 (d, J=9.4 Hz, 1H). LC/MS: Rt 2.8 mins.; m/e 391 (M+H), 389 (M−H).

Example 60

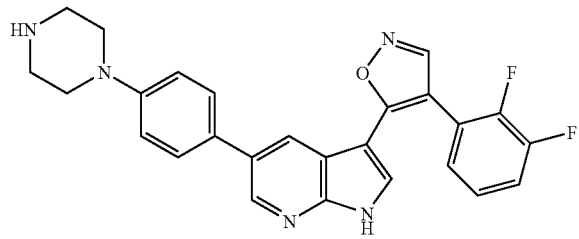

3-[4-(2,3-Difluoro-phenyl)-isoxazol-5-yl]-5-(4-piperazin-1-yl-phenyl)-1H-pyrrolo[2,3-b]pyridine (68)

¹H NMR (500 MHz, DMSO-d6) δ: 12.46 (s, 1H), 8.87 (s, 1H), 8.69 (br, 2H), 8.58 (d, 1H), 7.86 (d, 1H), 7.81 (d, 1H), 7.54 (m, 1H), 7.44 (d, J=8.6 Hz, 2H), 7.32 (m, 2H), 7.09 (d, J=8.6 Hz, 2H), 3.43 (br, 4H), 3.25 (br, 4H), 2.32 (s, 4.1H). LC/MS: Rt 2.4 mins; m/e 458.2 (M+H), 456.2 (M−H).

Example 61

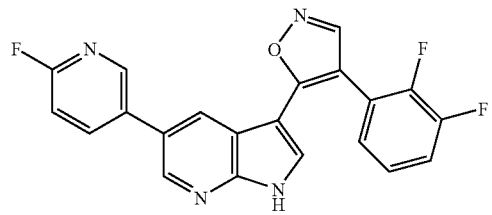

3-[4-(2,3-Difluoro-phenyl)-isoxazol-5-yl]-5-(6-fluoro-pyridin-3-yl)-1H-pyrrolo[2,3-b]pyridine (69)

¹H NMR (500 MHz, DMSO-d6) δ: 12.60 (s, 1H), 8.89 (s, 1H), 8.66 (d, 1H), 8.42 (d, 1H), 8.20 (dt, 1H), 7.96 (d, 1H), 7.91 (d, 1H), 7.52 (m, 1H), 7.35 (m, 2H), 7.29 (dd, 1H), 2.37 (s, 2.8H). LC/MS: Rt 3.8 mins.; m/e 393.1 (M+H), 391.2 (M−H).

Example 62

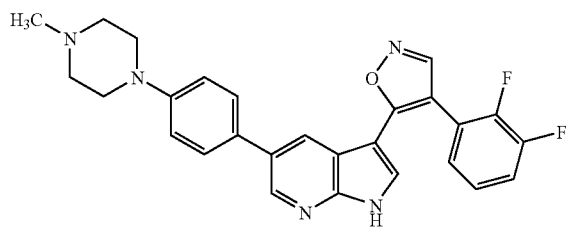

3-[4-(2,3-Difluoro-phenyl)-isoxazol-5-yl]-5-[4-(4-methyl-piperazin-1-yl)-phenyl]-1H-pyrrolo[2,3-b]pyridine methanesulfonate (70)

¹H NMR (500 MHz, DMSO-d6) δ: DMSO-d6: 12.45 (s, 1H), 8.87 (s, 1H), 8.57 (d, 1H), 7.87 (d, 1H), 7.79 (d, 1H), 7.55 (m, 1H), 7.42 (d, J=8.5 Hz, 2H), 7.34 (m, 2H), 7.07 (d, J=8.6 Hz, 2H), 3.20-3.02 (br, 4H), 2.72 (br, 4H), 2.30 (s, 6H). LC/MS: Rt 2.4 mins.; m/e 472.2 (M+H), 470.4 (M−H)

Example 63

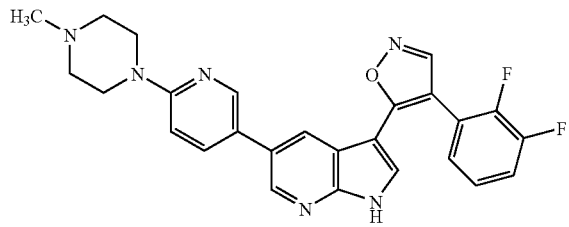

3-[4-(2,3-Difluoro-phenyl)-isoxazol-5-yl]-5-[6-(4-methyl-piperazin-1-yl)-pyridin-3-yl]-1H-pyrrolo[2,3-b]pyridine (71)

¹H NMR (500 MHz, DMSO-d6) δ: 12.50 (s, 1H), 9.70 (br, 1H), 8.88 (s, 1H), 8.59 (d, 1H), 8.37 (d, 1H), 7.86 (m, 2H), 7.79 (dd, 1H), 7.52 (m, 1H), 7.33 (m, 2H), 7.03 (d, 1H), 3.80 (br, 4H), 3.15 (br, 4H), 2.75 (s, 3H), 2.31 (s, 2.8H). LC/MS: Rt 2.2 mins.; m/e 473.3 (M+H), 471.4 (M−H).

Example 64

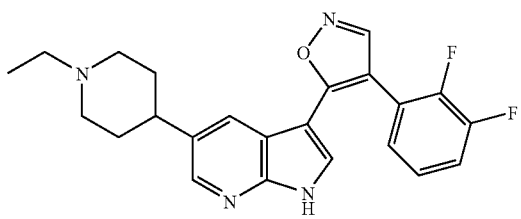

3-[4-(2,3-Difluoro-phenyl)-isoxazol-5-yl]-5-(1-ethyl-piperidin-4-yl)-1H-pyrrolo[2,3-b]pyridine (72)

¹H NMR (500 MHz, CD3OD) δ: 8.60 (s, 1H), 8.27 (d, 1H), 7.98 (d, 1H), 7.62 (s, 1H), 7.35 (m, 1H), 7.25 (m, 2H), 3.63 (d, br, 2H), 3.18 (q, 2H), 3.06 (m, 2H), 2.68 (s, 3H), 2.13 (d, br, 2H), 1.98 (m, 2H), 1.38 (t, 3H). LC/MS: Rt 2.1 mins.; m/e 409.4 (M+H), 407.4 (M−H).

General Method C:

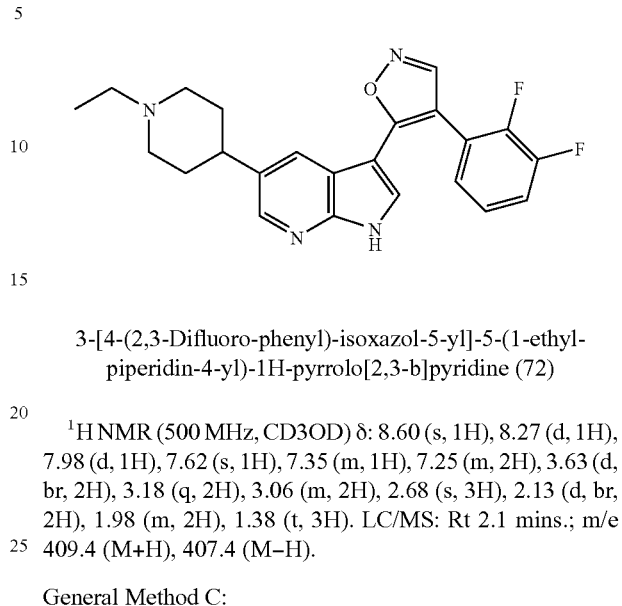

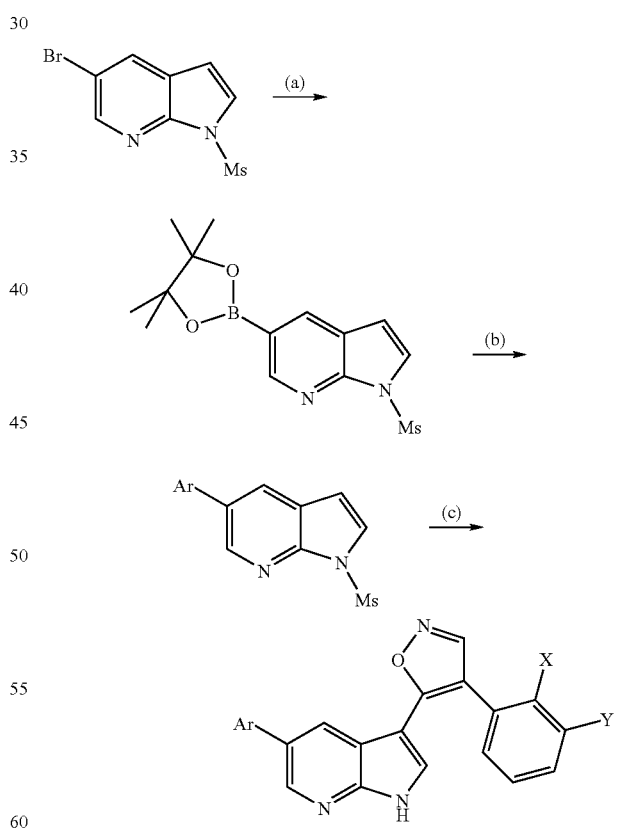

Reagents and Conditions: (a) bis(pinacolato)diboron, KOAc, PdCl₂(dppf), dioxane, 80 C; (b) Ar—Br or Ar—I, 2M Na₂CO₃, PdCl₂(dppf), DMF, 80 C; (c) (i) substituted-phenylacetyl chloride, AlCl₃, CH₂Cl₂, (ii) Bredereck's Reagent, THF, reflux, (iii) H₂NOH HCl, NaOAc, THF, reflux.

Example 65

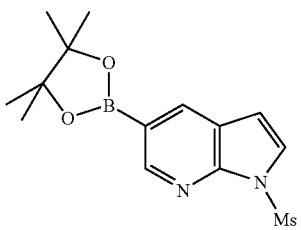

1-Methanesulfonyl-5-(4,4,5,5-tetramethyl-[1,3,2]-dioxaborolan-2-yl)-1H-pyrrolo[2,3-b]pyridine To a solution of 5-bromo-1-methanesulfonyl-1H-pyrrolo[2,3-b]pyridine (1.40 g, 5.1 mmol), bis(pinacolato)diboron (1.42 g, 5.6 mmol), and KOAC (15.3 mmol) in dioxane (30 mL) was added PdCl2(dppf) (250 mg, 0.31 mmol) under N2 atmosphere. The solution was heated at 80° C. for 3 h. The solvent was removed by evaporation, the residue was taken up to hexane (50 mL), and the precipitate was collected by filtration. The crude brownish solid was used without purification. MS (ES+): m/e=241.0 (M+H−C4H7); LC: 2.33 min. $^1$H NMR (500 MHz, DMSO-d6) δ: 8.62 (d, 1H), 8.38 (d, 1H), 7.74 (d, 1H), 6.83 (d, 1H) 3.72 (s, 3H), 1.34 (s, 12H) ppm.

Example 66

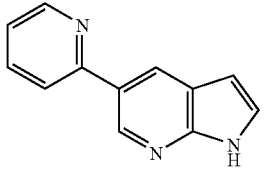

5-Pyridin-2-yl-1H-pyrrolo[2,3-b]pyridine

To a solution of 1-methanesulfonyl-5-(4,4,5,5-tetramethyl-[1,3,2]-dioxaborolan-2-yl)-1H-pyrrolo[2,3-b]pyridine (300 mg, 0.93 mmol) and 2-bromopyridine (150 mg, 0.95 mmol) in DMF (3 mL) was added aqueous Na2CO3 (2M, 1.9 mL, 3.8 mmol). To this suspension was then added PdCl2(dppf) (60 mg, 0.075 mmol) under N2 atmosphere. The flask was then covered with septa, heated at 80° C. for 9 h, and poured into water (30 mL). The aqueous solution was extracted with ethylacetate (3×30 mL). The combined organic layers were dried over Na2SO4, filtered, and evaporated. The resulting residue was dissolved in MeOH (10 mL) and treated with 6N NaOH solution (2 mL) at 50° C. for 3 h. After evaporating the MeOH, the aqueous residue was acidified with 6N HCl to pH=8. The precipitate was collected by filtration, washed with water, and dried on the pump for direct use (100 mg off-white solid, 0.51 mmol). MS (ES+): m/e=196.1 (M+H); LC: 2.04 min.

Example 67

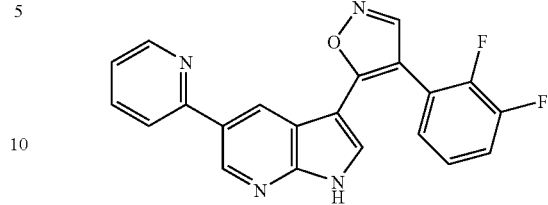

3-(4-(2,3-Difluoro-phenyl)-isoxazol-5-yl)-5-pyridin-2-yl-1H-pyrrolo[2,3-b]pyridine (73)

5-Pyridin-2-yl-1H-pyrrolo[2,3-b]pyridine (100 mg, 0.51 mmol) was converted to 3-[4-(2,3-difluoro-phenyl)-isoxazol-5-yl]-5-pyridin-2-yl-1H-pyrrolo[2,3-b]pyridine (50 mg, 0.13 mmol) by using Method A.

$^1$H NMR (500 MHz, DMSO-d6) δ: 12.60 (s, 1H), 8.89 (s, 1H), 8.69 (d, 1H), 8.34 (d, 1H), 8.31 (d, 1H), 7.95 (d, 1H), 7.93 (d, 1H), 7.57 (s, 1H), 7.50 (m, 1H), 7.35 (m, 1H), 7.30 (m, 1H), 3.93 (s, 3H). LC/MS: Rt 3.0 mins; m/e 375 (M+H), 373 (M−H).

Example 68

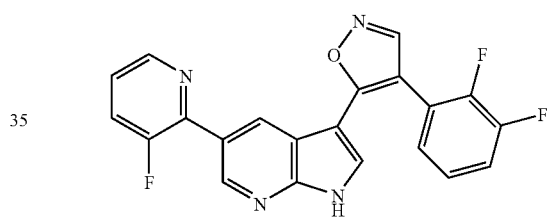

3-[4-(2,3-Difluoro-phenyl)-isoxazol-5-yl]-5-(3-fluoro-pyridin-2-yl)-1H-pyrrolo[2,3-b]pyridine (74)

$^1$H NMR (500 MHz, DMSO-d6) δ: 12.60 (s, 1H), 8.91 (s, 1H), 8.88 (s, 1H), 8.57 (m, 1H), 8.13 (s, 1H), 7.87 (d, 1H), 7.85 (ddd, 1H), 7.50 (m, 2H), 7.37 (m, 1H), 7.29 (m, 1H). LC/MS: Rt 3.7 mins.; m/e 392.9 (M+H), 391 (M−H)

Example 69

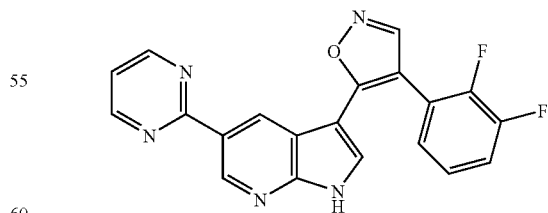

3-[4-(2,3-Difluoro-phenyl)-isoxazol-5-yl]-5-pyrimidin-2-yl-1H-pyrrolo[2,3-b]pyridine (75)

$^1$H NMR (500 MHz, DMSO-d6) δ: 12.63 (s, 1H), 9.36 (d, 1H), 8.96 (d, 1H), 8.91 (d, 2H), 8.89 (s, 1H), 7.84 (d, 1H), 7.53

(q, 1H), 7.46 (t, 1H), 7.39 (t, 1H), 7.30 (q, 1H). LC/MS: Rt 3.5 mins.; m/e 375.9 (M+H), 374 (M–H).

Example 70

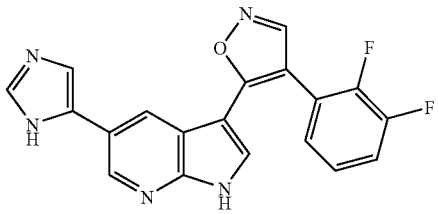

3-[4-(2,3-Difluoro-phenyl)-isoxazol-5-yl]-5-(3H-imidazol-4-yl)-1H-pyrrolo[2,3-b]pyridine (76)

$^1$H NMR (500 MHz, DMSO-d6) δ: 14.65 (br, 1H), 12.64 (s, 1H), 9.07 (s, 1H), 8.90 (s, 1H), 8.82 (d, 1H), 8.57 (d, 1H), 8.13 (s, 1H), 7.76 (d, 1H), 7.50 (m, 1H), 7.39 (m, 1H), 7.30 (m, 1H). LC/MS: Rt 2.1 mins; m/e 364 (M+H), 362.1 (M–H)

Example 71

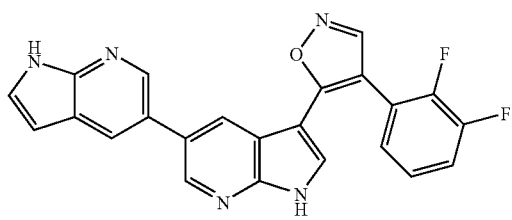

3-[4-(2,3-Difluoro-phenyl)-isoxazol-5-yl]-1H,1'H-[5,5']bi[pyrrolo[2,3-b]pyridinyl] (77)

$^1$H NMR (500 MHz, DMSO-d6) δ: 12.52 (s, 1H), 11.72 (s, 1H), 8.88 (s, 1H), 8.65 (d, 1H), 8.34 (d, 1H), 8.03 (d, 1H), 7.92 (s, 1H), 7.83 (d, 1H), 7.53 (m, 2H), 7.34 (m, 2H), 6.53 (dd, 1H)

Example 72

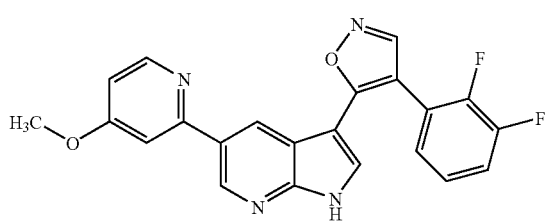

3-[4-(2,3-Difluoro-phenyl)-isoxazol-5-yl]-5-(4-methoxy-pyridin-2-yl)-1H-pyrrolo[2,3-b]pyridine (78)

$^1$H NMR (500 MHz, DMSO-d6) δ: 12.52 (s, 1H), 9.05 (d, 1H), 8.88 (s, 1H), 8.53 (d, 1H), 8.48 (d, 1H), 7.83 (s, 1H), 7.50 (q, 1H), 7.43 (d, 1H), 7.38 (t, 1H), 7.29 (m, 1H), 6.95 (dd, 1H), 3.95 (s, 3H). LC/MS: Rt 2.5 mins.; m/e 405 (M+H), 403.1 (M–H).

Example 73

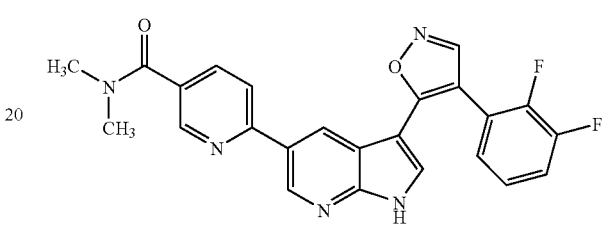

6-{3-[4-(2,3-Difluoro-phenyl)-isoxazol-5-yl]-1H-pyrrolo[2,3-b]pyridin-5-yl}-N,N-dimethyl-nicotinamide (79)

$^1$H NMR (500 MHz, DMSO-d6) δ: 12.58 (s, 1H), 9.08 (d, J=2.0 Hz, 1H), 8.89 (s, 1H), 8.74 (d, J=4.5 Hz, 1H), 8.48 (d, J=2.0 Hz, 1H), 7.88 (d, J=2.5 Hz, 1H), 7.81 (s, 1H), 7.48 (m, 1H), 7.38 (m, 1H), 7.33 (dd, J=1.0, 5.0 Hz, 1H), 7.28 (m, 1H), 3.05 (s, 3H), 2.93 (s, 3H). LC/MS: Rt 3.1 mins; m/e 446 (M+H), 444.1 (M–H).

Example 74

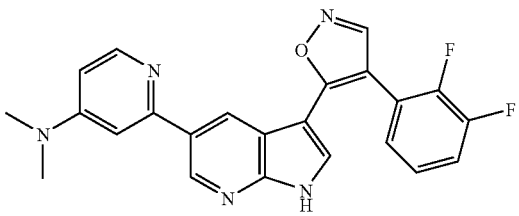

(2-{3-[4-(2,3-Difluoro-phenyl)-isoxazol-5-yl]-1H-pyrrolo[2,3-b]pyridin-5-yl}-pyridin-4-yl)-dimethyl-amine (80)

$^1$H NMR (500 MHz, DMSO-d6) δ: 12.71 (s, 1H), 8.91 (s, 2H), 8.53 (s, 1H), 8.24 (d, J=7.0 Hz, 1H), 7.87 (s, 1H), 7.50 (m, 1H), 7.31 (m, 1H), 7.30 (m, 1H), 7.18 (s, 1H), 6.91 (d, J=5.5 Hz, 1H), 3.24 (s, 6H) LC/MS: Rt 2.4 mins; m/e 418 (M+H), 416 (M–H).

Example 75

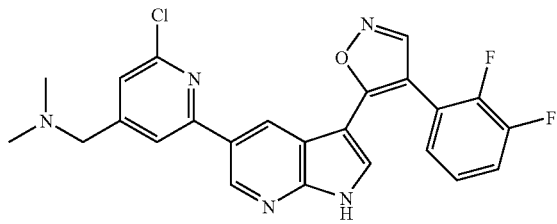

(2-Chloro-6-{3-[4-(2,3-difluoro-phenyl)-isoxazol-5-yl]-1H-pyrrolo[2,3-b]pyridin-5-yl}-pyridin-4-ylmethyl)-dimethyl-amine (81)

$^1$H NMR (500 MHz, CD3OD) δ: 9.05 (d, 1H), 8.79 (d, 1H), 8.62 (s, 1H), 8.04 (s, 1H), 7.70 (s, 1H), 7.54 (s, 1H), 7.36-7.24 (m, 3H), 4.42 (s, 2H), 2.97 (s, 6H). LC/MS: Rt 2.6 mins.; m/e 466 (M+H), 464.1 (M−H).

Example 76

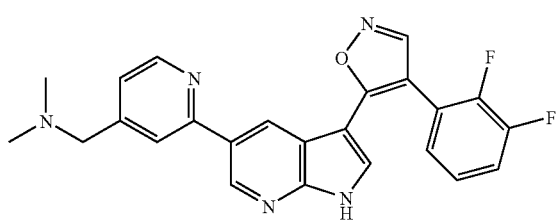

(2-{3-[4-(2,3-Difluoro-phenyl)-isoxazol-5-yl]-1H-pyrrolo[2,3-b]pyridin-5-yl}-pyridin-4-ylmethyl)-dimethyl-amine (82)

$^1$H NMR (500 MHz, DMSO-d6) δ: 12.57 (s, 1H), 9.81 (br, s, 1H), 9.08 (s, 1H), 8.91 (s, 1H), 8.76 (br, 1H), 8.63 (br, 1H), 8.02 (br, 1H), 7.85 (s, 1H), 7.55-7.28 (complex, 4H), 4.15 (br, 2H), 3.28 (s, 6H), 2.31 (s, 2.7H). LC/MS: Rt 2.4 mins.; m/e 432.3 (M+H), 430.3 (M−H).

Example 77

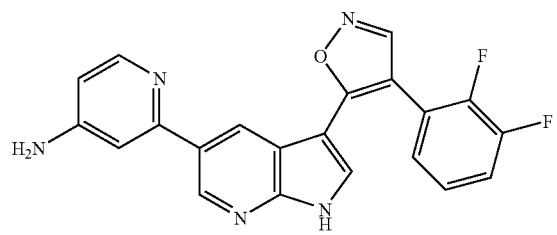

2-{3-[4-(2,3-Difluoro-phenyl)-isoxazol-5-yl]-1H-pyrrolo[2,3-b]pyridin-5-yl}-pyridin-4-ylamine (83)

$^1$H NMR (500 MHz, DMSO-d6) δ: 13.45 (s, 1H), 12.78 (s, 1H), 8.92 (s, 1H), 8.74 (d, 1H), 8.52 (d, 1H), 8.17 (d, br, 1H), 8.13 (br, 1H), 8.03 (br, 1H), 7.86 (d, 1H), 7.53 (q, 1H), 7.41 (t, 1H), 7.33 (q, 1H), 7.11 (d, 1H), 6.85 (dd, 1H), 2.32 (s, 3.5H). LC/MS: Rt 2.4 mins.; m/e 390.2 (M+H), 388.3 (M−H).

Example 78

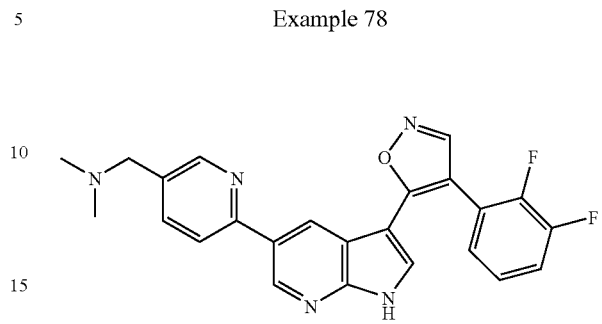

(6-{3-[4-(2,3-Difluoro-phenyl)-isoxazol-5-yl]-1H-pyrrolo[2,3-b]pyridin-5-yl}-pyridin-3-ylmethyl)-dimethyl-amine (84)

$^1$H NMR (500 MHz, DMSO-d6) δ: 12.60 (s, 1H), 9.72 (br, 1H), 9.10 (s, 1H), 8.90 (s, 1H), 8.77 (s, 1H), 8.64 (s, 1H), 8.09 (d, J=8.2 Hz, 1H), 8.03 (dd, J=8.2, 1.8 Hz, 1H), 7.84 (d, J=2.5 Hz, 1H), 7.51 (m, 1H), 7.38-7.30 (m, 2H), 4.39 (d, 2H), 2.81 (d, 6H), 2.34 (s, 3H). LC/MS: Rt 2.2 mins.; m/e 432.2 (M+H), 430.3 (M−H).

General Method D:

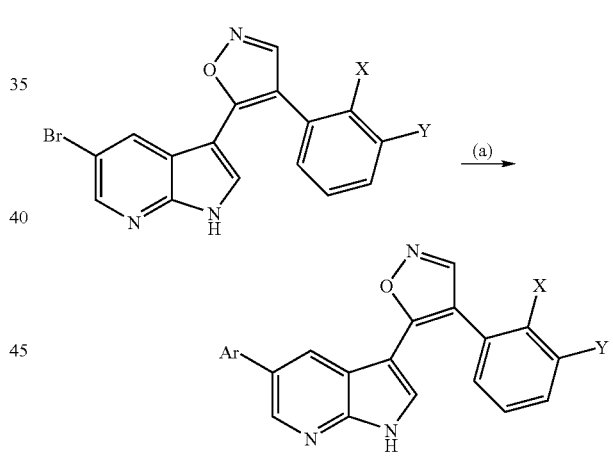

Reagents and Conditions: (a) R—B(OR)$_2$, 2M Na$_2$CO$_3$, PdCl$_2$(dppf), DMF.

Example 79

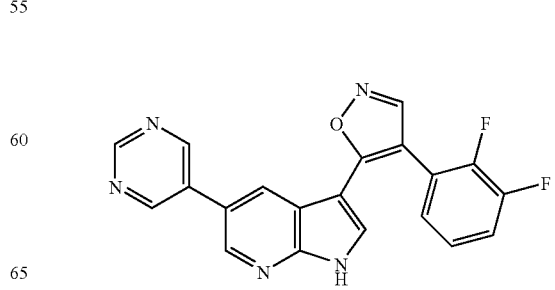

3-[4-(2,3-Difluoro-phenyl)-isoxazol-5-yl]-5-pyrimidin-5-yl-1H-pyrrolo[2,3-b]pyridine (85)

To a solution of 5-bromo-3-[4-(2,3-difluoro-phenyl)-isoxazol-5-yl]-1H-pyrrolo[2,3-b]pyridine (prepared by Method A, 50 mg, 0.13 mmol) and 5-pyrimidine boronic acid (33 mg, 0.27 mmol) in DME (1 mL) was added sat. NaHCO3 (1.2 M, 0.54 mL, 0.65 mmol) and tri-tert-butylphosphine (27 mg, 0.13 mmol). The suspension was stirred under N2 atmosphere while catalyst PdCl2(dppf) (5 mg, 0.006 mmol) was added. The reaction mixture was then heated at 80° C. for 5 h and diluted with ethyl acetate. The inorganic salt was removed by filtration, the filtrate was evaporated and purified by HPLC to afford the desired product as off-white solid (5.0 mg, 0.013 mmol, 10%).

$^1$H NMR (500 MHz, DMSO-d6) δ: 12.62 (br, 1H), 9.19 (s, 1H), 9.04 (s, 2H), 8.88 (s, 1H), 8.72 (d, 1H), 8.06 (d, 1H), 7.92 (s, 1H), 7.50 (m, 1H), 7.36 (m, 1H), 7.30 (m, 1H) ppm. LC/MS: Rt 3.1 mins.; m/e 375.9 (M+H), 374.1 (M−H)

Example 80

3-{3-[4-(2,3-Difluoro-phenyl)-isoxazol-5-yl]-1H-pyrrolo [2,3-b]pyridin-5-yl}-phenylamine (86)

$^1$H NMR (500 MHz, DMSO-d6) δ: 12.51 (s, 1H), 8.88 (s, 1H), 8.59 (d, 1H), 8.02 (d, 1H), 7.83 (s, 1H), 7.55 (m, 1H), 7.36 (m, 3H), 7.21 (s, 1H), 7.15 (d, br, 1H), 6.98 (d, br, 1H). LC/MS: Rt 2.8 mins.; m/e 389 (M+H), 387.1 (M−H).

Example 81

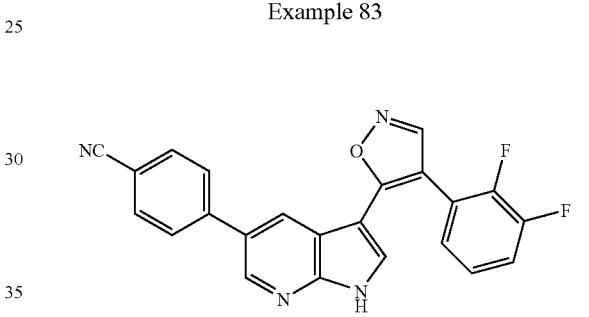

3-{3-[4-(2,3-Difluoro-phenyl)-isoxazol-5-yl]-1H-pyrrolo [2,3-b]pyridin-5-yl}-phenol (87)

$^1$H NMR (500 MHz, DMSO-d6) δ: 12.49 (s, 1H), 9.52 (s, 1H), 8.87 (s, 1H), 8.56 (d, 1H), 7.88 (d, 1H), 7.86 (d, 1H), 7.54 (m, 1H), 7.38 (m, 2H), 7.26 (t, 1H), 6.95 (m, 2H), 6.78 (dd, 1H). LC/MS: Rt 3.6 mins.; m/e 389.9 (M+H), 388 (M−H).

Example 82

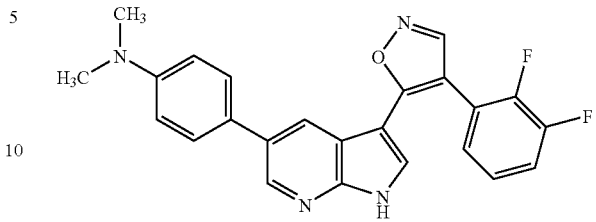

(4-{3-[4-(2,3-Difluoro-phenyl)-isoxazol-5-yl]-1H-pyrrolo[2,3-b]pyridin-5-yl}-phenyl)-dimethyl-amine (88)

$^1$H NMR (500 MHz, DMSO-d6) δ: 12.43 (s, 1H), 8.87 (s, 1H), 8.56 (d, 1H), 7.85 (d, 1H), 7.76 (d, 1H) 7.55 (m, 1H), 7.40-7.30 (m, 4H) 6.92 (d, 2H), 2.98 (s, 6H). LC/MS: Rt 3.4 MINS.; M/E 417 (M+H), 415 (M−H).

Example 83

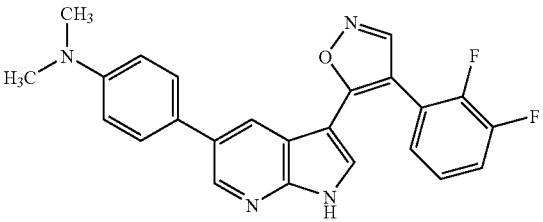

4-{3-[4-(2,3-Difluoro-phenyl)-isoxazol-5-yl]-1H-pyrrolo [2,3-b]pyridin-5-yl}-benzonitrile (89)

$^1$H NMR (500 MHz, DMSO-d6) δ: 12.60 (s, 1H), 8.89 (s, 1H), 8.71 (d, 1H), 7.97 (d, 1H), 7.93 (m, 3H), 7.77 (d, 2H), 7.54 (m, 1H), 7.35 (m, 2H). LC/MS: Rt 4.1 mins.; m/e 398.9 (M+H), 397 (M−H).

Example 84

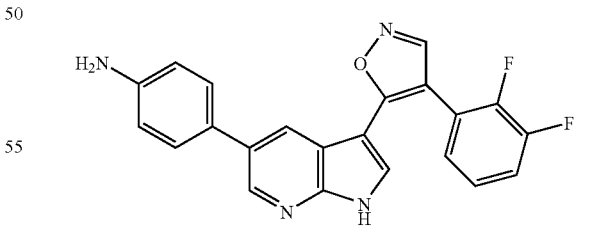

4-{3-[4-(2,3-Difluoro-phenyl)-isoxazol-5-yl]-1H-pyrrolo [2,3-b]pyridin-5-yl}-phenylamine (90)

$^1$H NMR (500 MHz, DMSO-d6) δ: 12.48 (s, 1H), 8.88 (s, 1H), 8.58 (d, 1H), 7.86 (d overlap, 2H), 7.54 (m, 1H), 7.48 (d, 2H), 7.35 (m, 2H), 7.10 (d, 2H) LC/MS: Rt 2.7 mins.; m/e 389 (M+H), 387 (M−H).

Example 85

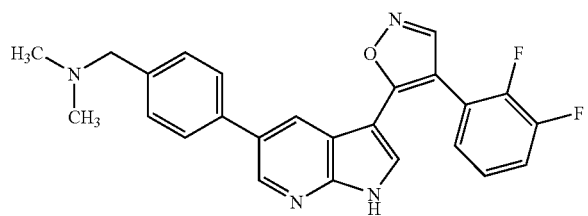

(4-{3-[4-(2,3-Difluoro-phenyl)-isoxazol-5-yl]-1H-pyrrolo[2,3-b]pyridin-5-yl}-benzyl)-dimethyl-amine (91)

$^1$H NMR (500 MHz, DMSO-d6) δ: 12.57 (s, 1H), 9.82 (br, 1H), 8.89 (s, 1H), 8.68 (d, 1H), 7.98 (d, 1H), 7.90 (d, 1H), 7.68 (d, 2H), 7.60 (d, 2H), 7.54 (m, 1H), 7.35 (m, 2H), 4.35 (s, 2H), 2.79 (s, 6H). LC/MS: Rt 2.4 mins.; m/e 431 (M+H), 429 (M−H).

Example 86

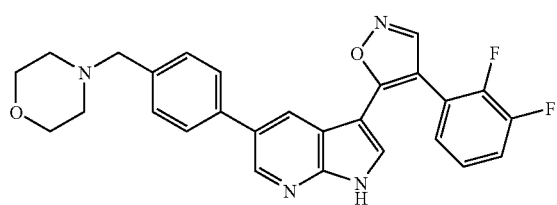

3-[4-(2,3-Difluoro-phenyl)-isoxazol-5-yl]-5-(4-morpholin-4-ylmethyl-phenyl)-1H-pyrrolo[2,3-b]pyridine (92)

$^1$H NMR (500 MHz, DMSO-d6) δ: 12.58 (s, 1H), 9.95 (br, 1H), 8.89 (s, 1H), 8.68 (d, 1H), 7.99 (d, 1H), 7.89 (d, 1H), 7.68 (d, 2H), 7.61 (d, 2H), 7.53 (m, 1H), 7.35 (m, 2H), 4.42 (s, 2H), 3.99 (d, br, 2H), 3.65 (t, br, 2H), 3.32 (d, br, 2H), 3.17 (t, br, 2H). LC/MS: Rt 2.4 mins.; m/e 473 (M+H), 471 (M−H).

Example 87

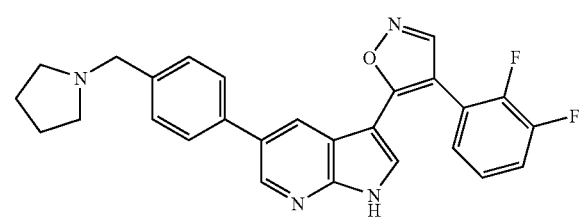

3-[4-(2,3-Difluoro-phenyl)-isoxazol-5-yl]-5-(4-pyrrolidin-1-ylmethyl-phenyl)-1H-pyrrolo[2,3-b]pyridine (93)

$^1$H NMR (500 MHz, DMSO-d6) δ: 12.51 (s, 1H), 8.87 (s, 1H), 8.61 (d, 1H), 7.90 (s, 1H), 7.82 (d, 1H), 7.57 (m, 1H), 7.45 (d, 2H), 7.39 (d, 2H), 7.35 (m, 2H), 3.61 (s, 2H), 2.45 (m, br, 4H), 1.71 (m, br, 4H). LC/MS: Rt 2.5 mins.; 457 (M+H), 455 (M−H).

Example 88

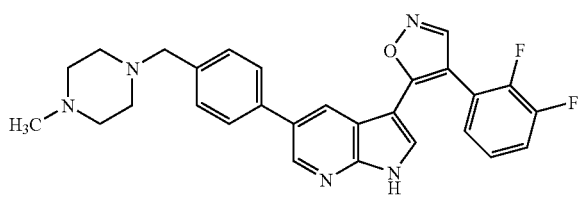

3-[4-(2,3-Difluoro-phenyl)-isoxazol-5-yl]-5-[4-(4-methyl-piperazin-1-ylmethyl)-phenyl]-1H-pyrrolo[2,3-b]pyridine (94)

$^1$H NMR (500 MHz, DMSO-d6) δ: 12.55 (s, 1H), 8.89 (s, 1H), 8.65 (d, 1H), 7.94 (d, 1H), 7.89 (d, 1H), 7.59 (d, 2H), 7.55 (m, 1H), 7.50 (d, 2H), 7.36 (m, 2H), 3.98 (s, 2H), 3.58-2.99 (complex, 8H), 2.84 (s, 3H). LC/MS: Rt 2.2 mins.; m/e 486 (M+H), 484 (M−H).

Example 89

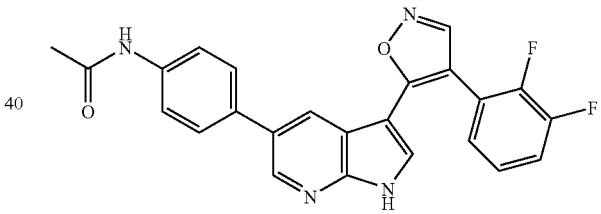

N-(4-{3-[4-(2,3-Difluoro-phenyl)-isoxazol-5-yl]-1H-pyrrolo[2,3-b]pyridin-5-yl}-phenyl)-acetamide (95)

$^1$H NMR (500 MHz, DMSO-d6) δ: 12.49 (s, 1H), 10.03 (s, 1H), 8.88 (s, 1H), 8.60 (s, 1H), 7.88 (d, 1H), 7.83 (d, 1H), 7.67 (d, 2H), 7.54 (m, 1H), 7.46 (d, 2H), 7.35 (m, 2H), 2.07 (s, 3H). LC/MS: Rt 3.4 mins.; m/e 431 (M+H), 429 (M−H).

Example 90

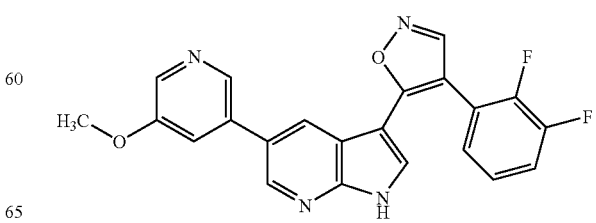

3-[4-(2,3-Difluoro-phenyl)-isoxazol-5-yl]-5-(5-methoxy-pyridin-3-yl)-1H-pyrrolo[2,3-b]pyridine (96)

¹H NMR (500 MHz, DMSO-d6) δ: 12.60 (s, 1H), 8.89 (s, 1H), 8.69 (d, 1H), 8.34 (d, 1H), 8.31 (d, 1H), 7.95 (d, 1H), 7.93 (d, 1H), 7.57 (s, 1H), 7.50 (m, 1H), 7.35 (m, 1H), 7.30 (m, 1H), 3.93 (s, 3H). LC/MS: Rt 2.9 mins.; m/e 405 (M+H), 403 (M−H).

Example 91

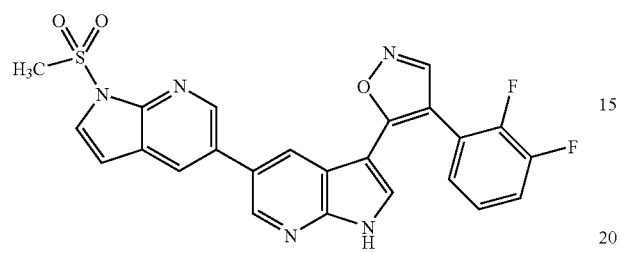

3'-[4-(2,3-Difluoro-phenyl)-isoxazol-5-yl]-1-methanesulfonyl-1H, 1'H-[5,5']bi[pyrrolo[2,3-b]pyridinyl] (97)

¹H NMR (500 MHz, DMSO-d6) δ: 12.58 (s, 1H), 8.89 (s, 1H), 8.71 (d, 1H), 8.66 (d, 1H), 8.24 (d, 1H), 8.02 (d, 1H), 7.90 (d, 1H), 7.80 (d, 1H), 7.57 (m, 1H), 7.37 (m, 1H), 7.33 (m, 1H), 6.88 (d, 1H), 3.77 (s, 3H). LC/MS: Rt 3.9 mins.; m/e 491.9 (M+H), 490 (M−H).

Example 92

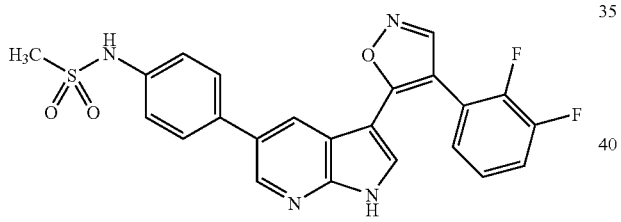

N-(4-{3-[4-(2,3-Difluoro-phenyl)-isoxazol-5-yl]-1H-pyrrolo[2,3-b]pyridin-5-yl}-phenyl)-methane sulfonamide (98)

¹H NMR (500 MHz, DMSO-d6) δ: 12.52 (s, 1H), 9.82 (s, 1H), 8.88 (s, 1H), 8.60 (d, 1H), 7.86 (m, 2H), 7.53 (m, 3H), 7.32 (m, 4H), 3.05 (s, 3H). LC/MS: Rt 3.7 mins.; m/e 466.90 (M+H), 465.0 (M−H).

Example 93

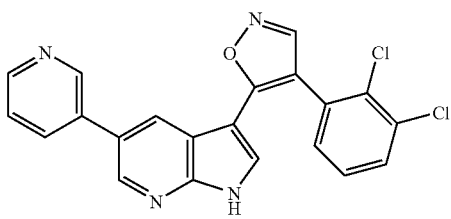

3-[4-(2,3-Dichloro-phenyl)-isoxazol-5-yl]-5-pyridin-3-yl-1H-pyrrolo[2,3-b]pyridine (99)

¹H NMR (500 MHz, DMSO-d6) δ: 12.57 (s, 1H), 8.87 (s, 1H), 8.84 (s, 1H), 8.69 (d, 1H), 8.66 (d, 1H), 8.11 (d, 1H), 7.93 (s, 1H), 7.76 (dd, 1H), 7.72 (d, 1H), 7.63 (dd, 1H), 7.51 (dd, 1H), 7.46 (dd, 1H). LC/MS: Rt 2.9 mins.; m/e 406.8 (M+H), 405 (M−H).

General method E:

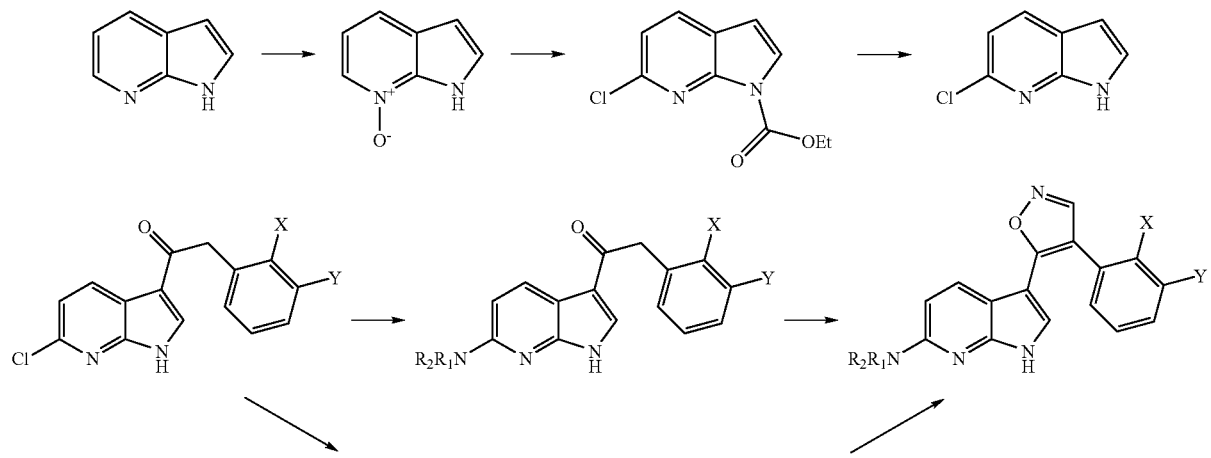

-continued

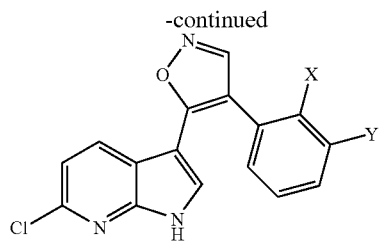

Preparation of 3-[4-(2,3-Difluoro-phenyl)-isoxazol-5-yl]-6-pyrrolidin-1-yl-1H-pyrrolo[2,3-b]pyridine, Example 97 (100)

Example 94

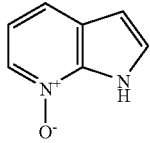

Step A: 1H-Pyrrolo[2,3-b]pyridine 7-oxide

To a solution of 7-azaindole (2.0 g, 16.93 mmol) in dry DME (60 mL) was added m-CPBA (70%) (6.3 g, 25.55 mmol). The resulting yellow solution was stirred at RT for 2 h during which time the product was precipitated out. The mixture was cooled and the light yellow product was isolated by filtration and washed with ether. A suspension of this yellow solid in water (60 mL) was basified to pH 9 with sat. K2CO3 solution. The solution was then cooled in refrigerator for a weekend. A white precipitate was collected by filtration and the filtrate was half evaporated and cooled again to repeat the crystallization procedure. The precipitates were combined and dried on the pump for the next reaction (1.5 g, 11.2 mmol, 66%). MS (ES+): m/e=135.1 (M+H); LC: 1.37 min.

Example 95

Step B: 6-Chloro-pyrrolo[2,3-b]pyridine-1-carboxylic Acid ethyl ester

To a solution of 1H-pyrrolo[2,3-b]pyridine 7-oxide (500 mg, 3.73 mmol) and HMDS (600 mg, 3.72 mmol) in dry THF was added ethylchloroformate (1.0 g, 9.21 mmol) dropwise at RT. The solution was stirred at RT for 1 h and evaporated. The residue was taken up to ethyl acetate and washed with sat. NaHCO3 solution. After evaporation, the crude product was purified by flash column to afford a colorless oil (600 mg, 72%). MS (ES+): m/e=225.1 (M+H); LC: 3.29 min.

Example 96

Step C: 6-Chloro-1H-pyrrolo[2,3-b]pyridine

To a solution of 6-Chloro-pyrrolo[2,3-b]pyridine-1-carboxylic acid ethyl ester (400 mg, 1.78 mmol) in MeOH (35 mL) was added 1N NaOH (13 mL). The solution was stirred at RT for 6 h and evaporated the solvent. The residue was neutralized with sat. NaHCO3 and the resulting precipitate was collected by filtration. After washing with water, the solid was dried on the pump for direct use (260 mg, 1.71 mmol, 96%). MS (ES+): m/e=153.1 (M+H); LC: 2.85 min.

Example 97

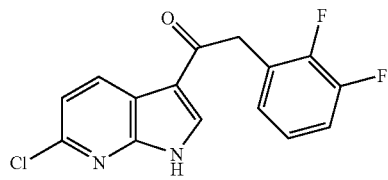

Step D: 1-(6-Chloro-1H-pyrrolo[2,3-b]pyridin-3-yl)-2-(2,3-difluoro-phenyl)-ethanone 6-Chloro-1H-pyrrolo[2,3-b]pyridine (250 mg, 1.64 mmol) was converted to 1-(6-chloro-1H-pyrrolo[2,3-b]pyridin-3-yl)-2-(2,3-difluoro-phenyl)-ethanone using Friedal_Crafts reaction as described in Method A.

Example 98

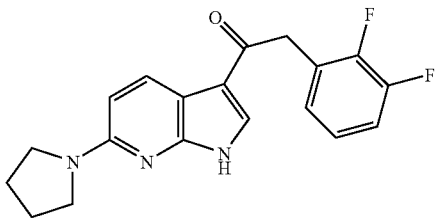

Step E: 2-(2,3-Difluoro-phenyl)-1-(6-pyrrolidin-1-yl-1H-pyrrolo [2,3-b]pyridin-3-yl)-ethanone A solution of 1-(6-chloro-1H-pyrrolo[2,3-b]pyridin-3-yl)-2-(2,3-difluoro-phenyl)-ethanone (100 mg, 0.29 mmol) and pyrrolidine (1 mL) in NMP (2 mL) was heated in a sealed tube with microwave at 220° C. for 15 min. The solution was poured into water and 0.5N HCl was added to precipitate the product. The crude product was collected by filtration, washed with water, and dried on the pump for direct use (80 mg, 0.23 mmol, 79%). MS (ES+): m/e=342.2 (M+H); LC: 2.92 min.

Example 99

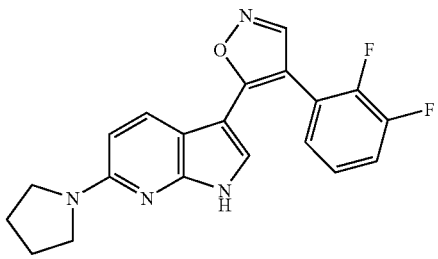

Step F: 3-[4-(2,3-Difluoro-phenyl)-isoxazol-5-yl]-6-pyrrolidin-1-yl-1H-pyrrolo[2,3-b]pyridine (100)

2-(2,3-Difluoro-phenyl)-1-(6-pyrrolidin-1-yl-1H-pyrrolo[2,3-b]pyridin-3-yl)-ethanone (80 mg, 0.23 mmol) was converted to 3-[4-(2,3-difluoro-phenyl)-isoxazol-5-yl]-6-pyrrolidin-1-yl-1H-pyrrolo[2,3-b]pyridine (22 mg, 0.06 mmol, 26%) by using the isoxazole formation procedures described in Method A. MS $^1$H NMR (500 MHz, DMSO-d6) δ: 11.75 (s, 1H), 8.78 (s, 1H), 7.65 (d, 1H), 7.50 (dd, 1H), 7.30 (m, 2H), 7.20 (s, 1H), 6.39 (d, 1H), 3.45 (brs, 4H), 1.95 (brs, 4H). LC/MS: Rt 3.14 mins.; m/e 367.2 (M+H), 365.4 (M−H).

Example 100

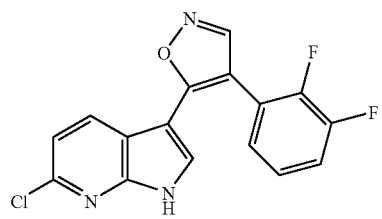

6-Chloro-3-[4-(2,3-difluoro-phenyl)-isoxazol-5-yl]-1H-pyrrolo[2,3-b]pyridine (101)

$^1$H NMR (500 MHz, DMSO-d6) δ: 12.60 (s, 1H), 8.89 (s, 1H), 7.91 (d, 1H), 7.82 (s, 1H), 7.51 (q, 1H), 7.30 (m, 2H), 7.25 (d, 1H). LC/MS: Rt 4.09 mins.; m/e 332.1 (M+H), 330.1 (M−H).

Example 101

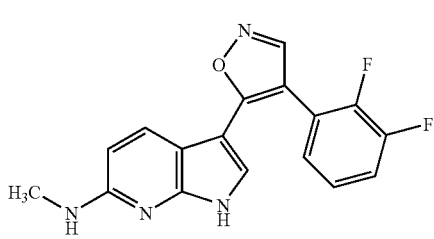

{3-[4-(2,3-Difluoro-phenyl)-isoxazol-5-yl]-1H-pyrrolo[2,3-b]pyridin-6-yl}-methyl-amine (102)

$^1$H NMR (500 MHz, DMSO-d6) δ: 11.69 (s, 1H), 8.78 (s, 1H), 7.56 (d, 1H), 7.50 (m, 1H), 7.31 (m, 1H), 7.15 (d, 1H), 6.36 (d, 1H), 2.81 (s, 3H). LC/MS: Rt 2.7 mins; m/e 327.2 (M+H), 325.2 (M−H).

Example 102

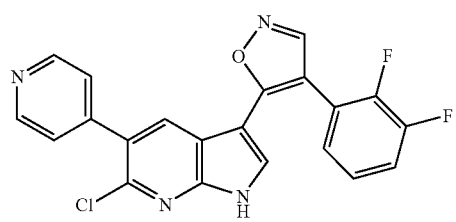

6-Chloro-3-[4-(2,3-difluoro-phenyl)-isoxazol-5-yl]-5-pyridin-4-yl-1H-pyrrolo[2,3-b]pyridine (103)

$^1$H NMR (500 MHz, DMSO-d6) δ: 12.84 (s, 1H), 8.88 (s, 1H), 8.77 (d, 2H), 7.99 (d, 1H), 7.79 (s, 1H), 7.61 (d, 2H), 7.51 (m, 1H), 7.32 (m, 2H). LC/MS: Rt 2.68 mins.; m/e 408.9 (M+H), 407 (M−H).

General method F:

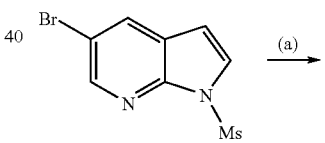

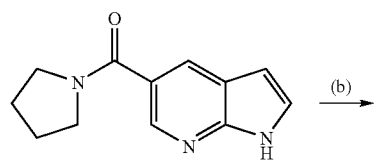

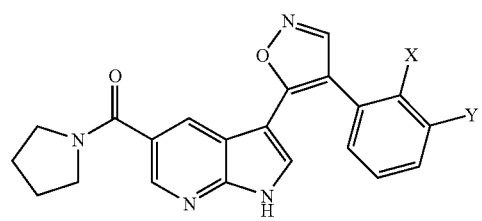

Reagents and Conditions: (a) pyrolidine, CO, PdCl$_2$(dppf), DMF, 80 C; (b) (i) substituted-phenylacetyl chloride, AlCl$_3$, CH$_2$Cl$_2$, (ii) Bredereck's Reagent, THF, reflux, (iii) H$_2$NOH HCl, NaOAc, THF, reflux.

Example 103

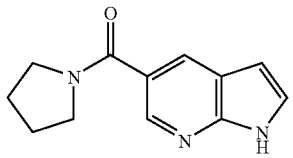

Pyrrolidin-1-yl-(1H-pyrrolo[2,3-b]pyridin-5-yl)-methanone

A mixture of 5-bromo-1-methanesulfonyl-1H-pyrrolo[2,3-b]pyridine (300 mg, 1.1 mmol), PdCl2(dppf) (55 mg, 0.07 mmol), and pyrrolidine (2 mL) in DMF (5 mL) was charged with CO balloon. The system was degassed with vacuum twice before it was heated to 80° C. for 6 h. The solution was cooled and poured into water. The aqueous solution was extracted with ethyl acetate (3×50 mL), the combined organic layers were dried over Na2SO4, and the solvent was removed by vacuum evaporation. The crude product was treated with 6N NaOH in MeOH for 2 h. MeOH was removed by evaporation. The aqueous solution was neutralized with 6N HCl to pH 8 and extracted with ethyl acetate. The combined organic layers were dried over Na2SO4 and the solvent was removed by vacuum evaporation to give a yellow solid (80 mg, 0.37 mmol, 34%), which was used directly for the next step. MS (ES+): m/e=216.1 (M+H); LC: 2.18 min.

Example 104

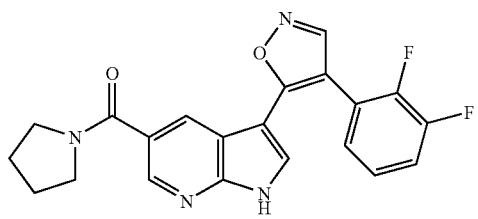

{3-[4-(2,3-Difluoro-phenyl)-isoxazol-5-yl]-1H-pyrrolo[2,3-b]pyridin-5-yl}-pyrrolidin-1-yl-methanone (104)

Pyrrolidin-1-yl-(1H-pyrrolo[2,3-b]pyridin-5-yl)-methanone (80 mg, 0.37 mmol) was converted to {3-[4-(2,3-Difluoro-phenyl)-isoxazol-5-yl]-1H-pyrrolo[2,3-b]pyridin-5-yl}-pyrrolidin-1-yl-methanone (20.0 mg, 0.05 mmol, 14%) by using Method A.

$^1$H NMR (500 MHz, DMSO-d6/CD3OD) δ: 8.84 (s, 1H), 8.50 (d, 1H), 7.99 (d, 1H), 7.86 (s, 1H), 7.47 (m, 1H), 7.34 (m, 1H), 7.28 (m, 1H), 3.50 (br, 2H), 3.32 (br, 2H), 1.85 (br, 4H). LC/MS: Rt 3.2 mins.; m/e 395 (M+H), 393 (M−H).

Example 105

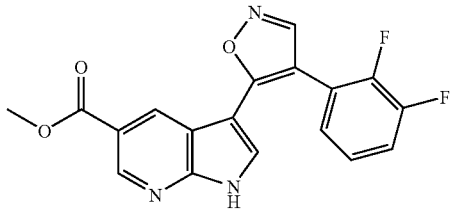

3-[4-(2,3-Difluoro-phenyl)-isoxazol-5-yl]-1H-pyrrolo[2,3-b]pyridine-5-carboxylic acid methyl ester (105)

was prepared by a similar carbonylation step but was carried out in methanol to give the title compound.

$^1$H NMR (500 MHz, DMSO-d6) δ: 12.84 (s, 1H), 8.91 (s, 1H), 8.89 (d, 1H), 8.34 (d, 1H), 7.96 (d, 1H), 7.54 (m, 1H), 7.34 (m, 2H), 3.87 (s, 3H). LC/MS: Rt 3.6 mins.; m/e 356 (M+H), 354 (M−H).

Preparation of triazolyl-azaindoles

General method G:

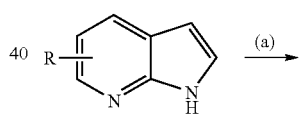

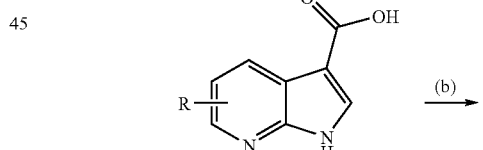

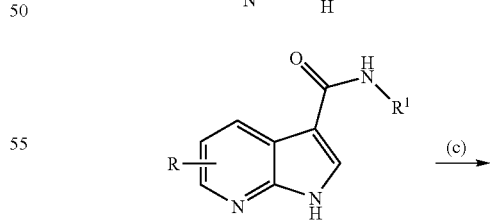

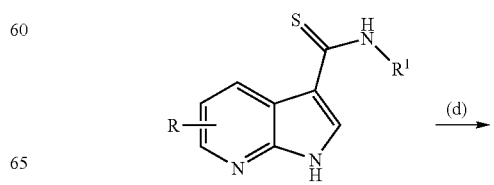

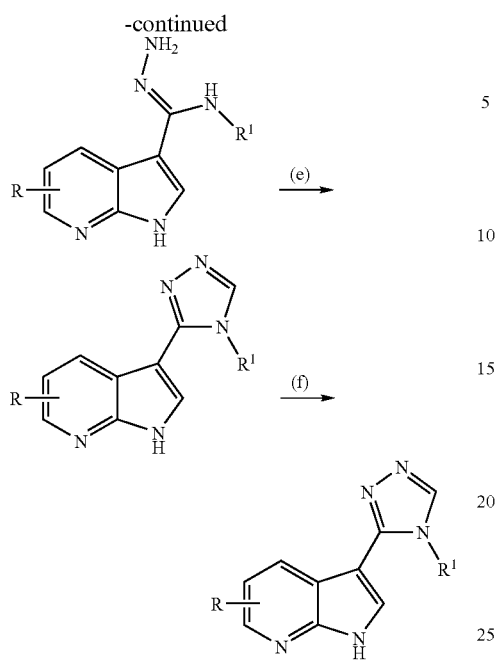

Reagents and Conditions: (a) (i) trichloroacetyl chloride, AlCl₃, CH₂Cl₂, (ii) Et₃N, H₂O, RT (b) (i) oxalyl chloride, DMF (cat.), CH₂Cl₂, (ii) Ar—NH2, Et₃N, CH₂Cl₂; (c) Lawesson's reagent, toluene, reflux; (d) hydrazine, EtOH & CH₂Cl₂; (e) triethylorthoformate, HCO2H; optional step (f) Suzuki coupling; when R=Br or I: R—B(OR)₂, 2M Na₂CO₃, PdCl2(dppf), DMF; when R=B(OH)₂: Ar—X (where X=Br, I, OTf), 2M Na₂CO₃, PdCl₂(dppf), DMF Example 106

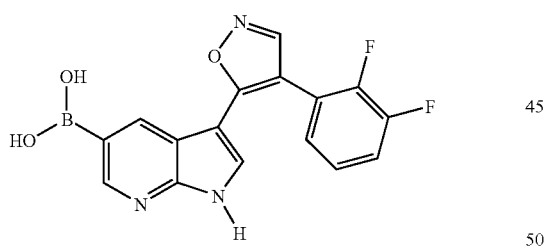

3-[4-(2,3-Difluoro-phenyl)-isoxazol-5-yl]-1H-pyrrolo[2,3-b]pyridine-5-boronic acid (158)

¹H NMR (500 MHz, DMSO-d6) δ: 12.32 (s, 1H), 8.85 (s, 1H), 8.69 (d, 1H), 8.52 (s, 1H), 8.13 (s, 2H), 7.64 (d, 1H), 7.50 (m, 1H), 7.34 (m, 1H), 7.28 (m, 1H). LC/MS: Rt 2.8 mins.; m/z 341.9 (M+H), 340.1 (M−H).

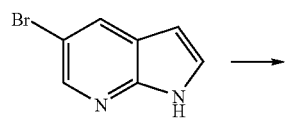

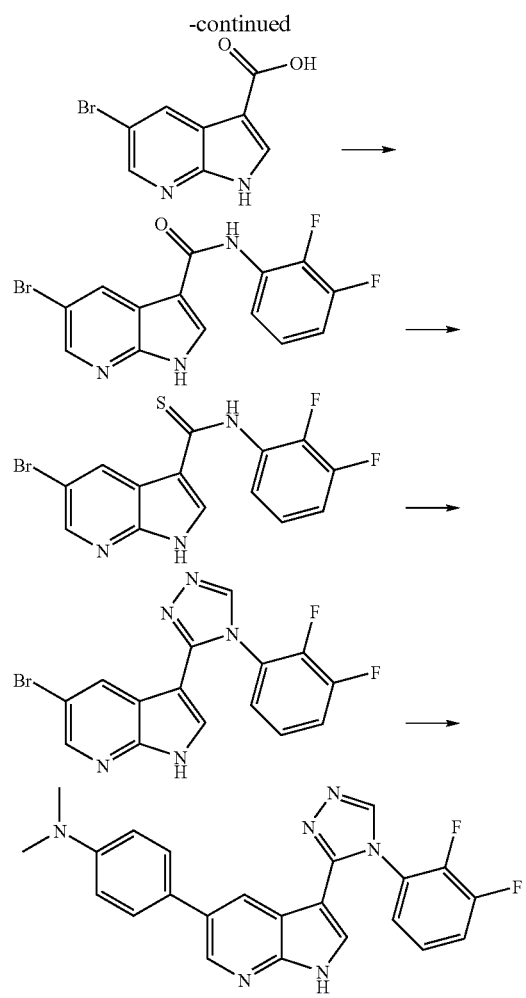

Example 107

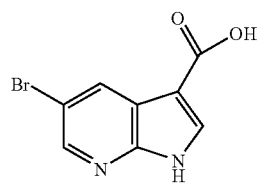

5-Bromo-1H-pyrrolo[2,3-b]pyridine-3-carboxylic acid

To a solution of 5-bromo-7-azaindole (2.0 g, 10.1 mmol) in DCM (50 mL) was added AlCl3 (6.8 g, 51.0 mmol). The suspension was stirred at RT for 10 min and trichloroacetyl chloride (2.8 g, 15.40 mmol) was added slowly. The mixture was stirred at RT for overnight and then poured into iced-water. The aqueous solution was extracted with DCM three times, and organic layers were combined and evaporated. The crude solid was dissolved in THF (50 mL) and treated with water (25 mL) and triethylamine (5 mL) at RT for 6 h. The solvents were then removed by evaporation and the resulting solid was poured into 1N HCl solution. The crude product was collected by filtration and washed with water. After drying on the pump for over night, a white solid was obtained (2.4 g, 9.96 mmol). MS (ES+): m/e=241.0 (M+H); LC: 2.7 min.

Example 108

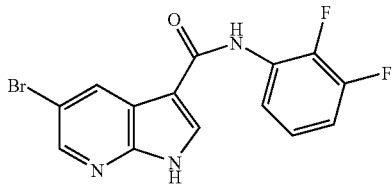

5-Bromo-1H-pyrrolo[2,3-b]pyridine-3-carboxylic acid (2,3-difluoro-phenyl)-amide

To a suspension of 5-bromo-1H-pyrrolo[2,3-b]pyridine-3-carboxylic acid (950 mg, 3.94 mmol) in DCM (20 mL) and DMF (0.1 mL) was added oxalyl chloride (600 mg, 4.72 mmol) slowly. The mixture was stirred at RT for 1 h. To this suspension was then added a solution of 2,3-difluorophenyl amine (610 mg, 4.72 mmol) and triethylamine (800 mg, 7.91 mmol) in DCM (5 mL). The reaction was kept at RT for another 2 h. The solvent was then evaporated, the residue was washed water, and dried for direct use. MS (ES+): m/e=352 (M+H); LC: 3.5 min.

Example 109

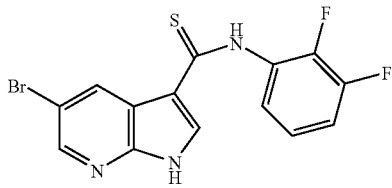

5-Bromo-1H-pyrrolo[2,3-b]pyridine-3-carbothioic Acid (2,3-difluoro-phenyl)-amide To a solution of 5-bromo-1H-pyrrolo[2,3-b]pyridine-3-carboxylic acid (2,3-difluoro-phenyl)-amide (300 mg, 0.85 mmol) in toluene (6 mL) was added Lawesson's reagent (210 mg, 0.52 mmol). The suspension was heated under reflux for 14 h. The solvent was removed by evaporation and the residue was dried on the pump for the next reaction. MS (ES+): m/e=368 (M+H); LC: 3.6 min.

Example 110

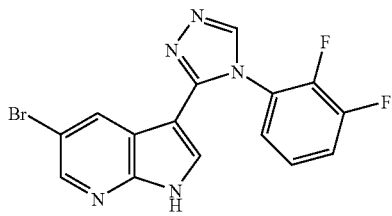

5-Bromo-3-[4-(2,3-difluoro-phenyl)-4H-[1,2,4]triazol-3-yl]-1H-pyrrolo[2,3-b]pyridine A crude material from above was dissolved in a co-solvents of ethanol (5 mL) and DCM (5 mL). Hydrazine (2 mL) was added at RT. The solution was stirred at RT for 4 h and evaporated. The residue was poured into aqueous NaHCO3 solution, filtered, washed with water, and dried. The crude product was dissolved in triethyl orthoformate (5 mL). To this solution was added HCOOH (1 mL) at 0° C. The reaction was allowed to warm up to RT and stayed for overnight. The solvents were removed by evaporation, the residue was taken up to ethyl acetate (50 mL) and washed with aq. NaHCO3. After drying over NaSO4, the solvent was evaporated to afford the desired triazole as yellow solid (120 mg, 0.32 mmol).

¹H NMR (500 MHz, DMSO-d6) δ: 12.32 (s, 1H), 8.86 (s, 1H), 8.62 (d, 1H), 8.42 (d, 1H), 7.75 (q, 1H), 7.57 (t, 1H), 7.46 (m, 1H), 7.07 (d, 1H) LC/MS: Rt 2.8 mins; m/e 377.1 (M+H).

Example 111

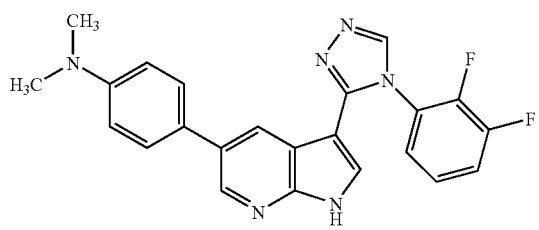

(4-{3-[4-(2,3-Difluoro-phenyl)-4H-[1,2,4]triazol-3-yl]-1H-pyrrolo[2,3-b]pyridin-5-yl}-phenyl)-dimethyl-amine (106)

The crude product (50 mg, 0.13 mmol) obtained above was converted to (4-{3-[4-(2,3-difluoro-phenyl)-4H-[1,2,4]triazol-3-yl]-1H-pyrrolo[2,3-b]pyridin-5-yl}-phenyl)-dimethyl-amine (19 mg, 0.05 mmol) by using Suzuki procedures as described in Method D.

¹H NMR (500 MHz, DMSO-d6) δ: 12.15 (s, 1H), 8.91 (s, 1H), 8.60 (s, 1H), 8.54 (s, 1H), 7.76 (m, 1H), 7.62 (m, 3H), 7.48 (m, 1H), 7.08 (m, br, 3H), 3.04 (s, 6H), 2.33 (s, 3H). LC/MS: Rt 2.2 mins.; m/e 417.3 (M+H), 415.3 (M−H).

Example 112

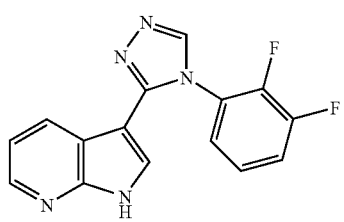

3-[4-(2,3-Difluoro-phenyl)-4H-[1,2,4]triazol-3-yl]-1H-pyrrolo[2,3-b]pyridine (107)

¹H NMR (500 MHz, DMSO-d6) δ: 12.12 (s, 1H), 8.90 (s, 1H), 8.45 (dd, 1H), 8.35 (dd, 1H), 7.75 (m, 1H), 7.58 (t, 1H), 7.47 (m, 1H), 7.25 (dd, 1H), 7.04 (s, 1H). LC/MS: Rt 2.06 mins.; m/e 298.2 (M+H), 296.2 (M−H).

Example 113

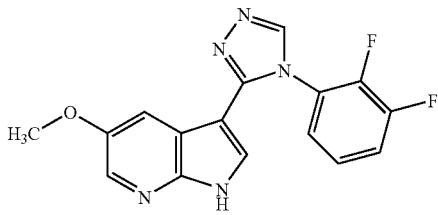

3-[4-(2,3-Difluoro-phenyl)-4H-[1,2,4]triazol-3-yl]-5-methoxy-1H-pyrrolo[2,3-b]pyridine (108)

¹H NMR (500 MHz, DMSO-d6) δ: 11.97 (s, 1H), 8.85 (s, 1H), 8.07 (d, 1H), 7.92 (d, 1H), 7.74 (m, 1H), 7.58 (m, 1H), 7.47 (m, 1H), 6.96 (d, 1H), 3.87 (s, 3H). LC/MS: Rt 2.35 mins.; m/e 328 (M+H), 326 (M−H).

Example 114

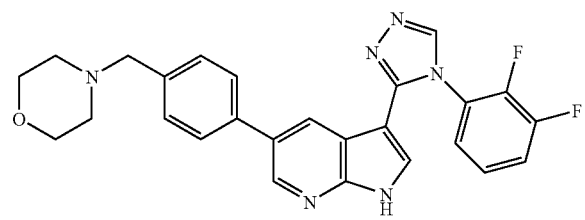

3-[4-(2,3-Difluoro-phenyl)-4H-[1,2,4]triazol-3-yl]-5-(4-morpholin-4-ylmethyl-phenyl)-1H-pyrrolo[2,3-b]pyridine (109)

¹H NMR (500 MHz, DMSO-d6) δ: 12.20 (s, 1H), 9.82 (brs, 1H), 8.88 (s, 1H), 8.71 (s, 1H), 8.69 (s, 1H), 7.86 (d, 2H), 7.77 (m, 1H), 7.66 (d, 2H), 7.59 (m, 1H), 7.49 (m, 1H), 7.06 (d, 1H), 4.45 (d, 2H), 3.97 (d, 2H), 3.65 (t, 2H), 3.35 (2H, covered by water), 3.17 (br, 2H), 2.28 (s, 3H). LC/MS: Rt 1.80 mins.; m/e 473.3 (M+H), 471.4 (M−H).

Example 115

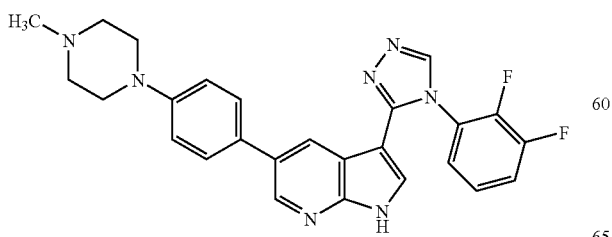

3-[4-(2,3-Difluoro-phenyl)-4H-[1,2,4]triazol-3-yl]-5-[4-(4-methyl-piperazin-1-yl)-phenyl]-1H-pyrrolo[2,3-b]pyridine (110)

¹H NMR (500 MHz, DMSO-d6) δ: 12.11 (s, 1H), 9.64 (br, 1H), 8.88 (s, 1H), 8.60 (d, 1H), 8.56 (d, 1H), 7.76 (q, 1H), 7.62 (d, 2H), 7.59 (m, 1H), 7.48 (m, 1H), 7.16 (d, 2H), 7.04 (d, 1H), 3.94 (d, 2H), 3.55 (d, 2H), 3.20 (q, 2H), 3.04 (t, 2H), 2.89 (d, 3H), 2.33 (s, 3.8H). LC/MS: Rt 1.8 mins.; m/e 472.3 (M+H), 470.4 (M−H).

Example 116

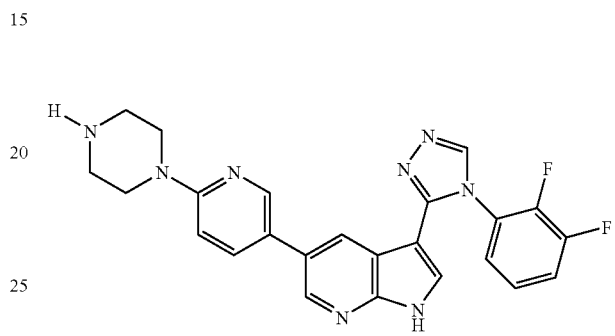

3-[4-(2,3-Difluoro-phenyl)-4H-[1,2,4]triazol-3-yl]-5-(6-piperazin-1-yl-pyridin-3-yl)-1H-pyrrolo[2,3-b]pyridine (111)

¹H NMR (500 MHz, DMSO-d6) δ: 8.81 (s, 1H), 8.52 (s, 1H), 8.48 (d, 1H), 8.43 (s, 1H), 7.84 (dd, 1H), 7.55 (q, 1H), 7.58 (t, 1H), 7.48 (m, 1H), 7.03 (s, 1H), 6.93 (dd, 1H), 3.45 (m, 8H), 2.35 (s, 8H). LC/MS: Rt 1.5 mins.; m/e 459.3 (M+H), 457.4 (M−H).

Example 117

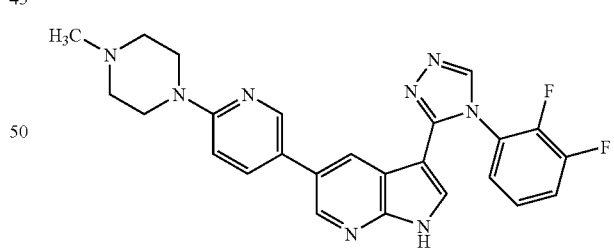

3-[4-(2,3-Difluoro-phenyl)-4H-[1,2,4]triazol-3-yl]-5-[6-(4-methyl-piperazin-1-yl)-pyridin-3-yl])-1H-pyrrolo[2,3-b]-pyridine (112)

¹H NMR (500 MHz, DMSO-d6) δ: 12.15 (s, 1H), 9.62 (br, 1H), 8.85 (s, 1H), 8.59 (s, 1H), 8.54 (s, 1H), 8.50 (s, 1H), 7.95 (d, 1H), 7.75 (m, 1H), 7.60 (m, 1H), 7.48 (m, 1H), 7.06 (s, 1H), 7.04 (s, 1H), 3.35-3.00 (mbr, 8H), 2.68 (br, 3H), 2.30 (s, 2.1H) LC/MS: Rt 1.6 mins.; m/e 473.3 (M+H), 471.4 (M−H).

Example 118

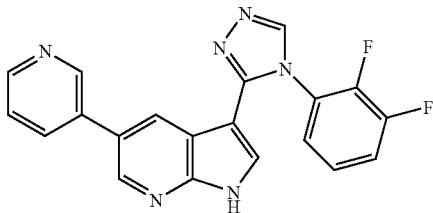

3-[4-(2,3-Difluoro-phenyl)-4H-[1,2,4]triazol-3-yl]-5-pyridin-3-yl-1H-pyrrolo[2,3-b]pyridine (113)

$^1$H NMR (500 MHz, DMSO-d6) δ: 12.35 (s, 1H), 9.21 (d, 1H), 8.91 (s, 1H), 8.80 (m, 3H), 8.68 (d, 1H), 7.95 (dd, 1H), 7.76 (q, 1H), 7.60 (t, 1H), 7.49 (m, 1H), 7.14 (d, 1H), 2.32 (s, 4H). LC/MS: Rt 1.6 mins.; m/e 375.2 (M+H), 373.2 (M−H).

Example 119

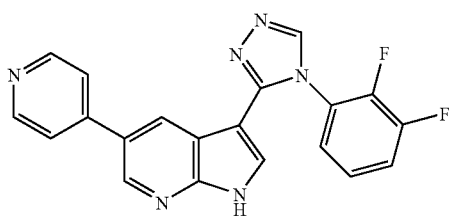

3-[4-(2,3-Difluoro-phenyl)-4H-[1,2,4]triazol-3-yl]-5-pyridin-4-yl-1H-pyrrolo[2,3-b]pyridine (114)

$^1$H NMR (500 MHz, DMSO-d6) δ: 12.49 (s, 1H), 8.98 (s, 2H), 8.92 (m, 3H), 8.41 (d, 2H), 7.75 (q, 1H), 7.60 (t, 1H), 7.49 (m, 1H), 7.19 (d, 1H), 2.31 (s, 3.5H). LC/MS: Rt 1.5 mins.; m/e 375.2 (M+H), 373.2 (M−H).

Example 120

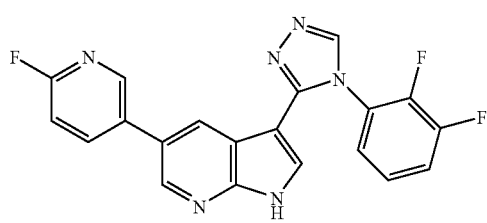

3-[4-(2,3-Difluoro-phenyl)-4H-[1,2,4]triazol-3-yl]-5-(6-fluoro-pyridin-3-yl)-1H-pyrrolo[2,3-b]-pyridine obtained as a yellow solid (yield 75%). MS: m/e 393.3 (M+1); LC: Rt 2.7 min

Example 121

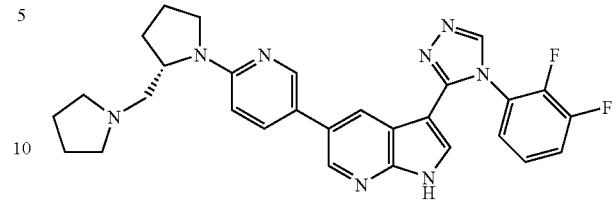

3-[4-(2,3-Difluoro-phenyl)-4H-[1,2,4]triazol-3-yl]-5-[6-(2-pyrrolidin-1-ylmethyl-pyrrolidin-1-yl)-pyridin-3-yl]-1H-pyrrolo[2,3-b]pyridine (115)

$^1$H NMR (500 MHz, DMSO-d6) δ: 8.81 (s, 1H), 8.52 (s, 1H), 8.48 (s, 1H), 8.38 (s, 1H), 7.78 (m, 2H), 7.57 (m, 1H), 7.47 (m, 1H), 7.01 (s, 1H), 6.57 (d, 1H), 4.18 (m, 1H), 3.54 (m, 2H), 3.17 (br, 2H), 2.65-2.55 (covered by DMSO, 4H), 2.10-1.90 (complex, 4H), 1.70 (m, 4H). LC/MS: Rt 2.00 mins.; m/e 527.30 (M+H).

Example 122

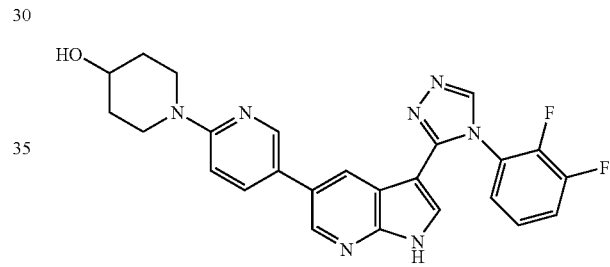

5'-{3-[4-(2,3-Difluoro-phenyl)-4H-[1,2,4]triazol-3-yl]-1H-pyrrolo[2,3-b]pyridin-5-yl}-3,4,5,6-tetrahydro-2H-[1,2']bi-pyridinyl-4-ol (116)

$^1$H NMR (500 MHz, DMSO-d6) δ: 12.10 (br, 1H), 8.81 (s, 1H), 8.52 (s, 1H), 8.47 (d, 1H), 8.42 (d, 1H), 7.82 (dd, 1H), 7.74 (m, 1H), 7.58 (t, 1H), 7.47 (m, 1H), 7.03 (s, 1H), 6.96 (d, 1H), 4.68 (br, 1H), 4.06 (d, br, 2H), 3.73 (m, br, 2H), 3.14 (t, 2H), 1.81 (d, br, 2H), 1.39 (dt, br, 2H). LC/MS: Rt 1.80 mins.; m/e 474.30 (M+H).

Example 123

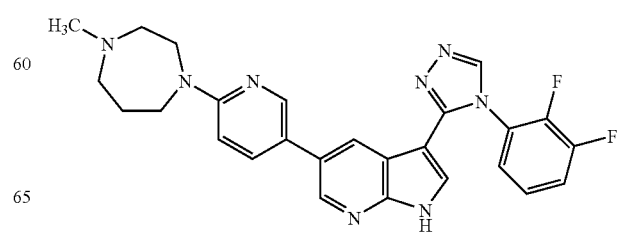

155

3-[4-(2,3-Difluoro-phenyl)-4H-[1,2,4]triazol-3-yl]-5-
[6-(4-methyl-[1,4]diazepan-1-yl)-pyridin-3-yl]-1H-
pyrrolo [2,3-b]-pyridine (117)

¹H NMR (500 MHz, DMSO-d6) δ: 12.09 (s, 1H), 8.86 (s, 1H), 8.56 (d, 1H), 8.49 (d, 1H), 8.40 (d, 1H), 7.81 (dd, 1H), 7.75 (m, 1H), 7.59 (t, 1H), 7.46 (m, 1H), 7.04 (s, 1H), 6.75 (d, 1H), 3.79 (dd, 2H), 3.65 (t, 2H), 2.63 (dd, 2H), 2.48 (covered by DMSO, 2H), 2.27 (s, 3H), 1.92 (m, 2H). LC/MS: Rt 1.40 mins.; m/e 487.40 (M+H).

Example 124

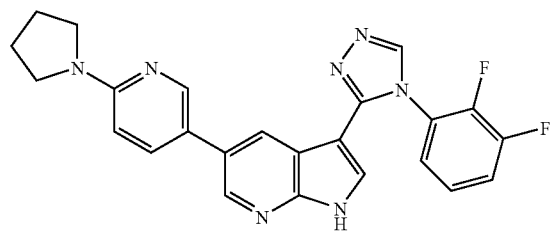

3-[4-(2,3-Difluoro-phenyl)-4H-[1,2,4]triazol-3-yl]-5-
(6-pyrrolidin-1-yl-pyridin-3-yl)-1H-pyrrolo[2,3-b]
pyridine (118)

¹H NMR (500 MHz, DMSO-d6) δ: 12.09 (s, 1H), 8.86 (s, 1H), 8.55 (d, 1H), 8.48 (s, 1H), 8.39 (d, 1H), 7.81 (dd, 1H), 7.74 (m, 1H), 7.59 (t, 1H), 7.47 (m, 1H), 7.04 (d, 1H), 6.57 (d, 1H), 3.44 (tbr, 4H), 1.97 (tbr, 4H). LC/MS: Rt 2.0 mins.; m/e 444.3 (M+H).

Example 125

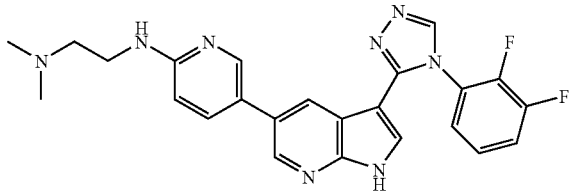

N'-(5-{3-[4-(2,3-Difluoro-phenyl)-4H-[1,2,4]triazol-
3-yl]-1H-pyrrolo[2,3-b]pyridin-5-yl}-pyridin-2-yl)-
N,N-dimethyl-ethane-1,2-diamine (119)

¹H NMR (500 MHz, DMSO-d6) δ: 12.17 (s, 1H), 9.72 (br, 1H), 8.87 (s, 1H), 8.59 (d, 2H), 8.40 (d, 1H), 8.00 (d, 1H), 7.76 (q, 1H), 7.59 (dd, 1H), 7.48 (m, 1H), 7.03 (d, 1H), 6.87 (d, 1H), 3.73 (t, 2H), 3.33 (t, 2H), 2.88 (s, 6H). LC/MS: Rt 1.3 mins.; m/e 461.3 (M+H).

156

Example 126

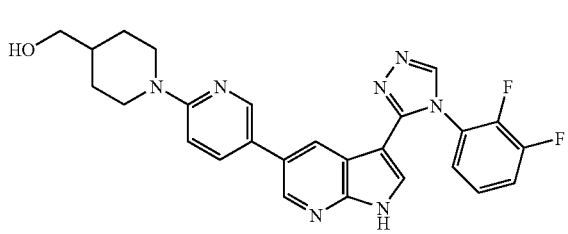

(5'-{3-[4-(2,3-Difluoro-phenyl)-4H-[1,2,4]triazol-3-
yl]-1H-pyrrolo[2,3-b]pyridin-5-yl}-3,4,5,6-tetrahy-
dro-2H-[1,2']bi-pyridinyl-4-yl)-methanol (120)

¹H NMR (500 MHz, DMSO-d6) δ: 12.20 (s, 1H), 8.90 (s, 1H), 8.62 (d, 1H), 8.58 (d, 1H), 8.37 (d, 1H), 8.12 (d, 1H), 7.77 (dd, 1H), 7.61 (dd, 1H), 7.49 (m, 1H), 7.32 (br, 1H), 7.09 (s, 1H), 4.34 (m, 3H), 3.31 (d, 1H), 3.08 (m, 2H), 1.80 (d, br, 2H), 1.74 (br, 1H), 1.30 (m, 2H). LC/MS: Rt 1.90 mins.; m/e 488.3 (M+H).

Example 127

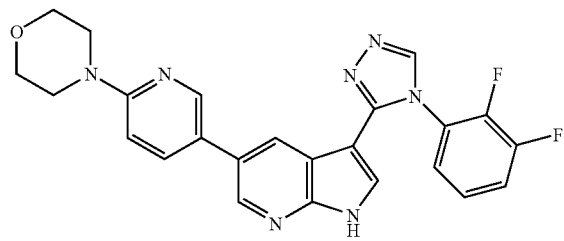

3-[4-(2,3-Difluoro-phenyl)-4H-[1,2,4]triazol-3-yl]-5-
(6-morpholin-4-yl-pyridin-3-yl)-1H-pyrrolo[2,3-b]
pyridine (121)

¹H NMR (500 MHz, DMSO-d6) δ: 12.20 (s, 1H), 8.90 (s, 1H), 8.62 (d, 1H), 8.57 (d, 1H), 8.43 (d, 1H), 8.13 (dd, 1H), 7.75 (dd, 1H), 7.59 (t, 1H), 7.48 (m, 1H), 7.21 (d, 1H), 7.09 (d, 1H), 3.77 (t, 4H), 3.60 (t, 4H). LC/MS: Rt 2.00 mins.; m/e 460.3 (M+H).

Example 128

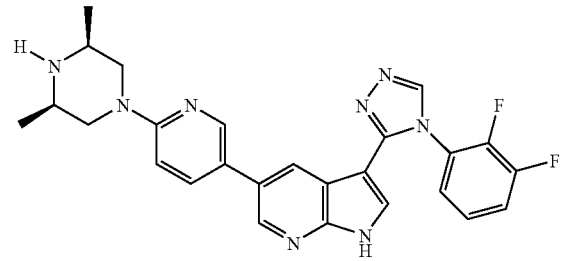

3-[4-(2,3-Difluoro-phenyl)-4H-[1,2,4]triazol-3-yl]-5-[6-(3,5-dimethyl-piperazin-1-yl)-pyridin-3-yl]-1H-pyrrolo[2,3-b]pyridine (122)

¹H NMR (500 MHz, DMSO-d6) δ: 12.20 (s, 1H), 9.12 (br, 1H), 8.90 (s, 1H), 8.61 (d, 1H), 8.56 (d, 1H), 8.50 (d, 1H), 8.01 (dd, 1H), 7.75 (dd, 1H), 7.59 (dd, 1H), 7.48 (m, 1H), 7.17 (d, 1H), 7.08 (d, 1H), 4.54 (d, 2H), 3.38 (br, 2H), 2.85 (dd, 2H), 1.31 (d, 6H). LC/MS: Rt 1.70 mins.; m/e 487.3 (M+H).

Example 129

5'-{3-[4-(2,3-Difluoro-phenyl)-4H-[1,2,4]triazol-3-yl]-1H-pyrrolo[2,3-b]pyridin-5-yl}-4-pyrrolidin-1-yl-3,4,5,6-tetrahydro-2H-[1,2']bipyridinyl (123)

¹H NMR (500 MHz, DMSO-d6) δ: 12.16 (s, 1H), 9.53 (br, 1H), 8.87 (s, 1H), 8.59 (d, 1H), 8.55 (d, 1H), 8.47 (d, 1H), 7.95 (dd, 1H), 7.75 (m, 1H), 7.59 (m, 1H), 7.48 (m, 1H), 7.10 (d, 1H), 7.05 (d, 1H), 4.48 (d, 2H), 3.55 (m, br, 2H), 3.43 (m, 1H), 3.11 (m, br, 2H), 2.92 (t, 2H), 2.14 (d, 2H), 2.05 (m, br, 2H), 1.85 (m, 2H), 1.59 (m, 2H). LC/MS: Rt 1.40 mins.; m/e 527.3 (M+H).

Example 130

(5-{3-[4-(2,3-Difluoro-phenyl)-4H-[1,2,4]triazol-3-yl]-1H-pyrrolo[2,3-b]pyridin-5-yl}-pyridin-2-yl)-(tetrahydro-furan-2-ylmethyl)-amine (124)

¹H NMR (500 MHz, DMSO-d6) δ: 12.22 (s, 1H), 8.88 (s, 1H), 8.61 (m, 2H), 8.26 (s, 1H), 8.18 (d, br, 1H), 7.76 (m, 1H), 7.59 (m, 1H), 7.49 (m, 1H), 7.14 (d, br, 1H), 7.06 (d, 1H), 4.06 (m, 1H), 3.80 (m, 1H), 3.70 (dd, 1H), 3.56 (dd, 1H), 3.42 (dd, 1H), 2.02 (m, 1H), 1.87 (m, 2H), 1.61 (m, 1H). LC/MS: Rt 1.90 mins.; m/e 474.3 (M+H).

Example 131

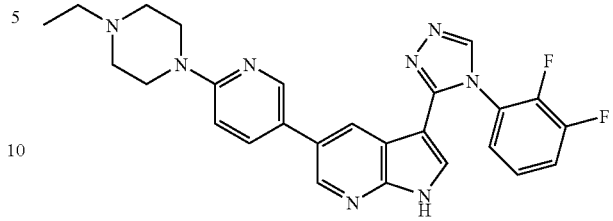

3-[4-(2,3-Difluoro-phenyl)-4H-[1,2,4]triazol-3-yl]-5-[6-(4-ethyl-piperazin-1-yl)-pyridin-3-yl]-1H-pyrrolo[2,3-b]pyridine (125)

¹H NMR (500 MHz, DMSO-d6) δ: 12.17 (s, 1H), 9.62 (br, 1H), 8.88 (s, 1H), 8.61 (d, 1H), 8.56 (d, 1H), 8.52 (d, 1H), 8.00 (dd, 1H), 7.75 (m, 1H), 7.59 (m, 1H), 7.48 (m, 1H), 7.13 (d, 1H), 7.06 (d, 1H), 4.50 (d, br, 2H), 3.61 (d, br, 2H), 3.21 (m, br, 4H), 3.09 (q, 2H), 1.27 (t, 3H). LC/MS: Rt 1.7 mins.; m/z 487.3 (M+H), 485.4 (M−H)

Example 132

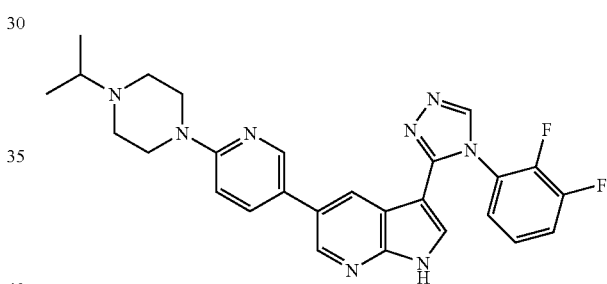

3-[4-(2,3-Difluoro-phenyl)-4H-[1,2,4]triazol-3-yl]-5-[6-(4-isopropyl-piperazin-1-yl)-pyridin-3-yl]-1H-pyrrolo[2,3-b]pyridine (126)

¹H NMR (500 MHz, DMSO-d6) δ:12.16 (s, 1H), 9.45 (br, 1H), 8.87 (s, 1H), 8.61 (d, 1H), 9.57 (d, 1H), 8.52 (d, 1H), 7.99 (dd, 1H), 7.75 (m, 1H), 7.58 (m, 1H), 7.48 (m, 1H), 7.12 (d, 1H), 7.05 (d, 1H), 4.53 (d, br, 2H), 3.57 (d, br, 2H), 3.16 (m, 5H), 1.30 (d, 6H). LC/MS: Rt 1.70 mins.; m/z 501.3 (M+H), 499.4 (M−H).

Example 133

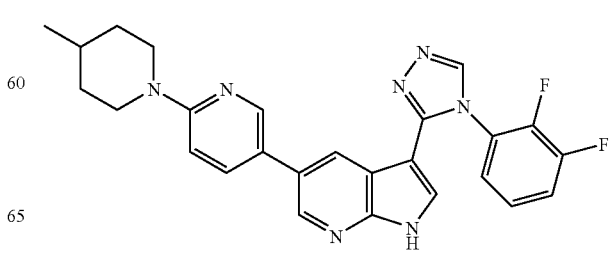

5'-{3-[4-(2,3-Difluoro-phenyl)-4H-[1,2,4]triazol-3-yl]-1H-pyrrolo[2,3-b]pyridin-5-yl}-4-methyl-3,4,5,6-tetrahydro-2H-[1,2']bipyridinyl (127)

¹H NMR (500 MHz, DMSO-d6) δ: 12.21 (s, 1H), 8.88 (s, 1H), 8.62 (d, 1H), 8.58 (d, 1H), 8.33 (d, 1H), 8.15 (d, br, 1H), 7.74 (m, 1H), 7.59 (m, 1H), 7.48 (m, 1H), 7.32 (d, br, 1H), 7.08 (d, 1H), 4.27 (d, br, 2H), 3.09 (t, br, 2H), 1.76 (d, br, 2H), 1.72 (m, 1H), 1.21 (m, 2H), 0.93 (d, 3H). LC/MS: Rt 2.30 mins.; m/z 472.3 (M+H), 470.4 (M–H)

Example 134

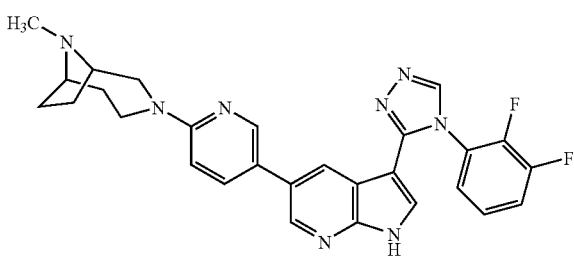

3-(5-{3-[4-(2,3-Difluoro-phenyl)-4H-[1,2,4]triazol-3-yl ]-1H-pyrrolo[2,3-b]pyridin-5-yl}-pyridin-2-yl)-9-methyl-3,9-diaza-bicyclo[4.2.1]nonane (128)

¹H NMR (500 MHz, DMSO-d6) δ: 12.13 (s, 1H), 9.75 (br, 1H), 8.87 (s, 1H), 8.59 (d, 1H), 8.55 (d, 1H), 8.43 (d, 1H), 7.93 (dd, 1H), 7.75 (m, 1H), 7.59 (m, 1H), 7.48 (m, 1H), 7.03 (d, 1H), 7.01 (d, 1H), 4.47 (d, br, 2H), 4.10 (br, 1H), 3.98 (m, br, 2H), 3.65 (dd, br, 1H), 2.87 (d, 3H), 2.42-1.90 (complex, 8H). LC/MS: Rt 1.60 mins.; 513.3 (M+H), 511.4 (M–H).

Example 135

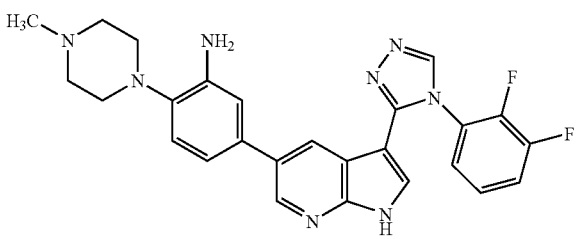

5-{3-[4-(2,3-Difluoro-phenyl)-4H-[1,2,4]triazol-3-yl]-1H-pyrrolo[2,3-b]pyridin-5-yl}-2-(4-methyl-piperazin-1-yl)-phenylamine (129)

¹H NMR (500 MHz, DMSO-d6) δ: 12.12 (s, 1H), 9.88 (br, 1H), 8.87 (s, 1H), 8.64 (d, 1H), 8.56 (d, 1H), 7.95 (s, 1H), 7.77 (dd, 1H), 7.60 (dd, 1H), 7.49 (m, 1H), 7.18 (d, 1H), 7.11 (d, 1H), 7.04 (d, 1H), 7.00 (d, 1H), 3.56 (d, br, 2H), 3.30 (m, 4H), 2.97 (t, 2H), 2.50 (s, 3H). LC/MS: Rt 1.70 mins.; m/e 487.3 (M+H).

Example 136

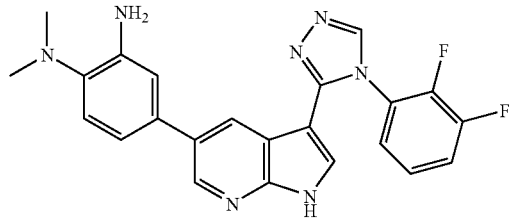

4-{3-[4-(2,3-Difluoro-phenyl)-4H-[1,2,4]triazol-3-yl]-1H-pyrrolo[2,3-b]pyridin-5-yl}-N¹,N¹-dimethyl-benzene-1,2-diamine (130)

¹H NMR (500 MHz, DMSO-d6) δ: 12.18 (s, 1H), 8.90 (s, 1H), 8.68 (d, 1H), 8.64 (d, 1H), 7.78 (m, 1H), 7.62 (m, 1H), 7.55 (d, 1H), 7.49 (m, 1H), 7.40 (d, 1H), 7.31 (d, 1H), 7.04 (d, 1H), 3.01 (s, 6H). LC/MS: Rt 1.90 mins.; m/e 432.3 (M+H).

Example 137

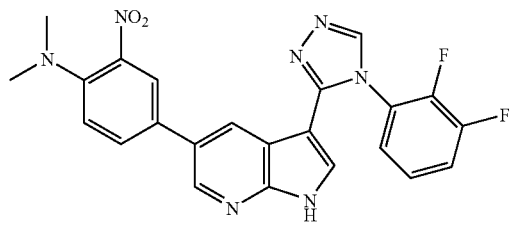

(4-{3-[4-(2,3-Difluoro-phenyl)-4H-[1,2,4]triazol-3-yl]-1H-pyrrolo[2,3-b]pyridin-5-yl}-2-nitro-phenyl)-dimethyl-amine (131)

¹H NMR (500 MHz, DMSO-d6) δ: 12.17 (s, 1H), 8.88 (s, 1H), 8.64 (s, 1H), 8.57 9s, 1H), 8.07 (s, 1H), 7.88 (d, 1H), 7.75 (m, 1H), 7.59 (m, 1H), 7.48 (m, 1H), 7.32 (d, 1H), 7.07 (s, 1H), 2.89 (s, 6H). LC/MS: Rt 3.30 mins.; m/e 462.3 (M+H).

General Method H:

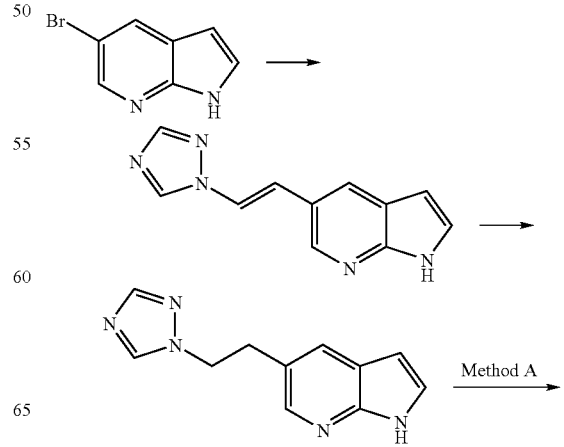

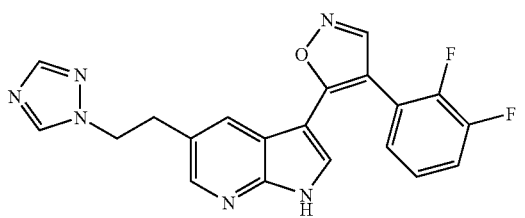

Example 138

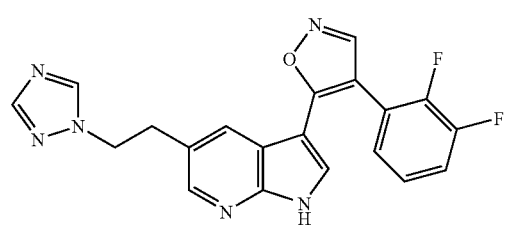

3-[4-(2,3-Difluoro-phenyl)-isoxazol-5-yl]-5-(2-[1,2,4]triazol-1-yl-ethyl)-1H-pyrrolo[2,3-b]pyridine (132)

The crude product obtained above (200 mg, 0.94 mmol) was converted to 3-[4-(2,3-difluoro-phenyl)-isoxazol-5-yl]-5-(2-[1,2,4]triazol-1-yl-ethyl)-1H-pyrrolo[2,3-b]pyridine (108 mg, 0.27 mmol) using Method A.

$^1$H NMR (500 MHz, DMSO-d6) δ: 12.28 (s, 1H), 8.84 (s, 1H), 8.29 (s, 1H), 8.05 (d, J=2 Hz, 1H), 7.95 (s, 1H), 7.69 (d, overlap, 2H), 7.52 (m, 1H), 7.31 (m, 2H), 4.40 (t, J=7.25 Hz, 2H), 3.17 (t, J=7.25 Hz, 2H). LC/MS: Rt 3.1 mins.; 393 (M+H), 391.1 (M−H).

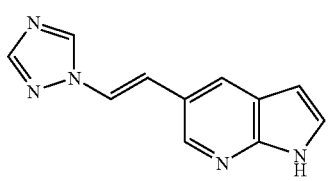

5-(2-[1,2,4]Triazol-1-yl-vinyl)-1H-pyrrolo[2,3-b]pyridine

A mixture of 5-bromo-azaindole (1 g, 5.1 mmol), 1-vinyl-triazole (600 mg, 6.3 mmol), and triethylamine (5 mL) was dissolved in DMF (25 mL). The solution was treated with N2 gas and PdCl2(dppf) (250 mg, 0.3 mmol) was added. The reaction was heated with stirring at 120° C. for 16 h and evaporated under vacuum. The residue DMF solution was poured into water, filtered, the solid was washed with ether. After drying on the pump for overnight, the crude solid was used for the next reaction directly (800 mg, 3.8 mmol). MS (ES+): m/e=212.1 (M+H); LC: 2.2 min.

Example 139

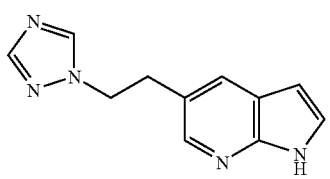

5-(2-[1,2,4]Triazol-1-yl-ethyl)-1H-pyrrolo[2,3-b]pyridine

A crude material from above (300 mg, 1.42 mmol) was dissolved in MeOH (15 mL). The solution was treated with hydrogen balloon in the presence of Pd/C (10%, 50 mg) for 4 h. The catalyst was removed by filtration through celite, the solvent was evaporated, and the residue (200 mg, 0.94 mmol) was dried on the pump for the next use. MS (ES+): m/e=214.1 (M+H); LC: 0.5 min.

Example 140

Example 141

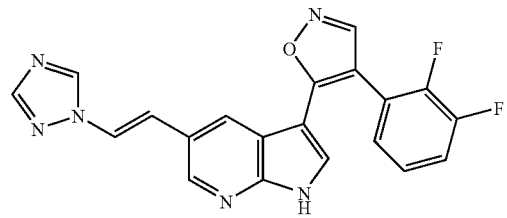

3-[4-(2,3-Difluoro-phenyl)-isoxazol-5-yl]-5-(2-[1,2,4]triazol-1-yl-vinyl)-1H-pyrrolo[2,3-b]pyridine (133)

$^1$H NMR (500 MHz, DMSO-d6) δ: 12.48 (s, 1H), 8.88 (s, 1H), 8.84 (s, 1H), 8.57 (d, 1H), 8.18 (s, 1H), 8.15 (d, 1H), 8.02 (d, 1H), 7.75 (d, 1H), 7.54 (m, 1H), 7.36 (d, 1H), 7.35 (m, overlap, 2H). LC/MS: Rt 3.4 mins.; m/e 390.9 (M+H), 389.1 (M−H).

General Method I:

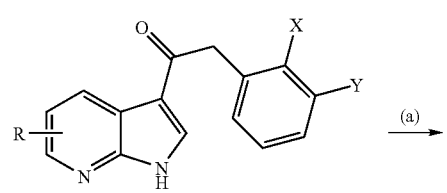

(a)

-continued

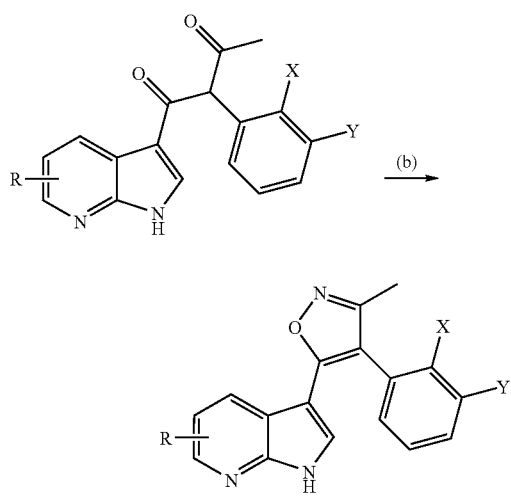

Reagents and Conditions: (a) (i) LHMDS, THF, −78° C., (ii) acetyl chloride (b) hydroxylamine hydrochloride, EtOH, reflux.

Example 142

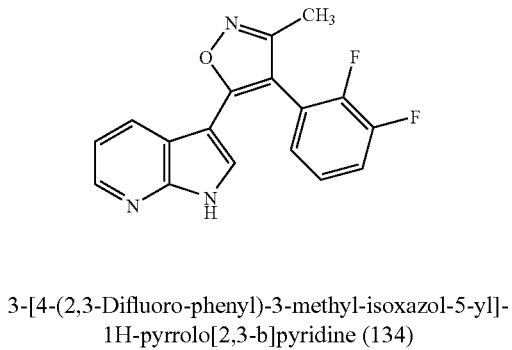

3-[4-(2,3-Difluoro-phenyl)-3-methyl-isoxazol-5-yl]-1H-pyrrolo[2,3-b]pyridine (134)

To a solution of 2-(2,3-difluoro-phenyl)-1-(1H-pyrrolo[2,3-b]pyridin-3-yl)-ethanone (200 mg, 0.73 mmol) in dry THF (5 mL) was added LiHDMS (1.0 M in THF, 2.2 mL, 2.2 mmol) at −78° C. The mixture was stirred at this temperature for 1.5 h and acetyl chloride (170 mg, 2.2 mmol) was added. The reaction was allowed to warm up to RT and continued to stir for another 2 h. The solution was then diluted with ethyl acetate and washed with 1N HCl. After evaporation, the crude product was purified by flash column to afford the desired product, which was treated with NH2OH HCl (100 mg, 1.44 mmol) in ethanol (10 mL) under reflux for 4 h to give 3-[4-(2,3-difluoro-phenyl)-3-methyl-isoxazol-5-yl]-1H-pyrrolo[2,3-b]pyridine (45 mg, 0.14 mmol) as white solid.

$^1$H NMR (500 MHz, DMSO-d6) δ: 12.29 (s, 1H), 8.33 (d, 1H), 7.92 (d, 1H), 7.55 (m, 2H), 7.35 (m, 2H) 7.16 (dd, 1H), 2.20 (s, 3H). LC/MS: Rt 3.3 mins.; m/e 312.1 (M+H), 310.1 (M−H).

Example 143

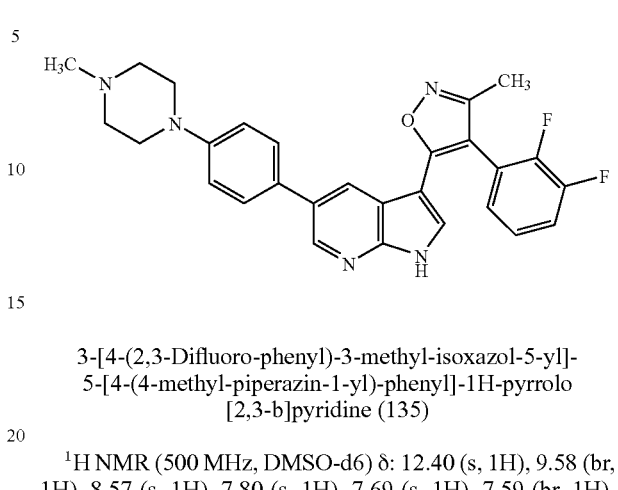

3-[4-(2,3-Difluoro-phenyl)-3-methyl-isoxazol-5-yl]-5-[4-(4-methyl-piperazin-1-yl)-phenyl]-1H-pyrrolo[2,3-b]pyridine (135)

$^1$H NMR (500 MHz, DMSO-d6) δ: 12.40 (s, 1H), 9.58 (br, 1H), 8.57 (s, 1H), 7.80 (s, 1H), 7.69 (s, 1H), 7.59 (br, 1H), 7.45 (d, 2H), 7.38 (s, 1H), 7.12 (d, 2H), 3.94 (d, 2H), 3.55 (d, 2H), 3.17 (m, 2H), 3.02 (m, 2H), 2.89 (s, 3H), 2.31 (s, 4H), 2.21 (s, 3H). LC/MS: Rt 2.4 mins.; 486.3 (M+H), 484.4 (M−H).

General Method J:

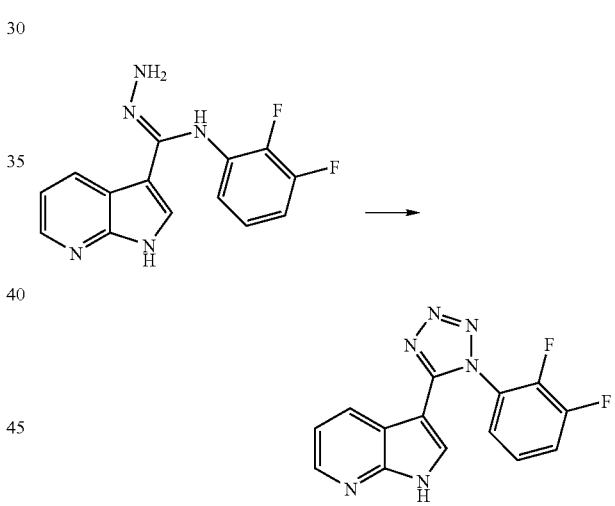

Example 144

3-[1-(2,3-Difluoro-phenyl)-1H-tetrazol-5-yl]-1H-pyrrolo[2,3-b]pyridine (11)

N-(2,3-Difluoro-phenyl)-N'-amino-1H-pyrrolo[2,3-b]pyridine-3-carboxamidine (prepared by using procedures described in Method G) (20 mg, 0.07 mmol) was dissolved in 2N HCl (2 mL)). A solution of NaNO$_2$ (6 mg) in water (1 mL) was added at 0° C. The mixture was stirred at 0° C. for 30 min and neutralized with 6N NaOH. The precipitate was collected by filtration and the crude product was purified by HPLC to afford a white solid (12 mg, 0.04 mmol).

$^1$H NMR (500 MHz, DMSO-d6) δ: 12.47 (s, 1H), 8.49 (dd, 1H), 8.40 (dd, 1H), 7.89 (m, 1H), 7.76 (m, 1H), 7.58 (m, 1H), 7.35 (d, 1H), 7.31 (dd, 1H). LC/MS: Rt 3.00 mins.; m/e 299 (M+H), 297.1 (M−H).

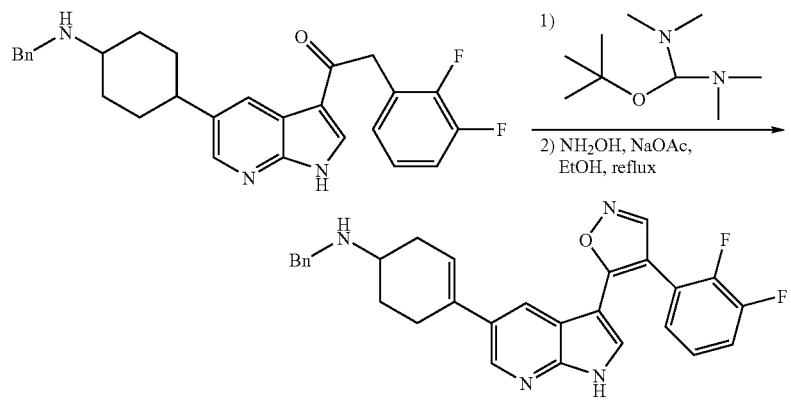
Preparation of Benzyl-(4-{3-[4-(2,3-difluoro-phenyl)-isoxazol-5-yl]-1H-pyrrolo[2,3-b]pyridin-5-yl}-cyclohex-3-enyl)-amine (11)
-continued
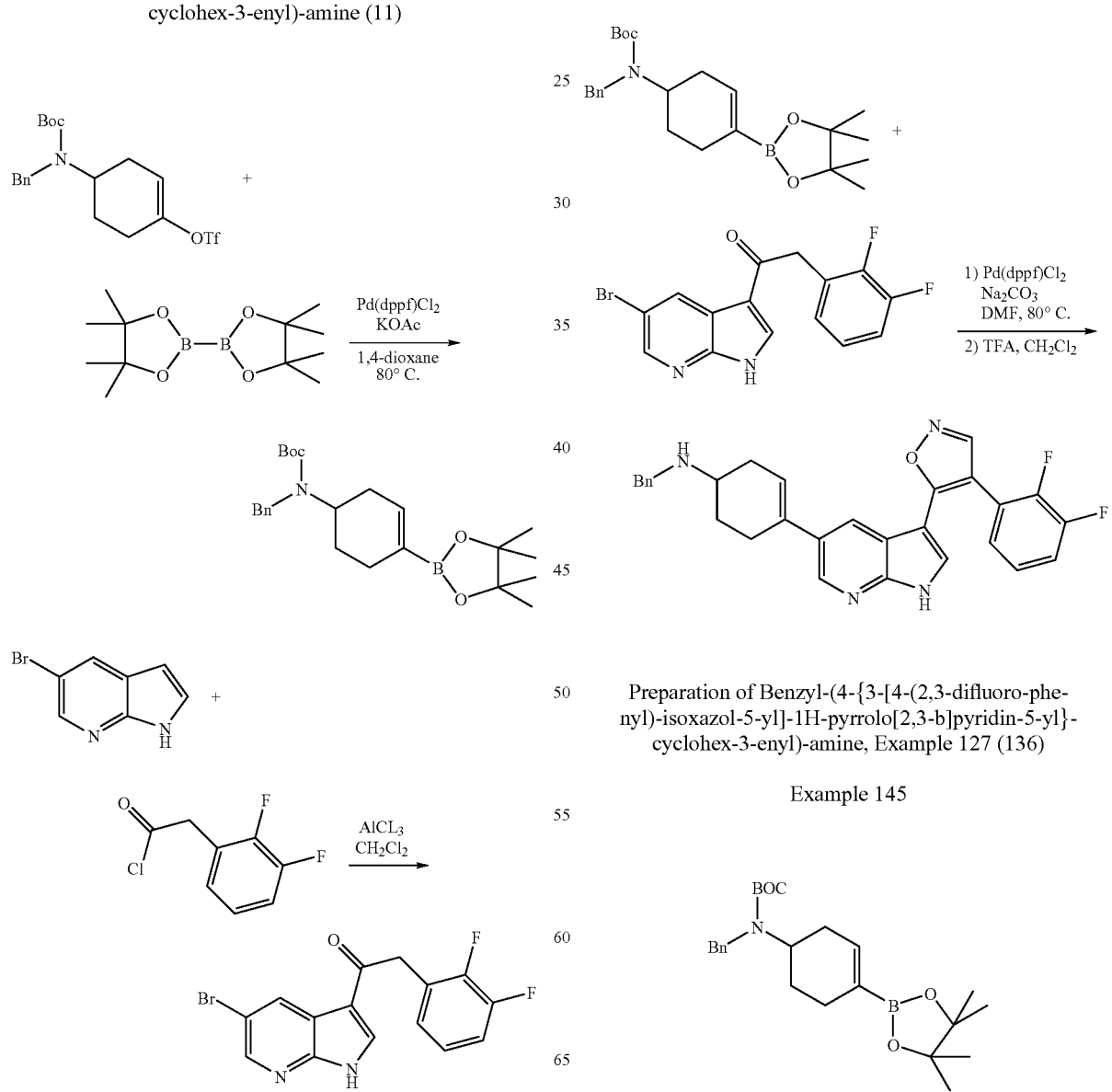
Preparation of Benzyl-(4-{3-[4-(2,3-difluoro-phenyl)-isoxazol-5-yl]-1H-pyrrolo[2,3-b]pyridin-5-yl}-cyclohex-3-enyl)-amine, Example 127 (136)
Example 145

Step A: Benzyl-[4-(4,4,5,5-tetramethyl-[1,3,2]dioxaborolan-2-yl)-cyclohex-3-enyl]-carbamic acid tert-butyl ester A mixture of 4-[benzyl(tert-butoxycarbonyl)amino]cycloexenyl trifluoromethanesulfonate (1.66 g, 3.81 mmol, prepared according to *Tetrahedron* 53 (1997) 1391-1402), bis(pinacolato)diboron (1.06 g, 4.17 mmol), KOAc (1.11 g, 11.3 mmol) and PdCl$_2$(dppf) (155 mg, 0.19 mmol) in dioxane (20 mL) was degassed at RT, stirred under N$_2$ at 80° C. for 15 hours and then concentrated. The residue was dissolved in EtOAc, and washed with water. Purification by Flash Chromatography (FC) (hexane/EtOAc 50:2 to 50:5) gave the title product (1.04 g) in 66.1% yield. FIA-MS: m/e=414.3 (M+1).

Example 146

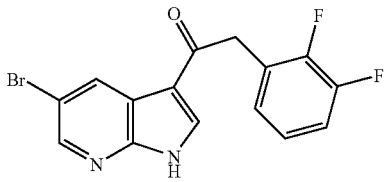

Step B: 1-(5-Bromo-1H-pyrrolo[2,3-b]pyridin-3-yl)-2-(2,3-difluoro-phenyl)-ethanone 2,3-Difluorophenylacetyl chloride(58.1 mmol) in CH$_2$Cl$_2$ (150 ml)was added to a suspension of 5-bromo-1H-pyrrolo[2,3-b]pyridine (8.0 g, 40.6 mmol) and AlCl$_3$ (46 g, 345 mmol) in CH$_2$Cl$_2$ (100 ml) at 0° C. After the addition, the cooling bath was removed and the reaction mixture was stirred at room temperature for 1.5 hrs. The reaction was cooled with ice-bath and methanol (100 ml) was added to the reaction mixture while maintaining the temperature below 30° C. The reaction mixture was evaporated and the residue was suspended in water. The solid was collected by vacuum filtration, washed with water and hexane to give the title compound (14.03 g) in 98% yield.

$^1$H-NMR (500 MHZ, CDCl$_3$): 10.93 (br.s, 1H), 8.95 (s, 1H), 8.39 (s, 1H), 8.10 (s, 1H), 7.01 (m, 3H), 4.16 (s, 2H).

Example 147

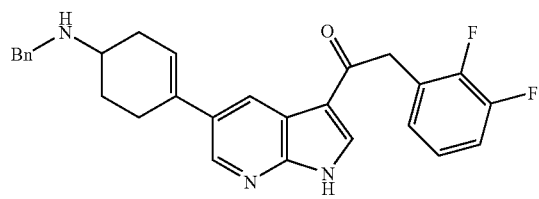

Step C: 1-[5-(4-Benzylamino-cyclohexyl)-1H-pyrrolo[2,3-b]pyridin-3-yl]-2-(2,3-difluoro-phenyl)-ethanone A mixture of benzyl-[4-(4,4,5,5-tetramethyl-[1,3,2]-dioxa-borolan-2-yl)-cyclohex-3-enyl]-carbamic acid tert-butyl ester (820 mg, 1.98 mmol from a)) and 1-(5-Bromo-1H-pyrrolo[2,3-b]pyridin-3-yl)-2-(2,3-difluoro-phenyl)-ethanone (702 mg, 2.0 mmol, from b)), Pd(dppf)Cl$_2$ (163 mg, 0.2 mmol), 2.0M aqueous Na$_2$CO$_3$ (2 ml, 4 mmol) in DMF (15 ml) was degassed and heated at 80° C. under N$_2$ for 3 days. The mixture was concentrated.

The residue was suspended in CH$_2$Cl$_2$, washed with saturated NH$_4$Cl. Purification by flash chromatography gave benzyl-(4-{3-[(2,3-difluoro-phenyl)-acetyl]-1H-pyrrolo[2,3-b]pyridin-5-yl}-cyclohex-3-enyl)-carbamic acid tert-butyl ester (545 mg). FIA-MS m/e=558.3(M+H), 556.3 (M−H).

A solution of the above carbamic acid tert-butyl ester (306 mg, 0.54 mmol) was dissolved in CH$_2$Cl$_2$ (1 ml), treated with TFA (3 ml) for 1 hour. The reaction was evaporated and the solid residue triturated with ether and hexane, and filtered to give the final desired product as a white solid (402 mg) in 80% overall yield. FIA-MS m/e=458.2 (M+H), 456.3 (M−H).

Example 148

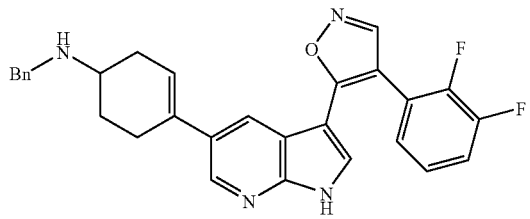

Step D: Benzyl-(4-{3-[4-(2,3-difluoro-phenyl)-isoxazol-5-yl]-1H-pyrrolo[2,3-b]pyridin-5-yl}-cyclohex-3-enyl)-amine (136)

A mixture of 1-[5-(4-benzylamino-cyclohexyl)-1H-pyrrolo[2,3-b]pyridin-3-yl]-2-(2,3-difluoro-phenyl)-ethanone (150 mg, 0.27 mmol. Preparation: see below) and t-butoxybis(dimethylamino)methane (0.27 ml, 1.0 mmol, Brederck's reagent) in THF (5 ml) was heated at 60° C. for 2 h. The reaction mixture was concentrated and dried under high vacuum for 0.5 h. The residue was dissolved in Ethanol (10 ml), refluxed with hydroxylamine hydrogen chloride (94 mg, 1.35 mmol) and sodium acetate (1.62 mmol) for 2.5 h. The mixture was concentrated and suspended in satd. NaHCO$_3$ and filtered. The solid was further purified by chromatography to give 50 mg of the desired product in 38.4% yield.

$^1$H NMR (500 MHz, DMSO-d6) δ: 12.41 (s, NH), 8.86 (s, 1H), 8.85 (m, 2H, NH2), 8.45 (d, 1H), 7.81 (d, 1H), 7.70 (d, 1H), 7.5 (m, 6H), 7.32 (m, 2H), 5.98 (br.s, 1H), 4.28 (t, 2H), 3.39 (m, 1H), 2.72 (m, 1H), 2.4 (m, 4H), 1.79 (m, 1H). LC/MS: Rt 2.62 mins.; m/e 483.3 (M+H), 481.3 (M−H).

Example 149

4-{3-[4-(2,3-Difluoro-phenyl)-isoxazol-5-yl]-1H-pyrrolo[2,3-b]pyridin-5-yl}-cyclohex-3-enylamine (137)

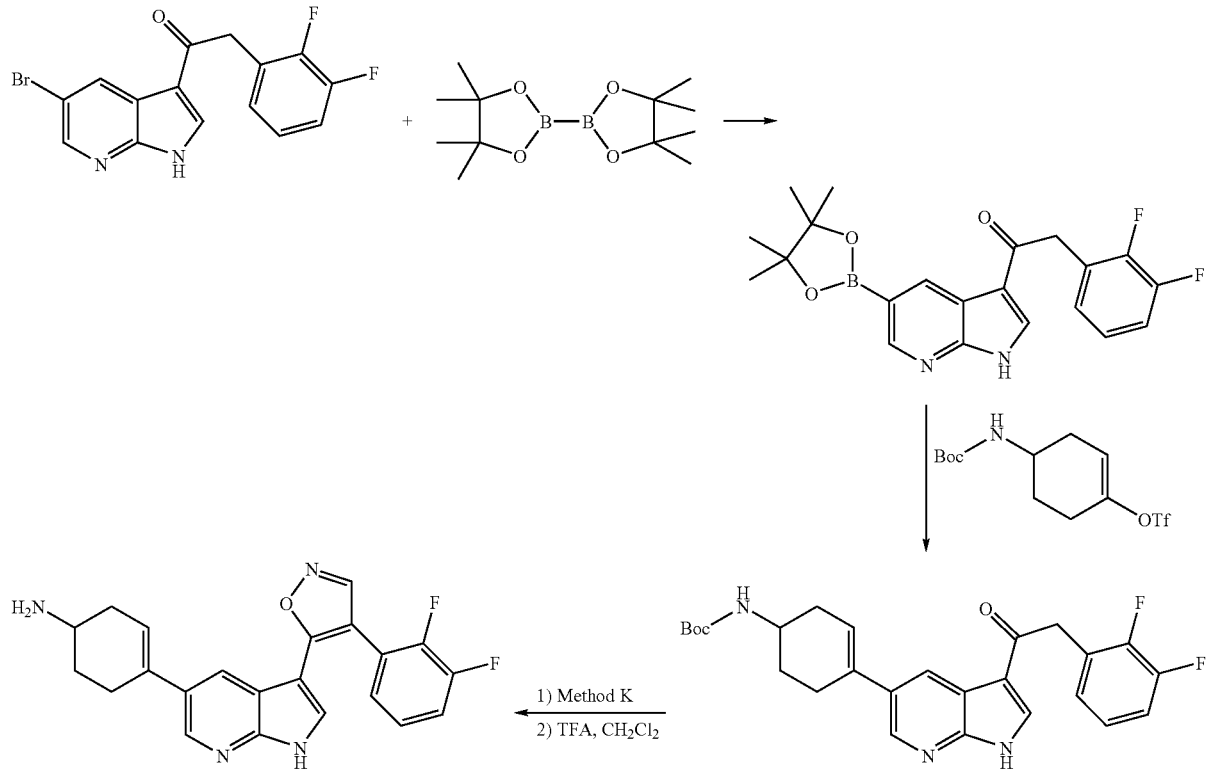

1) Method K
2) TFA, CH$_2$Cl$_2$

A suspension 1-(5-bromo-1H-pyrrolo[2,3-b]pyridin-3-yl)-2-(2,3-difluoro-phenyl)-ethanone (1.053 g, 3 mmol) and bis(pinacolato)diboron (840 mg, 3.3 mmol), PdCl$_2$(PPh$_3$)$_2$ (62 mg, 0.15 mmol) and KOAc (882 mg, 9.0 mmol) in 1,4-dioxane (18 ml) was heated at 80° C. under Argon for 3 hours, and then concentrated. The residue was suspended in water and filtration gave 1.15 g of 2-(2,3-Difluoro-phenyl)-1-[5-(4,4,5,5-tetramethyl-[1,3,2]dioxaborolan-2-yl)-1H-pyrrolo[2,3-b]pyridin-3-yl]-ethanone in 96% yield. LC-MS: m/e=399.3 (M+H), 397.3 (M−H).

To a solution of the above boronic ester (1.0 g, 2.5 mmol), trifluoro-methanesulfonic acid 4-tert-butoxycarbonylamino-cyclohex-1-enyl ester (690 mg, 2.0 mmol, prepared from (4-Oxo-cyclohexyl)-carbamic acid tert-butyl ester (Heterocycles 58 (2002) 471-504)) in a mixed solvent of DMF (15 ml) and DMSO (6 ml) was added aqueous 2.0M Na$_2$CO$_3$ (2 ml, 4 mmol) and PdCl$_2$(PPh$_3$) 2 The mixture was degassed and heated at 80° C. under Argon for 72 h, and then concentrated under high vacuum to remove DMF. The residue was suspended in aqueous NaHCO$_3$, then filtered. The solid was purified for FC to give (4-{3-[(2,3-difluoro-phenyl)-acetyl]-1H-pyrrolo[2,3-b]pyridin-5-yl}-cyclohex-3-enyl)-carbamic acid tert-butyl ester as a white solid (530 mg) in 56% yield, LC-MS: m/e=468.4 (M+H), 466.4 (M−H). $^1$H-NMR (500 MHz, CDCl$_3$) 13.41 (br.s, 1H), 9.23 (s, 1H), 8.44 (s, 1H), 8.38 (s, 1H), 7.09 (m, 3H), 6.24 (s, 1H), 4.56 (br. s, 1H), 4.32 (s, 2H), 3.90 (br.s, 1H), 2.63 (m, 3H), 2.13 (m, 2H), 1.28 (m, 1H), 1.49 (s, 9H).

Treatment of the above carbamic ester (330 mg, 0.7 mmol) with Bredeck's reagent followed with hydroxylamine hydrogen chloride (according to General Method K) then with TFA gave 300 mg of the final product.

$^1$H NMR (500 MHz, DMSO-d6) δ: 12.42 (s, 1H, NH), 8.86 (s, 1H), 8.43 (s, 1H), 7.90 (br.s, 3H, NH3), 7.80 (s, 1H), 7.70 (s, 1H), 7.51 (m, 1H), 7.32 (m, 2H), 5.94 (s, 1H), 3.36 (m, 1H), 2.56 (m, 1H), 2.45 (m, 2H), 2.36 (s, 3H), 2.23 (m, 1H), 2.08 (m, 1H), 1.75 (m, 1H). LC/MS: Rt 2.10 mins.; m/e 393.3 (M+H), 391.4 (M−H).

Example 150

(4-{3-[4-(2,3-Difluoro-phenyl)-isoxazol-5-yl]-1H-pyrrolo[2,3-b]pyridin-5-yl}-cyclohex-3-enyl)-dimethyl-amine (138)

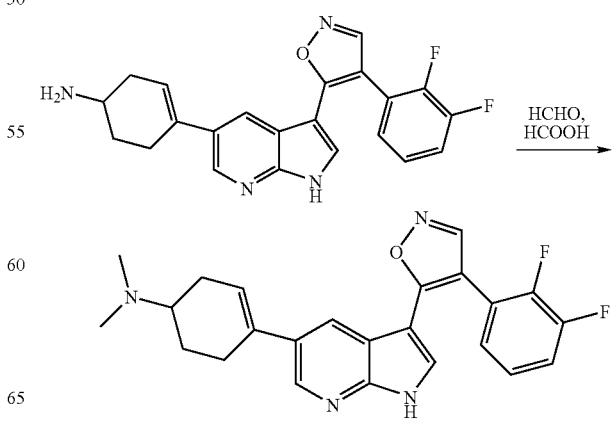

HCHO,
HCOOH

A mixture of 4-{3-[4-(2,3-Difluoro-phenyl)-isoxazol-5-yl]-1H-pyrrolo [2,3-b]pyridin-5-yl}-cyclohex-3-enylamine (47.8 mg, 0.12 mmol), 37% formaldehyde (0.5 ml) and formic acid (1 ml) was heated at 80° C. for 10 h. The mixture was concentrated and purified by HPLC to give 17.3 mg of the diamine product in 34.5% yield.

$^1$H NMR (500 MHz, DMSO-d6) δ: 12.43 (s, 1H, NH), 9.48 (s, 1H, MSOH), 8.86 (s, 1H), 8.45 (d, 1H), 7.82 (d, 1H), 7.68 (d, 1H), 7.52 (m, 1H), 7.34 (m, 1H), 7.30 (m, 1H), 5.98 (s, 1H), 3.45 (m, 1H), 3.83 (s, 3H, NCH3), 3.82 (s, 3H, NCH3), 2.7-2.4 (m, 4H), 2.31 (s, 3H, MSOH), 2.22 (m, 1H), 1.75 (m, 1H). LC/MS: Rt 2.22 mins.; m/e 421.4 (M+H), 419.4 (M−H).

Example 151

3-[4-(2,3-Difluoro-phenyl)-isoxazol-5-yl]-5-(4-morpholin-4-yl-cyclohex-1-enyl)-1H-pyrrolo[2,3-b]pyridine (139)

12 h, transferred to a solution of 4-{3-[4-(2,3-difluoro-phenyl)-isoxazol-5-yl]-1H-pyrrolo [2,3-b]pyridin-5-yl}-cyclohex-3-enylamine (50 mg, 0.12 mmol) in methanol (5 ml). The resulting solution was treated with sodium cyanoborohydride. After the reaction was completed, TFA was added, and the mixture was concentrated and purified by HPLC to give the morpholine product (20 mg) in 36% yield.

$^1$H NMR (500 MHz, DMSO-d6) δ: 12.43 (s, 1H, NH), 9.63 (br. s, MsOH), 8.86 (s, 1H), 8.46 (d, 1H), 7.82 (d, 1H), 7.69 (d, 1H), 7.51 (q, 1H), 7.34 (q, 1H), 7.29 (q, 1H), 5.99 (d, 1H), 4.05 (d, 2H), 3.72 (t, 2H), 3.56-3.48 (m, 3H), 3.18 (m, 2H), 2.61 (m, 2H), 2.44 (m, 2H), 2.33 (m, 1H), 2.32 (s, 3H, MsOH), 1.75 (ddd, 1H). LC/MS: Rt 2.22 mins.; m/e 463.4 (M+H), 461.4 (M−H).

Example 152

N-(4-{3-[4-(2,3-Difluoro-phenyl)-isoxazol-5-yl]-1H-pyrrolo[2,3-b]pyridin-5-yl}-cyclohex-3-enyl)-methanesulfonamide (140)

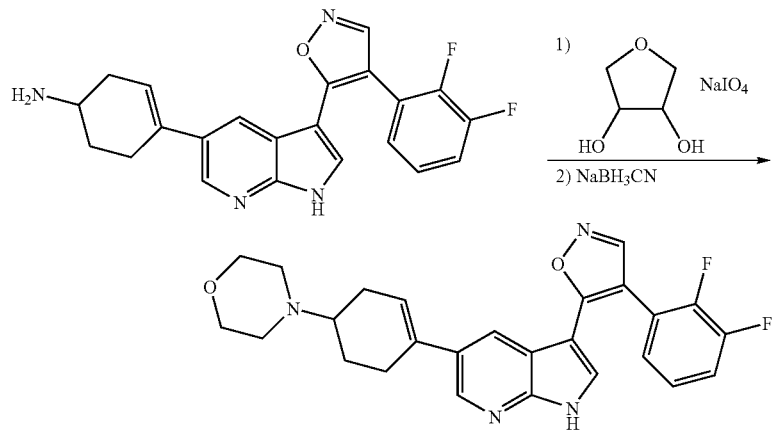
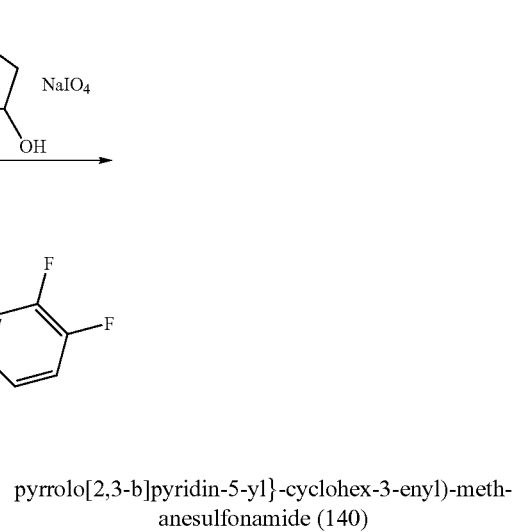

A solution of 1,4-anhydroerythritol (208 mg, 2 mmol) in water was treated with sodium periodate (400 mg, 4 mmol) for

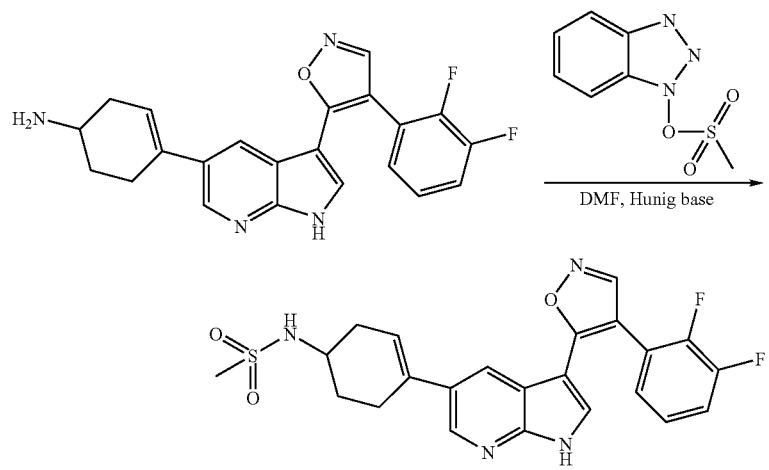

To a solution of 4-{3-[4-(2,3-Difluoro-phenyl)-isoxazol-5-yl]-1H-pyrrolo [2,3-b]pyridin-5-yl}-cyclohex-3-enylamine (47 mg, 0.12 mmol) in DMF (2 ml) was added methanesulfonic acid benzotriazol-1-yl ester (27 mg, 0.13 mmol) and Hunig base (10 drops) and stirred for 1 h. TFA was added, and the reaction mixture was purified by HPLC to give the methanesulfonamide (25.9 mg) in 46% yield.

¹H NMR (500 MHz, DMSO-d6) δ: 12.42 (s, 1H, NH), 8.86 (s, 1H), 8.42 (s, 1H), 7.82 (s, 1H), 7.63 (s, 1H), 7.53 (m, 1H), 7.31 (m, 2H), 7.09 (br.s, 1H), 5.90 (s, 1H), 3.46 (m, 1H), 2.96 (s, 3H), 2.7-2.4 (m, 3H) 2.39 (s, 3H, MsOH), 2.14 (m, 1H), 2.01 (m, 1H), 1.66 (m, 1H). LC/MS: Rt 3.38 mins.; m/e 471.3 (M+H), 469.3 (M−H).

Example 153

(4-{3-[4-(2,3-Difluoro-phenyl)-isoxazol-5-yl]-1H-pyrrol o[2,3-b]pyridin-5-yl}-cyclohexyl)-dimethylamine (141)

4.6 mmol) in CH2Cl2(15 ml) at 0° C. After the addition, the reaction was stirred for 1.5 hrs at 0° C. Methanol (5 ml) was added to the reaction. After 1 hr. the reaction was evaporated and the resulting residue purified by flash chromatography to afford 1-[5-(4-Amino-cyclohexyl)-1H-pyrrolo[2,3-b]pyridin-3-yl ]-2-(2,3-difluoro-phenyl)-ethanone (229 mg) in 70.5% yield. LC-MS: m/e=370.3 (M+H), 368.4 (M−H). After the treatment of the above cyclohexylamine (220 mg, 0.60 mmol) with 37% formaldehyde (2 ml) and formic acid (4 ml) at 80° C. for 15 h, pure 2-(2,3-Difluoro-phenyl)-1-[5-(4-dimethylamino-cyclohexyl)-1H-pyrrolo[2,3-b]pyridin-3-yl]-ethanone was obtained by FC (167 mg) in 70.1% yield. LC-MS: m/e: 398.4 (M+H), 396.4 (M−H).

The final desired product, (4-{3-[4-(2,3-difluoro-phenyl)-isoxazol-5-yl]-1H-pyrrol o[2,3-b]pyridin-5-yl}-cyclohexyl)-dimethyl-amine, was prepared according to Method K by treatment of 2-(2,3-Difluoro-phenyl)-1-[5-(4-dimethy-

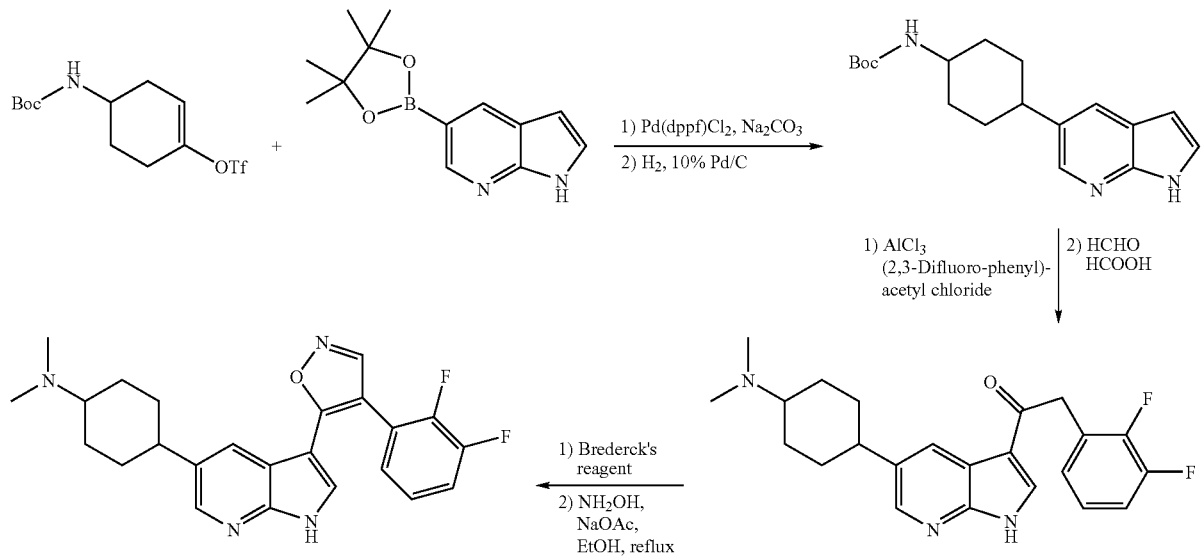

A mixture of trifluoro-methanesulfonic acid 4-tert-butoxycarbonylamino-cyclohex-1-enyl ester (730 mg, 20 mmol), 5-(4,4,5,5-tetramethyl-[1,3,2]dioxaborolan-2-yl)-1H-pyrrolo[2,3-b]pyridine (490 mg, 20 mmol), Pd(dppf)Cl₂ (80 mg) and 2.0M Na₂CO₃ (3 ml, 6 mmol) in DMF (20 ml) was heated at 80° C. under N₂ for 3 hours, and then concentrated. The residue was suspended in water, filtered and the solid was purified by FC to give [4-(1H-Pyrrolo[2,3-b]pyridin-5-yl)-cyclohex-3-enyl]-carbamic acid tert-butyl ester (600 mg) in 96% yield. FIA-MS: m/e=314.05 (M+H). A suspension of the above cyclohexene (300 mg) and 10% Pd/C (200 mg) in a 1:1 mixed solvent of EtOAc and MeOH (30 ml) was shaken under 50 psi H₂ for 20 h. Filtration gave [4-(1H-pyrrolo[2,3-b]pyridin-5-yl)-cyclohexyl]-carbamic acid tert-butyl ester (280 mg). FIA-MS: m/e=316.3 (M+H).

A solution of 2,3-difluorophenylacetyl chloride (1.0 mmol) in CH2Cl 2(3 ml) was added dropwise to a mixture of [4-(1H-pyrrolo[2,3-]pyridin-5-yl)-cyclohexyl]-carbamic acid tert-butyl ester (280 mg, 0.88 mmol) and AlCl3 (612 mg, lamino-cyclohexyl)-1H-pyrrolo[2,3-b]pyridin-3-yl]-ethanone (200 mg, 0.5 mmol) with Bredereck's reagent followed by hydroxylamine in 12.5% yield.

¹H NMR (500 MHz, DMSO-d6) δ: 12.33 (s, 1H, NH), 9.39 (br. s, OH), 8.85 (s, 1H), 8.23 (s, 1H), 7.78 (s, 1H), 7.57 (s, 1H), 7.52 (m, 1H), 7.33 (m, 2H), 3.22 (m, 1H), 2.77 (s, 6H), 2.64 (m, 1H), 2.33 (s, 3H), 2.09 (d, 2H), 1.90 (d, 2H), 1.59 (m, 2H), 1.45 (m, 2H). LC/MS: Rt 2.10 mins.; m/e 423.4 (M+H), 421.5 (M−H).

Scheme for I-142 and I-143

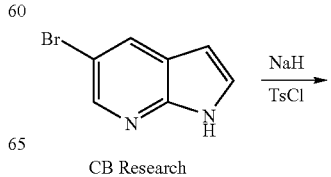

CB Research

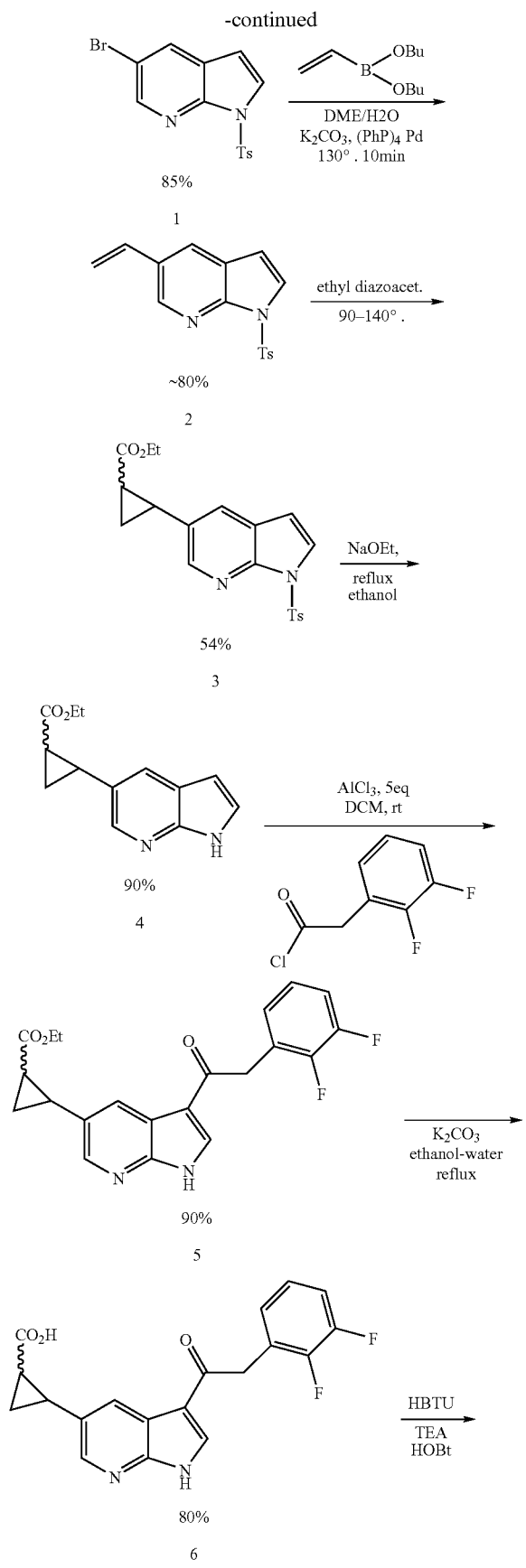
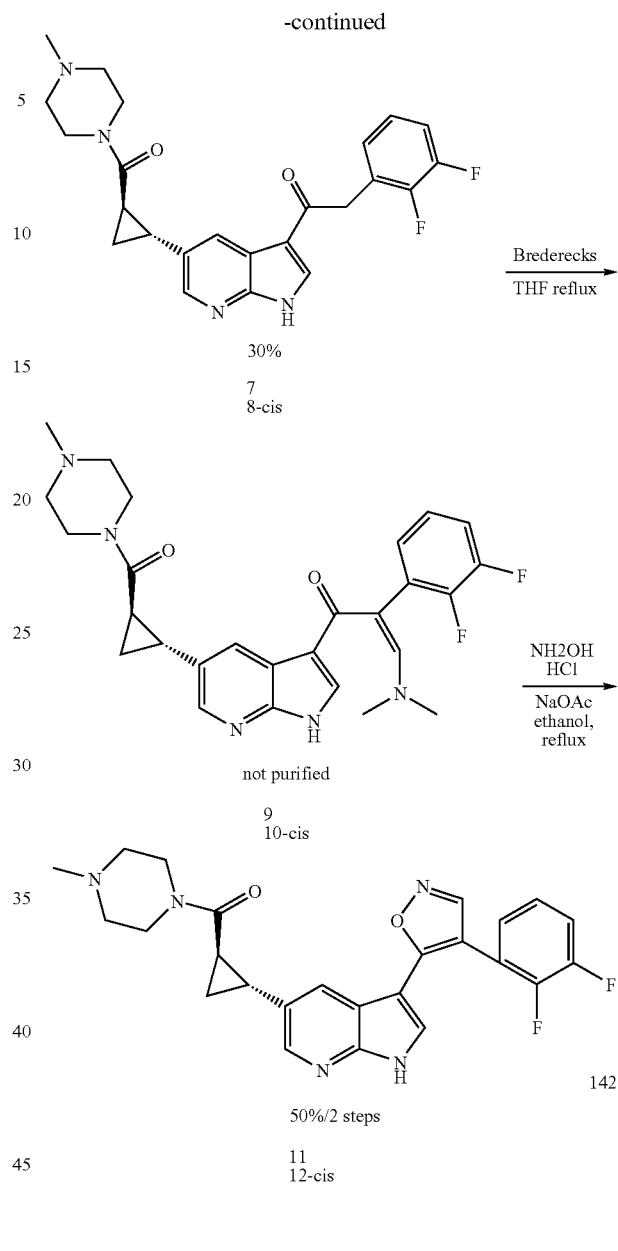

Example 154

Experimental for 5-cyclopropylazindole Compounds:

2:

1-(Toluene-4-sulfonyl)-5-vinyl-1H-pyrrolo[2,3-b]pyridine

5-Bromo-1-(toluene-4-sulfonyl)-1H-pyrrolo[2,3-b]pyridine, (300 mg, 0.85 mmol), vinylboronic acid dibutylester, (184 mg, 1.0 mmol), potassium carbonate, (420 mg, 3.0 mmol) and Pd(Ph$_3$P)$_4$ were combined in 3 mL DME and 1 mL water in a tube under nitrogen and heated in a microwave reactor to 130° C. for 10 min. The organic layer was then separated and evaporated. The residue was purified by silica chromatography (eluent: methylene chloride), affording 215 mg(85%) 1-(Toluene-4-sulfonyl)-5-vinyl-1H-pyrrolo[2,3-b]pyridine. MS ES+ 299.0.

3:

2-[1-(Toluene-4-sulfonyl)-1H-pyrrolo[2,3-b]pyridin-5-yl]-cyclopropanecarboxylic acid ethyl ester 1-(Toluene-4-sulfonyl)-5-vinyl-1H-pyrrolo[2,3-b]pyridine, (200 mg, 0.67 mmol), and ethyl diazoacetate, (730 μL, 7.0 mmol), were combined in 3 mL xylene and heated to 95° C. for 30 min, then to 115° C. for 4 hours. The solvent was evaporated onder vacuum and the residue purified by silica chromatography, (eluent: methylene chloride), affording 140 mg, (50%), 2-[1-(Toluene-4-sulfonyl)-1H-pyrrolo[2,3-b]pyridin-5-yl]-cyclopropanecarboxylic acid ethyl ester as a mixture of cis and trans isomers. MS ES+385.3.

4:

2-(1H-Pyrrolo[2,3-b]pyridin-5-yl)-cyclopropanecarboxylic Acid Ethyl Ester

2-[1-(Toluene-4-sulfonyl)-1H-pyrrolo[2,3-b]pyridin-5-yl]-cyclopropanecarboxylic acid ethyl ester, (153 mg, 0.4 mmol), was added to 2 mL ethanol and sodium ethoxide solution, (~2.68M, 300 μL, 0.8 mmol), was added. The mixture was heated to 70° C. for 3 hours. The mixture was cooled to rt and several mL sat. ammonium chloride solution were added. The mixture was extracted with dichloromethane and the organic layers evaporated affording 85 mg essentially pure 2-(1H-Pyrrolo[2,3-b]pyridin-5-yl)-cyclopropanecarboxylic acid ethyl ester, which was used without further purification. MS ES+231.1.

5:

2-{3-[(2,3-Difluoro-phenyl)-acetyl]-1H-pyrrolo[2,3-b]pyridin-5-yl}-cyclopropanecarboxylic Acid Ethyl Ester Was prepared from 2-(1H-Pyrrolo[2,3-b]pyridin-5-yl)-cyclopropanecarboxylic acid ethyl ester using a procedure similar to those described previously in this document. MS ES+385.2.

6:

2-{3-[(2,3-Difluoro-phenyl)-acetyl]-1H-pyrrolo[2,3-b]pyridin-5-yl}-cyclopropanecarboxylic Acid 2-{3-[(2,3-Difluoro-phenyl)-acetyl]-1H-pyrrolo[2,3-b]pyridin-5-yl}-cyclopropanecarboxylic acid ethyl ester, (130 mg, 0.33 mmol, was dissolved in 1 mL ethanol and 1 mL 10% potassium carbonate solution. The mixture was heated to reflux for ~16 hours. The reaction was then acidified with 6N HCl to a pH ~4-5 and extracted with dichloromethane. The essentially pure 2-{3-[(2,3-Difluoro-phenyl)-acetyl]-1H-pyrrolo[2,3-b]pyridin-5-yl}-cyclopropanecarboxylic acid was used without further purification in the next step. MS ES+ 357.

7(trans) and 8(cis):

2-(2,3-Difluoro-phenyl)-1-{5-[2-(4-methyl-piperazine-1-carbonyl)-cyclopropyl]-1H-pyrrolo[2,3-b]pyridin-3-yl}-ethanone 2-{3-[(2,3-Difluoro-phenyl)-acetyl]-1H-pyrrolo[2,3-b]pyridin-5-yl}-cyclopropanecarboxylic acid, (93 mg, 0.26 mmol), was combined with DIEA, (67 mg, 0.52 mmol), and HBTU, (113 mg, 0.3 mmol) in 1 mL DMF and stirred at rt for ~15 min. Then N-methyl piperazine, (26 mg, 0.26 mmol), was added and the reaction stirred at rt for 4 hours. The DMF was evaporated under vacuum, water added and the suspension extracted with dichloromethane. The solvent was evaporated under vacuum and the residue purified by silica chromatography, (eluent: 5% methanol/DCM), affording trans-2-(2,3-Difluoro-phenyl)-1-{5-[2-(4-methyl-piperazine-1-carbonyl)-cyclopropyl]-1H-pyrrolo[2,3-b]pyridin-3-yl}-ethanone, (35 mg, Rf 0.5) and the cis isomer (16 mg, Rf 0.3).

9:

trans-2-(2,3-Difluoro-phenyl)-3-dimethylamino-1-{5-[2-(4-methyl-piperazine-1-carbonyl)-cyclopropyl]-1H-pyrrolo[2,3-b]pyridin-3-yl}-propenone trans-2-(2,3-Difluoro-phenyl)-3-dimethylamino-1-{5-[2-(4-methyl-piperazine-1-carbonyl)-cyclopropyl]-1H-pyrrolo[2,3-b]pyridin-3-yl}-propenone was prepared from trans-2-(2,3-Difluoro-phenyl)-1-{5-[2-(4-methyl-piperazine-1-carbonyl)-cyclopropyl]-1H-pyrrolo[2,3-b]pyridin-3-yl}-ethanone, using a procedure similar to those described previously in this document. It was isolated, but not purified and converted directly to the corresponding isoxazole.

10:

cis-2-(2,3-Difluoro-phenyl)-3-dimethylamino-1-{5-[2-(4-methyl-piperazine-1-carbonyl)-cyclopropyl]-1H-pyrrolo[2,3-b]pyridin-3-yl}-propenone cis-2-(2,3-Difluoro-phenyl)-3-dimethylamino-1-{5-[2-(4-methyl-piperazine-1-carbonyl)-cyclopropyl]-1H-pyrrolo[2,3-b]pyridin-3-yl}-propenone was prepared from cis-2-(2,3-Difluoro-phenyl)-1-{5-[2-(4-methyl-piperazine-1-carbonyl)-cyclopropyl]-1H-pyrrolo[2,3-b]pyridin-3-yl}-ethanone, using a procedure similar to those described previously in this document. It was isolated, but not purified and converted directly to the corresponding isoxazole.

11:

trans-(2-{3-[4-(2,3-Difluoro-phenyl)-isoxazol-5-yl]-1H-pyrrolo[2,3-b]pyridin-5-yl}-cyclopropyl)-(4-methyl-piperazin-1-yl)-methanone (142)

trans-(2-{3-[4-(2,3-Difluoro-phenyl)-isoxazol-5-yl]-1H-pyrrolo[2,3-b]pyridin-5-yl}-cyclopropyl)-(4-methyl-piperazin-1-yl)-methanone (142) was prepared from trans-2-(2,3-Difluoro-phenyl)-3-dimethylamino-1-{5-[2-(4-methyl-piperazine-1-carbonyl)-cyclopropyl]-1H-pyrrolo[2,3-b]pyridin-3-yl}-propenone using a procedure similar to those described previously in this document. It was purified by prep hplc and isolated as the TFA salt. LC/MS: Rt 2.29 mins.; m/e 464.2 (M+H).

$^1$H NMR (500 MHz, MeOH-d4) δ: 8.60 (s, 1H), 8.22 (s, 1H), 7.80 (bs, 1H), 7.65 (s, 1H), 7.35 (m, 1H), 7.25 (m, 2H), 4.8-4.4 (m, 2H), 3.6-3.0 (m, 6H), 2.95 (s, 3H), 2.6 (m, 1H), 2.25 (m, 1H), 1.60 (m, 1H), 1.35 (m, 1H).

12:

cis-(2-{3-[4-(2,3-Difluoro-phenyl)-isoxazol-5-yl]-1H-pyrrolo[2,3-b]pyridin-5-yl}-cyclopropyl)-(4-methyl-piperazin-1-yl)-methanone (143)

cis-(2-{3-[4-(2,3-Difluoro-phenyl)-isoxazol-5-yl]-1H-pyrrolo[2,3-b]pyridin-5-yl}-cyclopropyl)-(4-methyl-piperazin-1-yl)-methanone (143) was prepared from cis-2-(2,3-

Difluoro-phenyl)-3-dimethylamino-1-{5-[2-(4-methyl-piperazine-1-carbonyl)-cyclopropyl]-1H-pyrrolo[2,3-b]pyridin-3-yl}-propenone using a procedure similar to those described previously in this document. It was purified by prep hplc and isolated as the TFA salt. LC/MS: Rt 2.24 mins.; m/e 464.2 (M+H)

¹H NMR (500 MHz, MeOH-d4) δ: 8.65 (s, 1H), 8.25 (bs, 1H), 8.05 (bs, 1H), 7.55 (s, 1H), 7.35 (m, 1H), 7.25 (m, 2H), 5.0-4.0 (m, 2H), 3.6-3.0 (m, 6H), 2.85 (bs, 3H), 2.75 (m, 1H), 2.45 (m, 1H), 1.75 (m, 1H), 1.45 (m, 1H).

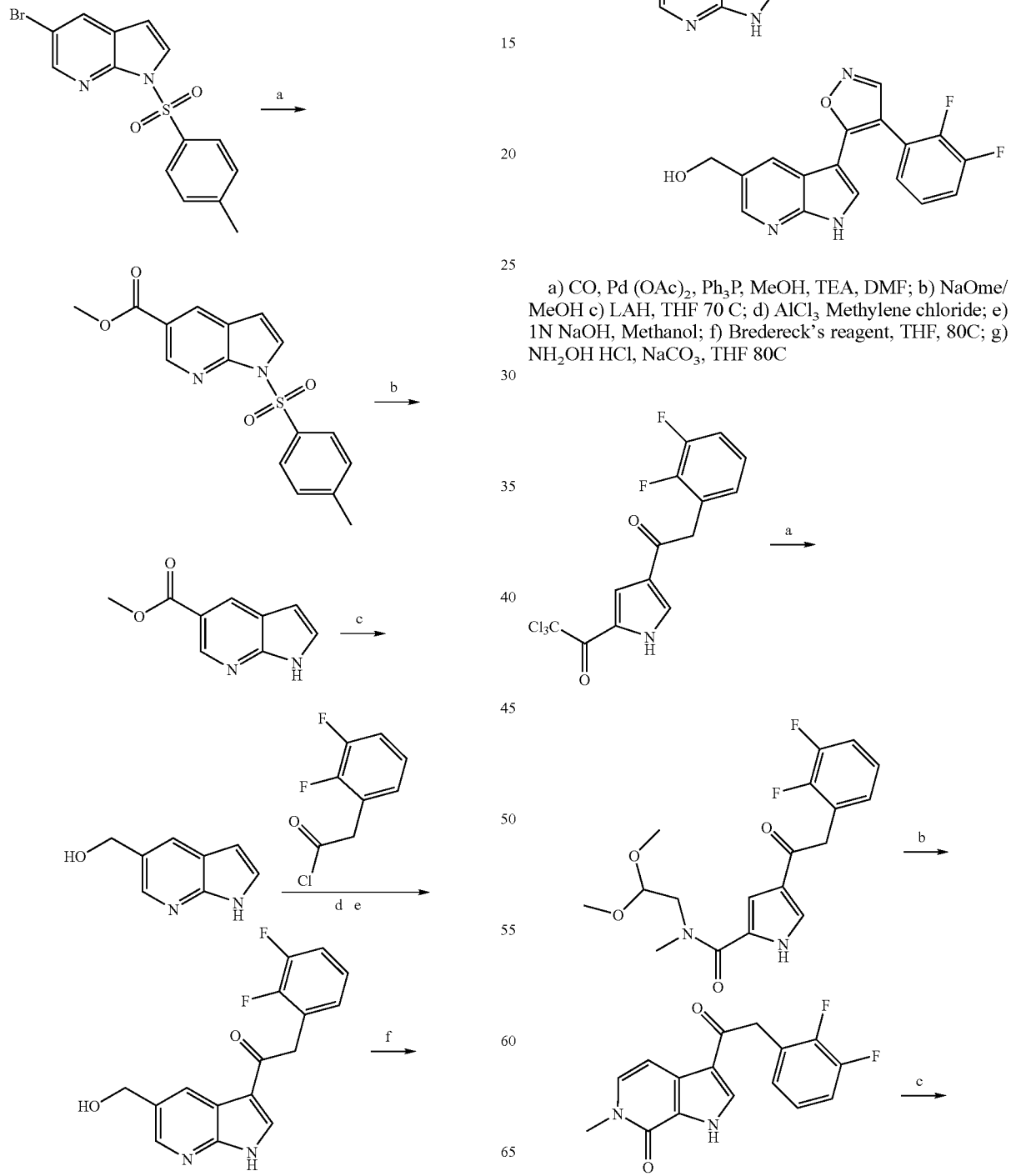

a) CO, Pd (OAc)₂, Ph₃P, MeOH, TEA, DMF; b) NaOme/MeOH c) LAH, THF 70 C; d) AlCl₃ Methylene chloride; e) 1N NaOH, Methanol; f) Bredereck's reagent, THF, 80C; g) NH₂OH HCl, NaCO₃, THF 80C -continued

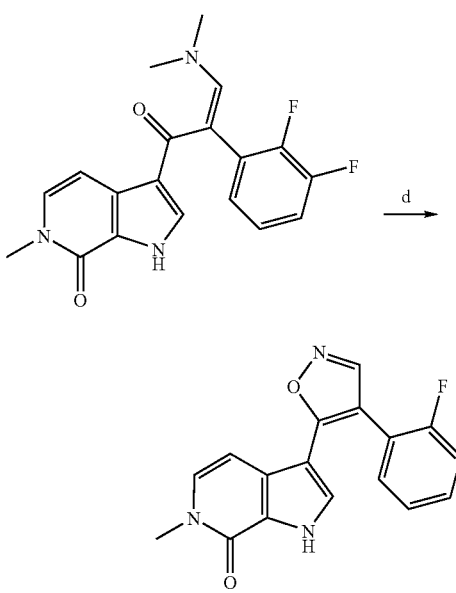

a) 1) (2,2-Dimethoxy-ethyl)-methyl-amine, 80C, acetonitrile; b) Et₂O, POCl₃; c) Bredereck's reagent, THF, 80C; d) NH₂OH HCl, NaCO₃, THF 80C.

Preparation of 3-[4-(2,3-Difluoro-phenyl)-isoxazol-5-yl]-6-methyl-1,6-dihydro-pyrrolo[2,3-c]pyridin-7-one Example 155

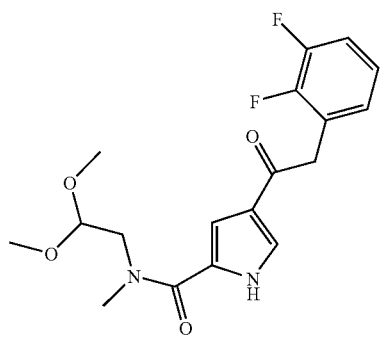

Step A: 4-[(2,3-Difluoro-phenyl)-acetyl]-1H-pyrrole-2-carboxylic Acid (2,2-dimethoxy-ethyl)-methyl-amide 2,2,2-Trichloro-1-{4-[(2,3-difluoro-phenyl)-acetyl]-1H-pyrrol-2-yl}-ethanone (300 mg, 0.82 mmol) and (2,2-Dimethoxy-ethyl)-methyl-amine (116 µL, 0.900 mmol) in acetonitrile were heated for 5 hr. Evaporation afforded 299 mg (99%) of 4-[(2,3-Difluoro-phenyl)-acetyl]-1H-pyrrole-2-carboxylic acid (2,2-dimethoxy-ethyl)-methyl-amide. ¹H NMR (500 MHz, CDCl₃) δ: 10.1-9.9 (1H, vbs), 7.02-6.96 (5H, cm), 4.51 (1H, s), 4.05 (2H, s) 3.59 (3H, bs), 3.39-3.36 (6H, s). LC/MS: Rt 3.13 mins.; m/e 367.26 (M+H), 365.34 (M−H).

Example 156

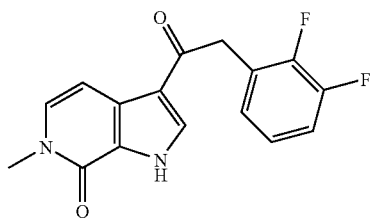

Step B: 3-[(2,3-Difluoro-phenyl)-acetyl]-6-methyl-1,6-dihydro-pyrrolo[2,3-c]pyridin-7-one To 4-[(2,3-Difluoro-phenyl)-acetyl]-1H-pyrrole-2-carboxylic acid (2,2-dimethoxy-ethyl)-methyl-amide (200 mg, 0.55 mmol) in dioxane (50 mL) was added POCl₃ (50 µL, 0.55 mmol) at 0C. The reaction solution was heated to 60C and stirred for 14 hr. The reaction was quenched with water and extracted with ethyl acetate, dried (Na₂SO₄). Flash chromatography (methylene chloride/methanol) gave 67 mg (41% yield)of title compound.
¹H NMR (500 MHz, DMSO-d6) δ: 12.8 (1H, bs), 8.34-8.33 (1H, d), 7.66-7.65 (1H, m) 7.36-7.32 (2H, cm) 7.16-7.15 (2H, m), 6.94-6.92 (1H, d), 4.35 (2H, s) 3.52 (3H, bs). LC/MS: 2.61 mins.; m/e 303.2 (M+H), 301.2 (M−H).

Example 157

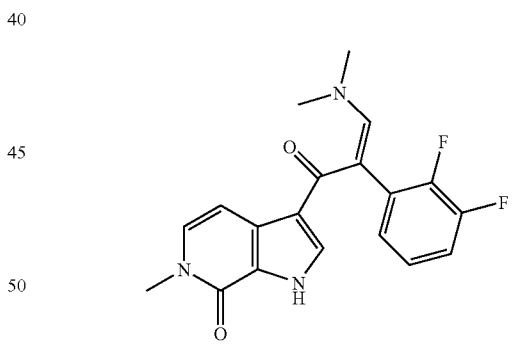

Step C: 3-[3-Dimethylamino-2-(2,3-difluoro-phenyl)-acryloyl]-6-methyl-1,6-dihydro-pyrrolo[2,3-c]pyridin-7-one To 3-[(2-Fluoro-phenyl)-acetyl]-6-methyl-1,6-dihydro-pyrrolo[2,3-c]pyridin-7-one(67 mg, 0.22 mmol) in THF (20 mL) was added Bredereck's reagent (183 µL, 0.89 mmol) and the reaction was heated to 80 C overnight. Concentration under reduced vacuum a red oil, used as obtained. LC/MS: Rt 2.32 mins.; m/e 330.3 (M⁺−27), M⁻256.3 (M−27) and Rt 2.60 m/e M− 329.3 (m−27).

Example 158

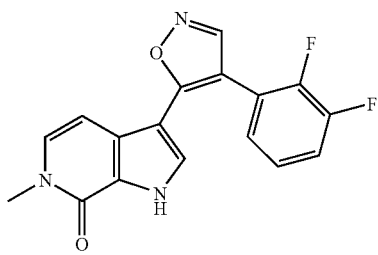

3-[4-(2,3-Difluoro-phenyl)-isoxazol-5-yl]-6-methyl-1,6-dihydro-pyrrolo[2,3-c]pyridin-7-one (144)

To 3-[3-Dimethylamino-2-(2-fluoro-phenyl)-acryloyl]-6-methyl-1, 6-dihydro-pyrrolo[2,3-c]pyridin-7-one (79 mg, 0.22 mmol) in tetrahydrofuran (20 mL) was added sodium hydrogen carbonate (19 mg, 0.0.27 mmol) and hydroxylamine Hydrochloride (23 mg, 0.27 mmol) and the mixture was heated to 80C. After 5 hr p-toluenesulfonic acid (catalytic amount) was added and the reaction mixture was heated for an additional 1 hr. The solution was cooled, diluted with ethyl acetate, washed with brine, dried (Na$_2$SO$_4$). Concentration gave an amber oil. Preparative reverse phase chromatography afforded 3-[4-(2-Fluoro-phenyl)-isoxazol-5-yl]-6-methyl-1, 6-dihydro-pyrrolo[2,3-c]pyridin-7-one (18.6 mg, 25% yield).

$^1$H NMR (500 MHz, DMSO-d6) δ: 12.37 (1H, bs), 8.85 (1H, s), 7.655-7.650 (1H, d), 7.51-7.50 (1H, q), 7.39-7.37 (1H, d), 7.34-7.28 (2H, cm), 7.09-7.06 (2H, m). LC/MS: Rt 3.21 mins.; m/e 328.1 (M+H), 326.2 (M−H).

Example 159

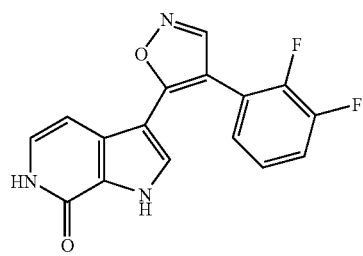

3-[4-(2,3-Difluoro-phenyl)-isoxazol-5-yl]-1,6-dihydro-pyrrolo[2,3-c]pyridin-7-one (145)

$^1$H NMR (500 MHz, DMSO-d6) δ: 12.65 (s, 0.75H), 12.31 (s, 0.25H), 11.17 (br, 0.75H), 11.09 (br, 0.25H), 9.23 (s, 0.25H), 8.82 (0.75H), 7.50 (m, 1H), 7.41 (s, 1H), 7.30 (m, 2H), 6.97 (m, 1H), 6.68 (d, 0.25H), 6.42 (d, 0.75H) LC/MS: Rt 3.06 mins.; m/z 314.1 (M+H), 312.2 (M−H)

Example 160

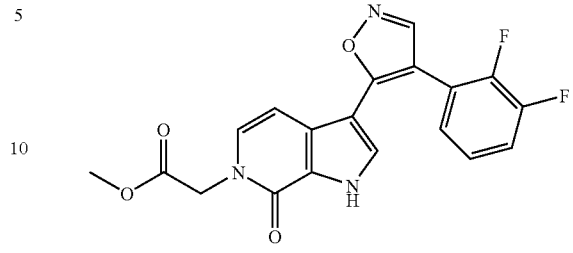

{3-[4-(2,3-Difluoro-phenyl)-isoxazol-5-yl]-7-oxo-1,7-di hydro-pyrrolo[2,3-c]pyridin-6-yl}-acetic acid methyl ester (146)

$^1$H NMR (500 MHz, DMSO-d6) δ: 12.73 (1H, bs), 8.84 (1H, s), 7.51-7.49 (H, cm), 7.464-7.468 (1H, d), 7.35-7.28 (2H, cm), 7.27-7.26 (1H, d), 6.47-6.46 (1H, d), 4.80 (2H, s), 3.68 (3H, s). LC/MS: Rt 3.21 mins.; m/z 385.91 (M+H), 384.05 (M−H)

Example 161

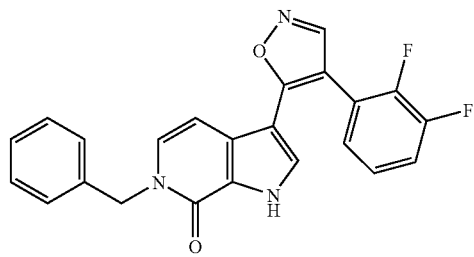

6-Benzyl-3-[4-(2,3-difluoro-phenyl)-isoxazol-5-yl]-1,6-dihydro-pyrrolo[2,3-c]pyridin-7-one (147)

$^1$H NMR (500 MHz, DMSO-d6) δ: 12.71 (1H, bs), 8.83 (1H, s), 7.53-7.47 (H, m), 7.44-7.43 (1H, d), 7.37-7.35 (1H, d), 7.34-7.24 (7H, cm), 6.49-6.47 (1H, d), 5.20 (1H, s). LC/MS: Rt 4.0 mins.; m/z 403.9 (M+H), 402.1 (M−H)

Preparation of 31

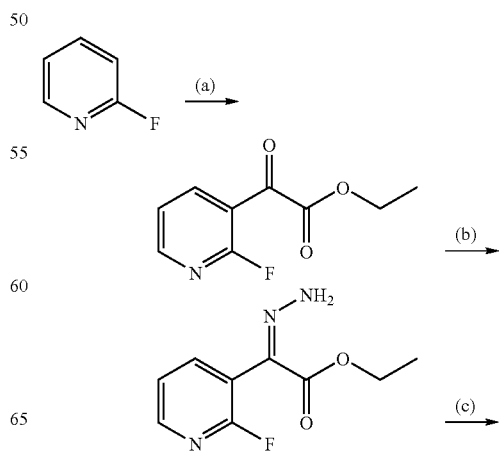

-continued

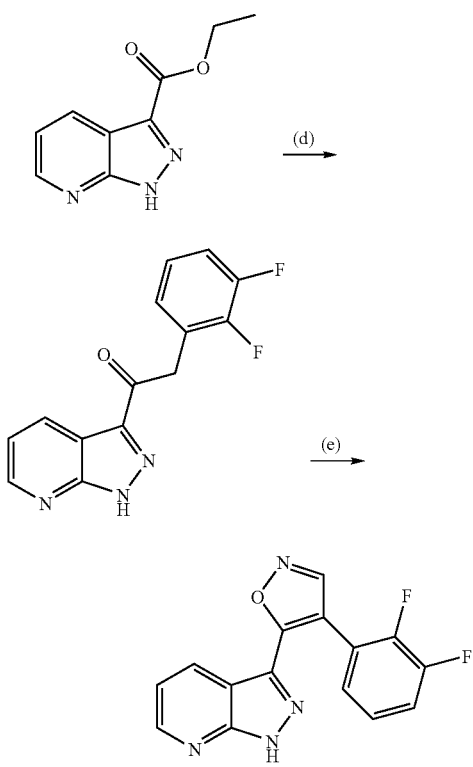

Reagents and Conditions: (a) (i) LHMDS, THF −78 C, (ii) diethyl oxalate; (b) H₂NNH₂, (i-PrO)₄T₁, CH₂Cl₂; (c) NMP, Microwave (250 C, 5 mins.); (d) LHMDS, 2,3-difluoroacetic acid, THF, 0 C; (e) (i) Bredereck's reagent, THF, reflux, (ii) hydroxylamine hydrochloride, NaOAc, THF, reflux.

3-(4-(2,3-difluorophenyl)isoxazol-5-yl)-1H-pyrazolo [3,4-b]pyridine (31)

Example 162

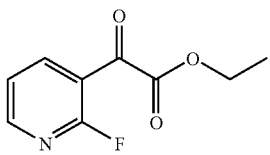

Step A: Ethyl 2-(2-fluoropyridin-3-yl)-2-oxoacetate

To a solution of 2-fluoropyridine (1.0 mL, 11.6 mmol) in THF (30 mL) at −78 under nitrogen was added a solution of lithiumdiisopropylamide in THF/heptane/ethylbenzyne. The resulting solution was allowed to stir for 1.5 hours then diethyl oxylate (1.89 mL, 13.9 mmol) was added dropwise via syringe. After 30 minutes, the resulting solution was diluted with EtOAc and washed with saturated NH4Cl then water. The organic layer was dried over MgSO4 and concentrated under vacuum to give an oil. Chromatography (20% to 30% EtOAc:hexane) gave 0.68 g (30% yield) of ethyl 2-(2-fluoropyridin-3-yl)-2-oxoacetate as an oil.

Example 163

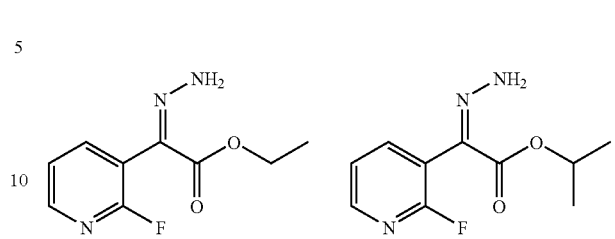

Step B: (Z)-Ethyl-2-(2fluoropyridin-3-yl)-2-hydrazonoacetate & (Z)-Isopropyl-2-(2fluoropyridin-3-yl)-2-hydrazonoacetate To a solution of ethyl 2-(2-fluoropyridin-3-yl)-2-oxoacetate (1.8 g, 9.14 mmol) in dicholromethane (25 mL) was added titanium isopropoxide (5.45 mL, 18.3 mmol) and hydrazine (0.89 mL, 18.3 mmol). The resulting yellow solution was allowed to stir at room temperature for 2.5 hours followed by the addition of water (2 mL) After 2.5 hours, the suspension was filtered through celite and washed with dichloromethane. Concentration of the solvent gave 1.29 grams of a 1:2 mixture of (Z)-ethyl-2-(2-fluoropyridin-3-yl)-2-hydrazonoacetate LC-MS Rt 1.5 min ES+ (212) and (Z)-isopropyl-2-(2-fluoropyridin-3-yl)-2-hydrazonoacetate LC-MS Rt 2.0 min ES+ (226) as a waxy solid.

Example 164

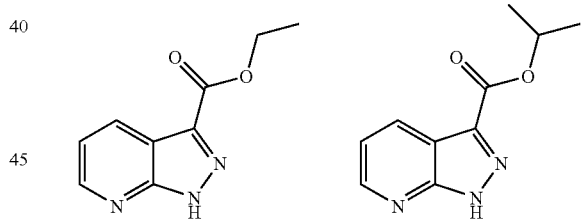

Step C: Ethyl 1H-pyrazolo[3,4-b]pyridine-3-carboxylate

A solution of (1.01 g, 4.96 mmol) of a 1:2 mixture (Z)-ethyl-2- (2-fluoropyridin-3-yl)-2-hydrazonoacetate and (Z)-isopropyl-2-(2-fluoropyridin-3-yl)-2-hydrazonoacetate in NMP (12 mL) was divided into three 5 mL microwave vessels then heated at 250 C for 5 min. The reactions were combined, diluted with EtOAc and washed with water, saturated sodium chloride then dried (MgSO4) and concentrated to dryness. Chromatography (SiO2, 4:1 to 1:1 EtOAc:hexane) gave 0.59 g (65% yield) of a 2:1 mixture of ethyl 1H-pyrazolo[3,4-b]pyridine-3-carboxylate LC-MS Rt 2.1 min ES+ (192.1), ES− (190.1) and isopropyl 1H-pyrazolo[3,4-b]pyridine-3-carboxylate LC-MS Rt 2.4 min ES+ (206.1), ES− (204.2) as a pink solid.

Example 165

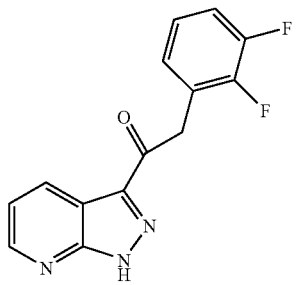

Step D: 2-(2,3-Difluorophenyl)-1-(1H-pyrazolo[3,4-b]pyridin-3-yl)ethanone

To a solution of 2,3-difluorophenylacetic acid (236 mg, 1.4 mmol) in THF at OC was added 3.85 mL (3.85 mmol) of a solution of lithium bis-trimethylsilylamide in THF. The resulting solution was then added to solution of a 2:1 mixture of ethyl 1H-pyrazolo[3,4-b]pyridine-3-carboxylate and isopropyl 1H-pyrazolo[3,4-b]pyridine-3-carboxylate (104 mg, 0.55 mmol) in THF. The resulting mixture was heated at 75C for 3 hours. The reaction progress was monitored by TLC and HPLC and quenched with saturated NH4Cl, diluted with EtOAc and washed with saturated NaHCO3 and brine. The organic layer was dried over MgSO4 and concentrated to give 137 mg (91% yield) of 2-(2,3-difluorophenyl)-1-(1H-pyrazolo[3,4-b]pyridin-3-yl)ethanone. LC-MS Rt=3.3 min ES+ (274.0) ES− (272.1).

Example 166

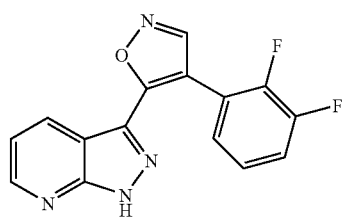

Preparation of 3-(4-(2,3-difluorophenyl)isoxazol-5-yl)-1H-pyrazolo[3,4-b]pyridine (31)

2-(2,3-Difluorophenyl)-1-(1H-pyrazolo[3,4-b]pyridin-3-yl)ethanone (137 mg, 0.5 mmol) was allowed to react according to the METHOD OF BREDERECKS to afford 112 mg (40% yield) of 3-(4-(2,3-difluorophenyl)isoxazol-5-yl)-1H-pyrazolo[3,4-b]pyridine.

$^1$H NMR (500 MHz, CD$_3$OD) δ: 8.75 (s, 1H), 8.60 (d, 2H), 8.46 (d, 2H), 7.48 (m, 1H), 7.35-7.29 (m, 2H) and 7.22 (bm, 1H); $^1$H NMR (Acetone-d6) δ: 8.81 (d, J=1.3 Hz, 1H) 8.66 (dd, J=1.5 and 4.5 Hz, 1H) 8.48 (dd, J=1.5 and 8.2 Hz, 1H) 7.57 (m, 1H) 7.39 (m, 2H) 7.28 (m, 1H). LC/MS Rt 3.30 mins.; m/e 299 (M+H), 297 (M−H)

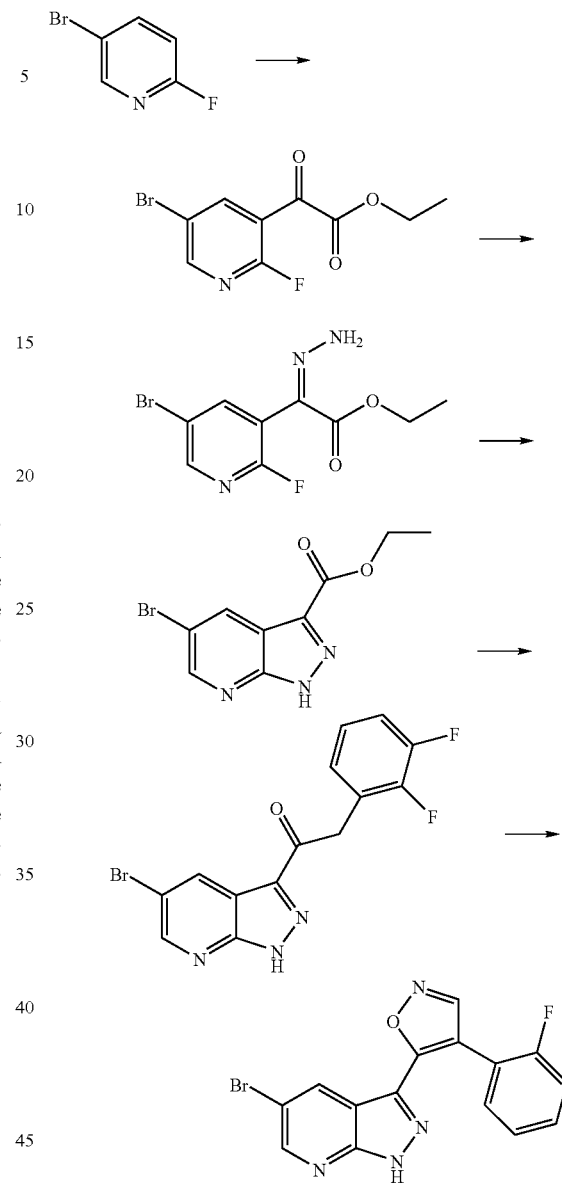

Reagents and Conditions: (a) (i) LHMDS, THF −78 C, (ii) diethyl oxalate; (b) H$_2$NNH$_2$, (i-PrO)$_4$T$_1$, CH$_2$Cl$_2$; (c) NMP, Microwave (250 C, 5 mins.); (d) LHMDS, 2,3-difluoroacetic acid, THF, 0 C; (e) (i) Bredereck's reagent, THF, reflux, (ii) hydroxylamine hydrochloride, NaOAc, THF, reflux.

Example 167

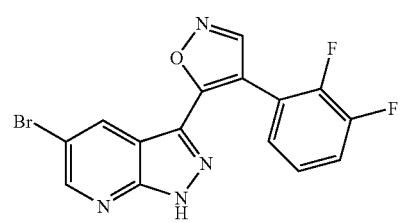

5-Bromo-3-(4-(2,3-difluorophenyl)isoxazol-5-yl)-1H-pyrazolo[3,4-b]pyridine (149)

5-Bromo-3-(4-(2,3-difluorophenyl)isoxazol-5-yl)-1H-pyrazolo[3,4-b]pyridine was prepared according to the method described for the preparation of 3-(4-(2,3-difluorophenyl)isoxazol-5-yl)-1H-pyrazolo[3,4-b]pyridine starting with 5-bromo-2-fluoropyridine.

$^1$H NMR (500 MHz, DMSO-d6) δ: 14.59 (S, 1H), 9.05 (S, 1H), 8.74 (d, 1H, J=2.0 Hz), 8.52 (d, 1H, J=2.0 Hz), 7.55-7.50 (m, 2H) and 7.34-7.30 ppm (m, 1H). LC/MS Rt 4.0 mins.; m/e 377 (M+H) 375 (M–H)

Example 168

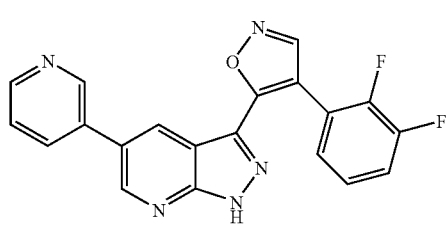

3-(4-(2,3-Difluorophenyl)isoxazol-5-yl)-5-(pyridin-3-yl)-1H-pyrazolo[3,4-b]pyridine (150)

3-(4-(2,3-difluorophenyl)isoxazol-5-yl)-5-(pyridin-3-yl)-1H-pyrazolo[3,4-b]pyridine was prepared according to METHOD FOR SUZUKI COUPLING to afford 3.8 mg (13% yield)

$^1$H NMR (500 MHz, DMSO-d6) δ: 14.52 (s, 1H), 9.07 (s, 1H), 9.03 (d, J=2.05 Hz, 2H), 8.68 (d, J=4.63 Hz, 1H), 8.59 (d, J=1.89 Hz, 1H), 8.29 (d, J=7.76 Hz, 1H), 7.64-7.61 (m, 1H), 7.55-7.50 (m, 2H), and 7.35-7.31 ppm (m, 1H). LC/MS Rt 2.5 mins.; m/e 376 (M+H), 374 (M–H)

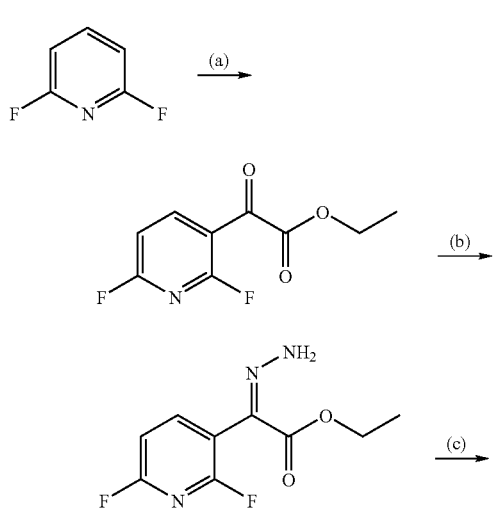

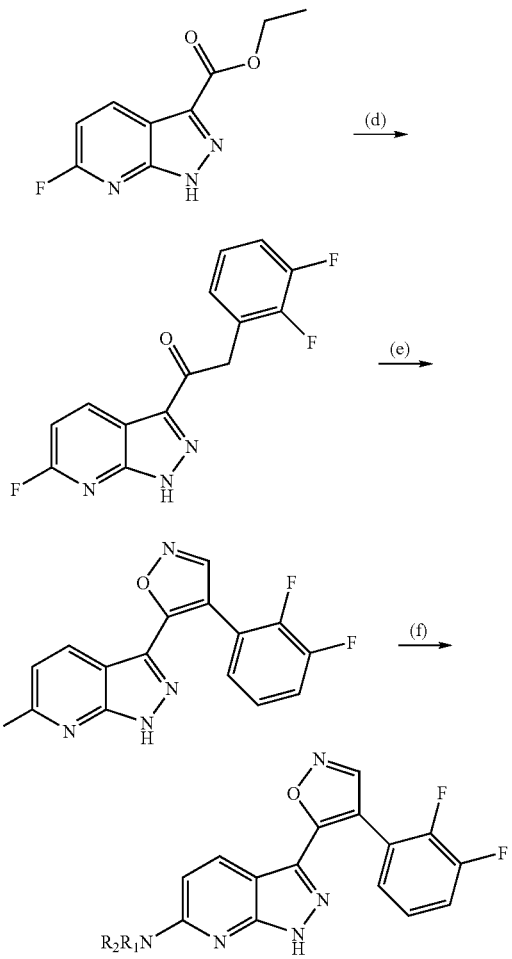

Reagents and Conditions: (a) (i) LHMDS, THF −78 C, (ii) diethyl oxalate; (b) H$_2$NNH$_2$, (i-PrO)$_4$Ti, CH$_2$Cl$_2$; (c) NMP, Microwave (250 C, 5 mins.); (d) LHMDS, 2,3-difluoroacetic acid, THF, 0 C; (e) (i) Bredereck's reagent, THF, reflux, (ii) hydroxylamine hydrochloride, NaOAc, THF, reflux; (f) HNR$_1$R$_2$, NMP.

Example 169

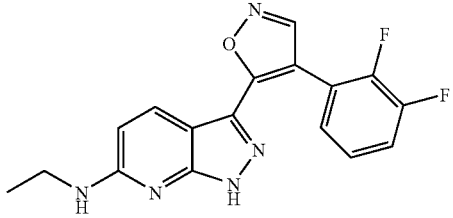

{3-[4-(2,3-Difluoro-phenyl)-isoxazol-5-yl]-1H-pyrazolo[3,4-b]pyridin-6-yl}-ethyl-amine (30)

$^1$H NMR (500 MHz, Acetone-d6) δ: 1.2 (t, 3H), 3.5 (q, 2H overlap d-solvent), 6.6 (d, 1H), 7.2 (m, 1H), 7.35 (m, 1H), 7.55 (t, 1H), 7.95 (d, 1H), 8.7 (s, 1H). LC/MS: Rt 3.3 mins.; m/e 342 (M+H), 340.2 (M–H).

Example 170

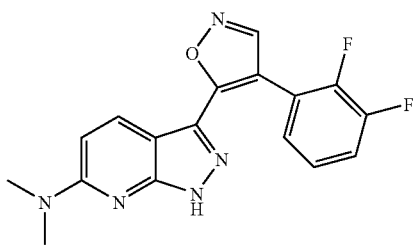

{3-[4-(2,3-Difluoro-phenyl)-isoxazol-5-yl]-1H-pyr-rolo[2,3-b]pyridin-6-yl}-dimethyl-amine (32)

$^1$H NMR (500 MHz, Acetone-d6) δ: 3.2 (s, 6H), 6.8 (d, 1H), 7.25 (m, 1H), 7.3 (m, 1H), 7.6 (t, 1H), 8.1 (d, 1H), 8.7 (s, 1H). LC/MS: Rt 3.6 mins.; m/e 342 (M+H), 340.1 (M–H)

Example 171

$K_i$ Determination for the Inhibition of c-Met

Compounds were screened for their ability to inhibit c-Met kinase activity using a standard coupled enzyme system (Fox et al., Protein Sci. 1998, 7, 2249). Reactions were carried out in a solution containing 100 mM HEPES (pH 7.5), 10 mM $MgCl_2$, 25 mM NaCl, 300 μM NADH, 1 mM DTT, and 1.5% DMSO. Final substrate concentrations in the assay were 200 μM ATP (Sigma Chemicals, St Louis, Mo.) and 10 μM poly-GluTyr (Sigma Chemical Company, St. Louis). Reactions were carried out at 30° C. and 80 nM c-Met. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and a test compound of the present invention. The assay stock buffer solution (175 μl) was incubated in a 96 well plate with 5 μl of the test compound of the present invention at final concentrations spanning 0.006 μM to 12.5 μM at 30° C. for 10 minutes. Typically, a 12-point titration was conducted by preparing serial dilutions (from 10 mM compound stocks) with DMSO of the test compounds of the present invention in daughter plates. The reaction was initiated by the addition of 20 μl of ATP (final concentration 200 μM). Rates of reaction were obtained using a Molecular Devices Spectramax plate reader (Sunnyvale, Calif.) over 10 minutes at 30° C. The $K_i$ values were determined from the rate data as a function of inhibitor concentration.

Compounds of the present invention were found to be inhibitors of c-Met. Compounds 1, 2, 37, 38, 40, 42, 43, 44, 46, 48, 49, 53, 57, 58, 59, 60, 61, 62, 63, 64, 65, 66, 67, 68, 69 70, 71, 72, 73, 74, 75, 76, 77, 78, 79, 81, 82, 83, 84, 85, 86, 87, 88, 89, 90, 91, 92, 93, 94, 95, 96, 97, 98, 99, 102, 105, 106, 109, 110, 112, 113, 114, 115, 116, 117, 118, 119, 120, 121, 122, 123, 124, 129, 130, 131, 133, 135, 136, 137, 138, 139, 140, 141, 142, 149, 153, 154, and 155 had Ki values of <0.2 μM. Compounds 31, 35, 39, 41, 45, 55, 103, 104, 108, 111, 132, 134, 143, 144, and 148 had Ki values of 0.2 μM-<1.0 μM.

Compounds 11, 29, 30, 32, 36, 47, 51, 52, 54, 56, 80, 100, 101, 107, 143, 145, 146, 147, 151, and 152 had Ki values of 1.0 μM-12.5 μM.

Example 172

GSK-3 Inhibition Assay

Compounds of the present invention were screened for their ability to inhibit GSK-3β, (AA 1-420) activity using a standard coupled enzyme system (Fox et al., Protein Sci. 1998, 7, 2249). Reactions were carried out in a solution containing 100 mM HEPES (pH 7.5), 10 mM MgCl2, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3b. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of the present invention. The assay stock buffer solution (175 μl) was incubated in a 96 well plate with 5 μl of the test compound of the present invention at final concentrations spanning 0.002 μM to 30 μM at 30° C. for 10 min. Typically, a 12 point titration was conducted by preparing serial dilutions (from 10 mM compound stocks) with DMSO of the test compounds of the present invention in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The Ki values were determined from the rate data as a function of inhibitor concentration.

Compounds of the present invention were found to inhibit GSK3. Compounds 63, 64, 67, 68, 69, 70, 72, 82, 86, 90, 97, 98, 99, 106, 109, 113, 114, 133, 135, 137, 138, 139, 140, 141, 149, and 155 had Ki values of <0.2 μM. Compounds 36, 37, 38, 43, 44, 49, 53, 57, 58, 59, 60, 61, 62, 65, 66, 71, 76, 77, 78, 79, 81, 83, 84, 88, 89, 92, 93, 94, 96, 105, 110, 112, 115, 116, 117, 118, 119, 132, 134, 136, 142, and 145 had Ki values of 0.2-<1.0 μM. Compounds 1, 2, 29, 33, 34, 35, 39, 40, 41, 42, 45, 46, 47, 48, 52, 55, 75, 80, 85, 87, 91, 95, 102, 103, 104, 108, 111, 143, 148, 150, 151, 153, and 154 had Ki values of 1.0-12.5 μM.

Example 173

JAK3 Inhibition Assay

Compound inhibition of JAK3 was assayed by the method described by G. R. Brown, et al., Bioorg. Med. Chem. Lett. 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween (PBST), was added 2 mM ATP, 5 mM MgCl2, and a solution of compound in DMSO. The reaction was started with JAK enzyme and the plates incubated for 60 minutes at 30° C. The plates were then washed with PBST, 100 mL HRP-Conjugated 4G10 antibody was added, and the plate incubated for 90 minutes at 30° C. The plate was again washed with PBST, 100 mL TMB solution is added, and the plates were incubated for another 30 minutes at 30° C. Sulfuric acid (100 mL of 1M) was added to stop the reaction and the plate is read at 450 nm to obtain the optical densities for analysis to determine IC50 values.

Compounds of the present invention were found to inhibit JAK3. Compounds 37, 38, 41, 43, 48, 49, 57, 58, 59, 65, 66, 67, 68, 70, 71, 73, 75, 76, 77, 79, 82, 83, 84, 86, 87, 88, 90, 91, 92, 93, 94, 95, 96, 98, 99, 105, 133, 135, 136, 137, 138, 139, 140, 153, 154, and 155 had Ki values of<0.2 µM. Compounds 1, 2, 35, 39, 42, 44, 46, 47, 51 53, 56, 61, 63, 64, 69, 74, 78, 81, 85, 97, 106, 109, 110, 116, 118, 124, 129, 130, 134, 141, 142, 145, and 149 had Ki values of 0.2-<1.0 µM. Compounds 31, 34, 36, 40, 45, 50, 52, 55, 60, 62, 72, 80, 102, 103, 104, 108, 111, 112, 113, 114, 115, 117, 119, 120, 121, 122, 123, 131, 132, 143, 144, 150, and 152 had Ki values of 1.0-12.5 µM.

Example 174

SYK Enzyme Assay

Compounds were screened for their ability to inhibit SYK using a standard coupled enzyme assay (Fox et al., *Protein Sci.* 1998, 7, 2249). Reactions were carried out in 100 mM HEPES (pH 7.5), 10 mM $MgCl_2$, 25 mM NaCl, 1 mM DTT and 1.5% DMSO. Final substrate concentrations in the assay were 200 µM ATP (Sigma chemical Co.) and 4 µM poly Gly-Tyr peptide (Sigma Chemical Co.). Assays were carried out at 30° C. and 200 nM SYK. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of SYK, DTT, and the test compound of interest of the present invention. 56 µl of the test reaction was placed in a 96 well plate followed by the addition of 1 µl of 2 mM DMSO stock containing the test compound of the present invnetion (final compound concentration 30 µM). The plate was pre-incubated for ~10 minutes at 30° C. and the reaction initiated by the addition of 10 µl of enzyme (final concentration 25 nM). Rates of reaction were obtained using a BioRad Ultramark plate reader (Hercules, Calif.) over a 5 minute read time at 30° C., and $K_i$ values for the compounds of the present invention were determined according to standard methods.

Compounds of the present invention were found to inhibit SYK. Compounds 1, 43, 67, 68, 70, 77, 86, 90, 99, 135, and 155 had Ki values of 0.2-<1.0 µM. Compounds 29, 35, 37, 38, 41, 42, 44, 61, 65, 71, 73, 76, 82, 84, 88, 91, 93, 98, 106, 133, and 134 had Ki values of 1.0-12.5 µM.

Example 175

KDR Enzyme Assay

Compounds were screened for their ability to inhibit KDR using a standard coupled enzyme assay (Fox et al., Protein Sci., (1998) 7, 2249). Assays were carried out in a mixture of 200 mM HEPES 7.5, 10 mM MgCl2, 25 mM NaCl, 1 mM DTT and 1.5% DMSO. Final substrate concentrations in the assay were 300 µM ATP (Sigma Chemicals) and 10 µM poly E4Y (Sigma). Assays were carried out at 37° C. and 30 nM KDR. Final concentrations of the components of the coupled enzyme system were 2.5 mM phosphoenolpyruvate, 200 µM NADH, 30 µg/ML pyruvate kinase and 10 µg/ml lactate dehydrogenase.

An assay stock buffer solution was prepared containing all of the reagents listed above, with the exception of ATP and the test compound of interest. 177 µl of the stock solution was placed in a 96 well plate followed by addition of 3 µl of 2 mM DMSO stock containing the test compound (final compound concentration 30 µM). The plate was preincubated for about 10 minutes at 37° C. and the reaction initiated by addition of 20 µl of ATP (final concentration 300 µM). Rates of reaction were obtained using a Molecular Devices plate reader (Sunnyvale, Calif.) over a 5 minute read time at 37° C. Compounds showing greater than 50% inhibition versus standard wells containing the assay mixture and DMSO without test compound were titrated to determine IC50 values determined.

Compounds of the present invention were found to inhibit KDR. Compounds 48, 49, 58, 65, 66, 67, 68, 69, 70, 71, 77, 78, 79, 80, 81, 82, 83, 84, 86, 88, 89, 90, 93, 94, 96, 97, 98, 99, 133, 137, 138, 140, 149, 154, and 155 had Ki values of<0.2 µM. Compounds 2, 35, 37, 38, 40, 42, 43, 44, 45, 46, 53, 55, 56, 57, 59, 61, 75, 76, 87, 91, 92, 95, 104, 105, 106, 109, 110, 112, 113, 114, 116, 117, 118, 119, 135, 136, 139, 142, 148, 150, and 153 had Ki values of 0.2-<1.0 µM. Compounds 1, 31, 36, 39, 41, 47, 51, 62, 63, 64, 73, 74, 85, 86, 102, 111, 115, 132, 134, and 141 had Ki values of 1.0-12.5 µM.

Example 176

Inhibition of FLT-3

Compounds were screened for their ability to inhibit FLT-3 activity using a radiometric filter-binding assay. This assay monitors the $^{33}P$ incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 µM ATP and 0.5 mg/mL pE4Y (both from Sigma Chemicals, St Louis, Mo.). The final concentration of compounds is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM $MgCl_2$, 25 mM NaCl, 1 mg/ml pE4Y and 180 µM ATP(containing 0.3 µCi of [γ-$^{33}$P] ATP for each reaction). Solution 2 contains 100 mM HEPES (pH 7.5), 10 mM $MgCl_2$, 25 mM NaCl, 2 mM DTT, 0.02% BSA and 3 nM FLT-3. The assay was run on a 96 well plate by mixing 50 µL each of Solution 1 and 2.5 mL of the test compounds. The reaction was initiated with Solution2. After incubation for 20 minutes at room temperature, the reaction was stopped with 50 µL of 20% TCA containing 0.4 mM of ATP. All of the reaction volume was then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an $IC_{50}$ or $K_i$.

Compounds of the present invention were found to inhibit FLT. Compounds 38, 57, 59, 65, 68, 70, 71, 76, 77, 79, 82, 84, 86, 87, 90, 91, 92, 93, 94, 95, 98, 99, 105, 133, 134, 137, 138, 139, 140, 142, 149, 153, and 155 had Ki values of<0.2 µM. Compounds 1, 43, 46, 47, 48, 49, 53, 58, 61, 62, 63, 64, 66, 69, 73, 75, 78, 81, 85, 96, 103, 106, 109, 110, 112, 115, 116, 117, 118, 119, 132, 136, 141, 143, and 154 had Ki values of 0.2-<1.0 µM. Compounds 2, 31, 34, 36, 39, 41, 42, 44, 45, 54, 55, 56, 60, 72, 74, 80, 83, 102, 104, 108, 111, 144, and 152 had Ki values of 1.0-12.5 µM.

Example 177

Inhibition of FMS

Compounds are screened for their ability to inhibit FMS activity using a radiometric filter-binding assay. This assay monitors the $^{33}$P incorporation into a substrate poly(Glu, Tyr) 4:1 (pE4Y). Reactions are carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay are 90 µM ATP and 0.5 mg/mL pE4Y (both from Sigma Chemicals, St Louis, Mo.). The final concentration of compounds is generally between 0.01 and 5 µM. Typically, a 12-point titration is conducted by preparing serial dilutions from 10 mM DMSO stock of test compound. Reactions were carried out at room temperature.

Two assay solutions are prepared. Solution 1 contains 100 mM HEPES (pH 7.5), 10 mM MgCl$_2$, 25 mM NaCl, 1 mg/ml pE4Y and 180 µM ATP (containing 0.3 µCi of [γ-$^{33}$P]ATP for each reaction). Solution 2 contains 100 mM HEPES (pH 7.5), 10 mM MgCl$_2$, 25 mM NaCl, 2 mM DTT, 0.02% BSA and 3 nM FMS. The assay is run on a 96 well plate by mixing 50 µL each of Solution 1 and 2.5 mL of the test compounds. The reaction is initiated with Solution2. After incubation for 20 minutes at room temperature, the reaction is stopped with 50 µL of 20% TCA containing 0.4 mM of ATP. All of the reaction volume is then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an IC$_{50}$ or K$_i$.

Example 178

Inhibition of c-KIT

Compounds are screened for their ability to inhibit c-KIT activity using a radiometric filter-binding assay. This assay monitors the $^{33}$P incorporation into a substrate poly(Glu, Tyr) 4:1 (pE4Y). Reactions are carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 700 µM ATP and 0.5 mg/mL pE4Y (both from Sigma Chemicals, St Louis, Mo.). The final concentration of compounds is generally between 0.01 and 5 µM. Typically, a 12-point titration is conducted by preparing serial dilutions from 10 mM DMSO stock of test compound. Reactions were carried out at room temperature.

Two assay solutions are prepared. Solution 1 contains 100 mM HEPES (pH 7.5), 10 mM MgCl$_2$, 25 mM NaCl, 1 mg/ml pE4Y and 1.4 mM ATP(containing 0.5 µCi of [γ-$^{33}$P]ATP for each reaction). Solution 2 contains 100 mM HEPES (pH 7.5), 10 mM MgCl$_2$, 25 mM NaCl, 2 mM DTT, 0.02% BSA and 25 nM c-KIT. The assay is run on a 96 well plate by mixing 33 µL of Solution1 and 1.65 µL of the test compounds. The reaction is initiated with 33 µL of Solution2. After incubation for 20 minutes at room temperature, the reaction was stopped with 50 µL of 10% TCA containing 0.2 mM of ATP. All of the reaction volume is then transferred to a filter plate and washed with 5% TCA by a Harvester9600 from TOMTEC (Hamden, Conn.). The amount of $^{33}$P incorporation into pE4y is analyzed by a Packard TopCount Microplate Scintillation Counter (Meriden, Conn.). The data is fitted using Prism software to get an IC$_{50}$ or K$_i$.

Compounds of the present invention were found to inhibit c-KIT. Compounds 1, 38, 43, 49, 53, 57, 59, 61, 65, 67, 68, 69, 70, 71, 72, 73, 76, 77, 78, 82, 83, 84, 85, 86, 87, 88, 90, 91, 92, 93, 94, 95, 96, 99, 105, 106, 109, 110, 114, 129, 130, 131, 135, 136, 137, 138, 139, 140, 141, 142, 149, 153, and 155 had K$_i$ values of<0.2 µM. Compounds 40, 46, 48, 55, 60, 62, 108, 111, 112, 113, 115, 116, 117, 118, 119, 120, 121, 122, 123, 124, and 144 had K$_i$ values of 0.2-<1.0 µM.

Example 179

Inhibition of AUR-2

Compounds are screened in the following manner for their ability to inhibit Aurora-2 using a standard coupled enzyme assay (Fox et al. (1998) *Protein Sci* 7, 2249). To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 µM peptide (LR-RASLG, American Peptide, Sunnyvale, Calif.) is added a DMSO solution of a compound of the present invention to a final concentration of 30 µM. The resulting mixture is incubated at 30° C. for 10 min. The reaction was initiated by the addition of 10 µL of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The K$_i$ values are determined from the rate data as a function of inhibitor concentration.

Compounds of the present invention were found to inhibit AUR-2. Compounds 37, 44, 49, 57, 59, 65, 68, 70, 71, 76, 86, 87, 90, 92, 93, 94, 95, 96, 98, 99, and 153 had K$_i$ values of<0.2 µM. Compounds 1, 2, 38, 42, 43, 46, 47, 48, 58, 75, 82, 83, 91, 134, and 145 had K$_i$ values of 0.2-<1.0 µM.

Example 180

TAK-1 Inhibition Assay

Compounds were screened for their ability to inhibit TAK1A kinase activity using a radiometric filter binding assay. Reactions were carried out in a solution containing Buffer A (100 mM HEPES (pH 7.5), 10 mM MgCl$_2$), 25 mM NaCl, 2 mM DTT, and 1.5% DMSO. Final substrate concentrations in the assay were 50 µM ATP (a mixture of unlabeled ATP (Sigma Chemicals, St Louis, Mo.) and $^{33}$P-labeled ATP (PerkinElmer Life Sciences, Boston, Mass.) for a final specific activity of 50 Ci/mol), and 12 µM bovine myelin basic protein (MBP, Vertex Pharmaceuticals, Cambridge, Mass.). Reactions were carried out at ambient temperature (~20° C.) using 20 nM TAK1A-TAB fusion protein. Under these conditions the extent of reaction is linear with time for a period of 2 hours.

A test compound of the present invention (1 µL in DMSO) was combined with ATP and Buffer A in a final volume of 47 µL in a 96 well plate. Typically, a 6 point titration was conducted by preparing serial dilutions (from 10 mM compound stocks) with DMSO of the test compounds of the present invention in daughter plates, for final concentrations spanning 0.046 µM to 3.73 µM. The reaction was initiated by the addition of 20 µl of an enzyme stock solution consisting of TAK1A-TAB fusion (described by Sugita, T. et al. in *Biochem. Biophys. Res. Comm.* 2002, 297, 1277-1281), MBP, Buffer A, NaCl, and DTT. The reaction was allowed to proceed for two hours at ambient temperature, then quenched with an equal volume of 10 mM unlabeled ATP in 10% trichloroacetic acid. A 110 µL aliquot of the quenched reaction was transferred to a Multiscreen PH filter plate (Millipore, Billerica, Mass.) and allowed to incubate at ambient temperature overnight (typically 16-20 hours). Following incubation the filter plates were washed with 3×150 μL aliquots of 5% trichloroacetic acid using a modified Biotek Elx405 plate washer. A 70 μL aliquot of Microscint 20 scintillation fluid (PerkinElmer) was added to each well, and the plate was then sealed and read on a TopCount NXT microplate scintillation counter (PerkinElmer). The $K_i$ values were determined from the rate data as a function of inhibitor concentration.

Compounds of the present invention were found to inhibit TAK-1. Compounds 68, 70, 71, 110, 135, 136, 137, 138, 140, and 155 had $K_i$ values of <0.2 μM. Compounds 48, 49, 53, 61, 69, 77, 78, 79, 84, 97, 98, 99, 106, 109, 115, 116, 117, 118, 133, 139, 141, and 142 had $K_i$ values of 0.2-<1.0 μM. Compounds 46, 62, 72, 111, 112, 113, 114, and 119 had $K_i$ values of 1.0-12.5 μM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:
1. A compound of formula I:

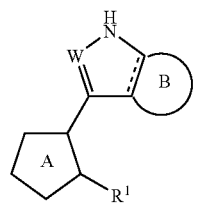

or a pharmaceutically acceptable salt thereof, wherein:
W is CH, wherein the H is optionally replaced with ($C_1$-$C_6$)-alkyl or $NH_2$;
Ring B is a pyridine ring, optionally substituted with 1-3 groups independently selected from $R^3$ or a 5-6 membered heterocyclic or heteroaryl ring containing one heteroatom selected from N, O, or S and optionally substituted with $R^o$;
$R^1$ is a phenyl optionally substituted with 1-3 $R^3$ groups;
wherein each $R^3$ is, independently, oxo, halogen, —B(OH)$_2$, —$R^o$, —$OR^o$, —$SR^o$, 1,2-methylenedioxy, 1,2-ethylenedioxy, —CO$_2$(C$_{1-4}$aliphatic), phenyl optionally substituted with $R^o$, —O(phenyl) optionally substituted with $R^o$, —(CH$_2$)$_{1-2}$(phenyl) optionally substituted with $R^o$, —CH=CH(phenyl) optionally substituted with $R^o$, —NO$_2$, —CN, —NHR$^o$, —N(R$^o$)$_2$, —NR$^o$C(O)R$^o$, —NR$^o$C(S)R$^o$, —NR$^o$C(O)N(R$^o$)$_2$, —NR$^o$C(S)N(R$^o$)$_2$, —NR$^o$CO$_2$R$^o$, —NR$^o$NR$^o$C(O)R$^o$, —NR$^o$NR$^o$C(O)N(R$^o$)$_2$, —NR$^o$NR$^o$CO$_2$R$^o$, —C(O)C(O)R$^o$, —C(O)CH$_2$C(O)R$^o$, —CO$_2$R$^o$, —C(O)R$^o$, —C(S)R$^o$, —C(O)N(R$^o$)$_2$, —C(S)N(R$^o$)$_2$, —OC(O)N(R$^o$)$_2$, —OC(O)R$^o$, —C(O)N(OR$_o$)R$^o$, —C(NOR$^o$)R$^o$, —S(O)$_2$R$^o$, —S(O)$_3$ R$^o$, —SO$_2$N(R$^o$)$_2$, —S(O)R$^o$, —NR$^o$SO$_2$N(R$^o$)$_2$, —NR$^o$SO$_2$R$^o$, —N(OR$_o$)R$^o$, —C(=NH)—N(R$^o$)$_2$, or —(CH$_2$)$_{0-2}$NHC(O)R$^o$;
wherein each independent occurrence of $R^o$ is selected from hydrogen, $C_{1-6}$ aliphatic, —O(phenyl), —CH$_2$(phenyl), wherein each $R^o$ is optionally substituted with J, wherein J is aryl, phenyl, heteroaryl, NH$_2$, NH(C$_{1-4}$aliphatic), N(C$_{1-4}$aliphatic)$_2$, NH(CH$_2$)phenyl, halogen, —NHSO$_2$(C$_{1-4}$aliphatic), —NHCO$_2$(C$_{1-4}$aliphatic), C$_{1-4}$aliphatic, OH, O(C$_{1-4}$aliphatic), NO$_2$, CN, CO$_2$H, —CO(5-6 membered heterocyclic ring), 5-6 membered heterocyclic ring, —CO$_2$(C$_{1-4}$aliphatic), —O(haloC$_{1-4}$aliphatic), or halo(C$_{1-4}$aliphatic), or two $R^o$ are taken together with the atom(s) to which each is bound to form a 5-8-membered heterocyclyl, aryl, or heteroaryl ring or a 3-8-membered cycloalkyl ring having 0-3 heteroatoms independently selected from nitrogen, oxygen, or sulfur;
wherein each group of J is optionally substituted with J', wherein J' is NH$_2$, NH(C$_{1-4}$aliphatic), N(C$_{1-4}$aliphatic)$_2$, NH(CH$_2$)phenyl, halogen, —NHSO$_2$(C$_{1-4}$aliphatic), —NHCO$_2$(C$_{1-4}$aliphatic), C$_{1-4}$aliphatic, OH, O(C$_{1-4}$aliphatic), NO$_2$, CN, CO$_2$H, —CO(5-6 membered heterocyclic ring), 5-6 membered heterocyclic ring, —CO$_2$(C$_{1-4}$aliphatic), —O(haloC$_{1-4}$aliphatic), or halo(C$_{1-4}$aliphatic), wherein each the J' groups is optionally substituted with C$_{1-4}$aliphatic, halogen, wherein each of the C$_{1-4}$aliphatic groups of J' is unsubstituted;
wherein each aliphatic or heteroaliphatic group or non-aromatic heterocyclic ring is optionally substituted with $R^3$, =O, =S, =NNHR*, =NN(R*)$_2$, =NNHC(O)R*, =NNHCO$_2$(alkyl), =NNHSO$_2$(alkyl), or =NR*, wherein each R* is independently selected from hydrogen or an optionally substituted C$_{1-6}$aliphatic, wherein optional substituents on the aliphatic group of R* are selected from 5-6 membered heterocyclic ring, heteroaryl, aryl, NH$_2$, NHSO$_2$R*, NH(C$_{1-4}$aliphatic), N(C$_{1-4}$aliphatic)$_2$, halogen, C$_{1-4}$aliphatic, OH, O(C$_{1-4}$aliphatic), CO(5-6 membered heterocyclic ring), NO$_2$, CN, CO$_2$H, CO$_2$(C$_{1-4}$aliphatic), O(halo C$_{1-4}$aliphatic), or halo(C$_{1-4}$aliphatic), wherein each of the foregoing C$_{1-4}$aliphatic groups of R* is unsubstituted;
wherein each nitrogen of a non-aromatic heterocyclic ring is optionally substituted with —(C$_{1-6}$aliphatic)$_2$, —R$^+$, —N(R$^+$)$_2$, —C(O)R$^+$, —CO$_2$R$^+$, —C(O)C(O)R$^+$, —C(O)CH$_2$C(O)R$^+$, —SO$_2$R+, —SO$_2$N(R$^+$)$_2$, —C(=S)N(R$^+$)$_2$, —C(=NH)—N(R$^+$)$_2$, or —NR$^+$SO$_2$R$^+$;
wherein R$^+$ is hydrogen, an optionally substituted C$_{1-6}$aliphatic, optionally substituted phenyl, optionally substituted —O(phenyl), optionally substituted —CH$_2$(phenyl), optionally substituted —(CH$_2$)$_{1-2}$(phenyl); optionally substituted —CH=CH(phenyl); or an unsubstituted 5-6 membered heteroaryl or heterocyclic ring having one to four heteroatoms independently selected from oxygen, nitrogen, or sulfur, wherein optional substituents on the aliphatic group or the phenyl ring of R$^+$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(halo C$_{1-4}$aliphatic), or halo(C$_{1-4}$aliphatic), wherein each of the foregoing C$_{1-4}$aliphatic groups of R$^+$ is unsubstituted, or
two R$^+$ are taken together with the atom(s) to which each is bound to form a 5-8-membered heterocyclyl, aryl, or heteroaryl ring or a 3-8-membered cycloalkyl ring having 0-3 heteroatoms independently selected from nitrogen, oxygen, or sulfur; and Ring A is an optionally substituted ring selected from:

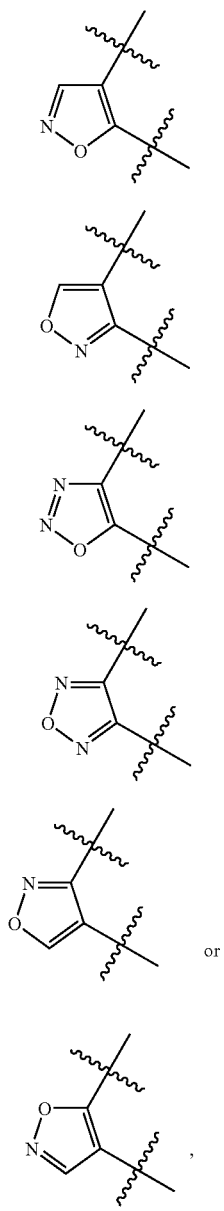

wherein said optional substituent of Ring A is selected from —OH, —NH₂, or —CH₃.

2. The compound according to claim 1, wherein R¹ is optionally substituted with one or more halogen or —OR°, wherein each R° is C$_{1-4}$aliphatic.

3. The compound according to claim 1, wherein Ring B is optionally substituted with one or more oxo; chloro; bromo; fluoro; —CH₂OH; —OH; —OCH₃; CH₃; —NHCH₃; —NHCH₂CH₃; —N(CH₃)₂; —NH—CH₂-tetrahydrofuranyl, pyrrolidinyl; piperidinyl; —COO(CH₃); —B(OH)₂; phenyl; benzyl; pyrindinyl; H; cyclopropyl; cyclohexyl; cyclohexenyl; —CH₂CH₃; —CH₂N(CH₃)₂; propynyl substituted with N(CH₃)₂; ethenyl; ethenyl substituted with triazolyl; —CH₂CH₂-triazolyl; NH(CH₃); NH(CH₂)phenyl; N(CH₃)₂; —NHSO₂(CH₃); —CO(piperazinyl) or —CO(pyrrolidinyl).

4. The compound according to claim 1, wherein Ring A is an optionally substituted isoxazolyl ring.

5. The compound according to claim 4, wherein Ring A is selected from the following rings:

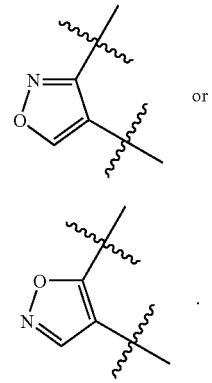

6. The compound according to claim 1, wherein W is CH.

7. A compound selected from the group consisting of:

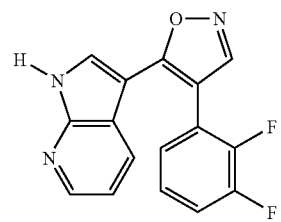

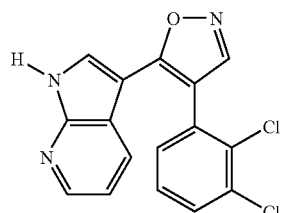

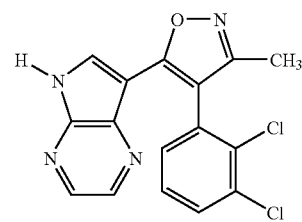

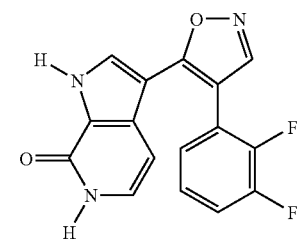

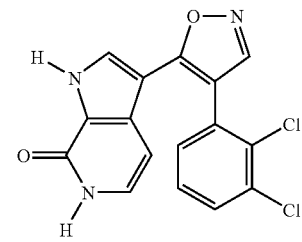

17
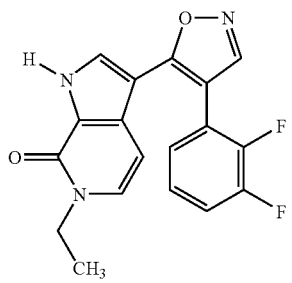
18
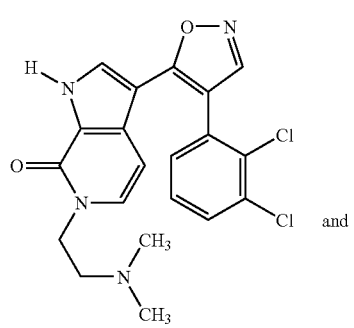
and
20
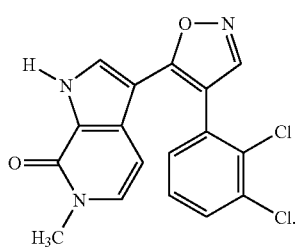
8. A compound selected from the group consisting of the following compounds:
35
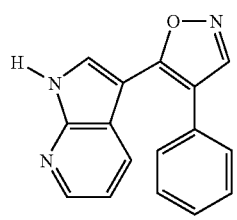
37
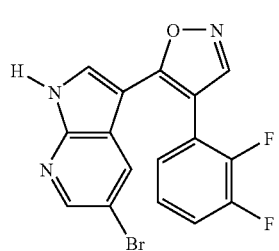
38
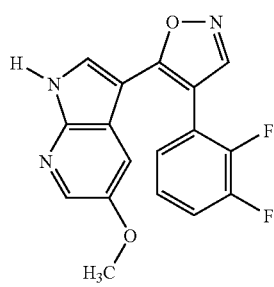
39
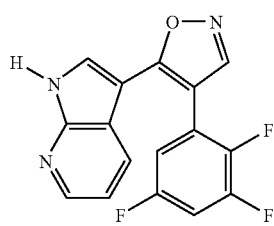
40
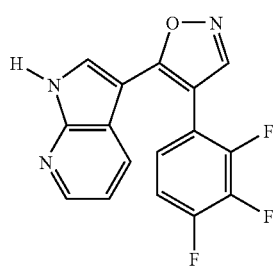
41
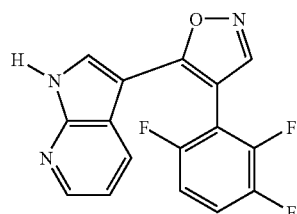
42
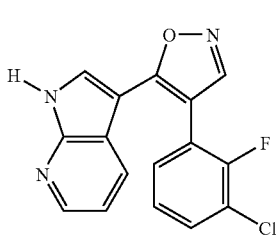
43
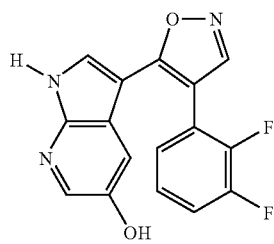

44
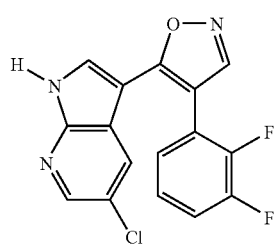
45
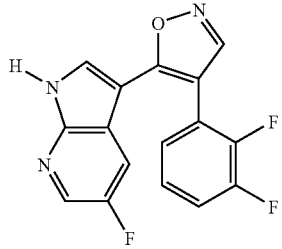
46
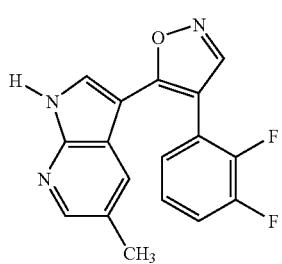
48
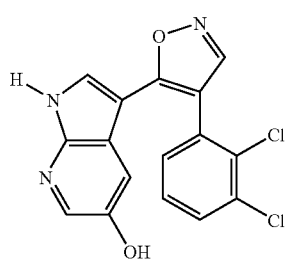
49
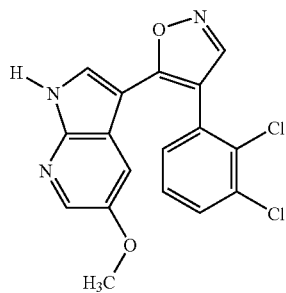
51
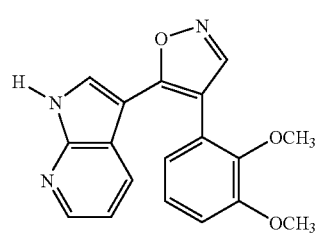
53
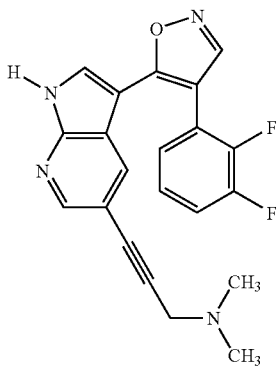
54
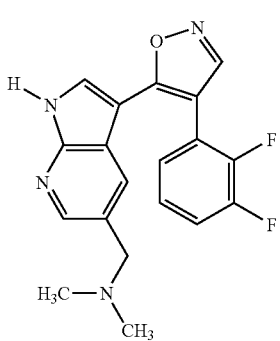
55
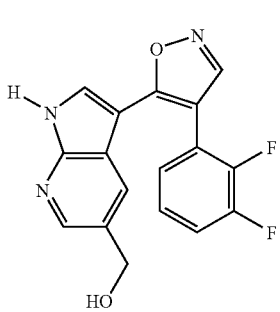
56
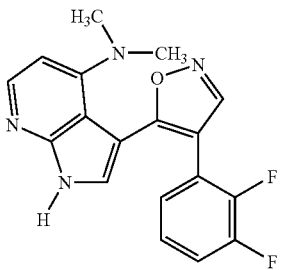

57 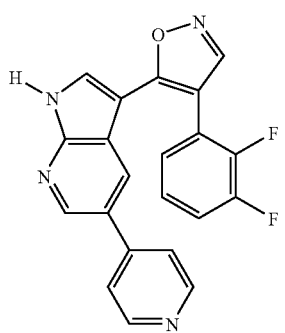
58 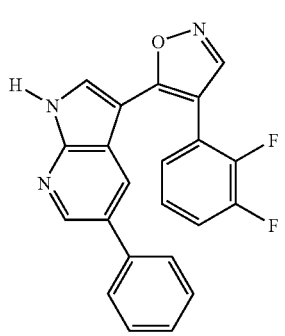
59 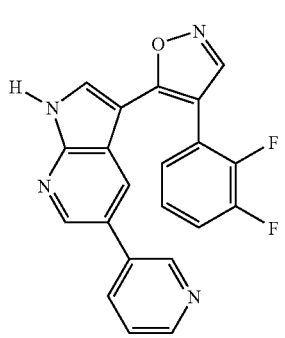
60 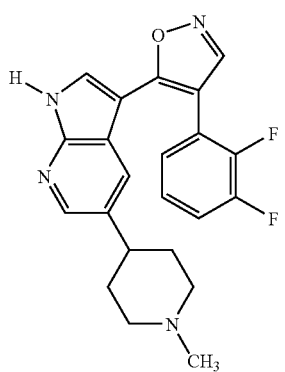
61 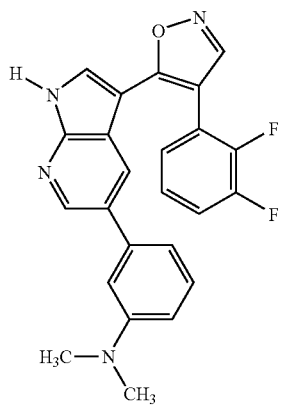
62 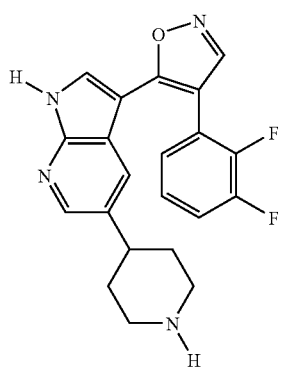
63 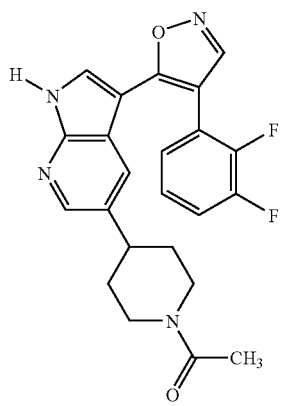
64 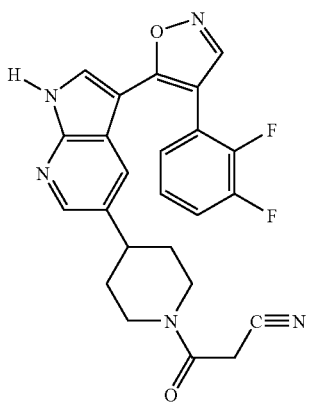

-continued
65
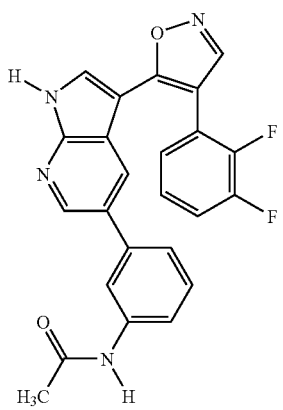
66
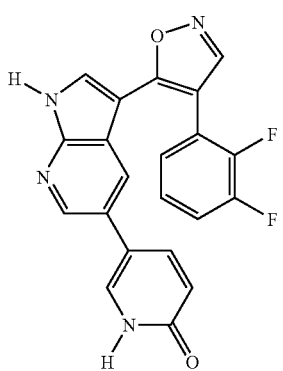
67
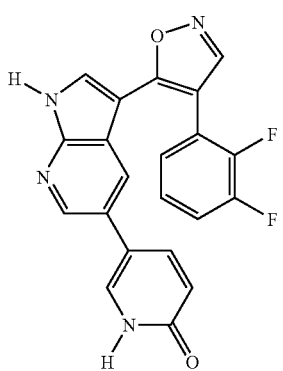
69
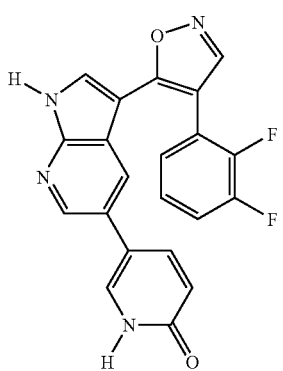
-continued
72
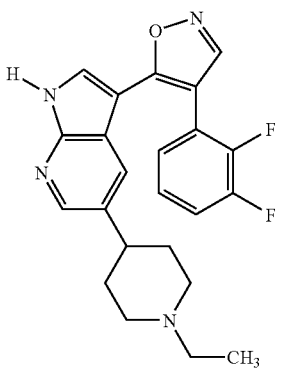
73
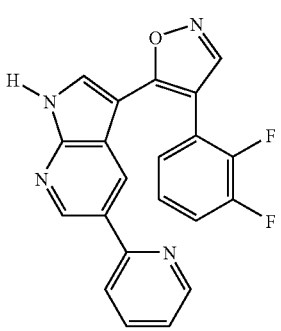
74
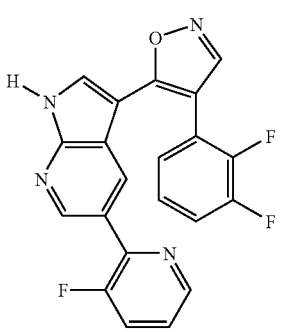
78
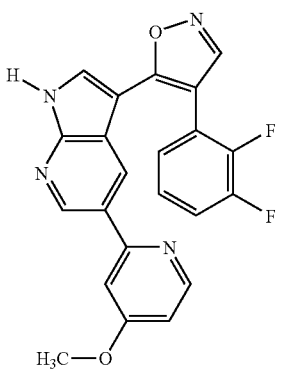

209
-continued
79
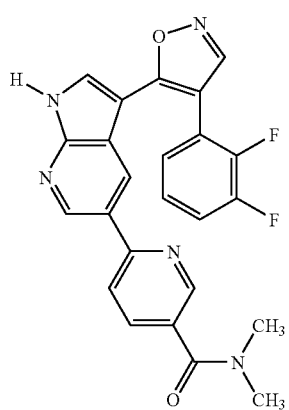
80
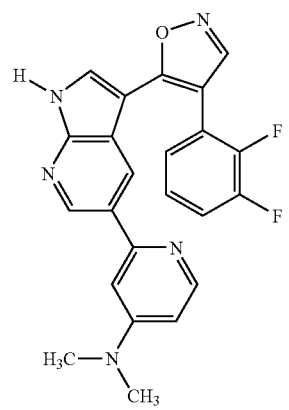
81
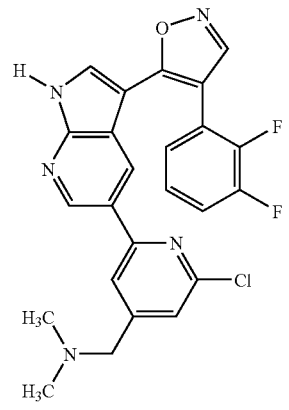
82
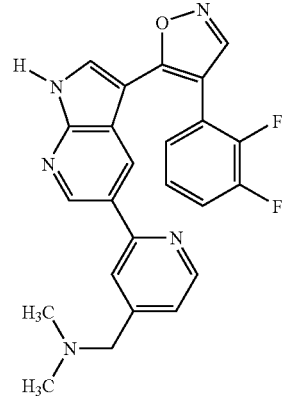
210
-continued
83
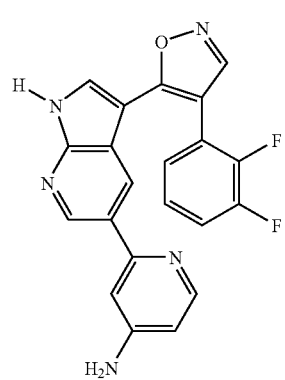
84
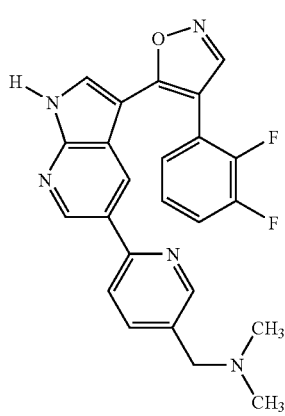
86
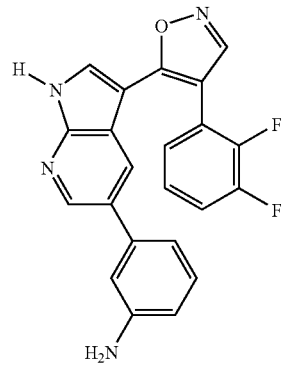
87
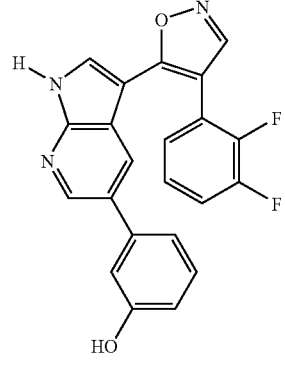

-continued
88
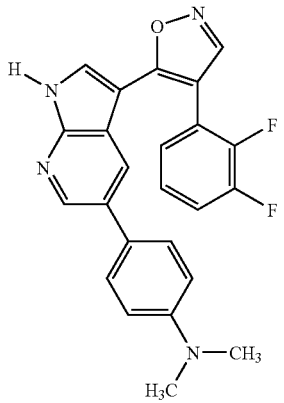
89
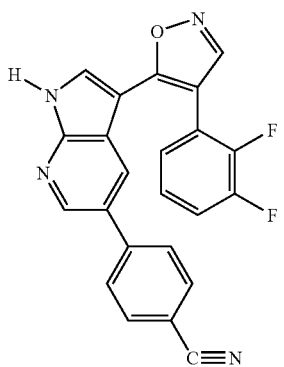
90
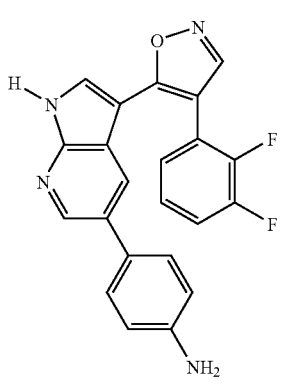
91
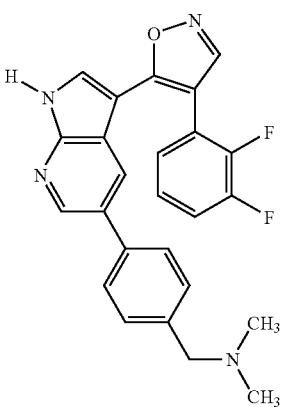
-continued
92
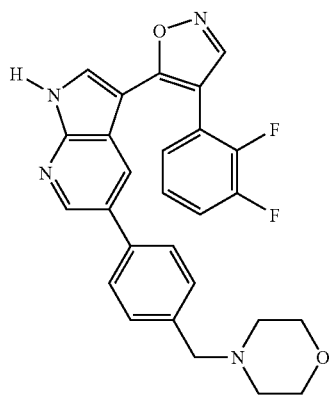
93
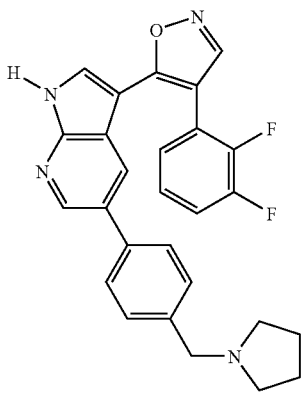
94
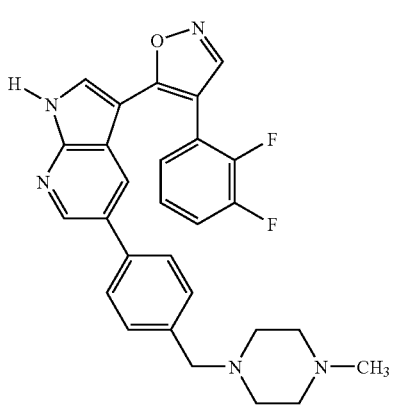
95
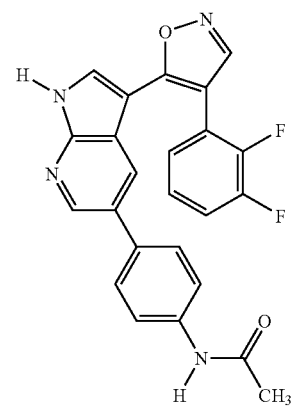

-continued
96 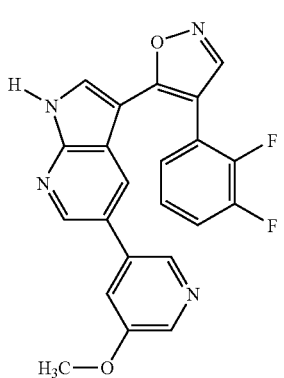
98 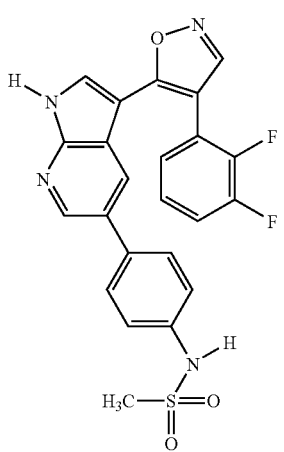
99 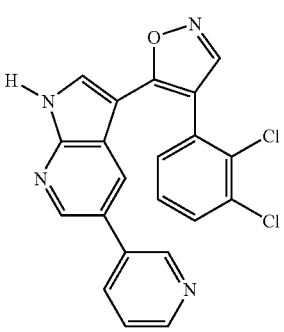
100 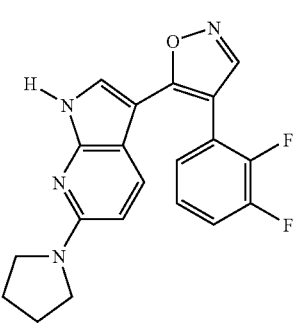
-continued
101 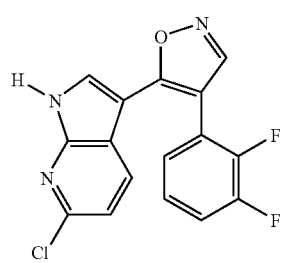
102 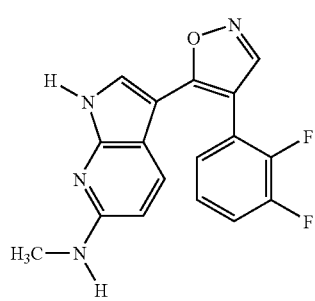
103 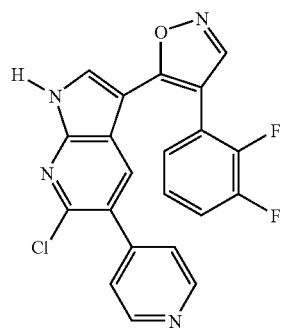
104 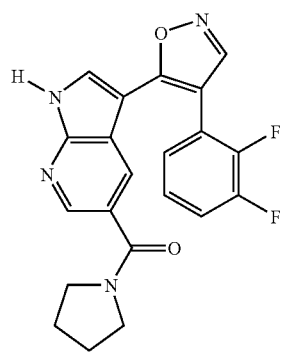
105 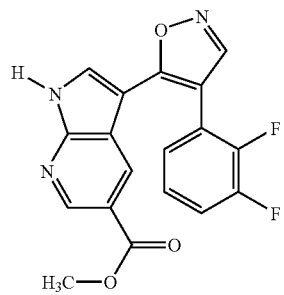

132
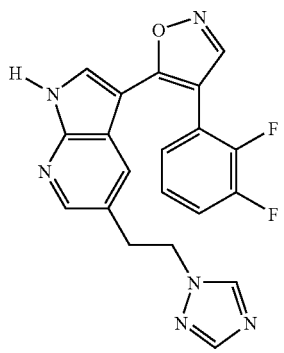
133
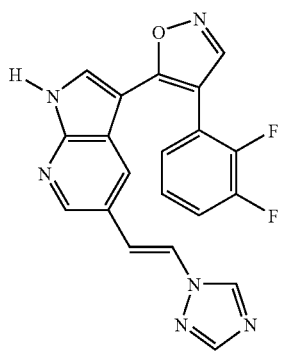
134
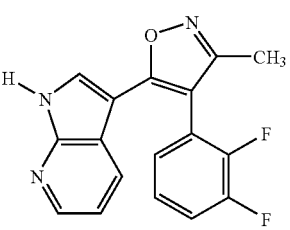
135
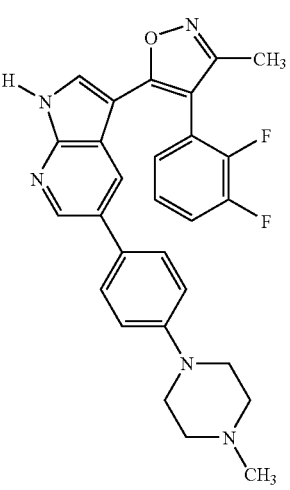
136
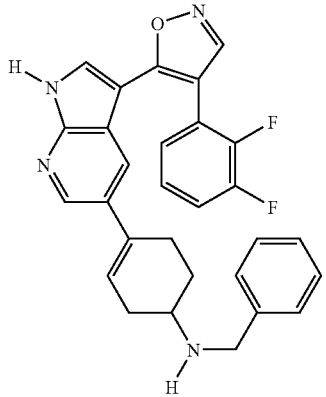
137
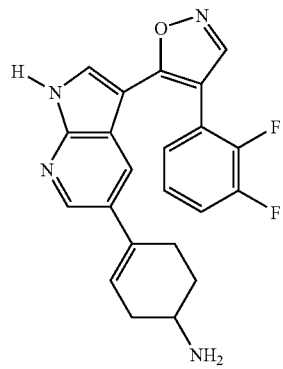
138
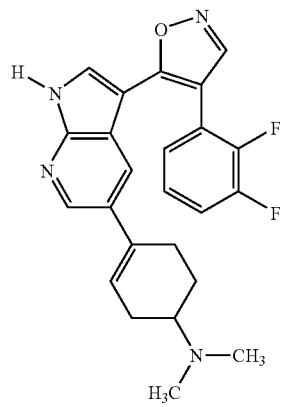
139
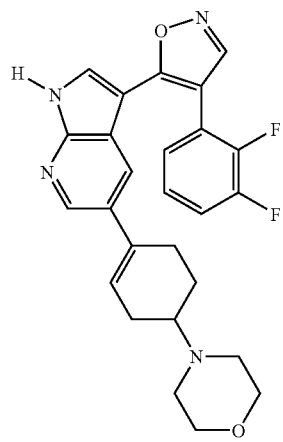

| 217 | 218 |
|---|---|
| -continued | -continued |
| 140 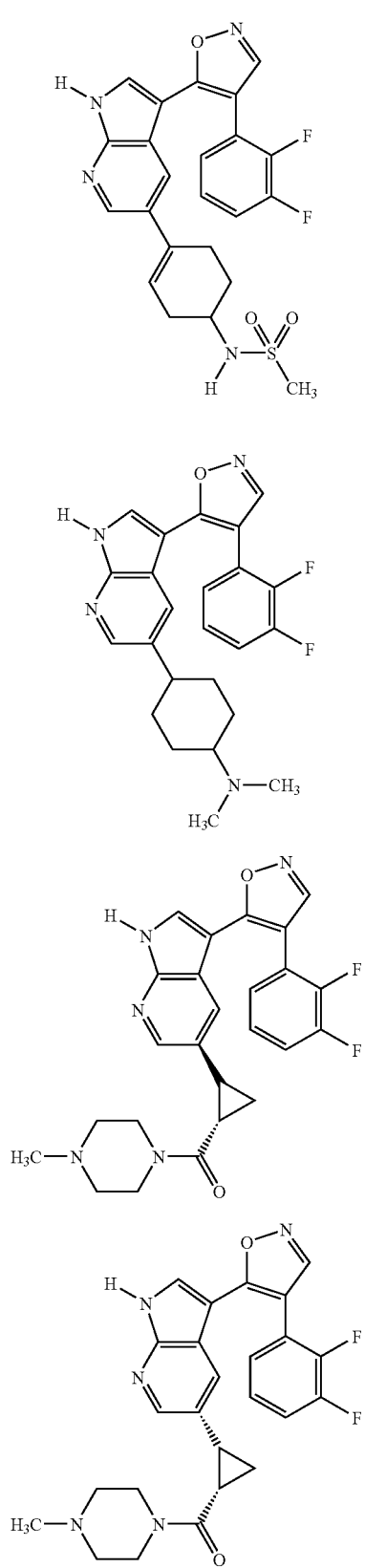 | 144 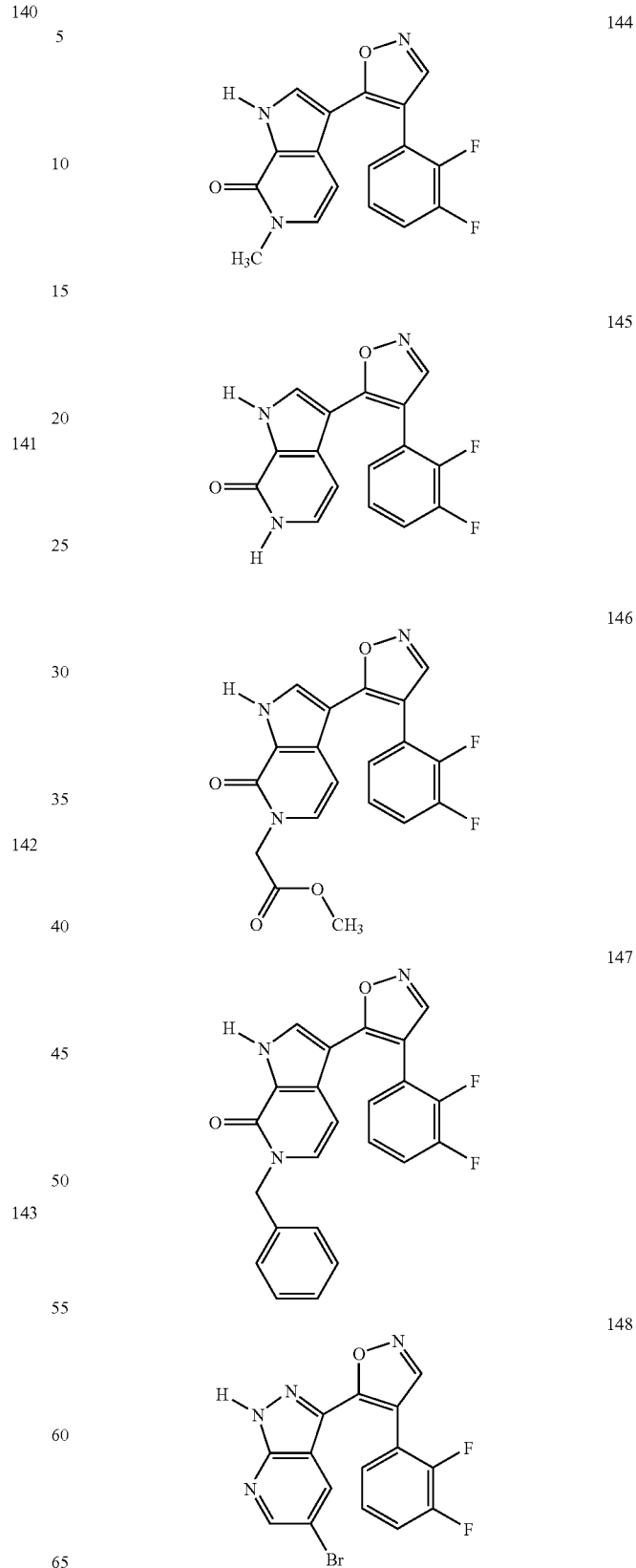 |
| 141 | 145 |
| 142 | 146 |
| 143 | 147 |
|  | 148 |

149 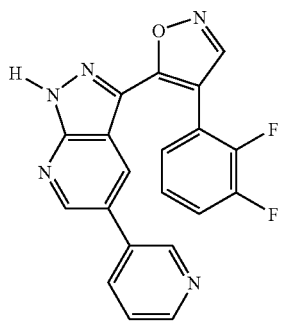

151 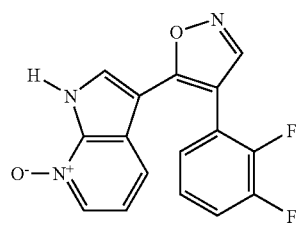

152 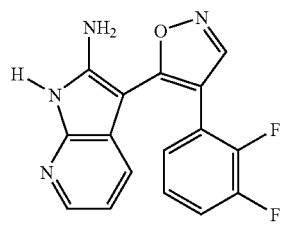

153 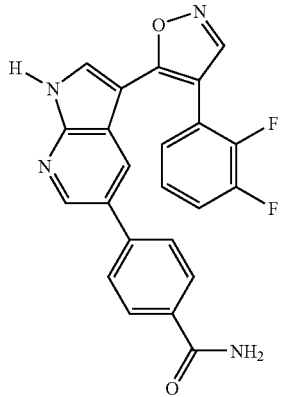

154 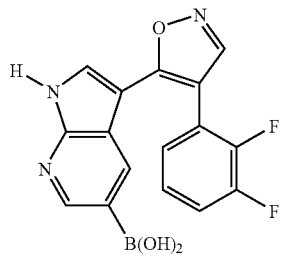

and

155 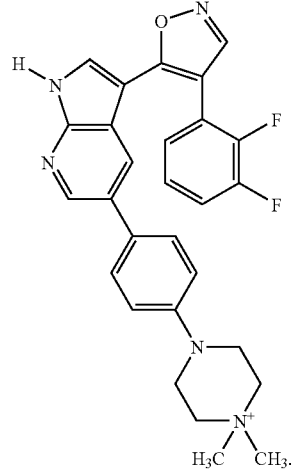

9. A composition comprising an effective amount of a compound according to claim 1, and a pharmaceutically acceptable carrier, adjuvant, or vehicle.

10. The composition according to claim 9, wherein said compound is in an amount sufficient to detectably inhibit c-Met, GSK3, JAK-3, SYK, or KDR protein kinase activity.

11. The composition according to claim 9, additionally comprising a therapeutic agent selected from a chemotherapeutic or anti-proliferative agent, an anti-inflammatory agent, an immunomodulatory or immunosuppressive agent, a neurotrophic factor, an agent for treating cardiovascular disease or, an agent for treating liver disease.

12. A method of inhibiting c-Met, GSK3, JAK-3, SYK, KDR, FLT-3, c-Kit, Aurora-2, or TAK-1 kinase activity in a biological sample in vitro; which method comprises contacting said biological sample with:
 a) a composition according to claim 9; or
 b) a compound according to claim 1.

* * * * *